United States Patent [19]
Warren et al.

[11] Patent Number: 6,066,783
[45] Date of Patent: *May 23, 2000

[54] GENES ENCODING INSECTICIDAL PROTEINS

[75] Inventors: Gregory W. Warren; Michael G. Koziel, both of Cary; Martha A. Mullins, Raleigh; Gordon J. Nye, Apex; Brian Carr; Nalini M. Desai, both of Cary; Kristy Kostichka, Durham, all of N.C.

[73] Assignee: Novartis Finance Corporation, New York, N.Y.

[ * ] Notice: This patent is subject to a terminal disclaimer.

[21] Appl. No.: 09/300,529

[22] Filed: Apr. 27, 1999

Related U.S. Application Data

[60] Continuation of application No. 08/469,334, Jun. 6, 1995, which is a division of application No. 08/463,483, Jun. 5, 1995, Pat. No. 5,849,870, which is a continuation-in-part of application No. 08/314,594, Sep. 28, 1994, abandoned, which is a continuation-in-part of application No. 08/218,018, Mar. 23, 1994, abandoned, which is a continuation-in-part of application No. 08/037,057, Mar. 25, 1993, abandoned.

[30] Foreign Application Priority Data

Mar. 23, 1994 [WO] WIPO ............... PCT/US94/03131

[51] Int. Cl.$^7$ .................. C07H 21/04; C12N 1/20; C12N 15/63; A01H 5/00
[52] U.S. Cl. ............ 800/302; 800/298; 536/23.71; 536/23.7; 536/23.1; 435/410; 435/412; 435/252.3; 435/252.33; 435/252.31; 435/320.1
[58] Field of Search .................... 800/302, 298; 536/23.7, 23.71, 23.1; 435/410, 412, 252.3, 252.33, 252.31, 320.1

[56] References Cited

U.S. PATENT DOCUMENTS

| | | | |
|---|---|---|---|
| 3,632,747 | 1/1972 | Satohiro et al. | 424/93 |
| 3,651,215 | 3/1972 | Satohiro et al. | 424/93 |
| 4,996,155 | 2/1991 | Sick et al. | 435/252.3 |
| 5,262,323 | 11/1993 | Baird et al. | 435/252.5 |

FOREIGN PATENT DOCUMENTS

| | | |
|---|---|---|
| 0498537A2 | 1/1992 | European Pat. Off. . |
| 0501650A2 | 2/1992 | European Pat. Off. . |
| WO 88/08880 | 11/1988 | WIPO . |
| WO 90/13651 | 11/1990 | WIPO . |
| WO 91/16432 | 10/1991 | WIPO . |
| WO 91/16434 | 10/1991 | WIPO . |
| US94/03131 | 7/1994 | WIPO . |
| WO 94/21795 | 9/1994 | WIPO . |

OTHER PUBLICATIONS

Arellano, A., et al., "Evidence of a New *Bacillus thuriengiensis* Toxin Active Against the Australian Sheep Blowfly *Lucilla cuprina*", Proceedings and Abstracts of the 5th International Colloquium on Invertebrate Pathology and Microbial Control, Adelaide, Austrailia, Aug. 20–24, 1990, p. 291.

Chambers et al., Isolation and Characterization of a Novel Isecticidal Crystal Protein Gene from *Bacillus thuringiensis* subsp. *aizawai*, Journal of Bacteriology 173(13): 3966–3976 (Jul., 1991).

Beecher, Douglas J., et al., "A Novel Bicomponent Hemolysin from *Bacillus cereus*", Inspection and Immunity, 58(7):2220–2227 (1990).

Estruch, Juan, et al, "VipA, a novel *Bacillus thuringiensis* vegetative insecticidal protein with a wide spectrum of activities against lepidopteran insects", Proc. Natl. Acad. Sci. USA, 93:5389–5394 (1996).

Faust, R.M., "Bacterial Diseases", In: *Insect Diseases*, G. Cantwell, ed., Marcel Dekker, NY 1974, pp. 90–102.

Faust, R.M., et al., "Bacteria and Their Toxins as Insecticides", In: *Microbial and Viral Pesticides*, E. Kurstak, Ed., Marcel Dekker, NY, 1982, pp. 84–89, 108–120.

Gleave, et al., "Screening by Poymerase Chain Reaction of *Bacillus thuringiensis* Serotypes for the Presence of cryV–like Insecticidal Protein Genes and Characterization of a cryV Gene Cloned from *B. thuringiensis* subsp. *kurstaki*," Appl. Environ. Microbiol. 59(5): 1683–1687 (1993).

Gilmore, Michael S., et al., "A *Bacillus cereus* Cytolytic Determinant, Cereolysin AB, Which Comprises the Phospholipase C and Sphingomyelinase Genes: Nucleotide Sequence and Genetic Linkage", Journal of Bacteriology, 171(2):744–753 (1989).

Heimpel, A.M., "The pH in the Gut and Blood of the Larch Sawfly, *Pristiphora erichsonii* (HTG.), and Other Insects with Reference to the Pathogenicity of *Bacillus cereus* FR. and FR.", Can. J. Zool., 33:99–106 (1955).

Heimpel, A.M., "Investigations of the Mode of Action of Strains of *Bacillus cereus* FR. and FR. Pathogenic for the Larch Sawfly, *Pristiphora erichsonii* (HTG.)", Can. J. Zool., 33:311–326 (1995).

Hofte, H., et al., "Insecticidal Crystal Proteins of *Bacillus thuringiensis*", Microbiological Reviews, 53(2):242–255 (1989).

Kostichka, et al. "Cloning of a cryV–type Isecticidal Protein Gene from *Bacillus thuringiensis*: the cry–V encoded Protein Is Expressed Early in Stationary Phase" J. Bacteriol. 178(7): 2141–2144 (1996).

Koziel, M.G., et al., "Field Performance of Elite Tansgenic Maize Plants Expressing an Insecticidal Protein Derived from *Bacillus thuringiensis*", Bio/Technology, 11:194–200 (1993).

Krieg, A., "Thuricin, a Bacteriocin Produced by *Bacillus thuringiensis*", J. Invert. Path., 15:291 (1970).

(List continued on next page.)

*Primary Examiner*—Nashaat Nashed
*Attorney, Agent, or Firm*—J. Timothy Meigs; Gary Pace

[57] ABSTRACT

The present invention is drawn to pesticidal strains and proteins. Bacillus strains which are capable of producing pesticidal proteins and auxiliary proteins during vegetative growth are provided. Also provided are the purified proteins, nucleotide sequences encoding the proteins and methods for using the strains, proteins and genes for controlling pests.

34 Claims, 1 Drawing Sheet

OTHER PUBLICATIONS

Krieg, A., "Concerning Alpha–exotoxin Produced by Vegetative Cells of *Bacillus thuringiensis* and *Bacillus cereus*", *J. Invert. Path.,* 17:134–135 (1971).

Kushner, D.J., et al., "Lecithinase Production by Strains of *Bacillus cereus* FR. and FR. Pathogenic for the Larch Sawfly, *Pristiphora erichsonii* (HTG.)", *Can. J. Microbiol.,* 3:547–551 (1957).

Luthy, P., et al., "*Bacillus thuringiensis* as a Bacterial Insecticide: Basic Consideration and Application", In: *Microbial and Viral Pesticides,* E. Kurstak, Ed., Marcel Dekker, NY 1982, pp. 37–39, 54–56.
Myers, P.S., et al., "Localization of a Mosquito–Larval Toxin of *Bacillus sphaericus* 1593", *Appl. Environ. Microbiol.,* 39(1):1205–1211 (1980).
Porter, A.G., et al., "Mosquitocidal Toxins of Bacilli and Their Genetic Manipulation for Effective Biological Control of Mosquitoes", *Microbiological Reviews,* 57(4):838–861 (1993).
Sekar, V., "The Insecticidal Crystal Protein Gene is Expressed in Vegetative Cells of *Bacillus thuringiensis* var. *temebropmos", Current Microbiology,* 17:347–349.
Shivakumar, A.G., et al., Abstract, :Cloned Crystal Protein Genes Express Vegetatively in *Bacillus subtilis, Plasmid,* 16(3):230 (1986).
Thanabalu, T., et al., "Proteolytic Processing of the Mosquitocidal Toxin from *Bacillus sphaericus* SSII–1", *J. Bacteriol.,* 174(15):5051–5056 (1992).
Yoshisue, H., et al., "Effects of *Bacillus thuringiensis* var. *israelensis* 20 kDa Protein on Production of the Bti 130–kDa Crystal Protein in *Escherichia coli", Bioscience, Biotechnology, and Biochemistry,* 56(9):1429–1433 (1992).
European International Search Report dated May 3, 1996.
Bernier et al., "*Bacillus thuringiensis* Strains A20 and A29 and Insecticidal Compounds Therefrom, and Compositions Containing These Compounds", Abstract No. 227249, *New Zealand Patent Office Journal,* 80(6):798, (1988).
Jellis et al., "*Bacillus thuringiensis* δ–Endotoxin Variants and Insecticidal Compositions", Abstract No. 228108, *New Zealand Patent Office Journal,* 81(3):359, (1992).
Schurter et al., "Genetic Manifpulation of *B. thuringiensis* and *B. cereus* Vectors and Insecticidal Composition", Abstract No. 229191, *New Zealand Patent Office Journal,* 81(3):363, (1992).
Tayabali et al., "Semiautomated Quantification of Cytotoxic Damage Induced in Cultured Insect Cells Exposed to Commercial *Bacillus thuringiensis* Biopesticides", *Journal of Applied Toxicology,* 15(5): 365–373 (1995).
Thanabalu et al., "Cytotoxicity and ADP–Ribosylating Activity of the Mosquitocidal Toxin from *Bacillus sphaericus* SSII–1: Possible Roles of the 27– and 70–Kilodalton Peptides", *Journal of Bacteriology,* 175(8): 2314–2320 (1993).
Vaithlingam et al., "Anti–Coleopteran Toxin and Gene", Abstract No. 226442, *New Zealand Patent Office Journal,* 80(7):931, (1991).
Wahisaka et al., "*Bacillus thuringiensis* Mutant and Bacterial Insecticide", Abstract No. 199725, *New Zealand Patent Office Journal,* (1982).
Walther et al., "Analysis of Mosquito Larvicidal Potential Exhibited by Vegetative Cells of *Bacillus thuringiensis* subsp. *israelensis", Applied and Environmental Microbiology,* 52(4):650–653 (1986).
Ward et al., "*Bacillus thuringiensis* var. *israelensis* δ–Endotoxin Cloning and Expression of the Toxin in Sporogenic and Asporogenic Strains of *Bacillus subtilis", Journal of Molecular Biology,* 191(1): 13–22 (1986).

Figure 1

Characterization of pCIB6022

|  | Activity vs. WCRW |
|---|---|
| pCIB6022 | +++ |
| pCIB6203 | — |
| pCIB6023 | — |
| pCIB6206 | — |
| pCIB6024 | — |

Functional Complementation of VIP Clones

| | Activity vs. WCRW |
|---|---|
| pCIB6203 / pCIB6023 | +++ |
| pCIB6203 / pCIB6206 | +++ |
| pCIB6023 / pCIB6024 | +++ |

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
      (A) LENGTH: 6049 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Bacillus cereus
      (B) STRAIN: AB78
      (C) INDIVIDUAL ISOLATE: NRRL B-21058

(ix) FEATURE:
    (A) NAME/KEY: CDS
    (B) LOCATION: 1082..2467
    (D) OTHER INFORMATION: /product= "VIP2A(a)"

(ix) FEATURE:
    (A) NAME/KEY: misc_feature
    (B) LOCATION: 2475..5126
    (D) OTHER INFORMATION: /note= "Coding sequence for the 100
        kd VIP1A(a) protein. This coding sequence is repeated
        in SEQ ID NO:4 and translated separately."

(xi) SEQUENCE DESCRIPTION: SEQ ID NO:1:

```
ATCGATACAA TGTTGTTTTA CTTAGACCGG TAGTCTCTGT AATTTGTTTA ATGCTATATT     60

CTTTACTTTG ATACATTTTA ATAGCCATTT CAACCTTATC AGTATGTTTT TGTGGTCTTC    120

CTCCTTTTTT TCCACGAGCT CTAGCTGCGT TTAATCCTGT TTTGGTACGT TCGCTAATAA    180

TATCTCTTTC TAATTCTGCA ATACTTGCCA TCATTCGAAA GAAGAATTTC CCCATAGCAT    240

TAGAGGTATC AATGTTGTCA TGAATAGAAA TAAAATCTAC ACCTAGCTCT TTGAATTTTT    300

CACTTAACTC AATTAGGTGT TTTGTAGAGC GAGAAATTCG ATCAAGTTTG TAAACAACTA    360

TCTTATCGCC TTTACGTAAT ACTTTTAGCA ACTCTTCGAG TTGAGGGCGC TCTTTTTTTA    420

TTCCTGTTAT TTTCTCCTGA TATAGCCTTT CTACACCATA TTGTTGCAAA GCATCTATTT    480

GCATATCGAG ATTTTGTTCT TCTGTGCTGA CACGAGCATA ACCAAAAATC AAATTGGTTT    540

CACTTCCTAT CTAAATATAT CTATTAAAAT AGCACCAAAA ACCTTATTAA ATTAAAATAA    600

GGAACTTTGT TTTTGGATAT GGATTTTGGT ACTCAATATG GATGAGTTTT TAACGCTTTT    660

GTTAAAAAAC AAACAAGTGC CATAAACGGT CGTTTTTGGG ATGACATAAT AAATAATCTG    720

TTTGATTAAC CTAACCTTGT ATCCTTACAG CCCAGTTTTA TTTGTACTTC AACTGACTGA    780

ATATGAAAAC AACATGAAGG TTTCATAAAA TTTATATATT TTCCATAACG GATGCTCTAT    840

CTTTAGGTTA TAGTTAAATT ATAAGAAAAA AACAAACGGA GGGAGTGAAA AAAAGCATCT    900

TCTCTATAAT TTTACAGGCT CTTTAATAAG AAGGGGGGAG ATTAGATAAT AAATATGAAT    960

ATCTATCTAT AATTGTTTGC TTCTACAATA ACTTATCTAA CTTTCATATA CAACAACAAA   1020

ACAGACTAAA TCCAGATTGT ATATTCATTT TCAGTTGTTC CTTTATAAAA TAATTTCATA   1080
```

```
A ATG AAA AGA ATG GAG GGA AAG TTG TTT ATG GTG TCA AAA AAA TTA        1126
  Met Lys Arg Met Glu Gly Lys Leu Phe Met Val Ser Lys Lys Leu
  1               5                   10                  15

CAA GTA GTT ACT AAA ACT GTA TTG CTT AGT ACA GTT TTC TCT ATA TCT     1174
Gln Val Val Thr Lys Thr Val Leu Leu Ser Thr Val Phe Ser Ile Ser
            20                  25                  30

TTA TTA AAT AAT GAA GTG ATA AAA GCT GAA CAA TTA AAT ATA AAT TCT     1222
Leu Leu Asn Asn Glu Val Ile Lys Ala Glu Gln Leu Asn Ile Asn Ser
        35                  40                  45

CAA AGT AAA TAT ACT AAC TTG CAA AAT CTA AAA ATC ACT GAC AAG GTA     1270
Gln Ser Lys Tyr Thr Asn Leu Gln Asn Leu Lys Ile Thr Asp Lys Val
    50                  55                  60

GAG GAT TTT AAA GAA GAT AAG GAA AAA GCG AAA GAA TGG GGG AAA GAA     1318
Glu Asp Phe Lys Glu Asp Lys Glu Lys Ala Lys Glu Trp Gly Lys Glu
65                  70                  75

AAA GAA AAA GAG TGG AAA CTA ACT GCT ACT GAA AAA GGA AAA ATG AAT     1366
Lys Glu Lys Glu Trp Lys Leu Thr Ala Thr Glu Lys Gly Lys Met Asn
80                  85                  90                  95

AAT TTT TTA GAT AAT AAA AAT GAT ATA AAG ACA AAT TAT AAA GAA ATT     1414
Asn Phe Leu Asp Asn Lys Asn Asp Ile Lys Thr Asn Tyr Lys Glu Ile
            100                 105                 110
```

```
ACT TTT TCT ATG GCA GGC TCA TTT GAA GAT GAA ATA AAA GAT TTA AAA    1462
Thr Phe Ser Met Ala Gly Ser Phe Glu Asp Glu Ile Lys Asp Leu Lys
            115                 120                 125

GAA ATT GAT AAG ATG TTT GAT AAA ACC AAT CTA TCA AAT TCT ATT ATC    1510
Glu Ile Asp Lys Met Phe Asp Lys Thr Asn Leu Ser Asn Ser Ile Ile
130                 135                 140

ACC TAT AAA AAT GTG GAA CCG ACA ACA ATT GGA TTT AAT AAA TCT TTA    1558
Thr Tyr Lys Asn Val Glu Pro Thr Thr Ile Gly Phe Asn Lys Ser Leu
    145                 150                 155

ACA GAA GGT AAT ACG ATT AAT TCT GAT GCA ATG GCA CAG TTT AAA GAA    1606
Thr Glu Gly Asn Thr Ile Asn Ser Asp Ala Met Ala Gln Phe Lys Glu
160                 165                 170                 175

CAA TTT TTA GAT AGG GAT ATT AAG TTT GAT AGT TAT CTA GAT ACG CAT    1654
Gln Phe Leu Asp Arg Asp Ile Lys Phe Asp Ser Tyr Leu Asp Thr His
                180                 185                 190

TTA ACT GCT CAA CAA GTT TCC AGT AAA GAA AGA GTT ATT TTG AAG GTT    1702
Leu Thr Ala Gln Gln Val Ser Ser Lys Glu Arg Val Ile Leu Lys Val
            195                 200                 205

ACG GTT CCG AGT GGG AAA GGT TCT ACT ACT CCA ACA AAA GCA GGT GTC    1750
Thr Val Pro Ser Gly Lys Gly Ser Thr Thr Pro Thr Lys Ala Gly Val
        210                 215                 220

ATT TTA AAT AAT AGT GAA TAC AAA ATG CTC ATT GAT AAT GGG TAT ATG    1798
Ile Leu Asn Asn Ser Glu Tyr Lys Met Leu Ile Asp Asn Gly Tyr Met
    225                 230                 235

GTC CAT GTA GAT AAG GTA TCA AAA GTG GTG AAA AAA GGG GTG GAG TGC    1846
Val His Val Asp Lys Val Ser Lys Val Val Lys Lys Gly Val Glu Cys
240                 245                 250                 255

TTA CAA ATT GAA GGG ACT TTA AAA AAG AGT CTT GAC TTT AAA AAT GAT    1894
Leu Gln Ile Glu Gly Thr Leu Lys Lys Ser Leu Asp Phe Lys Asn Asp
                260                 265                 270

ATA AAT GCT GAA GCG CAT AGC TGG GGT ATG AAG AAT TAT GAA GAG TGG    1942
Ile Asn Ala Glu Ala His Ser Trp Gly Met Lys Asn Tyr Glu Glu Trp
            275                 280                 285

GCT AAA GAT TTA ACC GAT TCG CAA AGG GAA GCT TTA GAT GGG TAT GCT    1990
Ala Lys Asp Leu Thr Asp Ser Gln Arg Glu Ala Leu Asp Gly Tyr Ala
        290                 295                 300

AGG CAA GAT TAT AAA GAA ATC AAT AAT TAT TTA AGA AAT CAA GGC GGA    2038
Arg Gln Asp Tyr Lys Glu Ile Asn Asn Tyr Leu Arg Asn Gln Gly Gly
    305                 310                 315

AGT GGA AAT GAA AAA CTA GAT GCT CAA ATA AAA AAT ATT TCT GAT GCT    2086
Ser Gly Asn Glu Lys Leu Asp Ala Gln Ile Lys Asn Ile Ser Asp Ala
320                 325                 330                 335

TTA GGG AAG AAA CCA ATA CCG GAA AAT ATT ACT GTG TAT AGA TGG TGT    2134
Leu Gly Lys Lys Pro Ile Pro Glu Asn Ile Thr Val Tyr Arg Trp Cys
                340                 345                 350

GGC ATG CCG GAA TTT GGT TAT CAA ATT AGT GAT CCG TTA CCT TCT TTA    2182
Gly Met Pro Glu Phe Gly Tyr Gln Ile Ser Asp Pro Leu Pro Ser Leu
            355                 360                 365

AAA GAT TTT GAA GAA CAA TTT TTA AAT ACA ATC AAA GAA GAC AAA GGA    2230
Lys Asp Phe Glu Glu Gln Phe Leu Asn Thr Ile Lys Glu Asp Lys Gly
        370                 375                 380

TAT ATG AGT ACA AGC TTA TCG AGT GAA CGT CTT GCA GCT TTT GGA TCT    2278
Tyr Met Ser Thr Ser Leu Ser Ser Glu Arg Leu Ala Ala Phe Gly Ser
    385                 390                 395

AGA AAA ATT ATA TTA CGA TTA CAA GTT CCG AAA GGA AGT ACG GGT GCG    2326
Arg Lys Ile Ile Leu Arg Leu Gln Val Pro Lys Gly Ser Thr Gly Ala
400                 405                 410                 415
```

```
TAT TTA AGT GCC ATT GGT GGA TTT GCA AGT GAA AAA GAG ATC CTA CTT      2374
Tyr Leu Ser Ala Ile Gly Gly Phe Ala Ser Glu Lys Glu Ile Leu Leu
                420                 425                 430

GAT AAA GAT AGT AAA TAT CAT ATT GAT AAA GTA ACA GAG GTA ATT ATT      2422
Asp Lys Asp Ser Lys Tyr His Ile Asp Lys Val Thr Glu Val Ile Ile
                435                 440                 445

AAA GGT GTT AAG CGA TAT GTA GTG GAT GCA ACA TTA TTA ACA AAT          2467
Lys Gly Val Lys Arg Tyr Val Val Asp Ala Thr Leu Leu Thr Asn
            450                 455                 460

TAAGGAGATG AAAAATATGA AGAAAAAGTT AGCAAGTGTT GTAACGTGTA CGTTATTAGC    2527

TCCTATGTTT TTGAATGGAA ATGTGAATGC TGTTTACGCA GACAGCAAAA CAAATCAAAT    2587

TTCTACAACA CAGAAAAATC AACAGAAAGA GATGGACCGA AAAGGATTAC TTGGGTATTA    2647

TTTCAAAGGA AAAGATTTTA GTAATCTTAC TATGTTTGCA CCGACACGTG ATAGTACTCT    2707

TATTTATGAT CAACAAACAG CAAATAAACT ATTAGATAAA AACAACAAG AATATCAGTC     2767

TATTCGTTGG ATTGGTTTGA TTCAGAGTAA AGAAACGGGA GATTTCACAT TTAACTTATC    2827

TGAGGATGAA CAGGCAATTA TAGAAATCAA TGGGAAAATT ATTTCTAATA AAGGGAAAGA    2887

AAAGCAAGTT GTCCATTTAG AAAAAGGAAA ATTAGTTCCA ATCAAAATAG AGTATCAATC    2947

AGATACAAAA TTTAATATTG ACAGTAAAAC ATTTAAAGAA CTTAAATTAT TTAAAATAGA    3007

TAGTCAAAAC CAACCCCAGC AAGTCCAGCA AGATGAACTG AGAAATCCTG AATTTAACAA    3067

GAAAGAATCA CAGGAATTCT TAGCGAAACC ATCGAAAATA AATCTTTTCA CTCAAAAAAT    3127

GAAAAGGGAA ATTGATGAAG ACACGGATAC GGATGGGGAC TCTATTCCTG ACCTTTGGGA    3187

AGAAAATGGG TATACGATTC ACAATAGAAT CGCTGTAAAG TGGGACGATT CTCTAGCAAG    3247

TAAAGGGTAT ACGAAATTTG TTTCAAATCC ACTAGAAAGT CACACAGTTG GTGATCCTTA    3307

TACAGATTAT GAAAAGGCAG CAAGAGATCT AGATTTGTCA AATGCAAAGG AAACGTTTAA    3367

CCCATTGGTA GCTGCTTTTC CAAGTGTGAA TGTTAGTATG GAAAAGGTGA TATTATCACC    3427

AAATGAAAAT TTATCCAATA GTGTAGAGTC TCATTCATCC ACGAATTGGT CTTATACAAA    3487

TACAGAAGGT GCTTCTGTTG AAGCGGGGAT TGGACCAAAA GGTATTTCGT TCGGAGTTAG    3547

CGTAAACTAT CAACACTCTG AAACAGTTGC ACAAGAATGG GGAACATCTA CAGGAAATAC    3607

TTCGCAATTC AATACGGCTT CAGCGGGATA TTTAAATGCA AATGTTCGAT ATAACAATGT    3667

AGGAACTGGT GCCATCTACG ATGTAAAACC TACAACAAGT TTTGTATTAA ATAACGATAC    3727

TATCGCAACT ATTACGGCGA AATCTAATTC TACAGCCTTA AATATATCTC TGGAGAAAG    3787

TTACCCGAAA AAAGGACAAA ATGGAATCGC AATAACATCA ATGGATGATT TAATTCCCA    3847

TCCGATTACA TTAAATAAAA AACAAGTAGA TAATCTGCTA ATAATAAAC CTATGATGTT    3907

GGAAACAAAC CAAACAGATG GTGTTTATAA GATAAAGAT ACACATGGAA ATATAGTAAC    3967

TGGCGGAGAA TGGAATGGTG TCATACAACA AATCAAGGCT AAAACAGCGT CTATTATTGT    4027

GGATGATGGG GAACGTGTAG CAGAAAAACG TGTAGCGGCA AAAGATTATG AAAATCCAGA    4087

AGATAAAACA CCGTCTTTAA CTTTAAAAGA TGCCCTGAAG CTTTCATATC AGATGAAAT     4147

AAAAGAAATA GAGGGATTAT TATATTATAA AAACAAACCG ATATACGAAT CGAGCGTTAT    4207

GACTTACTTA GATGAAAATA CAGCAAAAGA AGTGACCAAA CAATTAAATG ATACCACTGG    4267

GAAATTTAAA GATGTAAGTC ATTTATATGA TGTAAAACTG ACTCCAAAAA TGAATGTTAC    4327

AATCAAATTG TCTATACTTT ATGATAATGC TGAGTCTAAT GATAACTCAA TTGGTAAATG    4387

GACAAACACA ATATTGTTT CAGGTGGAAA TAACGGAAAA AAACAATATT CTTCTAATAA     4447
```

```
TCCGGATGCT AATTTGACAT TAAATACAGA TGCTCAAGAA AAATTAAATA AAAATCGTGA        4507

CTATTATATA AGTTTATATA TGAAGTCAGA AAAAAACACA CAATGTGAGA TTACTATAGA        4567

TGGGGAGATT TATCCGATCA CTACAAAAAC AGTGAATGTG AATAAAGACA ATTACAAAAG        4627

ATTAGATATT ATAGCTCATA ATATAAAAAG TAATCCAATT TCTTCACTTC ATATTAAAAC        4687

GAATGATGAA ATAACTTTAT TTTGGGATGA TATTTCTATA ACAGATGTAG CATCAATAAA        4747

ACCGGAAAAT TTAACAGATT CAGAAATTAA ACAGATTTAT AGTAGGTATG GTATTAAGTT        4807

AGAAGATGGA ATCCTTATTG ATAAAAAAGG TGGGATTCAT TATGGTGAAT TTATTAATGA        4867

AGCTAGTTTT AATATTGAAC CATTGCAAAA TTATGTGACC AAATATGAAG TTACTTATAG        4927

TAGTGAGTTA GGACCAAACG TGAGTGACAC ACTTGAAAGT GATAAAATTT ACAAGGATGG        4987

GACAATTAAA TTTGATTTTA CCAAATATAG TAAAAATGAA CAAGGATTAT TTTATGACAG        5047

TGGATTAAAT TGGGACTTTA AAATTAATGC TATTACTTAT GATGGTAAAG AGATGAATGT        5107

TTTTCATAGA TATAATAAAT AGTTATTATA TCTATGAAGC TGGTGCTAAA GATAGTGTAA        5167

AAGTTAATAT ACTGTAGGAT TGTAATAAAA GTAATGGAAT TGATATCGTA CTTTGGAGTG        5227

GGGGATACTT TGTAAATAGT TCTATCAGAA ACATTAGACT AAGAAAAGTT ACTACCCCCA        5287

CTTGAAAATG AAGATTCAAC TGATTACAAA CAACCTGTTA AATATTATAA GGTTTTAACA        5347

AAATATTAAA CTCTTTATGT TAATACTGTA ATATAAAGAG TTTAATTGTA TTCAAATGAA        5407

GCTTTCCCAC AAAATTAGAC TGATTATCTA ATGAAATAAT CAGTCTAATT TTGTAGAACA        5467

GGTCTGGTAT TATTGTACGT GGTCACTAAA AGATATCTAA TATTATTGGG CAAGGCGTTC        5527

CATGATTGAA TCCTCGAATG TCTTGCCCTT TCATTTATT TAAGAAGGAT TGTGGAGAAA        5587

TTATGGTTTA GATAATGAAG AAAGACTTCA CTTCTAATTT TTGATGTTAA ATAAATCAAA        5647

ATTTGGCGAT TCACATTGTT TAATCCACTG ATAAAACATA CTGGAGTGTT CTTAAAAAAT        5707

CAGCTTTTTT CTTTATAAAA TTTTGCTTAG CGTACGAAAT TCGTGTTTTG TTGGTGGGAC        5767

CCCATGCCCA TCAACTTAAG AGTAAATTAG TAATGAACTT TCGTTCATCT GGATTAAAAT        5827

AACCTCAAAT TAGGACATGT TTTTAAAAAT AAGCAGACCA AATAAGCCTA GAATAGGTAT        5887

CATTTTTAAA AATTATGCTG CTTTCTTTTG TTTTCCAAAT CCATTATACT CATAAGCAAC        5947

ACCCATAATG TCAAAGACTG TTTTTGTCTC ATATCGATAA GCTTGATATC GAATTCCTGC        6007

AGCCCGGGGG ATCCACTAGT TCTAGAGCGG CCGCCACCGC GG                           6049
```

(2) INFORMATION FOR SEQ ID NO:2:

(i) SEQUENCE CHARACTERISTICS:
        (A) LENGTH: 462 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Arg Met Glu Gly Lys Leu Phe Met Val Ser Lys Lys Leu Gln
  1               5                  10                  15

Val Val Thr Lys Thr Val Leu Leu Ser Thr Val Phe Ser Ile Ser Leu
             20                  25                  30

Leu Asn Asn Glu Val Ile Lys Ala Glu Gln Leu Asn Ile Asn Ser Gln
         35                  40                  45

Ser Lys Tyr Thr Asn Leu Gln Asn Leu Lys Ile Thr Asp Lys Val Glu
     50                  55                  60
```

-continued

```
Asp Phe Lys Glu Asp Lys Glu Lys Ala Lys Glu Trp Gly Lys Glu Lys
 65                  70                  75                  80

Glu Lys Glu Trp Lys Leu Thr Ala Thr Glu Lys Gly Lys Met Asn Asn
                 85                  90                  95

Phe Leu Asp Asn Lys Asn Asp Ile Lys Thr Asn Tyr Lys Glu Ile Thr
            100                 105                 110

Phe Ser Met Ala Gly Ser Phe Glu Asp Glu Ile Lys Asp Leu Lys Glu
        115                 120                 125

Ile Asp Lys Met Phe Asp Lys Thr Asn Leu Ser Asn Ser Ile Ile Thr
130                 135                 140

Tyr Lys Asn Val Glu Pro Thr Thr Ile Gly Phe Asn Lys Ser Leu Thr
145                 150                 155                 160

Glu Gly Asn Thr Ile Asn Ser Asp Ala Met Ala Gln Phe Lys Glu Gln
                165                 170                 175

Phe Leu Asp Arg Asp Ile Lys Phe Asp Ser Tyr Leu Asp Thr His Leu
            180                 185                 190

Thr Ala Gln Gln Val Ser Ser Lys Glu Arg Val Ile Leu Lys Val Thr
        195                 200                 205

Val Pro Ser Gly Lys Gly Ser Thr Thr Pro Thr Lys Ala Gly Val Ile
210                 215                 220

Leu Asn Asn Ser Glu Tyr Lys Met Leu Ile Asp Asn Gly Tyr Met Val
225                 230                 235                 240

His Val Asp Lys Val Ser Lys Val Val Lys Gly Val Glu Cys Leu
                245                 250                 255

Gln Ile Glu Gly Thr Leu Lys Lys Ser Leu Asp Phe Lys Asn Asp Ile
            260                 265                 270

Asn Ala Glu Ala His Ser Trp Gly Met Lys Asn Tyr Glu Glu Trp Ala
        275                 280                 285

Lys Asp Leu Thr Asp Ser Gln Arg Glu Ala Leu Asp Gly Tyr Ala Arg
        290                 295                 300

Gln Asp Tyr Lys Glu Ile Asn Asn Tyr Leu Arg Asn Gln Gly Gly Ser
305                 310                 315                 320

Gly Asn Glu Lys Leu Asp Ala Gln Ile Lys Asn Ile Ser Asp Ala Leu
                325                 330                 335

Gly Lys Lys Pro Ile Pro Glu Asn Ile Thr Val Tyr Arg Trp Cys Gly
            340                 345                 350

Met Pro Glu Phe Gly Tyr Gln Ile Ser Asp Pro Leu Pro Ser Leu Lys
        355                 360                 365

Asp Phe Glu Glu Gln Phe Leu Asn Thr Ile Lys Glu Asp Lys Gly Tyr
        370                 375                 380

Met Ser Thr Ser Leu Ser Ser Glu Arg Leu Ala Ala Phe Gly Ser Arg
385                 390                 395                 400

Lys Ile Ile Leu Arg Leu Gln Val Pro Lys Gly Ser Thr Gly Ala Tyr
                405                 410                 415

Leu Ser Ala Ile Gly Gly Phe Ala Ser Glu Lys Glu Ile Leu Leu Asp
            420                 425                 430

Lys Asp Ser Lys Tyr His Ile Asp Lys Val Thr Glu Val Ile Ile Lys
        435                 440                 445

Gly Val Lys Arg Tyr Val Val Asp Ala Thr Leu Leu Thr Asn
450                 455                 460
```

```
(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "Signal peptide for vacuolar
            targetting"

(xi) SEQUENCE DESCRIPTION: SEQ ID NO:3:

Ser Ser Ser Ser Phe Ala Asp Ser Asn Pro Ile Arg Val Thr Asp Arg
 1               5                  10                  15

Ala Ala Ser Thr
            20

(2) INFORMATION FOR SEQ ID NO:4:

(i) SEQUENCE CHARACTERISTICS:
        (A) LENGTH: 2655 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus cereus
        (B) STRAIN: AB78
        (C) INDIVIDUAL ISOLATE: NRRL B-21058

(ix) FEATURE:
        (A) NAME/KEY: CDS
        (B) LOCATION: 1..2652
        (D) OTHER INFORMATION: /product= "100 kDa protein VIP1A(a)"
            /note= "This sequence is identical to the portion of
            SEQ ID NO:1 between and including nucleotide 2475
            to 5126."

(xi) SEQUENCE DESCRIPTION: SEQ ID NO:4:

ATG AAA AAT ATG AAG AAA AAG TTA GCA AGT GTT GTA ACG TGT ACG TTA      48
Met Lys Asn Met Lys Lys Lys Leu Ala Ser Val Val Thr Cys Thr Leu
            465                 470                 475

TTA GCT CCT ATG TTT TTG AAT GGA AAT GTG AAT GCT GTT TAC GCA GAC      96
Leu Ala Pro Met Phe Leu Asn Gly Asn Val Asn Ala Val Tyr Ala Asp
        480                 485                 490

AGC AAA ACA AAT CAA ATT TCT ACA ACA CAG AAA AAT CAA CAG AAA GAG     144
Ser Lys Thr Asn Gln Ile Ser Thr Thr Gln Lys Asn Gln Gln Lys Glu
495                 500                 505                 510

ATG GAC CGA AAA GGA TTA CTT GGG TAT TAT TTC AAA GGA AAA GAT TTT     192
Met Asp Arg Lys Gly Leu Leu Gly Tyr Tyr Phe Lys Gly Lys Asp Phe
                515                 520                 525

AGT AAT CTT ACT ATG TTT GCA CCG ACA CGT GAT AGT ACT CTT ATT TAT     240
Ser Asn Leu Thr Met Phe Ala Pro Thr Arg Asp Ser Thr Leu Ile Tyr
        530                 535                 540

GAT CAA CAA ACA GCA AAT AAA CTA TTA GAT AAA AAA CAA CAA GAA TAT     288
Asp Gln Gln Thr Ala Asn Lys Leu Leu Asp Lys Lys Gln Gln Glu Tyr
    545                 550                 555
```

```
CAG TCT ATT CGT TGG ATT GGT TTG ATT CAG AGT AAA GAA ACG GGA GAT    336
Gln Ser Ile Arg Trp Ile Gly Leu Ile Gln Ser Lys Glu Thr Gly Asp
        560                 565                 570

TTC ACA TTT AAC TTA TCT GAG GAT GAA CAG GCA ATT ATA GAA ATC AAT    384
Phe Thr Phe Asn Leu Ser Glu Asp Glu Gln Ala Ile Ile Glu Ile Asn
575                 580                 585                 590

GGG AAA ATT ATT TCT AAT AAA GGG AAA GAA AAG CAA GTT GTC CAT TTA    432
Gly Lys Ile Ile Ser Asn Lys Gly Lys Glu Lys Gln Val Val His Leu
                595                 600                 605

GAA AAA GGA AAA TTA GTT CCA ATC AAA ATA GAG TAT CAA TCA GAT ACA    480
Glu Lys Gly Lys Leu Val Pro Ile Lys Ile Glu Tyr Gln Ser Asp Thr
        610                 615                 620

AAA TTT AAT ATT GAC AGT AAA ACA TTT AAA GAA CTT AAA TTA TTT AAA    528
Lys Phe Asn Ile Asp Ser Lys Thr Phe Lys Glu Leu Lys Leu Phe Lys
                625                 630                 635

ATA GAT AGT CAA AAC CAA CCC CAG CAA GTC CAG CAA GAT GAA CTG AGA    576
Ile Asp Ser Gln Asn Gln Pro Gln Gln Val Gln Gln Asp Glu Leu Arg
        640                 645                 650

AAT CCT GAA TTT AAC AAG AAA GAA TCA CAG GAA TTC TTA GCG AAA CCA    624
Asn Pro Glu Phe Asn Lys Lys Glu Ser Gln Glu Phe Leu Ala Lys Pro
655                 660                 665                 670

TCG AAA ATA AAT CTT TTC ACT CAA AAA ATG AAA AGG GAA ATT GAT GAA    672
Ser Lys Ile Asn Leu Phe Thr Gln Lys Met Lys Arg Glu Ile Asp Glu
                675                 680                 685

GAC ACG GAT ACG GAT GGG GAC TCT ATT CCT GAC CTT TGG GAA GAA AAT    720
Asp Thr Asp Thr Asp Gly Asp Ser Ile Pro Asp Leu Trp Glu Glu Asn
                    690                 695                 700

GGG TAT ACG ATT CAA AAT AGA ATC GCT GTA AAG TGG GAC GAT TCT CTA    768
Gly Tyr Thr Ile Gln Asn Arg Ile Ala Val Lys Trp Asp Asp Ser Leu
        705                 710                 715

GCA AGT AAA GGG TAT ACG AAA TTT GTT TCA AAT CCA CTA GAA AGT CAC    816
Ala Ser Lys Gly Tyr Thr Lys Phe Val Ser Asn Pro Leu Glu Ser His
720                 725                 730

ACA GTT GGT GAT CCT TAT ACA GAT TAT GAA AAG GCA GCA AGA GAT CTA    864
Thr Val Gly Asp Pro Tyr Thr Asp Tyr Glu Lys Ala Ala Arg Asp Leu
735                 740                 745                 750

GAT TTG TCA AAT GCA AAG GAA ACG TTT AAC CCA TTG GTA GCT GCT TTT    912
Asp Leu Ser Asn Ala Lys Glu Thr Phe Asn Pro Leu Val Ala Ala Phe
                755                 760                 765

CCA AGT GTG AAT GTT AGT ATG GAA AAG GTG ATA TTA TCA CCA AAT GAA    960
Pro Ser Val Asn Val Ser Met Glu Lys Val Ile Leu Ser Pro Asn Glu
                770                 775                 780

AAT TTA TCC AAT AGT GTA GAG TCT CAT TCA TCC ACG AAT TGG TCT TAT   1008
Asn Leu Ser Asn Ser Val Glu Ser His Ser Ser Thr Asn Trp Ser Tyr
        785                 790                 795

ACA AAT ACA GAA GGT GCT TCT GTT GAA GCG GGG ATT GGA CCA AAA GGT   1056
Thr Asn Thr Glu Gly Ala Ser Val Glu Ala Gly Ile Gly Pro Lys Gly
800                 805                 810

ATT TCG TTC GGA GTT AGC GTA AAC TAT CAA CAC TCT GAA ACA GTT GCA   1104
Ile Ser Phe Gly Val Ser Val Asn Tyr Gln His Ser Glu Thr Val Ala
815                 820                 825                 830

CAA GAA TGG GGA ACA TCT ACA GGA AAT ACT TCG CAA TTC AAT ACG GCT   1152
Gln Glu Trp Gly Thr Ser Thr Gly Asn Thr Ser Gln Phe Asn Thr Ala
                835                 840                 845

TCA GCG GGA TAT TTA AAT GCA AAT GTT CGA TAT AAC AAT GTA GGA ACT   1200
Ser Ala Gly Tyr Leu Asn Ala Asn Val Arg Tyr Asn Asn Val Gly Thr
        850                 855                 860
```

-continued

```
GGT GCC ATC TAC GAT GTA AAA CCT ACA ACA AGT TTT GTA TTA AAT AAC     1248
Gly Ala Ile Tyr Asp Val Lys Pro Thr Thr Ser Phe Val Leu Asn Asn
        865                 870                 875

GAT ACT ATC GCA ACT ATT ACG GCG AAA TCT AAT TCT ACA GCC TTA AAT     1296
Asp Thr Ile Ala Thr Ile Thr Ala Lys Ser Asn Ser Thr Ala Leu Asn
880                 885                 890

ATA TCT CCT GGA GAA AGT TAC CCG AAA AAA GGA CAA AAT GGA ATC GCA     1344
Ile Ser Pro Gly Glu Ser Tyr Pro Lys Lys Gly Gln Asn Gly Ile Ala
895                 900                 905                 910

ATA ACA TCA ATG GAT GAT TTT AAT TCC CAT CCG ATT ACA TTA AAT AAA     1392
Ile Thr Ser Met Asp Asp Phe Asn Ser His Pro Ile Thr Leu Asn Lys
                915                 920                 925

AAA CAA GTA GAT AAT CTG CTA AAT AAT AAA CCT ATG ATG TTG GAA ACA     1440
Lys Gln Val Asp Asn Leu Leu Asn Asn Lys Pro Met Met Leu Glu Thr
            930                 935                 940

AAC CAA ACA GAT GGT GTT TAT AAG ATA AAA GAT ACA CAT GGA AAT ATA     1488
Asn Gln Thr Asp Gly Val Tyr Lys Ile Lys Asp Thr His Gly Asn Ile
        945                 950                 955

GTA ACT GGC GGA GAA TGG AAT GGT GTC ATA CAA CAA ATC AAG GCT AAA     1536
Val Thr Gly Gly Glu Trp Asn Gly Val Ile Gln Gln Ile Lys Ala Lys
960                 965                 970

ACA GCG TCT ATT ATT GTG GAT GAT GGG GAA CGT GTA GCA GAA AAA CGT     1584
Thr Ala Ser Ile Ile Val Asp Asp Gly Glu Arg Val Ala Glu Lys Arg
975                 980                 985                 990

GTA GCG GCA AAA GAT TAT GAA AAT CCA GAA GAT AAA ACA CCG TCT TTA     1632
Val Ala Ala Lys Asp Tyr Glu Asn Pro Glu Asp Lys Thr Pro Ser Leu
                995                 1000                1005

ACT TTA AAA GAT GCC CTG AAG CTT TCA TAT CCA GAT GAA ATA AAA GAA     1680
Thr Leu Lys Asp Ala Leu Lys Leu Ser Tyr Pro Asp Glu Ile Lys Glu
            1010                1015                1020

ATA GAG GGA TTA TTA TAT TAT AAA AAC AAA CCG ATA TAC GAA TCG AGC     1728
Ile Glu Gly Leu Leu Tyr Tyr Lys Asn Lys Pro Ile Tyr Glu Ser Ser
        1025                1030                1035

GTT ATG ACT TAC TTA GAT GAA AAT ACA GCA AAA GAA GTG ACC AAA CAA     1776
Val Met Thr Tyr Leu Asp Glu Asn Thr Ala Lys Glu Val Thr Lys Gln
    1040                1045                1050

TTA AAT GAT ACC ACT GGG AAA TTT AAA GAT GTA AGT CAT TTA TAT GAT     1824
Leu Asn Asp Thr Thr Gly Lys Phe Lys Asp Val Ser His Leu Tyr Asp
1055                1060                1065                1070

GTA AAA CTG ACT CCA AAA ATG AAT GTT ACA ATC AAA TTG TCT ATA CTT     1872
Val Lys Leu Thr Pro Lys Met Asn Val Thr Ile Lys Leu Ser Ile Leu
                1075                1080                1085

TAT GAT AAT GCT GAG TCT AAT GAT AAC TCA ATT GGT AAA TGG ACA AAC     1920
Tyr Asp Asn Ala Glu Ser Asn Asp Asn Ser Ile Gly Lys Trp Thr Asn
            1090                1095                1100

ACA AAT ATT GTT TCA GGT GGA AAT AAC GGA AAA AAA CAA TAT TCT TCT     1968
Thr Asn Ile Val Ser Gly Gly Asn Asn Gly Lys Lys Gln Tyr Ser Ser
        1105                1110                1115

AAT AAT CCG GAT GCT AAT TTG ACA TTA AAT ACA GAT GCT CAA GAA AAA     2016
Asn Asn Pro Asp Ala Asn Leu Thr Leu Asn Thr Asp Ala Gln Glu Lys
    1120                1125                1130

TTA AAT AAA AAT CGT GAC TAT TAT ATA AGT TTA TAT ATG AAG TCA GAA     2064
Leu Asn Lys Asn Arg Asp Tyr Tyr Ile Ser Leu Tyr Met Lys Ser Glu
1135                1140                1145                1150

AAA AAC ACA CAA TGT GAG ATT ACT ATA GAT GGG GAG ATT TAT CCG ATC     2112
Lys Asn Thr Gln Cys Glu Ile Thr Ile Asp Gly Glu Ile Tyr Pro Ile
                1155                1160                1165
```

```
ACT ACA AAA ACA GTG AAT GTG AAT AAA GAC AAT TAC AAA AGA TTA GAT    2160
Thr Thr Lys Thr Val Asn Val Asn Lys Asp Asn Tyr Lys Arg Leu Asp
            1170                1175                1180

ATT ATA GCT CAT AAT ATA AAA AGT AAT CCA ATT TCT TCA CTT CAT ATT    2208
Ile Ile Ala His Asn Ile Lys Ser Asn Pro Ile Ser Ser Leu His Ile
            1185                1190                1195

AAA ACG AAT GAT GAA ATA ACT TTA TTT TGG GAT GAT ATT TCT ATA ACA    2256
Lys Thr Asn Asp Glu Ile Thr Leu Phe Trp Asp Asp Ile Ser Ile Thr
        1200                1205                1210

GAT GTA GCA TCA ATA AAA CCG GAA AAT TTA ACA GAT TCA GAA ATT AAA    2304
Asp Val Ala Ser Ile Lys Pro Glu Asn Leu Thr Asp Ser Glu Ile Lys
1215                1220                1225                1230

CAG ATT TAT AGT AGG TAT GGT ATT AAG TTA GAA GAT GGA ATC CTT ATT    2352
Gln Ile Tyr Ser Arg Tyr Gly Ile Lys Leu Glu Asp Gly Ile Leu Ile
                1235                1240                1245

GAT AAA AAA GGT GGG ATT CAT TAT GGT GAA TTT ATT AAT GAA GCT AGT    2400
Asp Lys Lys Gly Gly Ile His Tyr Gly Glu Phe Ile Asn Glu Ala Ser
            1250                1255                1260

TTT AAT ATT GAA CCA TTG CAA AAT TAT GTG ACC AAA TAT GAA GTT ACT    2448
Phe Asn Ile Glu Pro Leu Gln Asn Tyr Val Thr Lys Tyr Glu Val Thr
        1265                1270                1275

TAT AGT AGT GAG TTA GGA CCA AAC GTG AGT GAC ACA CTT GAA AGT GAT    2496
Tyr Ser Ser Glu Leu Gly Pro Asn Val Ser Asp Thr Leu Glu Ser Asp
1280                1285                1290

AAA ATT TAC AAG GAT GGG ACA ATT AAA TTT GAT TTT ACC AAA TAT AGT    2544
Lys Ile Tyr Lys Asp Gly Thr Ile Lys Phe Asp Phe Thr Lys Tyr Ser
1295                1300                1305                1310

AAA AAT GAA CAA GGA TTA TTT TAT GAC AGT GGA TTA AAT TGG GAC TTT    2592
Lys Asn Glu Gln Gly Leu Phe Tyr Asp Ser Gly Leu Asn Trp Asp Phe
                1315                1320                1325

AAA ATT AAT GCT ATT ACT TAT GAT GGT AAA GAG ATG AAT GTT TTT CAT    2640
Lys Ile Asn Ala Ile Thr Tyr Asp Gly Lys Glu Met Asn Val Phe His
            1330                1335                1340

AGA TAT AAT AAA TAG                                                2655
Arg Tyr Asn Lys
        1345
```

(2) INFORMATION FOR SEQ ID NO:5:

(i) SEQUENCE CHARACTERISTICS:
        (A) LENGTH: 884 amino acids
        (B) TYPE: amino acid
        (D) TOPOLOGY: linear (ii) MOLECULE TYPE: protein (xi) SEQUENCE DESCRIPTION: SEQ ID NO:5:

```
Met Lys Asn Met Lys Lys Leu Ala Ser Val Val Thr Cys Thr Leu
1               5                   10                  15

Leu Ala Pro Met Phe Leu Asn Gly Asn Val Asn Ala Val Tyr Ala Asp
                20                  25                  30

Ser Lys Thr Asn Gln Ile Ser Thr Thr Gln Lys Asn Gln Gln Lys Glu
            35                  40                  45

Met Asp Arg Lys Gly Leu Leu Gly Tyr Tyr Phe Lys Gly Lys Asp Phe
        50                  55                  60

Ser Asn Leu Thr Met Phe Ala Pro Thr Arg Asp Ser Thr Leu Ile Tyr
65                  70                  75                  80

Asp Gln Gln Thr Ala Asn Lys Leu Leu Asp Lys Lys Gln Glu Tyr
                85                  90                  95
```

-continued

```
Gln Ser Ile Arg Trp Ile Gly Leu Ile Gln Ser Lys Glu Thr Gly Asp
                100                 105                 110

Phe Thr Phe Asn Leu Ser Glu Asp Glu Gln Ala Ile Ile Glu Ile Asn
        115                 120                 125

Gly Lys Ile Ile Ser Asn Lys Gly Lys Glu Lys Gln Val Val His Leu
    130                 135                 140

Glu Lys Gly Lys Leu Val Pro Ile Lys Ile Glu Tyr Gln Ser Asp Thr
145                 150                 155                 160

Lys Phe Asn Ile Asp Ser Lys Thr Phe Lys Glu Leu Lys Leu Phe Lys
                165                 170                 175

Ile Asp Ser Gln Asn Gln Pro Gln Val Gln Gln Asp Glu Leu Arg
        180                 185                 190

Asn Pro Glu Phe Asn Lys Lys Glu Ser Gln Glu Phe Leu Ala Lys Pro
    195                 200                 205

Ser Lys Ile Asn Leu Phe Thr Gln Lys Met Lys Arg Glu Ile Asp Glu
    210                 215                 220

Asp Thr Asp Thr Asp Gly Asp Ser Ile Pro Asp Leu Trp Glu Glu Asn
225                 230                 235                 240

Gly Tyr Thr Ile Gln Asn Arg Ile Ala Val Lys Trp Asp Asp Ser Leu
                245                 250                 255

Ala Ser Lys Gly Tyr Thr Lys Phe Val Ser Asn Pro Leu Glu Ser His
        260                 265                 270

Thr Val Gly Asp Pro Tyr Thr Asp Tyr Glu Lys Ala Ala Arg Asp Leu
    275                 280                 285

Asp Leu Ser Asn Ala Lys Glu Thr Phe Asn Pro Leu Val Ala Ala Phe
    290                 295                 300

Pro Ser Val Asn Val Ser Met Glu Lys Val Ile Leu Ser Pro Asn Glu
305                 310                 315                 320

Asn Leu Ser Asn Ser Val Glu Ser His Ser Ser Thr Asn Trp Ser Tyr
                325                 330                 335

Thr Asn Thr Glu Gly Ala Ser Val Glu Ala Gly Ile Gly Pro Lys Gly
        340                 345                 350

Ile Ser Phe Gly Val Ser Val Asn Tyr Gln His Ser Glu Thr Val Ala
    355                 360                 365

Gln Glu Trp Gly Thr Ser Thr Gly Asn Thr Ser Gln Phe Asn Thr Ala
    370                 375                 380

Ser Ala Gly Tyr Leu Asn Ala Asn Val Arg Tyr Asn Asn Val Gly Thr
385                 390                 395                 400

Gly Ala Ile Tyr Asp Val Lys Pro Thr Thr Ser Phe Val Leu Asn Asn
                405                 410                 415

Asp Thr Ile Ala Thr Ile Thr Ala Lys Ser Asn Ser Thr Ala Leu Asn
        420                 425                 430

Ile Ser Pro Gly Glu Ser Tyr Pro Lys Lys Gly Gln Asn Gly Ile Ala
    435                 440                 445

Ile Thr Ser Met Asp Asp Phe Asn Ser His Pro Ile Thr Leu Asn Lys
    450                 455                 460

Lys Gln Val Asp Asn Leu Leu Asn Asn Lys Pro Met Met Leu Glu Thr
465                 470                 475                 480

Asn Gln Thr Asp Gly Val Tyr Lys Ile Lys Asp Thr His Gly Asn Ile
                485                 490                 495

Val Thr Gly Gly Glu Trp Asn Gly Val Ile Gln Gln Ile Lys Ala Lys
        500                 505                 510
```

-continued

```
Thr Ala Ser Ile Ile Val Asp Asp Gly Glu Arg Val Ala Glu Lys Arg
        515                 520                 525
Val Ala Ala Lys Asp Tyr Glu Asn Pro Glu Asp Lys Thr Pro Ser Leu
    530                 535                 540
Thr Leu Lys Asp Ala Leu Lys Leu Ser Tyr Pro Asp Glu Ile Lys Glu
545                 550                 555                 560
Ile Glu Gly Leu Leu Tyr Tyr Lys Asn Lys Pro Ile Tyr Glu Ser Ser
                565                 570                 575
Val Met Thr Tyr Leu Asp Glu Asn Thr Ala Lys Glu Val Thr Lys Gln
            580                 585                 590
Leu Asn Asp Thr Thr Gly Lys Phe Lys Asp Val Ser His Leu Tyr Asp
        595                 600                 605
Val Lys Leu Thr Pro Lys Met Asn Val Thr Ile Lys Leu Ser Ile Leu
    610                 615                 620
Tyr Asp Asn Ala Glu Ser Asn Asp Asn Ser Ile Gly Lys Trp Thr Asn
625                 630                 635                 640
Thr Asn Ile Val Ser Gly Gly Asn Asn Gly Lys Lys Gln Tyr Ser Ser
                645                 650                 655
Asn Asn Pro Asp Ala Asn Leu Thr Leu Asn Thr Asp Ala Gln Glu Lys
            660                 665                 670
Leu Asn Lys Asn Arg Asp Tyr Tyr Ile Ser Leu Tyr Met Lys Ser Glu
        675                 680                 685
Lys Asn Thr Gln Cys Glu Ile Thr Ile Asp Gly Glu Ile Tyr Pro Ile
    690                 695                 700
Thr Thr Lys Thr Val Asn Val Asn Lys Asp Asn Tyr Lys Arg Leu Asp
705                 710                 715                 720
Ile Ile Ala His Asn Ile Lys Ser Asn Pro Ile Ser Ser Leu His Ile
                725                 730                 735
Lys Thr Asn Asp Glu Ile Thr Leu Phe Trp Asp Asp Ile Ser Ile Thr
            740                 745                 750
Asp Val Ala Ser Ile Lys Pro Glu Asn Leu Thr Asp Ser Glu Ile Lys
        755                 760                 765
Gln Ile Tyr Ser Arg Tyr Gly Ile Lys Leu Glu Asp Gly Ile Leu Ile
    770                 775                 780
Asp Lys Lys Gly Gly Ile His Tyr Gly Glu Phe Ile Asn Glu Ala Ser
785                 790                 795                 800
Phe Asn Ile Glu Pro Leu Gln Asn Tyr Val Thr Lys Tyr Glu Val Thr
                805                 810                 815
Tyr Ser Ser Glu Leu Gly Pro Asn Val Ser Asp Thr Leu Glu Ser Asp
            820                 825                 830
Lys Ile Tyr Lys Asp Gly Thr Ile Lys Phe Asp Phe Thr Lys Tyr Ser
        835                 840                 845
Lys Asn Glu Gln Gly Leu Phe Tyr Asp Ser Gly Leu Asn Trp Asp Phe
    850                 855                 860
Lys Ile Asn Ala Ile Thr Tyr Asp Gly Lys Glu Met Asn Val Phe His
865                 870                 875                 880
Arg Tyr Asn Lys
```

(2) INFORMATION FOR SEQ ID NO:6:

(i) SEQUENCE CHARACTERISTICS:
       (A) LENGTH: 2004 base pairs
       (B) TYPE: nucleic acid

```
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bacillus cereus
            (B) STRAIN: AB78
            (C) INDIVIDUAL ISOLATE: NRRL B-21058

(ix) FEATURE:
            (A) NAME/KEY: CDS
            (B) LOCATION: 1..2001
            (D) OTHER INFORMATION: /product= "80 kDa protein VIP1A(a)"
                /note= "This sequence is identical to that found in
                SEQ ID NO:1 between and including nucleotide positions
                3126 and 5126"

(xi) SEQUENCE DESCRIPTION: SEQ ID NO:6:
```

| | | | | | | | | | | | | | | | | |
|---|---|---|---|---|---|---|---|---|---|---|---|---|---|---|---|---|
| ATG | AAA | AGG | GAA | ATT | GAT | GAA | GAC | ACG | GAT | ACG | GAT | GGG | GAC | TCT | ATT | 48 |
| Met | Lys | Arg | Glu | Ile | Asp | Glu | Asp | Thr | Asp | Thr | Asp | Gly | Asp | Ser | Ile | |
| 885 | | | | | 890 | | | | 895 | | | | | 900 | | |
| CCT | GAC | CTT | TGG | GAA | GAA | AAT | GGG | TAT | ACG | ATT | CAA | AAT | AGA | ATC | GCT | 96 |
| Pro | Asp | Leu | Trp | Glu | Glu | Asn | Gly | Tyr | Thr | Ile | Gln | Asn | Arg | Ile | Ala | |
| | | | | 905 | | | | | 910 | | | | | 915 | | |
| GTA | AAG | TGG | GAC | GAT | TCT | CTA | GCA | AGT | AAA | GGG | TAT | ACG | AAA | TTT | GTT | 144 |
| Val | Lys | Trp | Asp | Asp | Ser | Leu | Ala | Ser | Lys | Gly | Tyr | Thr | Lys | Phe | Val | |
| | | | 920 | | | | | 925 | | | | | 930 | | | |
| TCA | AAT | CCA | CTA | GAA | AGT | CAC | ACA | GTT | GGT | GAT | CCT | TAT | ACA | GAT | TAT | 192 |
| Ser | Asn | Pro | Leu | Glu | Ser | His | Thr | Val | Gly | Asp | Pro | Tyr | Thr | Asp | Tyr | |
| | | | 935 | | | | | 940 | | | | | 945 | | | |
| GAA | AAG | GCA | GCA | AGA | GAT | CTA | GAT | TTG | TCA | AAT | GCA | AAG | GAA | ACG | TTT | 240 |
| Glu | Lys | Ala | Ala | Arg | Asp | Leu | Asp | Leu | Ser | Asn | Ala | Lys | Glu | Thr | Phe | |
| | | 950 | | | | | 955 | | | | | 960 | | | | |
| AAC | CCA | TTG | GTA | GCT | GCT | TTT | CCA | AGT | GTG | AAT | GTT | AGT | ATG | GAA | AAG | 288 |
| Asn | Pro | Leu | Val | Ala | Ala | Phe | Pro | Ser | Val | Asn | Val | Ser | Met | Glu | Lys | |
| 965 | | | | | 970 | | | | | 975 | | | | | 980 | |
| GTG | ATA | TTA | TCA | CCA | AAT | GAA | AAT | TTA | TCC | AAT | AGT | GTA | GAG | TCT | CAT | 336 |
| Val | Ile | Leu | Ser | Pro | Asn | Glu | Asn | Leu | Ser | Asn | Ser | Val | Glu | Ser | His | |
| | | | | 985 | | | | | 990 | | | | | 995 | | |
| TCA | TCC | ACG | AAT | TGG | TCT | TAT | ACA | AAT | ACA | GAA | GGT | GCT | TCT | GTT | GAA | 384 |
| Ser | Ser | Thr | Asn | Trp | Ser | Tyr | Thr | Asn | Thr | Glu | Gly | Ala | Ser | Val | Glu | |
| | | | | 1000 | | | | | 1005 | | | | | 1010 | | |
| GCG | GGG | ATT | GGA | CCA | AAA | GGT | ATT | TCG | TTC | GGA | GTT | AGC | GTA | AAC | TAT | 432 |
| Ala | Gly | Ile | Gly | Pro | Lys | Gly | Ile | Ser | Phe | Gly | Val | Ser | Val | Asn | Tyr | |
| | | | 1015 | | | | | 1020 | | | | | 1025 | | | |
| CAA | CAC | TCT | GAA | ACA | GTT | GCA | CAA | GAA | TGG | GGA | ACA | TCT | ACA | GGA | AAT | 480 |
| Gln | His | Ser | Glu | Thr | Val | Ala | Gln | Glu | Trp | Gly | Thr | Ser | Thr | Gly | Asn | |
| | | | 1030 | | | | | 1035 | | | | | 1040 | | | |
| ACT | TCG | CAA | TTC | AAT | ACG | GCT | TCA | GCG | GGA | TAT | TTA | AAT | GCA | AAT | GTT | 528 |
| Thr | Ser | Gln | Phe | Asn | Thr | Ala | Ser | Ala | Gly | Tyr | Leu | Asn | Ala | Asn | Val | |
| 1045 | | | | | 1050 | | | | | 1055 | | | | | 1060 | |
| CGA | TAT | AAC | AAT | GTA | GGA | ACT | GGT | GCC | ATC | TAC | GAT | GTA | AAA | CCT | ACA | 576 |
| Arg | Tyr | Asn | Asn | Val | Gly | Thr | Gly | Ala | Ile | Tyr | Asp | Val | Lys | Pro | Thr | |
| | | | | 1065 | | | | | 1070 | | | | | 1075 | | |
| ACA | AGT | TTT | GTA | TTA | AAT | AAC | GAT | ACT | ATC | GCA | ACT | ATT | ACG | GCG | AAA | 624 |
| Thr | Ser | Phe | Val | Leu | Asn | Asn | Asp | Thr | Ile | Ala | Thr | Ile | Thr | Ala | Lys | |
| | | | 1080 | | | | | 1085 | | | | | 1090 | | | |

```
TCT AAT TCT ACA GCC TTA AAT ATA TCT CCT GGA GAA AGT TAC CCG AAA        672
Ser Asn Ser Thr Ala Leu Asn Ile Ser Pro Gly Glu Ser Tyr Pro Lys
            1095                1100                1105

AAA GGA CAA AAT GGA ATC GCA ATA ACA TCA ATG GAT GAT TTT AAT TCC        720
Lys Gly Gln Asn Gly Ile Ala Ile Thr Ser Met Asp Asp Phe Asn Ser
    1110                1115                1120

CAT CCG ATT ACA TTA AAT AAA AAA CAA GTA GAT AAT CTG CTA AAT AAT        768
His Pro Ile Thr Leu Asn Lys Lys Gln Val Asp Asn Leu Leu Asn Asn
1125                1130                1135                1140

AAA CCT ATG ATG TTG GAA ACA AAC CAA ACA GAT GGT GTT TAT AAG ATA        816
Lys Pro Met Met Leu Glu Thr Asn Gln Thr Asp Gly Val Tyr Lys Ile
                1145                1150                1155

AAA GAT ACA CAT GGA AAT ATA GTA ACT GGC GGA GAA TGG AAT GGT GTC        864
Lys Asp Thr His Gly Asn Ile Val Thr Gly Gly Glu Trp Asn Gly Val
            1160                1165                1170

ATA CAA CAA ATC AAG GCT AAA ACA GCG TCT ATT ATT GTG GAT GAT GGG        912
Ile Gln Gln Ile Lys Ala Lys Thr Ala Ser Ile Ile Val Asp Asp Gly
        1175                1180                1185

GAA CGT GTA GCA GAA AAA CGT GTA GCG GCA AAA GAT TAT GAA AAT CCA        960
Glu Arg Val Ala Glu Lys Arg Val Ala Ala Lys Asp Tyr Glu Asn Pro
    1190                1195                1200

GAA GAT AAA ACA CCG TCT TTA ACT TTA AAA GAT GCC CTG AAG CTT TCA       1008
Glu Asp Lys Thr Pro Ser Leu Thr Leu Lys Asp Ala Leu Lys Leu Ser
1205                1210                1215                1220

TAT CCA GAT GAA ATA AAA GAA ATA GAG GGA TTA TTA TAT TAT AAA AAC       1056
Tyr Pro Asp Glu Ile Lys Glu Ile Glu Gly Leu Leu Tyr Tyr Lys Asn
                1225                1230                1235

AAA CCG ATA TAC GAA TCG AGC GTT ATG ACT TAC TTA GAT GAA AAT ACA       1104
Lys Pro Ile Tyr Glu Ser Ser Val Met Thr Tyr Leu Asp Glu Asn Thr
            1240                1245                1250

GCA AAA GAA GTG ACC AAA CAA TTA AAT GAT ACC ACT GGG AAA TTT AAA       1152
Ala Lys Glu Val Thr Lys Gln Leu Asn Asp Thr Thr Gly Lys Phe Lys
        1255                1260                1265

GAT GTA AGT CAT TTA TAT GAT GTA AAA CTG ACT CCA AAA ATG AAT GTT       1200
Asp Val Ser His Leu Tyr Asp Val Lys Leu Thr Pro Lys Met Asn Val
    1270                1275                1280

ACA ATC AAA TTG TCT ATA CTT TAT GAT AAT GCT GAG TCT AAT GAT AAC       1248
Thr Ile Lys Leu Ser Ile Leu Tyr Asp Asn Ala Glu Ser Asn Asp Asn
1285                1290                1295                1300

TCA ATT GGT AAA TGG ACA AAC ACA AAT ATT GTT TCA GGT GGA AAT AAC       1296
Ser Ile Gly Lys Trp Thr Asn Thr Asn Ile Val Ser Gly Gly Asn Asn
                1305                1310                1315

GGA AAA AAA CAA TAT TCT TCT AAT AAT CCG GAT GCT AAT TTG ACA TTA       1344
Gly Lys Lys Gln Tyr Ser Ser Asn Asn Pro Asp Ala Asn Leu Thr Leu
            1320                1325                1330

AAT ACA GAT GCT CAA GAA AAA TTA AAT AAA AAT CGT GAC TAT TAT ATA       1392
Asn Thr Asp Ala Gln Glu Lys Leu Asn Lys Asn Arg Asp Tyr Tyr Ile
        1335                1340                1345

AGT TTA TAT ATG AAG TCA GAA AAA AAC ACA CAA TGT GAG ATT ACT ATA       1440
Ser Leu Tyr Met Lys Ser Glu Lys Asn Thr Gln Cys Glu Ile Thr Ile
    1350                1355                1360

GAT GGG GAG ATT TAT CCG ATC ACT ACA AAA ACA GTG AAT GTG AAT AAA       1488
Asp Gly Glu Ile Tyr Pro Ile Thr Thr Lys Thr Val Asn Val Asn Lys
1365                1370                1375                1380

GAC AAT TAC AAA AGA TTA GAT ATT ATA GCT CAT AAT ATA AAA AGT AAT       1536
Asp Asn Tyr Lys Arg Leu Asp Ile Ile Ala His Asn Ile Lys Ser Asn
                1385                1390                1395
```

```
CCA ATT TCT TCA CTT CAT ATT AAA ACG AAT GAT GAA ATA ACT TTA TTT    1584
Pro Ile Ser Ser Leu His Ile Lys Thr Asn Asp Glu Ile Thr Leu Phe
            1400                1405                1410

TGG GAT GAT ATT TCT ATA ACA GAT GTA GCA TCA ATA AAA CCG GAA AAT    1632
Trp Asp Asp Ile Ser Ile Thr Asp Val Ala Ser Ile Lys Pro Glu Asn
            1415                1420                1425

TTA ACA GAT TCA GAA ATT AAA CAG ATT TAT AGT AGG TAT GGT ATT AAG    1680
Leu Thr Asp Ser Glu Ile Lys Gln Ile Tyr Ser Arg Tyr Gly Ile Lys
            1430                1435                1440

TTA GAA GAT GGA ATC CTT ATT GAT AAA AAA GGT GGG ATT CAT TAT GGT    1728
Leu Glu Asp Gly Ile Leu Ile Asp Lys Lys Gly Gly Ile His Tyr Gly
1445                1450                1455                1460

GAA TTT ATT AAT GAA GCT AGT TTT AAT ATT GAA CCA TTG CCA AAT TAT    1776
Glu Phe Ile Asn Glu Ala Ser Phe Asn Ile Glu Pro Leu Pro Asn Tyr
            1465                1470                1475

GTG ACC AAA TAT GAA GTT ACT TAT AGT AGT GAG TTA GGA CCA AAC GTG    1824
Val Thr Lys Tyr Glu Val Thr Tyr Ser Ser Glu Leu Gly Pro Asn Val
            1480                1485                1490

AGT GAC ACA CTT GAA AGT GAT AAA ATT TAC AAG GAT GGG ACA ATT AAA    1872
Ser Asp Thr Leu Glu Ser Asp Lys Ile Tyr Lys Asp Gly Thr Ile Lys
            1495                1500                1505

TTT GAT TTT ACC AAA TAT AGT AAA AAT GAA CAA GGA TTA TTT TAT GAC    1920
Phe Asp Phe Thr Lys Tyr Ser Lys Asn Glu Gln Gly Leu Phe Tyr Asp
            1510                1515                1520

AGT GGA TTA AAT TGG GAC TTT AAA ATT AAT GCT ATT ACT TAT GAT GGT    1968
Ser Gly Leu Asn Trp Asp Phe Lys Ile Asn Ala Ile Thr Tyr Asp Gly
1525                1530                1535                1540

AAA GAG ATG AAT GTT TTT CAT AGA TAT AAT AAA TAG                    2004
Lys Glu Met Asn Val Phe His Arg Tyr Asn Lys
            1545                1550
```

(2) INFORMATION FOR SEQ ID NO:7:

(i) SEQUENCE CHARACTERISTICS:
        (A) LENGTH: 667 amino acids
        (B) TYPE: amino acid
        (D) TOPOLOGY: linear (ii) MOLECULE TYPE: protein (xi) SEQUENCE DESCRIPTION: SEQ ID NO:7:

```
Met Lys Arg Glu Ile Asp Glu Asp Thr Asp Thr Asp Gly Asp Ser Ile
1               5                   10                  15

Pro Asp Leu Trp Glu Glu Asn Gly Tyr Thr Ile Gln Asn Arg Ile Ala
            20                  25                  30

Val Lys Trp Asp Asp Ser Leu Ala Ser Lys Gly Tyr Thr Lys Phe Val
        35                  40                  45

Ser Asn Pro Leu Glu Ser His Thr Val Gly Asp Pro Tyr Thr Asp Tyr
    50                  55                  60

Glu Lys Ala Ala Arg Asp Leu Asp Leu Ser Asn Ala Lys Glu Thr Phe
65                  70                  75                  80

Asn Pro Leu Val Ala Ala Phe Pro Ser Val Asn Val Ser Met Glu Lys
                85                  90                  95

Val Ile Leu Ser Pro Asn Glu Asn Leu Ser Asn Ser Val Glu Ser His
            100                 105                 110

Ser Ser Thr Asn Trp Ser Tyr Thr Asn Thr Glu Gly Ala Ser Val Glu
        115                 120                 125

Ala Gly Ile Gly Pro Lys Gly Ile Ser Phe Gly Val Ser Val Asn Tyr
    130                 135                 140
```

-continued

```
Gln His Ser Glu Thr Val Ala Gln Glu Trp Gly Thr Ser Thr Gly Asn
145                 150                 155                 160

Thr Ser Gln Phe Asn Thr Ala Ser Ala Gly Tyr Leu Asn Ala Asn Val
                165                 170                 175

Arg Tyr Asn Asn Val Gly Thr Gly Ala Ile Tyr Asp Val Lys Pro Thr
            180                 185                 190

Thr Ser Phe Val Leu Asn Asn Asp Thr Ile Ala Thr Ile Thr Ala Lys
        195                 200                 205

Ser Asn Ser Thr Ala Leu Asn Ile Ser Pro Gly Glu Ser Tyr Pro Lys
210                 215                 220

Lys Gly Gln Asn Gly Ile Ala Ile Thr Ser Met Asp Asp Phe Asn Ser
225                 230                 235                 240

His Pro Ile Thr Leu Asn Lys Lys Gln Val Asp Asn Leu Leu Asn Asn
                245                 250                 255

Lys Pro Met Met Leu Glu Thr Asn Gln Thr Asp Gly Val Tyr Lys Ile
            260                 265                 270

Lys Asp Thr His Gly Asn Ile Val Thr Gly Gly Glu Trp Asn Gly Val
        275                 280                 285

Ile Gln Gln Ile Lys Ala Lys Thr Ala Ser Ile Ile Val Asp Asp Gly
290                 295                 300

Glu Arg Val Ala Glu Lys Arg Val Ala Ala Lys Asp Tyr Glu Asn Pro
305                 310                 315                 320

Glu Asp Lys Thr Pro Ser Leu Thr Leu Lys Asp Ala Leu Lys Leu Ser
                325                 330                 335

Tyr Pro Asp Glu Ile Lys Glu Ile Glu Gly Leu Leu Tyr Tyr Lys Asn
            340                 345                 350

Lys Pro Ile Tyr Glu Ser Ser Val Met Thr Tyr Leu Asp Glu Asn Thr
        355                 360                 365

Ala Lys Glu Val Thr Lys Gln Leu Asn Asp Thr Thr Gly Lys Phe Lys
370                 375                 380

Asp Val Ser His Leu Tyr Asp Val Lys Leu Thr Pro Lys Met Asn Val
385                 390                 395                 400

Thr Ile Lys Leu Ser Ile Leu Tyr Asp Asn Ala Glu Ser Asn Asp Asn
                405                 410                 415

Ser Ile Gly Lys Trp Thr Asn Thr Asn Ile Val Ser Gly Gly Asn Asn
            420                 425                 430

Gly Lys Lys Gln Tyr Ser Ser Asn Asn Pro Asp Ala Asn Leu Thr Leu
        435                 440                 445

Asn Thr Asp Ala Gln Glu Lys Leu Asn Lys Asn Arg Asp Tyr Tyr Ile
450                 455                 460

Ser Leu Tyr Met Lys Ser Glu Lys Asn Thr Gln Cys Glu Ile Thr Ile
465                 470                 475                 480

Asp Gly Glu Ile Tyr Pro Ile Thr Thr Lys Thr Val Asn Val Asn Lys
                485                 490                 495

Asp Asn Tyr Lys Arg Leu Asp Ile Ile Ala His Asn Ile Lys Ser Asn
            500                 505                 510

Pro Ile Ser Ser Leu His Ile Lys Thr Asn Asp Glu Ile Thr Leu Phe
        515                 520                 525

Trp Asp Asp Ile Ser Ile Thr Asp Val Ala Ser Ile Lys Pro Glu Asn
530                 535                 540

Leu Thr Asp Ser Glu Ile Lys Gln Ile Tyr Ser Arg Tyr Gly Ile Lys
545                 550                 555                 560
```

-continued

```
Leu Glu Asp Gly Ile Leu Ile Asp Lys Lys Gly Gly Ile His Tyr Gly
            565                 570                 575

Glu Phe Ile Asn Glu Ala Ser Phe Asn Ile Glu Pro Leu Pro Asn Tyr
        580                 585                 590

Val Thr Lys Tyr Glu Val Thr Tyr Ser Ser Glu Leu Gly Pro Asn Val
    595                 600                 605

Ser Asp Thr Leu Glu Ser Asp Lys Ile Tyr Lys Asp Gly Thr Ile Lys
    610                 615                 620

Phe Asp Phe Thr Lys Tyr Ser Lys Asn Glu Gln Gly Leu Phe Tyr Asp
625                 630                 635                 640

Ser Gly Leu Asn Trp Asp Phe Lys Ile Asn Ala Ile Thr Tyr Asp Gly
            645                 650                 655

Lys Glu Met Asn Val Phe His Arg Tyr Asn Lys
            660                 665
```

(2) INFORMATION FOR SEQ ID NO:8:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Bacillus cereus
        (B) STRAIN: AB78
        (C) INDIVIDUAL ISOLATE: NRRL B-21058

(ix) FEATURE:
(A) NAME/KEY: Peptide
(B) LOCATION: 1..16
(D) OTHER INFORMATION: /note= "N-terminal sequence of protein purified from strain AB78"

(xi) SEQUENCE DESCRIPTION: SEQ ID NO:8:

```
Lys Arg Glu Ile Asp Glu Asp Thr Asp Thr Asx Gly Asp Ser Ile Pro
1               5                   10                  15
```

(2) INFORMATION FOR SEQ ID NO:9:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: misc_feature
(B) LOCATION: 1..21
(D) OTHER INFORMATION: /note= "Oligonucleotide probe based on amino acids 3 to 9 of SEQ ID NO:8, using codon usage of Bacillus thuringiensis"

(xi) SEQUENCE DESCRIPTION: SEQ ID NO:9:

GAAATTGATC AAGATACNGA T                    21

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Bacillus thuringiensis
        (B) STRAIN: AB88

(ix) FEATURE:
        (A) NAME/KEY: Peptide
        (B) LOCATION: 1..14
        (D) OTHER INFORMATION: /note= "N-terminal amino acid
            sequence of protein known as anion exchange fraction 23 (smaller)"

(xi) SEQUENCE DESCRIPTION: SEQ ID NO:10:

Xaa Glu Pro Phe Val Ser Ala Xaa Xaa Xaa Gln Xaa Xaa Xaa
1 5 10

(2) INFORMATION FOR SEQ ID NO:11:

(i) SEQUENCE CHARACTERISTICS:
(A) LENGTH: 13 amino acids
(B) TYPE: amino acid
(C) STRANDEDNESS: single
(D) TOPOLOGY: linear (vi) ORIGINAL SOURCE:
(A) ORGANISM: Bacillus thuringiensis (xi) SEQUENCE DESCRIPTION: SEQ ID NO:11:

Xaa Glu Tyr Glu Asn Val Glu Pro Phe Val Ser Ala Xaa
1 5 10

(2) INFORMATION FOR SEQ ID NO:12:

(i) SEQUENCE CHARACTERISTICS:
(A) LENGTH: 14 amino acids
(B) TYPE: amino acid
(C) STRANDEDNESS: single
(D) TOPOLOGY: linear (vi) ORIGINAL SOURCE:
(A) ORGANISM: Bacillus thurigiensis (xi) SEQUENCE DESCRIPTION: SEQ ID NO:12:

Met Asn Lys Asn Asn Thr Lys Leu Pro Thr Arg Ala Leu Pro
1 5 10

(2) INFORMATION FOR SEQ ID NO:13:

(i) SEQUENCE CHARACTERISTICS:
(A) LENGTH: 15 amino acids
(B) TYPE: amino acid
(C) STRANDEDNESS: single
(D) TOPOLOGY: linear

```
    (ii) MOLECULE TYPE: peptide (iii) HYPOTHETICAL: NO (v) FRAGMENT TYPE: N-terminal (vi) ORIGINAL SOURCE:
         (A) ORGANISM: Bacillus thuringiensis
         (B) STRAIN: AB88

(ix) FEATURE:
         (A) NAME/KEY: Peptide
         (B) LOCATION: 1..15
         (D) OTHER INFORMATION: /note= "N-terminal amino acid
             sequence of 35 kDa VIP active against Agrotis ipsilon"

(xi) SEQUENCE DESCRIPTION: SEQ ID NO:13:

Ala Leu Ser Glu Asn Thr Gly Lys Asp Gly Gly Tyr Ile Val Pro
1               5                   10                  15

(2) INFORMATION FOR SEQ ID NO:14:

(i) SEQUENCE CHARACTERISTICS:
         (A) LENGTH: 9 amino acids
         (B) TYPE: amino acid
         (C) STRANDEDNESS: single
         (D) TOPOLOGY: linear (vi) ORIGINAL SOURCE:
         (A) ORGANISM: Bacillus thuringiensis (xi) SEQUENCE DESCRIPTION: SEQ ID NO:14:

Met Asp Asn Asn Pro Asn Ile Asn Glu
1               5

(2) INFORMATION FOR SEQ ID NO:15:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: N-terminal (ix) FEATURE:
         (A) NAME/KEY: Peptide
         (B) LOCATION: 1..9
         (D) OTHER INFORMATION: /note= "N-terminal sequence of 80
             kDa delta-endotoxin"

(xi) SEQUENCE DESCRIPTION: SEQ ID NO:15:

Met Asp Asn Asn Pro Asn Ile Asn Glu
1               5

(2) INFORMATION FOR SEQ ID NO:16:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: N-terminal
```

(vi) ORIGINAL SOURCE:
            (A) ORGANISM: Bacillus thuringiensis (ix) FEATURE:
            (A) NAME/KEY: Peptide
            (B) LOCATION: 1..11
            (D) OTHER INFORMATION: /note= "N-terminal sequence from 60
                kDa delta-endotoxin"

(xi) SEQUENCE DESCRIPTION: SEQ ID NO:16:

Met Asn Val Leu Asn Ser Gly Arg Thr Thr Ile
1               5                   10

(2) INFORMATION FOR SEQ ID NO:17:

(i) SEQUENCE CHARACTERISTICS:
            (A) LENGTH: 2655 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: misc_feature
            (B) LOCATION: 1..2652
            (D) OTHER INFORMATION: /note= "Maize optimized DNA
                sequence for 100 kd VIP1A(a) protein from AB78"

(xi) SEQUENCE DESCRIPTION: SEQ ID NO:17:

```
ATGAAGAACA TGAAGAAGAA GCTGGCCAGC GTGGTGACCT GCACCCTGCT GGCCCCCATG      60

TTCCTGAACG GCAACGTGAA CGCCGTGTAC GCCGACAGCA AGACCAACCA GATCAGCACC     120

ACCCAGAAGA ACCAGCAGAA GGAGATGGAC CGCAAGGGCC TGCTGGGCTA CTACTTCAAG     180

GGCAAGGACT TCAGCAACCT GACCATGTTC GCCCCCACGC GTGACAGCAC CCTGATCTAC     240

GACCAGCAGA CCGCCAACAA GCTGCTGGAC AAGAAGCAGC AGGAGTACCA GAGCATCCGC     300

TGGATCGGCC TGATCCAGAG CAAGGAGACC GGCGACTTCA CCTTCAACCT GAGCGAGGAC     360

GAGCAGGCCA TCATCGAGAT CAACGGCAAG ATCATCAGCA CAAGGGCAA GGAGAAGCAG      420

GTGGTGCACC TGGAGAAGGG CAAGCTGGTG CCCATCAAGA TCGAGTACCA GAGCGACACC     480

AAGTTCAACA TCGACAGCAA GACCTTCAAG GAGCTGAAGC TTTTCAAGAT CGACAGCCAG     540

AACCAGCCCC AGCAGGTGCA GCAGGACGAG CTGCGCAACC CCGAGTTCAA CAAGAAGGAG     600

AGCCAGGAGT TCCTGGCCAA GCCCAGCAAG ATCAACCTGT TCACCCAGCA GATGAAGCGC     660

GAGATCGACG AGGACACCGA CACCGACGGC GACAGCATCC CCGACCTGTG GGAGGAGAAC     720

GGCTACACCA TCCAGAACCG CATCGCCGTG AAGTGGGACG ACAGCCTGGC TAGCAAGGGC     780

TACACCAAGT TCGTGAGCAA CCCCCTGGAG AGCCACACCG TGGGCGACCC CTACACCGAC     840

TACGAGAAGG CCGCCCGCGA CCTGGACCTG AGCAACGCCA AGGAGACCTT CAACCCCCTG     900

GTGGCCGCCT TCCCCAGCGT GAACGTGAGC ATGGAGAAGG TGATCCTGAG CCCCAACGAG     960

AACCTGAGCA ACAGCGTGGA GAGCCACTCG AGCACCAACT GGAGCTACAC CAACACCGAG    1020

GGCGCCAGCG TGGAGGCCGG CATCGGTCCC AAGGGCATCA GCTTCGGCGT GAGCGTGAAC    1080

TACCAGCACA GCGAGACCGT GGCCCAGGAG TGGGGCACCA GCACCGGCAA CACCAGCCAG    1140

TTCAACACCG CCAGCGCCGG CTACCTGAAC GCCAACGTGC GCTACAACAA CGTGGGCACC    1200

GGCGCCATCT ACGACGTGAA GCCCACCACC AGCTTCGTGC TGAACAACGA CACCATCGCC    1260
```

-continued

```
ACCATCACCG CCAAGTCGAA TTCCACCGCC CTGAACATCA GCCCCGGCGA GAGCTACCCC   1320
AAGAAGGGCC AGAACGGCAT CGCCATCACC AGCATGGACG ACTTCAACAG CCACCCCATC   1380
ACCCTGAACA AGAAGCAGGT GGACAACCTG CTGAACAACA AGCCCATGAT GCTGGAGACC   1440
AACCAGACCG ACGGCGTCTA CAAGATCAAG GACACCCACG GCAACATCGT GACCGGCGGC   1500
GAGTGGAACG GCGTGATCCA GCAGATCAAG GCCAAGACCG CCAGCATCAT CGTCGACGAC   1560
GGCGAGCGCG TGGCCGAGAA GCGCGTGGCC GCCAAGGACT ACGAGAACCC CGAGGACAAG   1620
ACCCCCAGCC TGACCCTGAA GGACGCCCTG AAGCTGAGCT ACCCCGACGA GATCAAGGAG   1680
ATCGAGGGCC TGCTGTACTA CAAGAACAAG CCCATCTACG AGAGCAGCGT GATGACCTAT   1740
CTAGACGAGA ACACCGCCAA GGAGGTGACC AAGCAGCTGA ACGACACCAC CGGCAAGTTC   1800
AAGGACGTGA GCCACCTGTA CGACGTGAAG CTGACCCCCA AGATGAACGT GACCATCAAG   1860
CTGAGCATCC TGTACGACAA CGCCGAGAGC AACGACAACA GCATCGGCAA GTGGACCAAC   1920
ACCAACATCG TGAGCGGCGG CAACAACGGC AAGAAGCAGT ACAGCAGCAA CAACCCCGAC   1980
GCCAACCTGA CCCTGAACAC CGACGCCCAG GAGAAGCTGA ACAAGAACCG CGACTACTAC   2040
ATCAGCCTGT ACATGAAGAG CGAGAAGAAC ACCCAGTGCG AGATCACCAT CGACGGCGAG   2100
ATATACCCCA TCACCACCAA GACCGTGAAC GTGAACAAGG ACAACTACAA GCGCCTGGAC   2160
ATCATCGCCC ACAACATCAA GAGCAACCCC ATCAGCAGCC TGCACATCAA GACCAACGAC   2220
GAGATCACCC TGTTCTGGGA CGACATATCG ATTACCGACG TCGCCAGCAT CAAGCCCGAG   2280
AACCTGACCG ACAGCGAGAT CAAGCAGATA TACAGTCGCT ACGGCATCAA GCTGGAGGAC   2340
GGCATCCTGA TCGACAAGAA GGGCGGCATC CACTACGGCG AGTTCATCAA CGAGGCCAGC   2400
TTCAACATCG AGCCCCTGCA GAACTACGTG ACCAAGTACG AGGTGACCTA CAGCAGCGAG   2460
CTGGGCCCCA ACGTGAGCGA CACCCTGGAG AGCGACAAGA TTTACAAGGA CGGCACCATC   2520
AAGTTCGACT TCACCAAGTA CAGCAAGAAC GAGCAGGGCC TGTTCTACGA CAGCGGCCTG   2580
AACTGGGACT TCAAGATCAA CGCCATCACC TACGACGGCA AGGAGATGAA CGTGTTCCAC   2640
CGCTACAACA AGTAG                                                   2655
```

(2) INFORMATION FOR SEQ ID NO:18:

(i) SEQUENCE CHARACTERISTICS:
(A) LENGTH: 2004 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: misc_feature
(B) LOCATION: 1..2004
(D) OTHER INFORMATION: /note= "Maize optimized DNA sequence for VIP1A(a) 80 kd protein from AB78"

(xi) SEQUENCE DESCRIPTION: SEQ ID NO:18:

```
ATGAAGCGCG AGATCGACGA GGACACCGAC ACCGACGGCG ACAGCATCCC CGACCTGTGG     60
GAGGAGAACG GCTACACCAT CCAGAACCGC ATCGCCGTGA AGTGGGACGA CAGCCTGGCT    120
AGCAAGGGCT ACACCAAGTT CGTGAGCAAC CCCCTGGAGA GCCACACCGT GGGCGACCCC    180
TACACCGACT ACGAGAAGGC CGCCCGCGAC CTGGACCTGA GCAACGCCAA GGAGACCTTC    240
```

```
AACCCCCTGG TGGCCGCCTT CCCCAGCGTG AACGTGAGCA TGGAGAAGGT GATCCTGAGC    300

CCCAACGAGA ACCTGAGCAA CAGCGTGGAG AGCCACTCGA GCACCAACTG GAGCTACACC    360

AACACCGAGG GCGCCAGCGT GGAGGCCGGC ATCGGTCCCA AGGGCATCAG CTTCGGCGTG    420

AGCGTGAACT ACCAGCACAG CGAGACCGTG GCCCAGGAGT GGGGCACCAG CACCGGCAAC    480

ACCAGCCAGT TCAACACCGC CAGCGCCGGC TACCTGAACG CCAACGTGCG CTACAACAAC    540

GTGGGCACCG GCGCCATCTA CGACGTGAAG CCCACCACCA GCTTCGTGCT GAACAACGAC    600

ACCATCGCCA CCATCACCGC CAAGTCGAAT TCCACCGCCC TGAACATCAG CCCCGGCGAG    660

AGCTACCCCA GAAGGGCCA GAACGGCATC GCCATCACCA GCATGGACGA CTTCAACAGC    720

CACCCCATCA CCCTGAACAA GAAGCAGGTG GACAACCTGC TGAACAACAA GCCCATGATG    780

CTGGAGACCA ACCAGACCGA CGGCGTCTAC AAGATCAAGG ACACCCACGG CAACATCGTG    840

ACCGGCGGCG AGTGGAACGG CGTGATCCAG CAGATCAAGG CCAAGACCGC CAGCATCATC    900

GTCGACGACG GCGAGCGCGT GGCCGAGAAG CGCGTGGCCG CCAAGGACTA CGAGAACCCC    960

GAGGACAAGA CCCCCAGCCT GACCCTGAAG GACGCCCTGA AGCTGAGCTA CCCCGACGAG    1020

ATCAAGGAGA TCGAGGGCCT GCTGTACTAC AAGAACAAGC CCATCTACGA GAGCAGCGTG    1080

ATGACCTATC TAGACGAGAA CACCGCCAAG GAGGTGACCA AGCAGCTGAA CGACACCACC    1140

GGCAAGTTCA AGGACGTGAG CCACCTGTAC GACGTGAAGC TGACCCCCAA GATGAACGTG    1200

ACCATCAAGC TGAGCATCCT GTACGACAAC GCCGAGAGCA ACGACAACAG CATCGGCAAG    1260

TGGACCAACA CCAACATCGT GAGCGGCGGC AACAACGGCA AGAAGCAGTA CAGCAGCAAC    1320

AACCCCGACG CCAACCTGAC CCTGAACACC GACGCCCAGG AGAAGCTGAA CAAGAACCGC    1380

GACTACTACA TCAGCCTGTA CATGAAGAGC GAGAAGAACA CCCAGTGCGA GATCACCATC    1440

GACGGCGAGA TATACCCCAT CACCACCAAG ACCGTGAACG TGAACAAGGA CAACTACAAG    1500

CGCCTGGACA TCATCGCCCA CAACATCAAG AGCAACCCCA TCAGCAGCCT GCACATCAAG    1560

ACCAACGACG AGATCACCCT GTTCTGGGAC GACATATCGA TTACCGACGT CGCCAGCATC    1620

AAGCCCGAGA ACCTGACCGA CAGCGAGATC AAGCAGATAT ACAGTCGCTA CGGCATCAAG    1680

CTGGAGGACG GCATCCTGAT CGACAAGAAG GGCGGCATCC ACTACGGCGA GTTCATCAAC    1740

GAGGCCAGCT TCAACATCGA GCCCCTGCAG AACTACGTGA CCAAGTACGA GGTGACCTAC    1800

AGCAGCGAGC TGGGCCCCAA CGTGAGCGAC ACCCTGGAGA GCGACAAGAT TTACAAGGAC    1860

GGCACCATCA AGTTCGACTT CACCAAGTAC AGCAAGAACG AGCAGGGCCT GTTCTACGAC    1920

AGCGGCCTGA ACTGGGACTT CAAGATCAAC GCCATCACCT ACGACGGCAA GGAGATGAAC    1980

GTGTTCCACC GCTACAACAA GTAG                                          2004
```

(2) INFORMATION FOR SEQ ID NO:19:

(i) SEQUENCE CHARACTERISTICS:
        (A) LENGTH: 4074 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1386
        (D) OTHER INFORMATION: /product= "VIP2A(b) from Btt"

-continued (ix) FEATURE:
(A) NAME/KEY: CDS
(B) LOCATION: 1394..3895
(D) OTHER INFORMATION: /product= "VIP1A(b) from Btt"

(ix) FEATURE:
(A) NAME/KEY: misc_feature
(B) LOCATION: 1..4074
(D) OTHER INFORMATION: /note= "Cloned DNA sequence from Btt which contains the genes for both VIP1A(b) and VIP2A(b)"

(xi) SEQUENCE DESCRIPTION: SEQ ID NO:19:

ATG CAA AGA ATG GAG GGA AAG TTG TTT GTG GTG TCA AAA ACA TTA CAA 48
Met Gln Arg Met Glu Gly Lys Leu Phe Val Val Ser Lys Thr Leu Gln
670 675 680

GTA GTT ACT AGA ACT GTA TTG CTT AGT ACA GTT TAC TCT ATA ACT TTA 96
Val Val Thr Arg Thr Val Leu Leu Ser Thr Val Tyr Ser Ile Thr Leu
685 690 695

TTA AAT AAT GTA GTG ATA AAA GCT GAC CAA TTA AAT ATA AAT TCT CAA 144
Leu Asn Asn Val Val Ile Lys Ala Asp Gln Leu Asn Ile Asn Ser Gln
700 705 710 715

AGT AAA TAT ACT AAC TTG CAA AAT CTA AAA ATC CCT GAT AAT GCA GAG 192
Ser Lys Tyr Thr Asn Leu Gln Asn Leu Lys Ile Pro Asp Asn Ala Glu
720 725 730

GAT TTT AAA GAA GAT AAG GGG AAA GCG AAA GAA TGG GGG AAA GAG AAA 240
Asp Phe Lys Glu Asp Lys Gly Lys Ala Lys Glu Trp Gly Lys Glu Lys
735 740 745

GGG GAA GAG TGG AGG CCT CCT GCT ACT GAG AAA GGA GAA ATG AAT AAT 288
Gly Glu Glu Trp Arg Pro Pro Ala Thr Glu Lys Gly Glu Met Asn Asn
750 755 760

TTT TTA GAT AAT AAA AAT GAT ATA AAG ACC AAT TAT AAA GAA ATT ACT 336
Phe Leu Asp Asn Lys Asn Asp Ile Lys Thr Asn Tyr Lys Glu Ile Thr
765 770 775

TTT TCT ATG GCA GGT TCA TGT GAA GAT GAA ATA AAA GAT TTA GAA GAA 384
Phe Ser Met Ala Gly Ser Cys Glu Asp Glu Ile Lys Asp Leu Glu Glu
780 785 790 795

ATT GAT AAG ATC TTT GAT AAA GCC AAT CTC TCG AGT TCT ATT ATC ACC 432
Ile Asp Lys Ile Phe Asp Lys Ala Asn Leu Ser Ser Ser Ile Ile Thr
800 805 810

TAT AAA AAT GTG GAA CCA GCA ACA ATT GGA TTT AAT AAA TCT TTA ACA 480
Tyr Lys Asn Val Glu Pro Ala Thr Ile Gly Phe Asn Lys Ser Leu Thr
815 820 825

GAA GGT AAT ACG ATT AAT TCT GAT GCA ATG GCA CAG TTT AAA GAA CAA 528
Glu Gly Asn Thr Ile Asn Ser Asp Ala Met Ala Gln Phe Lys Glu Gln
830 835 840

TTT TTA GGT AAG GAT ATG AAG TTT GAT AGT TAT CTA GAT ACT CAT TTA 576
Phe Leu Gly Lys Asp Met Lys Phe Asp Ser Tyr Leu Asp Thr His Leu
845 850 855

ACT GCT CAA CAA GTT TCC AGT AAA AAA AGA GTT ATT TTG AAG GTT ACG 624
Thr Ala Gln Gln Val Ser Ser Lys Lys Arg Val Ile Leu Lys Val Thr
860 865 870 875

GTT CCG AGT GGG AAA GGT TCT ACT ACT CCA ACA AAA GCA GGT GTC ATT 672
Val Pro Ser Gly Lys Gly Ser Thr Thr Pro Thr Lys Ala Gly Val Ile
880 885 890

TTA AAC AAT AAT GAA TAC AAA ATG CTC ATT GAT AAT GGG TAT GTG CTC 720
Leu Asn Asn Asn Glu Tyr Lys Met Leu Ile Asp Asn Gly Tyr Val Leu
895 900 905

CAT GTA GAT AAG GTA TCA AAA GTA GTA AAA AAA GGG ATG GAG TGC TTA 768
His Val Asp Lys Val Ser Lys Val Val Lys Lys Gly Met Glu Cys Leu
910 915 920

```
CAA GTT GAA GGG ACT TTA AAA AAG AGT CTC GAC TTT AAA AAT GAT ATA      816
Gln Val Glu Gly Thr Leu Lys Lys Ser Leu Asp Phe Lys Asn Asp Ile
925                 930                 935

AAT GCT GAA GCG CAT AGC TGG GGG ATG AAA ATT TAT GAA GAC TGG GCT      864
Asn Ala Glu Ala His Ser Trp Gly Met Lys Ile Tyr Glu Asp Trp Ala
940                 945                 950                 955

AAA AAT TTA ACC GCT TCG CAA AGG GAA GCT TTA GAT GGG TAT GCT AGG      912
Lys Asn Leu Thr Ala Ser Gln Arg Glu Ala Leu Asp Gly Tyr Ala Arg
                960                 965                 970

CAA GAT TAT AAA GAA ATC AAT AAT TAT TTG CGC AAT CAA GGC GGG AGT      960
Gln Asp Tyr Lys Glu Ile Asn Asn Tyr Leu Arg Asn Gln Gly Gly Ser
            975                 980                 985

GGA AAT GAA AAG CTG GAT GCC CAA TTA AAA AAT ATT TCT GAT GCT TTA     1008
Gly Asn Glu Lys Leu Asp Ala Gln Leu Lys Asn Ile Ser Asp Ala Leu
        990                 995                 1000

GGG AAG AAA CCC ATA CCA GAA AAT ATT ACC GTG TAT AGA TGG TGT GGC     1056
Gly Lys Lys Pro Ile Pro Glu Asn Ile Thr Val Tyr Arg Trp Cys Gly
    1005                1010                1015

ATG CCG GAA TTT GGT TAT CAA ATT AGT GAT CCG TTA CCT TCT TTA AAA     1104
Met Pro Glu Phe Gly Tyr Gln Ile Ser Asp Pro Leu Pro Ser Leu Lys
1020                1025                1030                1035

GAT TTT GAA GAA CAA TTT TTA AAT ACA ATT AAA GAA GAC AAA GGG TAT     1152
Asp Phe Glu Glu Gln Phe Leu Asn Thr Ile Lys Glu Asp Lys Gly Tyr
                1040                1045                1050

ATG AGT ACA AGC TTA TCG AGT GAA CGT CTT GCA GCT TTT GGA TCT AGA     1200
Met Ser Thr Ser Leu Ser Ser Glu Arg Leu Ala Ala Phe Gly Ser Arg
            1055                1060                1065

AAA ATT ATA TTA CGC TTA CAA GTT CCG AAA GGA AGT ACG GGG GCG TAT     1248
Lys Ile Ile Leu Arg Leu Gln Val Pro Lys Gly Ser Thr Gly Ala Tyr
        1070                1075                1080

TTA AGT GCC ATT GGT GGA TTT GCA AGT GAA AAA GAG ATC CTA CTT GAT     1296
Leu Ser Ala Ile Gly Gly Phe Ala Ser Glu Lys Glu Ile Leu Leu Asp
    1085                1090                1095

AAA GAT AGT AAA TAT CAT ATT GAT AAA GCA ACA GAG GTA ATC ATT AAA     1344
Lys Asp Ser Lys Tyr His Ile Asp Lys Ala Thr Glu Val Ile Ile Lys
1100                1105                1110                1115

GGT GTT AAG CGA TAT GTA GTG GAT GCA ACA TTA TTA ACA AAT              1386
Gly Val Lys Arg Tyr Val Val Asp Ala Thr Leu Leu Thr Asn
                1120                1125

TAAGGAG ATG AAA AAT ATG AAG AAA AAG TTA GCA AGT GTT GTA ACC TGT     1435
        Met Lys Asn Met Lys Lys Lys Leu Ala Ser Val Val Thr Cys
        1                   5                   10

ATG TTA TTA GCT CCT ATG TTT TTG AAT GGA AAT GTG AAT GCT GTT AAC     1483
Met Leu Leu Ala Pro Met Phe Leu Asn Gly Asn Val Asn Ala Val Asn
15                  20                  25                  30

GCG GAT AGT AAA ATA AAT CAG ATT TCT ACA ACG CAG GAA AAC CAA CAG     1531
Ala Asp Ser Lys Ile Asn Gln Ile Ser Thr Thr Gln Glu Asn Gln Gln
                35                  40                  45

AAA GAG ATG GAC CGA AAG GGA TTA TTG GGA TAT TAT TTC AAA GGA AAA     1579
Lys Glu Met Asp Arg Lys Gly Leu Leu Gly Tyr Tyr Phe Lys Gly Lys
            50                  55                  60

GAT TTT AAT AAT CTT ACT ATG TTT GCA CCG ACA CGT GAT AAT ACC CTT     1627
Asp Phe Asn Asn Leu Thr Met Phe Ala Pro Thr Arg Asp Asn Thr Leu
        65                  70                  75

ATG TAT GAC CAA CAA ACA GCG AAT GCA TTA TTA GAT AAA AAA CAA CAA     1675
Met Tyr Asp Gln Gln Thr Ala Asn Ala Leu Leu Asp Lys Lys Gln Gln
    80                  85                  90
```

```
                                                -continued

GAA TAT CAG TCC ATT CGT TGG ATT GGT TTG ATT CAG CGT AAA GAA ACG      1723
Glu Tyr Gln Ser Ile Arg Trp Ile Gly Leu Ile Gln Arg Lys Glu Thr
 95             100                 105                 110

GGC GAT TTC ACA TTT AAC TTA TCA AAG GAT GAA CAG GCA ATT ATA GAA      1771
Gly Asp Phe Thr Phe Asn Leu Ser Lys Asp Glu Gln Ala Ile Ile Glu
                115                 120                 125

ATC GAT GGG AAA ATC ATT TCT AAT AAA GGG AAA GAA AAG CAA GTT GTC      1819
Ile Asp Gly Lys Ile Ile Ser Asn Lys Gly Lys Glu Lys Gln Val Val
            130                 135                 140

CAT TTA GAA AAA GAA AAA TTA GTT CCA ATC AAA ATA GAG TAT CAA TCA      1867
His Leu Glu Lys Glu Lys Leu Val Pro Ile Lys Ile Glu Tyr Gln Ser
        145                 150                 155

GAT ACG AAA TTT AAT ATT GAT AGT AAA ACA TTT AAA GAA CTT AAA TTA      1915
Asp Thr Lys Phe Asn Ile Asp Ser Lys Thr Phe Lys Glu Leu Lys Leu
160                 165                 170

TTT AAA ATA GAT AGT CAA AAC CAA TCT CAA CAA GTT CAA CTG AGA AAC      1963
Phe Lys Ile Asp Ser Gln Asn Gln Ser Gln Gln Val Gln Leu Arg Asn
175                 180                 185                 190

CCT GAA TTT AAC AAA AAA GAA TCA CAG GAA TTT TTA GCA AAA GCA TCA      2011
Pro Glu Phe Asn Lys Lys Glu Ser Gln Glu Phe Leu Ala Lys Ala Ser
                195                 200                 205

AAA ACA AAC CTT TTT AAG CAA AAA ATG AAA AGA GAT ATT GAT GAA GAT      2059
Lys Thr Asn Leu Phe Lys Gln Lys Met Lys Arg Asp Ile Asp Glu Asp
            210                 215                 220

ACG GAT ACA GAT GGA GAC TCC ATT CCT GAT CTT TGG GAA GAA AAT GGG      2107
Thr Asp Thr Asp Gly Asp Ser Ile Pro Asp Leu Trp Glu Glu Asn Gly
        225                 230                 235

TAC ACG ATT CAA AAT AAA GTT GCT GTC AAA TGG GAT GAT TCG CTA GCA      2155
Tyr Thr Ile Gln Asn Lys Val Ala Val Lys Trp Asp Asp Ser Leu Ala
240                 245                 250

AGT AAG GGA TAT ACA AAA TTT GTT TCG AAT CCA TTA GAC AGC CAC ACA      2203
Ser Lys Gly Tyr Thr Lys Phe Val Ser Asn Pro Leu Asp Ser His Thr
255                 260                 265                 270

GTT GGC GAT CCC TAT ACT GAT TAT GAA AAG GCC GCA AGG GAT TTA GAT      2251
Val Gly Asp Pro Tyr Thr Asp Tyr Glu Lys Ala Ala Arg Asp Leu Asp
                275                 280                 285

TTA TCA AAT GCA AAG GAA ACG TTC AAC CCA TTG GTA GCT GCT TTT CCA      2299
Leu Ser Asn Ala Lys Glu Thr Phe Asn Pro Leu Val Ala Ala Phe Pro
            290                 295                 300

AGT GTG AAT GTT AGT ATG GAA AAG GTG ATA TTA TCA CCA AAT GAA AAT      2347
Ser Val Asn Val Ser Met Glu Lys Val Ile Leu Ser Pro Asn Glu Asn
        305                 310                 315

TTA TCC AAT AGT GTA GAG TCT CAT TCA TCC ACG AAT TGG TCT TAT ACG      2395
Leu Ser Asn Ser Val Glu Ser His Ser Ser Thr Asn Trp Ser Tyr Thr
320                 325                 330

AAT ACA GAA GGA GCT TCC ATT GAA GCT GGT GGC GGT CCA TTA GGC CTT      2443
Asn Thr Glu Gly Ala Ser Ile Glu Ala Gly Gly Gly Pro Leu Gly Leu
335                 340                 345                 350

TCT TTT GGC GTG AGT GTT ACT TAT CAA CAC TCT GAA ACA GTT GCA CAA      2491
Ser Phe Gly Val Ser Val Thr Tyr Gln His Ser Glu Thr Val Ala Gln
                355                 360                 365

GAA TGG GGA ACA TCT ACA GGA AAT ACT TCA CAA TTC AAT ACG GCT TCA      2539
Glu Trp Gly Thr Ser Thr Gly Asn Thr Ser Gln Phe Asn Thr Ala Ser
            370                 375                 380

GCG GGA TAT TTA AAT GCA AAT GTT CGG TAT AAC AAT GTA GGG ACT GGT      2587
Ala Gly Tyr Leu Asn Ala Asn Val Arg Tyr Asn Asn Val Gly Thr Gly
        385                 390                 395
```

```
GCC ATC TAT GAT GTA AAA CCT ACA ACA AGT TTT GTA TTA AAT AAC AAT     2635
Ala Ile Tyr Asp Val Lys Pro Thr Thr Ser Phe Val Leu Asn Asn Asn
            400                 405                 410

ACC ATC GCA ACG ATT ACA GCA AAA TCA AAT TCA ACA GCT TTA CGT ATA     2683
Thr Ile Ala Thr Ile Thr Ala Lys Ser Asn Ser Thr Ala Leu Arg Ile
415                 420                 425                 430

TCT CCG GGG GAT AGT TAT CCA GAA ATA GGA GAA AAC GCT ATT GCG ATT     2731
Ser Pro Gly Asp Ser Tyr Pro Glu Ile Gly Glu Asn Ala Ile Ala Ile
                    435                 440                 445

ACA TCT ATG GAT GAT TTT AAT TCT CAT CCA ATT ACA TTA AAT AAA CAA     2779
Thr Ser Met Asp Asp Phe Asn Ser His Pro Ile Thr Leu Asn Lys Gln
            450                 455                 460

CAG GTA AAT CAA TTG ATA AAT AAT AAG CCA ATT ATG CTA GAG ACA GAC     2827
Gln Val Asn Gln Leu Ile Asn Asn Lys Pro Ile Met Leu Glu Thr Asp
        465                 470                 475

CAA ACA GAT GGT GTT TAT AAA ATA AGA GAT ACA CAT GGA AAT ATT GTA     2875
Gln Thr Asp Gly Val Tyr Lys Ile Arg Asp Thr His Gly Asn Ile Val
        480                 485                 490

ACT GGT GGA GAA TGG AAT GGT GTA ACA CAA CAA ATT AAA GCA AAA ACA     2923
Thr Gly Gly Glu Trp Asn Gly Val Thr Gln Gln Ile Lys Ala Lys Thr
495                 500                 505                 510

GCG TCT ATT ATT GTG GAT GAC GGG AAA CAG GTA GCA GAA AAA CGT GTG     2971
Ala Ser Ile Ile Val Asp Asp Gly Lys Gln Val Ala Glu Lys Arg Val
                    515                 520                 525

GCG GCA AAA GAT TAT GGT CAT CCA GAA GAT AAA ACA CCA CCT TTA ACT     3019
Ala Ala Lys Asp Tyr Gly His Pro Glu Asp Lys Thr Pro Pro Leu Thr
            530                 535                 540

TTA AAA GAT ACC CTG AAG CTT TCA TAC CCA GAT GAA ATA AAA GAA ACT     3067
Leu Lys Asp Thr Leu Lys Leu Ser Tyr Pro Asp Glu Ile Lys Glu Thr
        545                 550                 555

AAT GGA TTG TTG TAC TAT GAT GAC AAA CCA ATC TAT GAA TCG AGT GTC     3115
Asn Gly Leu Leu Tyr Tyr Asp Asp Lys Pro Ile Tyr Glu Ser Ser Val
        560                 565                 570

ATG ACT TAT CTG GAT GAA AAT ACG GCA AAA GAA GTC AAA AAA CAA ATA     3163
Met Thr Tyr Leu Asp Glu Asn Thr Ala Lys Glu Val Lys Lys Gln Ile
575                 580                 585                 590

AAT GAT ACA ACC GGA AAA TTT AAG GAT GTA AAT CAC TTA TAT GAT GTA     3211
Asn Asp Thr Thr Gly Lys Phe Lys Asp Val Asn His Leu Tyr Asp Val
                    595                 600                 605

AAA CTG ACT CCA AAA ATG AAT TTT ACG ATT AAA ATG GCT TCC TTG TAT     3259
Lys Leu Thr Pro Lys Met Asn Phe Thr Ile Lys Met Ala Ser Leu Tyr
            610                 615                 620

GAT GGG GCT GAA AAT AAT CAT AAC TCT TTA GGA ACC TGG TAT TTA ACA     3307
Asp Gly Ala Glu Asn Asn His Asn Ser Leu Gly Thr Trp Tyr Leu Thr
        625                 630                 635

TAT AAT GTT GCT GGT GGA AAT ACT GGG AAG AGA CAA TAT CGT TCA GCT     3355
Tyr Asn Val Ala Gly Gly Asn Thr Gly Lys Arg Gln Tyr Arg Ser Ala
        640                 645                 650

CAT TCT TGT GCA CAT GTA GCT CTA TCT TCA GAA GCG AAA AAG AAA CTA     3403
His Ser Cys Ala His Val Ala Leu Ser Ser Glu Ala Lys Lys Lys Leu
655                 660                 665                 670

AAT CAA AAT GCG AAT TAC TAT CTT AGC ATG TAT ATG AAG GCT GAT TCT     3451
Asn Gln Asn Ala Asn Tyr Tyr Leu Ser Met Tyr Met Lys Ala Asp Ser
                    675                 680                 685

ACT ACG GAA CCT ACA ATA GAA GTA GCT GGG GAA AAA TCT GCA ATA ACA     3499
Thr Thr Glu Pro Thr Ile Glu Val Ala Gly Glu Lys Ser Ala Ile Thr
            690                 695                 700
```

```
                                                       -continued

AGT AAA AAA GTA AAA TTA AAT AAT CAA AAT TAT CAA AGA GTT GAT ATT      3547
Ser Lys Lys Val Lys Leu Asn Asn Gln Asn Tyr Gln Arg Val Asp Ile
        705                 710                 715

TTA GTG AAA AAT TCT GAA AGA AAT CCA ATG GAT AAA ATA TAT ATA AGA      3595
Leu Val Lys Asn Ser Glu Arg Asn Pro Met Asp Lys Ile Tyr Ile Arg
720                 725                 730

GGA AAT GGC ACG ACA AAT GTT TAT GGG GAT GAT GTT ACT ATC CCA GAG      3643
Gly Asn Gly Thr Thr Asn Val Tyr Gly Asp Asp Val Thr Ile Pro Glu
735                 740                 745                 750

GTA TCA GCT ATA AAT CCG GCT AGT CTA TCA GAT GAA GAA ATT CAA GAA      3691
Val Ser Ala Ile Asn Pro Ala Ser Leu Ser Asp Glu Glu Ile Gln Glu
            755                 760                 765

ATA TTT AAA GAC TCA ACT ATT GAA TAT GGA AAT CCT AGT TTC GTT GCT      3739
Ile Phe Lys Asp Ser Thr Ile Glu Tyr Gly Asn Pro Ser Phe Val Ala
        770                 775                 780

GAT GCC GTA ACA TTT AAA AAT ATA AAA CCT TTA CAA AAT TAT GTA AAG      3787
Asp Ala Val Thr Phe Lys Asn Ile Lys Pro Leu Gln Asn Tyr Val Lys
785                 790                 795

GAA TAT GAA ATA TAT CAT AAA TCT CAT CGA TAT GAA AAG AAA ACG GTC      3835
Glu Tyr Glu Ile Tyr His Lys Ser His Arg Tyr Glu Lys Lys Thr Val
800                 805                 810

TTT GAT ATC ATG GGT GTT CAT TAT GAG TAT AGT ATA GCT AGG GAA CAA      3883
Phe Asp Ile Met Gly Val His Tyr Glu Tyr Ser Ile Ala Arg Glu Gln
815                 820                 825                 830

AAG AAA GCC GCA TAATTTTAAA AATAAAACTC GTTAGAGTTT ATTTAGCATG          3935
Lys Lys Ala Ala

GTATTTTTAA GAATAATCAA TATGTTGAAC CGTTTGTAGC TGTTTTGGAA GGGAATTTCA    3995

TTTTATTTGG TCTCTTAAGT TGATGGGCAT GGGATATGTT CAGCATCCAA GCGTTTNGGG    4055

GGTTANAAAA TCCAATTTT                                                 4074

(2) INFORMATION FOR SEQ ID NO:20:

(i) SEQUENCE CHARACTERISTICS:
        (A) LENGTH: 462 amino acids
        (B) TYPE: amino acid
        (D) TOPOLOGY: linear (ii) MOLECULE TYPE: protein (xi) SEQUENCE DESCRIPTION: SEQ ID NO:20:

Met Gln Arg Met Glu Gly Lys Leu Phe Val Val Ser Lys Thr Leu Gln
1               5                   10                  15

Val Val Thr Arg Thr Val Leu Leu Ser Thr Val Tyr Ser Ile Thr Leu
            20                  25                  30

Leu Asn Asn Val Val Ile Lys Ala Asp Gln Leu Asn Ile Asn Ser Gln
        35                  40                  45

Ser Lys Tyr Thr Asn Leu Gln Asn Leu Lys Ile Pro Asp Asn Ala Glu
    50                  55                  60

Asp Phe Lys Glu Asp Lys Gly Lys Ala Lys Glu Trp Gly Lys Glu Lys
65                  70                  75                  80

Gly Glu Glu Trp Arg Pro Pro Ala Thr Glu Lys Gly Glu Met Asn Asn
                85                  90                  95

Phe Leu Asp Asn Lys Asn Asp Ile Lys Thr Asn Tyr Lys Glu Ile Thr
            100                 105                 110

Phe Ser Met Ala Gly Ser Cys Glu Asp Glu Ile Lys Asp Leu Glu Glu
        115                 120                 125
```

-continued

```
Ile Asp Lys Ile Phe Asp Lys Ala Asn Leu Ser Ser Ile Ile Thr
    130                 135                 140
Tyr Lys Asn Val Glu Pro Ala Thr Ile Gly Phe Asn Lys Ser Leu Thr
145                 150                 155                 160
Glu Gly Asn Thr Ile Asn Ser Asp Ala Met Ala Gln Phe Lys Glu Gln
                165                 170                 175
Phe Leu Gly Lys Asp Met Lys Phe Asp Ser Tyr Leu Asp Thr His Leu
            180                 185                 190
Thr Ala Gln Gln Val Ser Ser Lys Arg Val Ile Leu Lys Val Thr
        195                 200                 205
Val Pro Ser Gly Lys Gly Ser Thr Pro Thr Lys Ala Gly Val Ile
    210                 215                 220
Leu Asn Asn Asn Glu Tyr Lys Met Leu Ile Asp Asn Gly Tyr Val Leu
225                 230                 235                 240
His Val Asp Lys Val Ser Lys Val Val Lys Lys Gly Met Glu Cys Leu
                245                 250                 255
Gln Val Glu Gly Thr Leu Lys Lys Ser Leu Asp Phe Lys Asn Asp Ile
            260                 265                 270
Asn Ala Glu Ala His Ser Trp Gly Met Lys Ile Tyr Glu Asp Trp Ala
        275                 280                 285
Lys Asn Leu Thr Ala Ser Gln Arg Glu Ala Leu Asp Gly Tyr Ala Arg
    290                 295                 300
Gln Asp Tyr Lys Glu Ile Asn Asn Tyr Leu Arg Asn Gln Gly Gly Ser
305                 310                 315                 320
Gly Asn Glu Lys Leu Asp Ala Gln Leu Lys Asn Ile Ser Asp Ala Leu
                325                 330                 335
Gly Lys Lys Pro Ile Pro Glu Asn Ile Thr Val Tyr Arg Trp Cys Gly
            340                 345                 350
Met Pro Glu Phe Gly Tyr Gln Ile Ser Asp Pro Leu Pro Ser Leu Lys
        355                 360                 365
Asp Phe Glu Glu Gln Phe Leu Asn Thr Ile Lys Glu Asp Lys Gly Tyr
    370                 375                 380
Met Ser Thr Ser Leu Ser Ser Glu Arg Leu Ala Ala Phe Gly Ser Arg
385                 390                 395                 400
Lys Ile Ile Leu Arg Leu Gln Val Pro Lys Gly Ser Thr Gly Ala Tyr
                405                 410                 415
Leu Ser Ala Ile Gly Gly Phe Ala Ser Glu Lys Glu Ile Leu Leu Asp
            420                 425                 430
Lys Asp Ser Lys Tyr His Ile Asp Lys Ala Thr Glu Val Ile Ile Lys
        435                 440                 445
Gly Val Lys Arg Tyr Val Val Asp Ala Thr Leu Leu Thr Asn
    450                 455                 460
```

(2) INFORMATION FOR SEQ ID NO:21:

(i) SEQUENCE CHARACTERISTICS:
        (A) LENGTH: 834 amino acids
        (B) TYPE: amino acid
        (D) TOPOLOGY: linear (ii) MOLECULE TYPE: protein (xi) SEQUENCE DESCRIPTION: SEQ ID NO:21:

```
Met Lys Asn Met Lys Lys Lys Leu Ala Ser Val Val Thr Cys Met Leu
 1               5                  10                  15
```

-continued

```
Leu Ala Pro Met Phe Leu Asn Gly Asn Val Asn Ala Val Asn Ala Asp
            20                  25                  30

Ser Lys Ile Asn Gln Ile Ser Thr Thr Gln Glu Asn Gln Gln Lys Glu
        35                  40                  45

Met Asp Arg Lys Gly Leu Leu Gly Tyr Tyr Phe Lys Gly Lys Asp Phe
    50                  55                  60

Asn Asn Leu Thr Met Phe Ala Pro Thr Arg Asp Asn Thr Leu Met Tyr
65                  70                  75                  80

Asp Gln Gln Thr Ala Asn Ala Leu Leu Asp Lys Lys Gln Gln Glu Tyr
                85                  90                  95

Gln Ser Ile Arg Trp Ile Gly Leu Ile Gln Arg Lys Glu Thr Gly Asp
            100                 105                 110

Phe Thr Phe Asn Leu Ser Lys Asp Glu Gln Ala Ile Ile Glu Ile Asp
        115                 120                 125

Gly Lys Ile Ile Ser Asn Lys Gly Lys Glu Lys Gln Val Val His Leu
    130                 135                 140

Glu Lys Glu Lys Leu Val Pro Ile Lys Ile Glu Tyr Gln Ser Asp Thr
145                 150                 155                 160

Lys Phe Asn Ile Asp Ser Lys Thr Phe Lys Glu Leu Lys Leu Phe Lys
                165                 170                 175

Ile Asp Ser Gln Asn Gln Ser Gln Gln Val Gln Leu Arg Asn Pro Glu
            180                 185                 190

Phe Asn Lys Lys Glu Ser Gln Glu Phe Leu Ala Lys Ala Ser Lys Thr
        195                 200                 205

Asn Leu Phe Lys Gln Lys Met Lys Arg Asp Ile Asp Glu Asp Thr Asp
    210                 215                 220

Thr Asp Gly Asp Ser Ile Pro Asp Leu Trp Glu Asn Gly Tyr Thr
225                 230                 235                 240

Ile Gln Asn Lys Val Ala Val Lys Trp Asp Asp Ser Leu Ala Ser Lys
                245                 250                 255

Gly Tyr Thr Lys Phe Val Ser Asn Pro Leu Asp Ser His Thr Val Gly
            260                 265                 270

Asp Pro Tyr Thr Asp Tyr Glu Lys Ala Ala Arg Asp Leu Asp Leu Ser
        275                 280                 285

Asn Ala Lys Glu Thr Phe Asn Pro Leu Val Ala Ala Phe Pro Ser Val
    290                 295                 300

Asn Val Ser Met Glu Lys Val Ile Leu Ser Pro Asn Glu Asn Leu Ser
305                 310                 315                 320

Asn Ser Val Glu Ser His Ser Ser Thr Asn Trp Ser Tyr Thr Asn Thr
                325                 330                 335

Glu Gly Ala Ser Ile Glu Ala Gly Gly Pro Leu Gly Leu Ser Phe
            340                 345                 350

Gly Val Ser Val Thr Tyr Gln His Ser Glu Thr Val Ala Gln Glu Trp
        355                 360                 365

Gly Thr Ser Thr Gly Asn Thr Ser Gln Phe Asn Thr Ala Ser Ala Gly
    370                 375                 380

Tyr Leu Asn Ala Asn Val Arg Tyr Asn Val Gly Thr Gly Ala Ile
385                 390                 395                 400

Tyr Asp Val Lys Pro Thr Thr Ser Phe Val Leu Asn Asn Thr Ile
                405                 410                 415

Ala Thr Ile Thr Ala Lys Ser Asn Ser Thr Ala Leu Arg Ile Ser Pro
            420                 425                 430
```

-continued

```
Gly Asp Ser Tyr Pro Glu Ile Gly Glu Asn Ala Ile Ala Ile Thr Ser
            435                 440                 445

Met Asp Asp Phe Asn Ser His Pro Ile Thr Leu Asn Lys Gln Gln Val
    450                 455                 460

Asn Gln Leu Ile Asn Asn Lys Pro Ile Met Leu Glu Thr Asp Gln Thr
465                 470                 475                 480

Asp Gly Val Tyr Lys Ile Arg Asp Thr His Gly Asn Ile Val Thr Gly
                485                 490                 495

Gly Glu Trp Asn Gly Val Thr Gln Gln Ile Lys Ala Lys Thr Ala Ser
            500                 505                 510

Ile Ile Val Asp Asp Gly Lys Gln Val Ala Glu Lys Arg Val Ala Ala
            515                 520                 525

Lys Asp Tyr Gly His Pro Glu Asp Lys Thr Pro Pro Leu Thr Leu Lys
    530                 535                 540

Asp Thr Leu Lys Leu Ser Tyr Pro Asp Glu Ile Lys Glu Thr Asn Gly
545                 550                 555                 560

Leu Leu Tyr Tyr Asp Asp Lys Pro Ile Tyr Glu Ser Ser Val Met Thr
                565                 570                 575

Tyr Leu Asp Glu Asn Thr Ala Lys Glu Val Lys Lys Gln Ile Asn Asp
            580                 585                 590

Thr Thr Gly Lys Phe Lys Asp Val Asn His Leu Tyr Asp Val Lys Leu
            595                 600                 605

Thr Pro Lys Met Asn Phe Thr Ile Lys Met Ala Ser Leu Tyr Asp Gly
    610                 615                 620

Ala Glu Asn Asn His Asn Ser Leu Gly Thr Trp Tyr Leu Thr Tyr Asn
625                 630                 635                 640

Val Ala Gly Gly Asn Thr Gly Lys Arg Gln Tyr Arg Ser Ala His Ser
                645                 650                 655

Cys Ala His Val Ala Leu Ser Ser Glu Ala Lys Lys Leu Asn Gln
            660                 665                 670

Asn Ala Asn Tyr Tyr Leu Ser Met Tyr Met Lys Ala Asp Ser Thr Thr
            675                 680                 685

Glu Pro Thr Ile Glu Val Ala Gly Glu Lys Ser Ala Ile Thr Ser Lys
    690                 695                 700

Lys Val Lys Leu Asn Asn Gln Asn Tyr Gln Arg Val Asp Ile Leu Val
705                 710                 715                 720

Lys Asn Ser Glu Arg Asn Pro Met Asp Lys Ile Tyr Ile Arg Gly Asn
                725                 730                 735

Gly Thr Thr Asn Val Tyr Gly Asp Asp Val Thr Ile Pro Glu Val Ser
            740                 745                 750

Ala Ile Asn Pro Ala Ser Leu Ser Asp Glu Glu Ile Gln Glu Ile Phe
            755                 760                 765

Lys Asp Ser Thr Ile Glu Tyr Gly Asn Pro Ser Phe Val Ala Asp Ala
    770                 775                 780

Val Thr Phe Lys Asn Ile Lys Pro Leu Gln Asn Tyr Val Lys Glu Tyr
785                 790                 795                 800

Glu Ile Tyr His Lys Ser His Arg Tyr Glu Lys Lys Thr Val Phe Asp
                805                 810                 815

Ile Met Gly Val His Tyr Glu Tyr Ser Ile Ala Arg Glu Gln Lys Lys
            820                 825                 830

Ala Ala
```

-continued (2) INFORMATION FOR SEQ ID NO:22:

(i) SEQUENCE CHARACTERISTICS:
(A) LENGTH: 4041 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..4038
(D) OTHER INFORMATION: /product= "VIP1A(a)/VIP2A(a) fusion product"

(xi) SEQUENCE DESCRIPTION: SEQ ID NO:22:

```
ATG AAA AGA ATG GAG GGA AAG TTG TTT ATG GTG TCA AAA AAA TTA CAA       48
Met Lys Arg Met Glu Gly Lys Leu Phe Met Val Ser Lys Lys Leu Gln
835                 840                 845                 850

GTA GTT ACT AAA ACT GTA TTG CTT AGT ACA GTT TTC TCT ATA TCT TTA       96
Val Val Thr Lys Thr Val Leu Leu Ser Thr Val Phe Ser Ile Ser Leu
                855                 860                 865

TTA AAT AAT GAA GTG ATA AAA GCT GAA CAA TTA AAT ATA AAT TCT CAA      144
Leu Asn Asn Glu Val Ile Lys Ala Glu Gln Leu Asn Ile Asn Ser Gln
            870                 875                 880

AGT AAA TAT ACT AAC TTG CAA AAT CTA AAA ATC ACT GAC AAG GTA GAG      192
Ser Lys Tyr Thr Asn Leu Gln Asn Leu Lys Ile Thr Asp Lys Val Glu
        885                 890                 895

GAT TTT AAA GAA GAT AAG GAA AAA GCG AAA GAA TGG GGG AAA GAA AAA      240
Asp Phe Lys Glu Asp Lys Glu Lys Ala Lys Glu Trp Gly Lys Glu Lys
    900                 905                 910

GAA AAA GAG TGG AAA CTA ACT GCT ACT GAA AAA GGA AAA ATG AAT AAT      288
Glu Lys Glu Trp Lys Leu Thr Ala Thr Glu Lys Gly Lys Met Asn Asn
915                 920                 925                 930

TTT TTA GAT AAT AAA AAT GAT ATA AAG ACA AAT TAT AAA GAA ATT ACT      336
Phe Leu Asp Asn Lys Asn Asp Ile Lys Thr Asn Tyr Lys Glu Ile Thr
                935                 940                 945

TTT TCT ATG GCA GGC TCA TTT GAA GAT GAA ATA AAA GAT TTA AAA GAA      384
Phe Ser Met Ala Gly Ser Phe Glu Asp Glu Ile Lys Asp Leu Lys Glu
            950                 955                 960

ATT GAT AAG ATG TTT GAT AAA ACC AAT CTA TCA AAT TCT ATT ATC ACC      432
Ile Asp Lys Met Phe Asp Lys Thr Asn Leu Ser Asn Ser Ile Ile Thr
        965                 970                 975

TAT AAA AAT GTG GAA CCG ACA ACA ATT GGA TTT AAT AAA TCT TTA ACA      480
Tyr Lys Asn Val Glu Pro Thr Thr Ile Gly Phe Asn Lys Ser Leu Thr
    980                 985                 990

GAA GGT AAT ACG ATT AAT TCT GAT GCA ATG GCA CAG TTT AAA GAA CAA      528
Glu Gly Asn Thr Ile Asn Ser Asp Ala Met Ala Gln Phe Lys Glu Gln
995                 1000                1005                1010

TTT TTA GAT AGG GAT ATT AAG TTT GAT AGT TAT CTA GAT ACG CAT TTA      576
Phe Leu Asp Arg Asp Ile Lys Phe Asp Ser Tyr Leu Asp Thr His Leu
                1015                1020                1025

ACT GCT CAA CAA GTT TCC AGT AAA GAA AGA GTT ATT TTG AAG GTT ACG      624
Thr Ala Gln Gln Val Ser Ser Lys Glu Arg Val Ile Leu Lys Val Thr
            1030                1035                1040

GTT CCG AGT GGG AAA GGT TCT ACT ACT CCA ACA AAA GCA GGT GTC ATT      672
Val Pro Ser Gly Lys Gly Ser Thr Thr Pro Thr Lys Ala Gly Val Ile
        1045                1050                1055

TTA AAT AAT AGT GAA TAC AAA ATG CTC ATT GAT AAT GGG TAT ATG GTC      720
Leu Asn Asn Ser Glu Tyr Lys Met Leu Ile Asp Asn Gly Tyr Met Val
    1060                1065                1070
```

```
CAT GTA GAT AAG GTA TCA AAA GTG GTG AAA AAA GGG GTG GAG TGC TTA        768
His Val Asp Lys Val Ser Lys Val Val Lys Lys Gly Val Glu Cys Leu
1075              1080            1085            1090

CAA ATT GAA GGG ACT TTA AAA AAG AGT CTT GAC TTT AAA AAT GAT ATA        816
Gln Ile Glu Gly Thr Leu Lys Lys Ser Leu Asp Phe Lys Asn Asp Ile
            1095            1100            1105

AAT GCT GAA GCG CAT AGC TGG GGT ATG AAG AAT TAT GAA GAG TGG GCT        864
Asn Ala Glu Ala His Ser Trp Gly Met Lys Asn Tyr Glu Glu Trp Ala
                1110            1115            1120

AAA GAT TTA ACC GAT TCG CAA AGG GAA GCT TTA GAT GGG TAT GCT AGG        912
Lys Asp Leu Thr Asp Ser Gln Arg Glu Ala Leu Asp Gly Tyr Ala Arg
            1125            1130            1135

CAA GAT TAT AAA GAA ATC AAT AAT TAT TTA AGA AAT CAA GGC GGA AGT        960
Gln Asp Tyr Lys Glu Ile Asn Asn Tyr Leu Arg Asn Gln Gly Gly Ser
            1140            1145            1150

GGA AAT GAA AAA CTA GAT GCT CAA ATA AAA AAT ATT TCT GAT GCT TTA       1008
Gly Asn Glu Lys Leu Asp Ala Gln Ile Lys Asn Ile Ser Asp Ala Leu
1155            1160            1165            1170

GGG AAG AAA CCA ATA CCG GAA AAT ATT ACT GTG TAT AGA TGG TGT GGC       1056
Gly Lys Lys Pro Ile Pro Glu Asn Ile Thr Val Tyr Arg Trp Cys Gly
                1175            1180            1185

ATG CCG GAA TTT GGT TAT CAA ATT AGT GAT CCG TTA CCT TCT TTA AAA       1104
Met Pro Glu Phe Gly Tyr Gln Ile Ser Asp Pro Leu Pro Ser Leu Lys
            1190            1195            1200

GAT TTT GAA GAA CAA TTT TTA AAT ACA ATC AAA GAA GAC AAA GGA TAT       1152
Asp Phe Glu Glu Gln Phe Leu Asn Thr Ile Lys Glu Asp Lys Gly Tyr
            1205            1210            1215

ATG AGT ACA AGC TTA TCG AGT GAA CGT CTT GCA GCT TTT GGA TCT AGA       1200
Met Ser Thr Ser Leu Ser Ser Glu Arg Leu Ala Ala Phe Gly Ser Arg
            1220            1225            1230

AAA ATT ATA TTA CGA TTA CAA GTT CCG AAA GGA AGT ACG GGT GCG TAT       1248
Lys Ile Ile Leu Arg Leu Gln Val Pro Lys Gly Ser Thr Gly Ala Tyr
1235            1240            1245            1250

TTA AGT GCC ATT GGT GGA TTT GCA AGT GAA AAA GAG ATC CTA CTT GAT       1296
Leu Ser Ala Ile Gly Gly Phe Ala Ser Glu Lys Glu Ile Leu Leu Asp
                1255            1260            1265

AAA GAT AGT AAA TAT CAT ATT GAT AAA GTA ACA GAG GTA ATT ATT AAA       1344
Lys Asp Ser Lys Tyr His Ile Asp Lys Val Thr Glu Val Ile Ile Lys
            1270            1275            1280

GGT GTT AAG CGA TAT GTA GTG GAT GCA ACA TTA TTA ACA AAT ATG AAA       1392
Gly Val Lys Arg Tyr Val Val Asp Ala Thr Leu Leu Thr Asn Met Lys
            1285            1290            1295

AAT ATG AAG AAA AAG TTA GCA AGT GTT GTA ACG TGT ACG TTA TTA GCT       1440
Asn Met Lys Lys Lys Leu Ala Ser Val Val Thr Cys Thr Leu Leu Ala
            1300            1305            1310

CCT ATG TTT TTG AAT GGA AAT GTG AAT GCT GTT TAC GCA GAC AGC AAA       1488
Pro Met Phe Leu Asn Gly Asn Val Asn Ala Val Tyr Ala Asp Ser Lys
1315            1320            1325            1330

ACA AAT CAA ATT TCT ACA ACA CAG AAA AAT CAA CAG AAA GAG ATG GAC       1536
Thr Asn Gln Ile Ser Thr Thr Gln Lys Asn Gln Gln Lys Glu Met Asp
                1335            1340            1345

CGA AAA GGA TTA CTT GGG TAT TAT TTC AAA GGA AAA GAT TTT AGT AAT       1584
Arg Lys Gly Leu Leu Gly Tyr Tyr Phe Lys Gly Lys Asp Phe Ser Asn
            1350            1355            1360

CTT ACT ATG TTT GCA CCG ACA CGT GAT AGT ACT CTT ATT TAT GAT CAA       1632
Leu Thr Met Phe Ala Pro Thr Arg Asp Ser Thr Leu Ile Tyr Asp Gln
            1365            1370            1375
```

```
CAA ACA GCA AAT AAA CTA TTA GAT AAA AAA CAA CAA GAA TAT CAG TCT        1680
Gln Thr Ala Asn Lys Leu Leu Asp Lys Lys Gln Gln Glu Tyr Gln Ser
            1380                1385                1390

ATT CGT TGG ATT GGT TTG ATT CAG AGT AAA GAA ACG GGA GAT TTC ACA        1728
Ile Arg Trp Ile Gly Leu Ile Gln Ser Lys Glu Thr Gly Asp Phe Thr
1395                1400                1405                1410

TTT AAC TTA TCT GAG GAT GAA CAG GCA ATT ATA GAA ATC AAT GGG AAA        1776
Phe Asn Leu Ser Glu Asp Glu Gln Ala Ile Ile Glu Ile Asn Gly Lys
                1415                1420                1425

ATT ATT TCT AAT AAA GGG AAA GAA AAG CAA GTT GTC CAT TTA GAA AAA        1824
Ile Ile Ser Asn Lys Gly Lys Glu Lys Gln Val Val His Leu Glu Lys
            1430                1435                1440

GGA AAA TTA GTT CCA ATC AAA ATA GAG TAT CAA TCA GAT ACA AAA TTT        1872
Gly Lys Leu Val Pro Ile Lys Ile Glu Tyr Gln Ser Asp Thr Lys Phe
            1445                1450                1455

AAT ATT GAC AGT AAA ACA TTT AAA GAA CTT AAA TTA TTT AAA ATA GAT        1920
Asn Ile Asp Ser Lys Thr Phe Lys Glu Leu Lys Leu Phe Lys Ile Asp
            1460                1465                1470

AGT CAA AAC CAA CCC CAG CAA GTC CAG CAA GAT GAA CTG AGA AAT CCT        1968
Ser Gln Asn Gln Pro Gln Gln Val Gln Gln Asp Glu Leu Arg Asn Pro
1475                1480                1485                1490

GAA TTT AAC AAG AAA GAA TCA CAG GAA TTC TTA GCG AAA CCA TCG AAA        2016
Glu Phe Asn Lys Lys Glu Ser Gln Glu Phe Leu Ala Lys Pro Ser Lys
                1495                1500                1505

ATA AAT CTT TTC ACT CAA AAA ATG AAA AGG GAA ATT GAT GAA GAC ACG        2064
Ile Asn Leu Phe Thr Gln Lys Met Lys Arg Glu Ile Asp Glu Asp Thr
            1510                1515                1520

GAT ACG GAT GGG GAC TCT ATT CCT GAC CTT TGG GAA GAA AAT GGG TAT        2112
Asp Thr Asp Gly Asp Ser Ile Pro Asp Leu Trp Glu Glu Asn Gly Tyr
            1525                1530                1535

ACG ATT CAA AAT AGA ATC GCT GTA AAG TGG GAC GAT TCT CTA GCA AGT        2160
Thr Ile Gln Asn Arg Ile Ala Val Lys Trp Asp Asp Ser Leu Ala Ser
            1540                1545                1550

AAA GGG TAT ACG AAA TTT GTT TCA AAT CCA CTA GAA AGT CAC ACA GTT        2208
Lys Gly Tyr Thr Lys Phe Val Ser Asn Pro Leu Glu Ser His Thr Val
1555                1560                1565                1570

GGT GAT CCT TAT ACA GAT TAT GAA AAG GCA GCA AGA GAT CTA GAT TTG        2256
Gly Asp Pro Tyr Thr Asp Tyr Glu Lys Ala Ala Arg Asp Leu Asp Leu
                1575                1580                1585

TCA AAT GCA AAG GAA ACG TTT AAC CCA TTG GTA GCT GCT TTT CCA AGT        2304
Ser Asn Ala Lys Glu Thr Phe Asn Pro Leu Val Ala Ala Phe Pro Ser
            1590                1595                1600

GTG AAT GTT AGT ATG GAA AAG GTG ATA TTA TCA CCA AAT GAA AAT TTA        2352
Val Asn Val Ser Met Glu Lys Val Ile Leu Ser Pro Asn Glu Asn Leu
            1605                1610                1615

TCC AAT AGT GTA GAG TCT CAT TCA TCC ACG AAT TGG TCT TAT ACA AAT        2400
Ser Asn Ser Val Glu Ser His Ser Ser Thr Asn Trp Ser Tyr Thr Asn
1620                1625                1630

ACA GAA GGT GCT TCT GTT GAA GCG GGG ATT GGA CCA AAA GGT ATT TCG        2448
Thr Glu Gly Ala Ser Val Glu Ala Gly Ile Gly Pro Lys Gly Ile Ser
1635                1640                1645                1650

TTC GGA GTT AGC GTA AAC TAT CAA CAC TCT GAA ACA GTT GCA CAA GAA        2496
Phe Gly Val Ser Val Asn Tyr Gln His Ser Glu Thr Val Ala Gln Glu
                1655                1660                1665

TGG GGA ACA TCT ACA GGA AAT ACT TCG CAA TTC AAT ACG GCT TCA GCG        2544
Trp Gly Thr Ser Thr Gly Asn Thr Ser Gln Phe Asn Thr Ala Ser Ala
            1670                1675                1680
```

```
GGA TAT TTA AAT GCA AAT GTT CGA TAT AAC AAT GTA GGA ACT GGT GCC        2592
Gly Tyr Leu Asn Ala Asn Val Arg Tyr Asn Asn Val Gly Thr Gly Ala
        1685                1690                1695

ATC TAC GAT GTA AAA CCT ACA ACA AGT TTT GTA TTA AAT AAC GAT ACT        2640
Ile Tyr Asp Val Lys Pro Thr Thr Ser Phe Val Leu Asn Asn Asp Thr
    1700                1705                1710

ATC GCA ACT ATT ACG GCG AAA TCT AAT TCT ACA GCC TTA AAT ATA TCT        2688
Ile Ala Thr Ile Thr Ala Lys Ser Asn Ser Thr Ala Leu Asn Ile Ser
1715                1720                1725                1730

CCT GGA GAA AGT TAC CCG AAA AAA GGA CAA AAT GGA ATC GCA ATA ACA        2736
Pro Gly Glu Ser Tyr Pro Lys Lys Gly Gln Asn Gly Ile Ala Ile Thr
            1735                1740                1745

TCA ATG GAT GAT TTT AAT TCC CAT CCG ATT ACA TTA AAT AAA AAA CAA        2784
Ser Met Asp Asp Phe Asn Ser His Pro Ile Thr Leu Asn Lys Lys Gln
        1750                1755                1760

GTA GAT AAT CTG CTA AAT AAT AAA CCT ATG ATG TTG GAA ACA AAC CAA        2832
Val Asp Asn Leu Leu Asn Asn Lys Pro Met Met Leu Glu Thr Asn Gln
    1765                1770                1775

ACA GAT GGT GTT TAT AAG ATA AAA GAT ACA CAT GGA AAT ATA GTA ACT        2880
Thr Asp Gly Val Tyr Lys Ile Lys Asp Thr His Gly Asn Ile Val Thr
1780                1785                1790

GGC GGA GAA TGG AAT GGT GTC ATA CAA CAA ATC AAG GCT AAA ACA GCG        2928
Gly Gly Glu Trp Asn Gly Val Ile Gln Gln Ile Lys Ala Lys Thr Ala
1795                1800                1805                1810

TCT ATT ATT GTG GAT GAT GGG GAA CGT GTA GCA GAA AAA CGT GTA GCG        2976
Ser Ile Ile Val Asp Asp Gly Glu Arg Val Ala Glu Lys Arg Val Ala
            1815                1820                1825

GCA AAA GAT TAT GAA AAT CCA GAA GAT AAA ACA CCG TCT TTA ACT TTA        3024
Ala Lys Asp Tyr Glu Asn Pro Glu Asp Lys Thr Pro Ser Leu Thr Leu
            1830                1835                1840

AAA GAT GCC CTG AAG CTT TCA TAT CCA GAT GAA ATA AAA GAA ATA GAG        3072
Lys Asp Ala Leu Lys Leu Ser Tyr Pro Asp Glu Ile Lys Glu Ile Glu
        1845                1850                1855

GGA TTA TTA TAT TAT AAA AAC AAA CCG ATA TAC GAA TCG AGC GTT ATG        3120
Gly Leu Leu Tyr Tyr Lys Asn Lys Pro Ile Tyr Glu Ser Ser Val Met
        1860                1865                1870

ACT TAC TTA GAT GAA AAT ACA GCA AAA GAA GTG ACC AAA CAA TTA AAT        3168
Thr Tyr Leu Asp Glu Asn Thr Ala Lys Glu Val Thr Lys Gln Leu Asn
1875                1880                1885                1890

GAT ACC ACT GGG AAA TTT AAA GAT GTA AGT CAT TTA TAT GAT GTA AAA        3216
Asp Thr Thr Gly Lys Phe Lys Asp Val Ser His Leu Tyr Asp Val Lys
            1895                1900                1905

CTG ACT CCA AAA ATG AAT GTT ACA ATC AAA TTG TCT ATA CTT TAT GAT        3264
Leu Thr Pro Lys Met Asn Val Thr Ile Lys Leu Ser Ile Leu Tyr Asp
        1910                1915                1920

AAT GCT GAG TCT AAT GAT AAC TCA ATT GGT AAA TGG ACA AAC ACA AAT        3312
Asn Ala Glu Ser Asn Asp Asn Ser Ile Gly Lys Trp Thr Asn Thr Asn
        1925                1930                1935

ATT GTT TCA GGT GGA AAT AAC GGA AAA AAA CAA TAT TCT TCT AAT AAT        3360
Ile Val Ser Gly Gly Asn Asn Gly Lys Lys Gln Tyr Ser Ser Asn Asn
        1940                1945                1950

CCG GAT GCT AAT TTG ACA TTA AAT ACA GAT GCT CAA GAA AAA TTA AAT        3408
Pro Asp Ala Asn Leu Thr Leu Asn Thr Asp Ala Gln Glu Lys Leu Asn
1955                1960                1965                1970

AAA AAT CGT GAC TAT TAT ATA AGT TTA TAT ATG AAG TCA GAA AAA AAC        3456
Lys Asn Arg Asp Tyr Tyr Ile Ser Leu Tyr Met Lys Ser Glu Lys Asn
            1975                1980                1985
```

-continued

| | |
|---|---|
| ACA CAA TGT GAG ATT ACT ATA GAT GGG GAG ATT TAT CCG ATC ACT ACA<br>Thr Gln Cys Glu Ile Thr Ile Asp Gly Glu Ile Tyr Pro Ile Thr Thr<br>                    1990                 1995                2000 | 3504 |
| AAA ACA GTG AAT GTG AAT AAA GAC AAT TAC AAA AGA TTA GAT ATT ATA<br>Lys Thr Val Asn Val Asn Lys Asp Asn Tyr Lys Arg Leu Asp Ile Ile<br>2005                 2010                2015 | 3552 |
| GCT CAT AAT ATA AAA AGT AAT CCA ATT TCT TCA CTT CAT ATT AAA ACG<br>Ala His Asn Ile Lys Ser Asn Pro Ile Ser Ser Leu His Ile Lys Thr<br>                    2020                 2025                2030 | 3600 |
| AAT GAT GAA ATA ACT TTA TTT TGG GAT GAT ATT TCT ATA ACA GAT GTA<br>Asn Asp Glu Ile Thr Leu Phe Trp Asp Asp Ile Ser Ile Thr Asp Val<br>2035                 2040                2045               2050 | 3648 |
| GCA TCA ATA AAA CCG GAA AAT TTA ACA GAT TCA GAA ATT AAA CAG ATT<br>Ala Ser Ile Lys Pro Glu Asn Leu Thr Asp Ser Glu Ile Lys Gln Ile<br>                    2055                 2060                2065 | 3696 |
| TAT AGT AGG TAT GGT ATT AAG TTA GAA GAT GGA ATC CTT ATT GAT AAA<br>Tyr Ser Arg Tyr Gly Ile Lys Leu Glu Asp Gly Ile Leu Ile Asp Lys<br>2070                 2075                 2080 | 3744 |
| AAA GGT GGG ATT CAT TAT GGT GAA TTT ATT AAT GAA GCT AGT TTT AAT<br>Lys Gly Gly Ile His Tyr Gly Glu Phe Ile Asn Glu Ala Ser Phe Asn<br>                    2085                 2090                2095 | 3792 |
| ATT GAA CCA TTG CAA AAT TAT GTG ACC AAA TAT GAA GTT ACT TAT AGT<br>Ile Glu Pro Leu Gln Asn Tyr Val Thr Lys Tyr Glu Val Thr Tyr Ser<br>2100                 2105                 2110 | 3840 |
| AGT GAG TTA GGA CCA AAC GTG AGT GAC ACA CTT GAA AGT GAT AAA ATT<br>Ser Glu Leu Gly Pro Asn Val Ser Asp Thr Leu Glu Ser Asp Lys Ile<br>2115                 2120                 2125               2130 | 3888 |
| TAC AAG GAT GGG ACA ATT AAA TTT GAT TTT ACC AAA TAT AGT AAA AAT<br>Tyr Lys Asp Gly Thr Ile Lys Phe Asp Phe Thr Lys Tyr Ser Lys Asn<br>                    2135                 2140                2145 | 3936 |
| GAA CAA GGA TTA TTT TAT GAC AGT GGA TTA AAT TGG GAC TTT AAA ATT<br>Glu Gln Gly Leu Phe Tyr Asp Ser Gly Leu Asn Trp Asp Phe Lys Ile<br>2150                 2155                 2160 | 3984 |
| AAT GCT ATT ACT TAT GAT GGT AAA GAG ATG AAT GTT TTT CAT AGA TAT<br>Asn Ala Ile Thr Tyr Asp Gly Lys Glu Met Asn Val Phe His Arg Tyr<br>                    2165                 2170                2175 | 4032 |
| AAT AAA TAG<br>Asn Lys<br>    2180 | 4041 |

(2) INFORMATION FOR SEQ ID NO:23:

(i) SEQUENCE CHARACTERISTICS:
        (A) LENGTH: 1346 amino acids
        (B) TYPE: amino acid
        (D) TOPOLOGY: linear (ii) MOLECULE TYPE: protein (xi) SEQUENCE DESCRIPTION: SEQ ID NO:23:

Met Lys Arg Met Glu Gly Lys Leu Phe Met Val Ser Lys Lys Leu Gln
 1                 5                  10                 15

Val Val Thr Lys Thr Val Leu Leu Ser Thr Val Phe Ser Ile Ser Leu
             20                  25                 30

Leu Asn Asn Glu Val Ile Lys Ala Glu Gln Leu Asn Ile Asn Ser Gln
     35                  40                 45

Ser Lys Tyr Thr Asn Leu Gln Asn Leu Lys Ile Thr Asp Lys Val Glu
 50                55                  60

Asp Phe Lys Glu Asp Lys Glu Lys Ala Lys Glu Trp Gly Lys Glu Lys
 65                70                75                  80

-continued

```
Glu Lys Glu Trp Lys Leu Thr Ala Thr Glu Lys Gly Lys Met Asn Asn
                 85                  90                  95
Phe Leu Asp Asn Lys Asn Asp Ile Lys Thr Asn Tyr Lys Glu Ile Thr
                100                 105                 110
Phe Ser Met Ala Gly Ser Phe Glu Asp Glu Ile Lys Asp Leu Lys Glu
            115                 120                 125
Ile Asp Lys Met Phe Asp Lys Thr Asn Leu Ser Asn Ser Ile Ile Thr
        130                 135                 140
Tyr Lys Asn Val Glu Pro Thr Thr Ile Gly Phe Asn Lys Ser Leu Thr
145                 150                 155                 160
Glu Gly Asn Thr Ile Asn Ser Asp Ala Met Ala Gln Phe Lys Glu Gln
                165                 170                 175
Phe Leu Asp Arg Asp Ile Lys Phe Asp Ser Tyr Leu Asp Thr His Leu
                180                 185                 190
Thr Ala Gln Gln Val Ser Ser Lys Glu Arg Val Ile Leu Lys Val Thr
            195                 200                 205
Val Pro Ser Gly Lys Gly Ser Thr Thr Pro Thr Lys Ala Gly Val Ile
        210                 215                 220
Leu Asn Asn Ser Glu Tyr Lys Met Leu Ile Asp Asn Gly Tyr Met Val
225                 230                 235                 240
His Val Asp Lys Val Ser Lys Val Val Lys Gly Val Glu Cys Leu
                245                 250                 255
Gln Ile Glu Gly Thr Leu Lys Lys Ser Leu Asp Phe Lys Asn Asp Ile
                260                 265                 270
Asn Ala Glu Ala His Ser Trp Gly Met Lys Asn Tyr Glu Glu Trp Ala
            275                 280                 285
Lys Asp Leu Thr Asp Ser Gln Arg Glu Ala Leu Asp Gly Tyr Ala Arg
        290                 295                 300
Gln Asp Tyr Lys Glu Ile Asn Asn Tyr Leu Arg Asn Gln Gly Gly Ser
305                 310                 315                 320
Gly Asn Glu Lys Leu Asp Ala Gln Ile Lys Asn Ile Ser Asp Ala Leu
                325                 330                 335
Gly Lys Lys Pro Ile Pro Glu Asn Ile Thr Val Tyr Arg Trp Cys Gly
                340                 345                 350
Met Pro Glu Phe Gly Tyr Gln Ile Ser Asp Pro Leu Pro Ser Leu Lys
            355                 360                 365
Asp Phe Glu Glu Gln Phe Leu Asn Thr Ile Lys Glu Asp Lys Gly Tyr
        370                 375                 380
Met Ser Thr Ser Leu Ser Ser Glu Arg Leu Ala Ala Phe Gly Ser Arg
385                 390                 395                 400
Lys Ile Ile Leu Arg Leu Gln Val Pro Lys Gly Ser Thr Gly Ala Tyr
                405                 410                 415
Leu Ser Ala Ile Gly Gly Phe Ala Ser Glu Lys Glu Ile Leu Leu Asp
                420                 425                 430
Lys Asp Ser Lys Tyr His Ile Asp Lys Val Thr Glu Val Ile Ile Lys
            435                 440                 445
Gly Val Lys Arg Tyr Val Val Asp Ala Thr Leu Leu Thr Asn Met Lys
        450                 455                 460
Asn Met Lys Lys Lys Leu Ala Ser Val Val Thr Cys Thr Leu Leu Ala
465                 470                 475                 480
Pro Met Phe Leu Asn Gly Asn Val Asn Ala Val Tyr Ala Asp Ser Lys
                485                 490                 495
```

-continued

```
Thr Asn Gln Ile Ser Thr Thr Gln Lys Asn Gln Gln Lys Glu Met Asp
            500                 505                 510

Arg Lys Gly Leu Leu Gly Tyr Tyr Phe Lys Gly Lys Asp Phe Ser Asn
            515                 520                 525

Leu Thr Met Phe Ala Pro Thr Arg Asp Ser Thr Leu Ile Tyr Asp Gln
            530                 535                 540

Gln Thr Ala Asn Lys Leu Leu Asp Lys Lys Gln Gln Glu Tyr Gln Ser
545                 550                 555                 560

Ile Arg Trp Ile Gly Leu Ile Gln Ser Lys Glu Thr Gly Asp Phe Thr
                565                 570                 575

Phe Asn Leu Ser Glu Asp Glu Gln Ala Ile Ile Glu Ile Asn Gly Lys
            580                 585                 590

Ile Ile Ser Asn Lys Gly Lys Glu Lys Gln Val Val His Leu Glu Lys
            595                 600                 605

Gly Lys Leu Val Pro Ile Lys Ile Glu Tyr Gln Ser Asp Thr Lys Phe
            610                 615                 620

Asn Ile Asp Ser Lys Thr Phe Lys Glu Leu Lys Leu Phe Lys Ile Asp
625                 630                 635                 640

Ser Gln Asn Gln Pro Gln Gln Val Gln Gln Asp Glu Leu Arg Asn Pro
                645                 650                 655

Glu Phe Asn Lys Lys Glu Ser Gln Glu Phe Leu Ala Lys Pro Ser Lys
            660                 665                 670

Ile Asn Leu Phe Thr Gln Lys Met Lys Arg Glu Ile Asp Glu Asp Thr
            675                 680                 685

Asp Thr Asp Gly Asp Ser Ile Pro Asp Leu Trp Glu Glu Asn Gly Tyr
            690                 695                 700

Thr Ile Gln Asn Arg Ile Ala Val Lys Trp Asp Asp Ser Leu Ala Ser
705                 710                 715                 720

Lys Gly Tyr Thr Lys Phe Val Ser Asn Pro Leu Glu Ser His Thr Val
                725                 730                 735

Gly Asp Pro Tyr Thr Asp Tyr Glu Lys Ala Ala Arg Asp Leu Asp Leu
            740                 745                 750

Ser Asn Ala Lys Glu Thr Phe Asn Pro Leu Val Ala Ala Phe Pro Ser
            755                 760                 765

Val Asn Val Ser Met Glu Lys Val Ile Leu Ser Pro Asn Glu Asn Leu
            770                 775                 780

Ser Asn Ser Val Glu Ser His Ser Ser Thr Asn Trp Ser Tyr Thr Asn
785                 790                 795                 800

Thr Glu Gly Ala Ser Val Glu Ala Gly Ile Gly Pro Lys Gly Ile Ser
                805                 810                 815

Phe Gly Val Ser Val Asn Tyr Gln His Ser Glu Thr Val Ala Gln Glu
            820                 825                 830

Trp Gly Thr Ser Thr Gly Asn Thr Ser Gln Phe Asn Thr Ala Ser Ala
            835                 840                 845

Gly Tyr Leu Asn Ala Asn Val Arg Tyr Asn Asn Val Gly Thr Gly Ala
            850                 855                 860

Ile Tyr Asp Val Lys Pro Thr Thr Ser Phe Val Leu Asn Asn Asp Thr
865                 870                 875                 880

Ile Ala Thr Ile Thr Ala Lys Ser Asn Ser Thr Ala Leu Asn Ile Ser
                885                 890                 895

Pro Gly Glu Ser Tyr Pro Lys Lys Gly Gln Asn Gly Ile Ala Ile Thr
            900                 905                 910
```

-continued

```
Ser Met Asp Asp Phe Asn Ser His Pro Ile Thr Leu Asn Lys Lys Gln
            915                 920                 925

Val Asp Asn Leu Leu Asn Asn Lys Pro Met Met Leu Glu Thr Asn Gln
            930                 935                 940

Thr Asp Gly Val Tyr Lys Ile Lys Asp Thr His Gly Asn Ile Val Thr
945                 950                 955                 960

Gly Gly Glu Trp Asn Gly Val Ile Gln Gln Ile Lys Ala Lys Thr Ala
                965                 970                 975

Ser Ile Ile Val Asp Asp Gly Glu Arg Val Ala Glu Lys Arg Val Ala
            980                 985                 990

Ala Lys Asp Tyr Glu Asn Pro Glu Asp Lys Thr Pro Ser Leu Thr Leu
            995                 1000                1005

Lys Asp Ala Leu Lys Leu Ser Tyr Pro Asp Glu Ile Lys Glu Ile Glu
            1010                1015                1020

Gly Leu Leu Tyr Tyr Lys Asn Lys Pro Ile Tyr Glu Ser Ser Val Met
1025                1030                1035                1040

Thr Tyr Leu Asp Glu Asn Thr Ala Lys Glu Val Thr Lys Gln Leu Asn
            1045                1050                1055

Asp Thr Thr Gly Lys Phe Lys Asp Val Ser His Leu Tyr Asp Val Lys
            1060                1065                1070

Leu Thr Pro Lys Met Asn Val Thr Ile Lys Leu Ser Ile Leu Tyr Asp
            1075                1080                1085

Asn Ala Glu Ser Asn Asp Asn Ser Ile Gly Lys Trp Thr Asn Thr Asn
            1090                1095                1100

Ile Val Ser Gly Gly Asn Asn Gly Lys Lys Gln Tyr Ser Ser Asn Asn
1105                1110                1115                1120

Pro Asp Ala Asn Leu Thr Leu Asn Thr Asp Ala Gln Glu Lys Leu Asn
            1125                1130                1135

Lys Asn Arg Asp Tyr Tyr Ile Ser Leu Tyr Met Lys Ser Glu Lys Asn
            1140                1145                1150

Thr Gln Cys Glu Ile Thr Ile Asp Gly Glu Ile Tyr Pro Ile Thr Thr
            1155                1160                1165

Lys Thr Val Asn Val Asn Lys Asp Asn Tyr Lys Arg Leu Asp Ile Ile
            1170                1175                1180

Ala His Asn Ile Lys Ser Asn Pro Ile Ser Ser Leu His Ile Lys Thr
1185                1190                1195                1200

Asn Asp Glu Ile Thr Leu Phe Trp Asp Asp Ile Ser Ile Thr Asp Val
            1205                1210                1215

Ala Ser Ile Lys Pro Glu Asn Leu Thr Asp Ser Glu Ile Lys Gln Ile
            1220                1225                1230

Tyr Ser Arg Tyr Gly Ile Lys Leu Glu Asp Gly Ile Leu Ile Asp Lys
            1235                1240                1245

Lys Gly Gly Ile His Tyr Gly Glu Phe Ile Asn Glu Ala Ser Phe Asn
1250                1255                1260

Ile Glu Pro Leu Gln Asn Tyr Val Thr Lys Tyr Glu Val Thr Tyr Ser
1265                1270                1275                1280

Ser Glu Leu Gly Pro Asn Val Ser Asp Thr Leu Glu Ser Asp Lys Ile
            1285                1290                1295

Tyr Lys Asp Gly Thr Ile Lys Phe Asp Phe Thr Lys Tyr Ser Lys Asn
            1300                1305                1310

Glu Gln Gly Leu Phe Tyr Asp Ser Gly Leu Asn Trp Asp Phe Lys Ile
            1315                1320                1325
```

-continued

```
Asn Ala Ile Thr Tyr Asp Gly Lys Glu Met Asn Val Phe His Arg Tyr
    1330                1335                1340

Asn Lys
1345
```

(2) INFORMATION FOR SEQ ID NO:24:

(i) SEQUENCE CHARACTERISTICS:
(A) LENGTH: 1399 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..1386
(D) OTHER INFORMATION: /note= "Maize optimized DNA sequence for VIP2A(a) protein from AB78"

(xi) SEQUENCE DESCRIPTION: SEQ ID NO:24:

```
ATGAAGCGCA TGGAGGGCAA GCTGTTCATG GTGAGCAAGA AGCTCCAGGT GGTGACCAAG     60

ACCGTGCTGC TGAGCACCGT GTTCAGCATC AGCCTGCTGA ACAACGAGGT GATCAAGGCC    120

GAGCAGCTGA ACATCAACAG CCAGAGCAAG TACACCAACC TCCAGAACCT GAAGATCACC    180

GACAAGGTGG AGGACTTCAA GGAGGACAAG GAGAAGGCCA AGGAGTGGGG CAAGGAGAAG    240

GAGAAGGAGT GGAAGCTTAC CGCCACCGAG AAGGGCAAGA TGAACAACTT CCTGGACAAC    300

AAGAACGACA TCAAGACCAA CTACAAGGAG ATCACCTTCA GCATGGCCGG CAGCTTCGAG    360

GACGAGATCA AGGACCTGAA GGAGATCGAC AAGATGTTCG ACAAGACCAA CCTGAGCAAC    420

AGCATCATCA CCTACAAGAA CGTGGAGCCC ACCACCATCG GCTTCAACAA GAGCCTGACC    480

GAGGGCAACA CCATCAACAG CGACGCCATG GCCCAGTTCA AGGAGCAGTT CCTGGACCGC    540

GACATCAAGT TCGACAGCTA CCTGGACACC CACCTGACCG CCCAGCAGGT GAGCAGCAAG    600

GAGCGCGTGA TCCTGAAGGT GACCGTCCCC AGCGGCAAGG GCAGCACCAC CCCCACCAAG    660

GCCGGCGTGA TCCTGAACAA CAGCGAGTAC AAGATGCTGA TCGACAACGG CTACATGGTG    720

CACGTGGACA AGGTGAGCAA GGTGGTGAAG AAGGGCGTGG AGTGCCTCCA GATCGAGGGC    780

ACCCTGAAGA AGAGTCTAGA CTTCAAGAAC GACATCAACG CCGAGGCCCA CAGCTGGGGC    840

ATGAAGAACT ACGAGGAGTG GGCCAAGGAC CTGACCGACA GCCAGCGCGA GGCCCTGGAC    900

GGCTACGCCC GCCAGGACTA CAAGGAGATC AACAACTACC TGCGCAACCA GGGCGGCAGC    960

GGCAACGAGA AGCTGGACGC CCAGATCAAG AACATCAGCG ACGCCCTGGG CAAGAAGCCC   1020

ATCCCCGAGA ACATCACCGT GTACCGCTGG TGCGGCATGC CCGAGTTCGG CTACCAGATC   1080

AGCGACCCCC TGCCCAGCCT GAAGGACTTC GAGGAGCAGT TCCTGAACAC CATCAAGGAG   1140

GACAAGGGCT ACATGAGCAC CAGCCTGAGC AGCGAGCGCC TGGCCGCCTT CGGCAGCCGC   1200

AAGATCATCC TGCGCCTGCA GGTGCCCAAG GGCAGCACCG GCGCCTACCT GAGCGCCATC   1260

GGCGGCTTCG CCAGCGAGAA GGAGATCCTG CTGGACAAGG ACAGCAAGTA CCACATCGAC   1320

AAGGTGACCG AGGTGATCAT CAAGGGCGTG AAGCGCTACG TGGTGGACGC CACCCTGCTG   1380

ACCAACTAGA TCTGAGCTC                                                1399
```

(2) INFORMATION FOR SEQ ID NO:25:

(i) SEQUENCE CHARACTERISTICS:
(A) LENGTH: 19 amino acids
(B) TYPE: amino acid

-continued (C) STRANDEDNESS: single
(D) TOPOLOGY: linear (ii) MOLECULE TYPE: peptide (ix) FEATURE:
(A) NAME/KEY: Peptide
(B) LOCATION: 1..19
(D) OTHER INFORMATION: /note= "Secretion signal peptide to secrete VIP2 out of a cell"

(xi) SEQUENCE DESCRIPTION: SEQ ID NO:25:

```
Gly Trp Ser Trp Ile Phe Leu Phe Leu Leu Ser Gly Ala Ala Gly Val
1               5                   10                  15

His Cys Leu
```

(2) INFORMATION FOR SEQ ID NO:26:

(i) SEQUENCE CHARACTERISTICS:
(A) LENGTH: 2655 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Synthetic DNA"

(iii) HYPOTHETICAL: NO (ix) FEATURE:
(A) NAME/KEY: misc_feature
(B) LOCATION: 1..2655
(D) OTHER INFORMATION: /note= "maize optimized DNA sequence encoding VIP1A(a)"

(xi) SEQUENCE DESCRIPTION: SEQ ID NO:26:

```
ATGAAGAACA TGAAGAAGAA GCTGGCCAGC GTGGTGACCT GCACCCTGCT GGCCCCCATG     60

TTCCTGAACG GCAACGTGAA CGCCGTGTAC GCCGACAGCA AGACCAACCA GATCAGCACC    120

ACCCAGAAGA ACCAGCAGAA GGAGATGGAC CGCAAGGGCC TGCTGGGCTA CTACTTCAAG    180

GGCAAGGACT TCAGCAACCT GACCATGTTC GCCCCCACGC GTGACAGCAC CCTGATCTAC    240

GACCAGCAGA CCGCCAACAA GCTGCTGGAC AAGAAGCAGC AGGAGTACCA GAGCATCCGC    300

TGGATCGGCC TGATCCAGAG CAAGGAGACC GGCGACTTCA CCTTCAACCT GAGCGAGGAC    360

GAGCAGGCCA TCATCGAGAT CAACGGCAAG ATCATCAGCA ACAAGGGCAA GGAGAAGCAG    420

GTGGTGCACC TGGAGAAGGG CAAGCTGGTG CCCATCAAGA TCGAGTACCA GAGCGACACC    480

AAGTTCAACA TCGACAGCAA GACCTTCAAG GAGCTGAAGC TTTTCAAGAT CGACAGCCAG    540

AACCAGCCCC AGCAGGTGCA GCAGGACGAG CTGCGCAACC CCGAGTTCAA CAAGAAGGAG    600

AGCCAGGAGT TCCTGGCCAA GCCCAGCAAG ATCAACCTGT TCACCCAGCA GATGAAGCGC    660

GAGATCGACG AGGACACCGA CACCGACGGC GACAGCATCC CCGACCTGTG GGAGGAGAAC    720

GGCTACACCA TCCAGAACCG CATCGCCGTG AAGTGGGACG ACAGCCTGGC TAGCAAGGGC    780

TACACCAAGT TCGTGAGCAA CCCCCTGGAG AGCCACACCG TGGGCGACCC CTACACCGAC    840

TACGAGAAGG CCGCCCGCGA CCTGGACCTG AGCAACGCCA AGGAGACCTT CAACCCCCTG    900

GTGGCCGCCT TCCCCAGCGT GAACGTGAGC ATGGAGAAGG TGATCCTGAG CCCCAACGAG    960

AACCTGAGCA ACAGCGTGGA GAGCCACTCG AGCACCAACT GGAGCTACAC CAACACCGAG   1020

GGCGCCAGCG TGGAGGCCGG CATCGGTCCC AAGGGCATCA GCTTCGGCGT GAGCGTGAAC   1080

TACCAGCACA GCGAGACCGT GGCCCAGGAG TGGGGCACCA GCACCGGCAA CACCAGCCAG   1140
```

-continued

```
TTCAACACCG CCAGCGCCGG CTACCTGAAC GCCAACGTGC GCTACAACAA CGTGGGCACC   1200

GGCGCCATCT ACGACGTGAA GCCCACCACC AGCTTCGTGC TGAACAACGA CACCATCGCC   1260

ACCATCACCG CCAAGTCGAA TTCCACCGCC CTGAACATCA GCCCCGGCGA GAGCTACCCC   1320

AAGAAGGGCC AGAACGGCAT CGCCATCACC AGCATGGACG ACTTCAACAG CCACCCCATC   1380

ACCCTGAACA AGAAGCAGGT GGACAACCTG CTGAACAACA AGCCCATGAT GCTGGAGACC   1440

AACCAGACCG ACGGCGTCTA CAAGATCAAG GACACCCACG GCAACATCGT GACGGGCGGC   1500

GAGTGGAACG GCGTGATCCA GCAGATCAAG GCCAAGACCG CCAGCATCAT CGTCGACGAC   1560

GGCGAGCGCG TGGCCGAGAA GCGCGTGGCC GCCAAGGACT ACGAGAACCC CGAGGACAAG   1620

ACCCCCAGCC TGACCCTGAA GGACGCCCTG AAGCTGAGCT ACCCCGACGA GATCAAGGAG   1680

ATCGAGGGCT TGCTGTACTA CAAGAACAAG CCCATCTACG AGAGCAGCGT GATGACCTAT   1740

CTAGACGAGA ACACCGCCAA GGAGGTGACC AAGCAGCTGA ACGACACCAC CGGCAAGTTC   1800

AAGGACGTGA GCCACCTGTA CGACGTGAAG CTGACCCCCA AGATGAACGT GACCATCAAG   1860

CTGAGCATCC TGTACGACAA CGCCGAGAGC AACGACAACA GCATCGGCAA GTGGACCAAC   1920

ACCAACATCG TGAGCGGCGG CAACAACGGC AAGAAGCAGT ACAGCAGCAA CAACCCCGAC   1980

GCCAACCTGA CCCTGAACAC CGACGCCCAG GAGAAGCTGA ACAAGAACCG CGACTACTAC   2040

ATCAGCCTGT ACATGAAGAG CGAGAAGAAC ACCCAGTGCG AGATCACCAT CGACGGCGAG   2100

ATATACCCCA TCACCACCAA GACCGTGAAC GTGAACAAGG ACAACTACAA GCGCCTGGAC   2160

ATCATCGCCC ACAACATCAA GAGCAACCCC ATCAGCAGCC TGCACATCAA GACCAACGAC   2220

GAGATCACCC TGTTCTGGGA CGACATATCG ATTACCGACG TCGCCAGCAT CAAGCCCGAG   2280

AACCTGACCG ACAGCGAGAT CAAGCAGATA TACAGTCGCT ACGGCATCAA GCTGGAGGAC   2340

GGCATCCTGA TCGACAAGAA AGGCGGCATC CACTACGGCG AGTTCATCAA CGAGGCCAGC   2400

TTCAACATCG AGCCCCTGCA GAACTACGTG ACCAAGTACG AGGTGACCTA CAGCAGCGAG   2460

CTGGGCCCCA ACGTGAGCGA CACCCTGGAG AGCGACAAGA TTTACAAGGA CGGCACCATC   2520

AAGTTCGACT TCACCAAGTA CAGCAAGAAC GAGCAGGGCC TGTTCTACGA CAGCGGCCTG   2580

AACTGGGACT TCAAGATCAA CGCCATCACC TACGACGGCA AGGAGATGAA CGTGTTCCAC   2640

CGCTACAACA AGTAG                                                    2655
```

(2) INFORMATION FOR SEQ ID NO:27:

(i) SEQUENCE CHARACTERISTICS:
- (A) LENGTH: 1389 base pairs
- (B) TYPE: nucleic acid
- (C) STRANDEDNESS: single
- (D) TOPOLOGY: linear (ii) MOLECULE TYPE: other nucleic acid
- (A) DESCRIPTION: /desc = "Synthetic DNA"

(iii) HYPOTHETICAL: NO (ix) FEATURE:
- (A) NAME/KEY: misc_feature
- (B) LOCATION: 1..1389
- (D) OTHER INFORMATION: /note= "maize optimized DNA sequence encoding VIP2A(a)"

(xi) SEQUENCE DESCRIPTION: SEQ ID NO:27:

```
ATGAAGCGCA TGGAGGGCAA GCTGTTCATG GTGAGCAAGA AGCTCCAGGT GGTGACCAAG     60

ACCGTGCTGC TGAGCACCGT GTTCAGCATC AGCCTGCTGA ACAACGAGGT GATCAAGGCC    120
```

```
GAGCAGCTGA ACATCAACAG CCAGAGCAAG TACACCAACC TCCAGAACCT GAAGATCACC      180

GACAAGGTGG AGGACTTCAA GGAGGACAAG GAGAAGGCCA AGGAGTGGGG CAAGGAGAAG      240

GAGAAGGAGT GGAAGCTTAC CGCCACCGAG AAGGGCAAGA TGAACAACTT CCTGGACAAC      300

AAGAACGACA TCAAGACCAA CTACAAGGAG ATCACCTTCA GCATAGCCGG CAGCTTCGAG      360

GACGAGATCA AGGACCTGAA GGAGATCGAC AAGATGTTCG ACAAGACCAA CCTGAGCAAC      420

AGCATCATCA CCTACAAGAA CGTGGAGCCC ACCACCATCG GCTTCAACAA GAGCCTGACC      480

GAGGGCAACA CCATCAACAG CGACGCCATG GCCCAGTTCA AGGAGCAGTT CCTGGACCGC      540

GACATCAAGT TCGACAGCTA CCTGGACACC CACCTGACCG CCCAGCAGGT GAGCAGCAAG      600

GAGCGCGTGA TCCTGAAGGT GACCGTCCCC AGCGGCAAGG GCAGCACCAC CCCCACCAAG      660

GCCGGCGTGA TCCTGAACAA CAGCGAGTAC AAGATGCTGA TCGACAACGG CTACATGGTG      720

CACGTGGACA AGGTGAGCAA GGTGGTGAAG AAGGGCGTGG AGTGCCTCCA GATCGAGGGC      780

ACCCTGAAGA AGAGTCTAGA CTTCAAGAAC GACATCAACG CCGAGGCCCA CAGCTGGGGC      840

ATGAAGAACT ACGAGGAGTG GGCCAAGGAC CTGACCGACA GCCAGCGCGA GGCCCTGGAC      900

GGCTACGCCC GCCAGGACTA CAAGGAGATC AACAACTACC TGCGCAACCA GGGCGGCAGC      960

GGCAACGAGA GCTGGACGC CCAGATCAAG AACATCAGCG ACGCCCTGGG CAAGAAGCCC     1020
```
(Note: one-letter continues)

```
ATCCCCGAGA ACATCACCGT GTACCGCTGG TGCGGCATGC CCGAGTTCGG CTACCAGATC     1080

AGCGACCCCC TGCCCAGCCT GAAGGACTTC GAGGAGCAGT TCCTGAACAC CATCAAGGAG     1140

GACAAGGGCT ACATGAGCAC CAGCCTGAGC AGCGAGCGCC TGGCCGCCTT CGGCAGCCGC     1200

AAGATCATCC TGCGCCTGCA GGTGCCCAAG GGCAGCACTG GTGCCTACCT GAGCGCCATC     1260

GGCGGCTTCG CCAGCGAGAA GGAGATCCTG CTGGATAAGG ACAGCAAGTA CCACATCGAC     1320

AAGGTGACCG AGGTGATCAT CAAGGGCGTG AAGCGCTACG TGGTGGACGC CACCCTGCTG     1380

ACCAACTAG                                                             1389
```

(2) INFORMATION FOR SEQ ID NO:28:

(i) SEQUENCE CHARACTERISTICS:
        (A) LENGTH: 2378 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION: 9..2375
        (D) OTHER INFORMATION: /note= "Native DNA sequence
            encoding VIP3A(a) protein from AB88 as contained in
            pCIB7104"

(xi) SEQUENCE DESCRIPTION: SEQ ID NO:28:

```
AGATGAAC ATG AAC AAG AAT AAT ACT AAA TTA AGC ACA AGA GCC TTA CCA       50
         Met Asn Lys Asn Asn Thr Lys Leu Ser Thr Arg Ala Leu Pro
           1               5                  10

AGT TTT ATT GAT TAT TTT AAT GGC ATT TAT GGA TTT GCC ACT GGT ATC        98
Ser Phe Ile Asp Tyr Phe Asn Gly Ile Tyr Gly Phe Ala Thr Gly Ile
 15              20                  25                  30

AAA GAC ATT ATG AAC ATG ATT TTT AAA ACG GAT ACA GGT GGT GAT CTA       146
Lys Asp Ile Met Asn Met Ile Phe Lys Thr Asp Thr Gly Gly Asp Leu
             35                  40                  45
```

```
ACC CTA GAC GAA ATT TTA AAG AAT CAG CAG TTA CTA AAT GAT ATT TCT    194
Thr Leu Asp Glu Ile Leu Lys Asn Gln Gln Leu Leu Asn Asp Ile Ser
         50                  55                  60

GGT AAA TTG GAT GGG GTG AAT GGA AGC TTA AAT GAT CTT ATC GCA CAG    242
Gly Lys Leu Asp Gly Val Asn Gly Ser Leu Asn Asp Leu Ile Ala Gln
         65                  70                  75

GGA AAC TTA AAT ACA GAA TTA TCT AAG GAA ATA TTA AAA ATT GCA AAT    290
Gly Asn Leu Asn Thr Glu Leu Ser Lys Glu Ile Leu Lys Ile Ala Asn
         80                  85                  90

GAA CAA AAT CAA GTT TTA AAT GAT GTT AAT AAC AAA CTC GAT GCG ATA    338
Glu Gln Asn Gln Val Leu Asn Asp Val Asn Asn Lys Leu Asp Ala Ile
 95                 100                 105                 110

AAT ACG ATG CTT CGG GTA TAT CTA CCT AAA ATT ACC TCT ATG TTG AGT    386
Asn Thr Met Leu Arg Val Tyr Leu Pro Lys Ile Thr Ser Met Leu Ser
            115                 120                 125

GAT GTA ATG AAA CAA AAT TAT GCG CTA AGT CTG CAA ATA GAA TAC TTA    434
Asp Val Met Lys Gln Asn Tyr Ala Leu Ser Leu Gln Ile Glu Tyr Leu
            130                 135                 140

AGT AAA CAA TTG CAA GAG ATT TCT GAT AAG TTG GAT ATT ATT AAT GTA    482
Ser Lys Gln Leu Gln Glu Ile Ser Asp Lys Leu Asp Ile Ile Asn Val
            145                 150                 155

AAT GTA CTT ATT AAC TCT ACA CTT ACT GAA ATT ACA CCT GCG TAT CAA    530
Asn Val Leu Ile Asn Ser Thr Leu Thr Glu Ile Thr Pro Ala Tyr Gln
    160                 165                 170

AGG ATT AAA TAT GTG AAC GAA AAA TTT GAG GAA TTA ACT TTT GCT ACA    578
Arg Ile Lys Tyr Val Asn Glu Lys Phe Glu Glu Leu Thr Phe Ala Thr
175                 180                 185                 190

GAA ACT AGT TCA AAA GTA AAA AAG GAT GGC TCT CCT GCA GAT ATT CTT    626
Glu Thr Ser Ser Lys Val Lys Lys Asp Gly Ser Pro Ala Asp Ile Leu
            195                 200                 205

GAT GAG TTA ACT GAG TTA ACT GAA CTA GCG AAA AGT GTA ACA AAA AAT    674
Asp Glu Leu Thr Glu Leu Thr Glu Leu Ala Lys Ser Val Thr Lys Asn
            210                 215                 220

GAT GTG GAT GGT TTT GAA TTT TAC CTT AAT ACA TTC CAC GAT GTA ATG    722
Asp Val Asp Gly Phe Glu Phe Tyr Leu Asn Thr Phe His Asp Val Met
            225                 230                 235

GTA GGA AAT AAT TTA TTC GGG CGT TCA GCT TTA AAA ACT GCA TCG GAA    770
Val Gly Asn Asn Leu Phe Gly Arg Ser Ala Leu Lys Thr Ala Ser Glu
    240                 245                 250

TTA ATT ACT AAA GAA AAT GTG AAA ACA AGT GGC AGT GAG GTC GGA AAT    818
Leu Ile Thr Lys Glu Asn Val Lys Thr Ser Gly Ser Glu Val Gly Asn
255                 260                 265                 270

GTT TAT AAC TTC TTA ATT GTA TTA ACA GCT CTG CAA GCC CAA GCT TTT    866
Val Tyr Asn Phe Leu Ile Val Leu Thr Ala Leu Gln Ala Gln Ala Phe
            275                 280                 285

CTT ACT TTA ACA ACA TGC CGA AAA TTA TTA GGC TTA GCA GAT ATT GAT    914
Leu Thr Leu Thr Thr Cys Arg Lys Leu Leu Gly Leu Ala Asp Ile Asp
            290                 295                 300

TAT ACT TCT ATT ATG AAT GAA CAT TTA AAT AAG GAA AAA GAG GAA TTT    962
Tyr Thr Ser Ile Met Asn Glu His Leu Asn Lys Glu Lys Glu Glu Phe
            305                 310                 315

AGA GTA AAC ATC CTC CCT ACA CTT TCT AAT ACT TTT TCT AAT CCT AAT   1010
Arg Val Asn Ile Leu Pro Thr Leu Ser Asn Thr Phe Ser Asn Pro Asn
            320                 325                 330

TAT GCA AAA GTT AAA GGA AGT GAT GAA GAT GCA AAG ATG ATT GTG GAA   1058
Tyr Ala Lys Val Lys Gly Ser Asp Glu Asp Ala Lys Met Ile Val Glu
335                 340                 345                 350
```

```
GCT AAA CCA GGA CAT GCA TTG ATT GGG TTT GAA ATT AGT AAT GAT TCA       1106
Ala Lys Pro Gly His Ala Leu Ile Gly Phe Glu Ile Ser Asn Asp Ser
            355                 360                 365

ATT ACA GTA TTA AAA GTA TAT GAG GCT AAG CTA AAA CAA AAT TAT CAA       1154
Ile Thr Val Leu Lys Val Tyr Glu Ala Lys Leu Lys Gln Asn Tyr Gln
        370                 375                 380

GTC GAT AAG GAT TCC TTA TCG GAA GTT ATT TAT GGT GAT ATG GAT AAA       1202
Val Asp Lys Asp Ser Leu Ser Glu Val Ile Tyr Gly Asp Met Asp Lys
                385                 390                 395

TTA TTG TGC CCA GAT CAA TCT GAA CAA ATC TAT TAT ACA AAT AAC ATA       1250
Leu Leu Cys Pro Asp Gln Ser Glu Gln Ile Tyr Tyr Thr Asn Asn Ile
            400                 405                 410

GTA TTT CCA AAT GAA TAT GTA ATT ACT AAA ATT GAT TTC ACT AAA AAA       1298
Val Phe Pro Asn Glu Tyr Val Ile Thr Lys Ile Asp Phe Thr Lys Lys
415                 420                 425                 430

ATG AAA ACT TTA AGA TAT GAG GTA ACA GCG AAT TTT TAT GAT TCT TCT       1346
Met Lys Thr Leu Arg Tyr Glu Val Thr Ala Asn Phe Tyr Asp Ser Ser
                435                 440                 445

ACA GGA GAA ATT GAC TTA AAT AAG AAA AAA GTA GAA TCA AGT GAA GCG       1394
Thr Gly Glu Ile Asp Leu Asn Lys Lys Lys Val Glu Ser Ser Glu Ala
            450                 455                 460

GAG TAT AGA ACG TTA AGT GCT AAT GAT GAT GGG GTG TAT ATG CCG TTA       1442
Glu Tyr Arg Thr Leu Ser Ala Asn Asp Asp Gly Val Tyr Met Pro Leu
        465                 470                 475

GGT GTC ATC AGT GAA ACA TTT TTG ACT CCG ATT AAT GGG TTT GGC CTC       1490
Gly Val Ile Ser Glu Thr Phe Leu Thr Pro Ile Asn Gly Phe Gly Leu
        480                 485                 490

CAA GCT GAT GAA AAT TCA AGA TTA ATT ACT TTA ACA TGT AAA TCA TAT       1538
Gln Ala Asp Glu Asn Ser Arg Leu Ile Thr Leu Thr Cys Lys Ser Tyr
495                 500                 505                 510

TTA AGA GAA CTA CTG CTA GCA ACA GAC TTA AGC AAT AAA GAA ACT AAA       1586
Leu Arg Glu Leu Leu Leu Ala Thr Asp Leu Ser Asn Lys Glu Thr Lys
                515                 520                 525

TTG ATC GTC CCG CCA AGT GGT TTT ATT AGC AAT ATT GTA GAG AAC GGG       1634
Leu Ile Val Pro Pro Ser Gly Phe Ile Ser Asn Ile Val Glu Asn Gly
            530                 535                 540

TCC ATA GAA GAG GAC AAT TTA GAG CCG TGG AAA GCA AAT AAT AAG AAT       1682
Ser Ile Glu Glu Asp Asn Leu Glu Pro Trp Lys Ala Asn Asn Lys Asn
        545                 550                 555

GCG TAT GTA GAT CAT ACA GGC GGA GTG AAT GGA ACT AAA GCT TTA TAT       1730
Ala Tyr Val Asp His Thr Gly Gly Val Asn Gly Thr Lys Ala Leu Tyr
        560                 565                 570

GTT CAT AAG GAC GGA GGA ATT TCA CAA TTT ATT GGA GAT AAG TTA AAA       1778
Val His Lys Asp Gly Gly Ile Ser Gln Phe Ile Gly Asp Lys Leu Lys
575                 580                 585                 590

CCG AAA ACT GAG TAT GTA ATC CAA TAT ACT GTT AAA GGA AAA CCT TCT       1826
Pro Lys Thr Glu Tyr Val Ile Gln Tyr Thr Val Lys Gly Lys Pro Ser
                595                 600                 605

ATT CAT TTA AAA GAT GAA AAT ACT GGA TAT ATT CAT TAT GAA GAT ACA       1874
Ile His Leu Lys Asp Glu Asn Thr Gly Tyr Ile His Tyr Glu Asp Thr
            610                 615                 620

AAT AAT AAT TTA GAA GAT TAT CAA ACT ATT AAT AAA CGT TTT ACT ACA       1922
Asn Asn Asn Leu Glu Asp Tyr Gln Thr Ile Asn Lys Arg Phe Thr Thr
        625                 630                 635

GGA ACT GAT TTA AAG GGA GTG TAT TTA ATT TTA AAA AGT CAA AAT GGA       1970
Gly Thr Asp Leu Lys Gly Val Tyr Leu Ile Leu Lys Ser Gln Asn Gly
        640                 645                 650
```

```
GAT GAA GCT TGG GGA GAT AAC TTT ATT ATT TTG GAA ATT AGT CCT TCT    2018
Asp Glu Ala Trp Gly Asp Asn Phe Ile Ile Leu Glu Ile Ser Pro Ser
655                 660                 665                 670

GAA AAG TTA TTA AGT CCA GAA TTA ATT AAT ACA AAT AAT TGG ACG AGT    2066
Glu Lys Leu Leu Ser Pro Glu Leu Ile Asn Thr Asn Asn Trp Thr Ser
                    675                 680                 685

ACG GGA TCA ACT AAT ATT AGC GGT AAT ACA CTC ACT CTT TAT CAG GGA    2114
Thr Gly Ser Thr Asn Ile Ser Gly Asn Thr Leu Thr Leu Tyr Gln Gly
                690                 695                 700

GGA CGA GGG ATT CTA AAA CAA AAC CTT CAA TTA GAT AGT TTT TCA ACT    2162
Gly Arg Gly Ile Leu Lys Gln Asn Leu Gln Leu Asp Ser Phe Ser Thr
            705                 710                 715

TAT AGA GTG TAT TTT TCT GTG TCC GGA GAT GCT AAT GTA AGG ATT AGA    2210
Tyr Arg Val Tyr Phe Ser Val Ser Gly Asp Ala Asn Val Arg Ile Arg
720                 725                 730

AAT TCT AGG GAA GTG TTA TTT GAA AAA AGA TAT ATG AGC GGT GCT AAA    2258
Asn Ser Arg Glu Val Leu Phe Glu Lys Arg Tyr Met Ser Gly Ala Lys
735                 740                 745                 750

GAT GTT TCT GAA ATG TTC ACT ACA AAA TTT GAG AAA GAT AAC TTT TAT    2306
Asp Val Ser Glu Met Phe Thr Thr Lys Phe Glu Lys Asp Asn Phe Tyr
                755                 760                 765

ATA GAG CTT TCT CAA GGG AAT AAT TTA TAT GGT GGT CCT ATT GTA CAT    2354
Ile Glu Leu Ser Gln Gly Asn Asn Leu Tyr Gly Gly Pro Ile Val His
            770                 775                 780

TTT TAC GAT GTC TCT ATT AAG TAA                                    2378
Phe Tyr Asp Val Ser Ile Lys
            785
```

(2) INFORMATION FOR SEQ ID NO:29:

(i) SEQUENCE CHARACTERISTICS:
        (A) LENGTH: 789 amino acids
        (B) TYPE: amino acid
        (D) TOPOLOGY: linear (ii) MOLECULE TYPE: protein (xi) SEQUENCE DESCRIPTION: SEQ ID NO:29:

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160
```

-continued

```
Leu Ile Asn Ser Thr Leu Thr Glu Ile Thr Pro Ala Tyr Gln Arg Ile
            165                 170                 175

Lys Tyr Val Asn Glu Lys Phe Glu Leu Thr Phe Ala Thr Glu Thr
        180                 185                 190

Ser Ser Lys Val Lys Lys Asp Gly Ser Pro Ala Asp Ile Leu Asp Glu
            195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Gln Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575
```

```
Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
    770                 775                 780

Asp Val Ser Ile Lys
785

(2) INFORMATION FOR SEQ ID NO:30:

(i) SEQUENCE CHARACTERISTICS:
        (A) LENGTH: 2403 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: misc_feature
        (B) LOCATION: 11..2389
        (D) OTHER INFORMATION: /note= "maize optimized DNA
            sequence encoding VIP3A(a)"

(xi) SEQUENCE DESCRIPTION: SEQ ID NO:30:

GGATCCACCA ATGAACATGA ACAAGAACAA CACCAAGCTG AGCACCCGCG CCCTGCCGAG      60

CTTCATCGAC TACTTCAACG GCATCTACGG CTTCGCCACC GGCATCAAGG ACATCATGAA     120

CATGATCTTC AAGACCGACA CCGGCGGCGA CCTGACCCTG GACGAGATCC TGAAGAACCA     180

GCAGCTGCTG AACGACATCA GCGGCAAGCT GGACGGCGTG AACGGCAGCC TGAACGACCT     240

GATCGCCCAG GCAACCTGA ACACCGAGCT GAGCAAGGAG ATCCTTAAGA TCGCCAACGA      300

GCAGAACCAG GTGCTGAACG ACGTGAACAA CAAGCTGGAC GCCATCAACA CCATGCTGCG     360

CGTGTACCTG CCGAAGATCA CCAGCATGCT GAGCGACGTG ATGAAGCAGA ACTACGCCCT     420
```

-continued

```
GAGCCTGCAG ATCGAGTACC TGAGCAAGCA GCTGCAGGAG ATCAGCGACA AGCTGGACAT      480

CATCAACGTG AACGTCCTGA TCAACAGCAC CCTGACCGAG ATCACCCCGG CCTACCAGCG      540

CATCAAGTAC GTGAACGAGA AGTTCGAAGA GCTGACCTTC GCCACCGAGA CCAGCAGCAA      600

GGTGAAGAAG GACGGCAGCC CGGCCGACAT CCTGGACGAG CTGACCGAGC TGACCGAGCT      660

GGCCAAGAGC GTGACCAAGA ACGACGTGGA CGGCTTCGAG TTCTACCTGA ACACCTTCCA      720

CGACGTGATG GTGGGCAACA ACCTGTTCGG CCGCAGCGCC CTGAAGACCG CCAGCGAGCT      780

GATCACCAAG GAGAACGTGA AGACCAGCGG CAGCGAGGTG GGCAACGTGT ACAACTTCCT      840

GATCGTGCTG ACCGCCCTGC AGGCCCAGGC CTTCCTGACC CTGACCACCT GTCGCAAGCT      900

GCTGGGCCTG GCCGACATCG ACTACACCAG CATCATGAAC GAGCACTTGA ACAAGGAGAA      960

GGAGGAGTTC CGCGTGAACA TCCTGCCGAC CCTGAGCAAC ACCTTCAGCA ACCCGAACTA     1020

CGCCAAGGTG AAGGGCAGCG ACGAGGACGC CAAGATGATC GTGGAGGCTA AGCCGGGCCA     1080

CGCGTTGATC GGCTTCGAGA TCAGCAACGA CAGCATCACC GTGCTGAAGG TGTACGAGGC     1140

CAAGCTGAAG CAGAACTACC AGGTGGACAA GGACAGCTTG AGCGAGGTGA CTACGGCGA     1200

CATGGACAAG CTGCTGTGTC CGGACCAGAG CGAGCAAATC TACTACACCA ACAACATCGT     1260

GTTCCCGAAC GAGTACGTGA TCACCAAGAT CGACTTCACC AAGAAGATGA AGACCCTGCG     1320

CTACGAGGTG ACCGCCAACT TCTACGACAG CAGCACCGGC GAGATCGACC TGAACAAGAA     1380

GAAGGTGGAG AGCAGCGAGG CCGAGTACCG CACCCTGAGC GCGAACGACG ACGGCGTCTA     1440

CATGCCACTG GGCGTGATCA GCGAGACCTT CCTGACCCCG ATCAACGGCT TTGGCCTGCA     1500

GGCCGACGAG AACAGCCGCC TGATCACCCT GACCTGTAAG AGCTACCTGC GCGAGCTGCT     1560

GCTAGCCACC GACCTGAGCA ACAAGGAGAC CAAGCTGATC GTGCCACCGA GCGGCTTCAT     1620

CAGCAACATC GTGGAGAACG GCAGCATCGA GGAGGACAAC CTGGAGCCGT GGAAGGCCAA     1680

CAACAAGAAC GCCTACGTGG ACCACACCGG CGGCGTGAAC GGCACCAAGG CCCTGTACGT     1740

GCACAAGGAC GGCGGCATCA GCCAGTTCAT CGGCGACAAG CTGAAGCCGA AGACCGAGTA     1800

CGTGATCCAG TACACCGTGA AGGGCAAGCC ATCGATTCAC CTGAAGGACG AGAACACCGG     1860

CTACATCCAC TACGAGGACA CCAACAACAA CCTGGAGGAC TACCAGACCA TCAACAAGCG     1920

CTTCACCACC GGCACCGACC TGAAGGGCGT GTACCTGATC CTGAAGAGCC AGAACGGCGA     1980

CGAGGCCTGG GGCGACAACT TCATCATCCT GGAGATCAGC CCGAGCGAGA AGCTGCTGAG     2040

CCCGGAGCTG ATCAACACCA ACAACTGGAC CAGCACCGGC AGCACCAACA TCAGCGGCAA     2100

CACCCTGACC CTGTACCAGG GCGGCCGCGG CATCCTGAAG CAGAACCTGC AGCTGGACAG     2160

CTTCAGCACC TACCGCGTGT ACTTCAGCGT GAGCGGCGAC GCCAACGTGC GCATCCGCAA     2220

CAGCCGCGAG GTGCTGTTCG AGAAGAGGTA CATGAGCGGC GCCAAGGACG TGAGCGAGAT     2280

GTTCACCACC AAGTTCGAGA AGGACAACTT CTACATCGAG CTGAGCCAGG GCAACAACCT     2340

GTACGGCGGC CCGATCGTGC ACTTCTACGA CGTGAGCATC AAGTTAACGT AGAGCTCAGA     2400

TCT                                                                  2403
```

(2) INFORMATION FOR SEQ ID NO:31:

(i) SEQUENCE CHARACTERISTICS:
        (A) LENGTH: 2612 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
    (A) NAME/KEY: CDS
    (B) LOCATION: 118..2484
    (D) OTHER INFORMATION: /note= "Native DNA sequence
        encoding VIP3A(b) from AB424"

(xi) SEQUENCE DESCRIPTION: SEQ ID NO:31:

| | |
|---|---|
| ATTGAAATTG ATAAAAAGTT ATGAGTGTTT AATAATCAGT AATTACCAAT AAAGAATTAA | 60 |
| GAATACAAGT TTACAAGAAA TAAGTGTTAC AAAAAATAGC TGAAAAGGAA GATGAAC | 117 |

| | | | | | | | | | | | | | | | |
|---|---|---|---|---|---|---|---|---|---|---|---|---|---|---|---|
| ATG | AAC | AAG | AAT | AAT | ACT | AAA | TTA | AGC | ACA | AGA | GCC | TTA | CCA | AGT | TTT | 165 |
| Met | Asn | Lys | Asn | Asn | Thr | Lys | Leu | Ser | Thr | Arg | Ala | Leu | Pro | Ser | Phe | |
| 790 | | | | | 795 | | | | | 800 | | | | | 805 | |

| ATT | GAT | TAT | TTC | AAT | GGC | ATT | TAT | GGA | TTT | GCC | ACT | GGT | ATC | AAA | GAC | 213 |
|---|---|---|---|---|---|---|---|---|---|---|---|---|---|---|---|---|
| Ile | Asp | Tyr | Phe | Asn | Gly | Ile | Tyr | Gly | Phe | Ala | Thr | Gly | Ile | Lys | Asp | |
| | | | | 810 | | | | | 815 | | | | | 820 | | |

| ATT | ATG | AAC | ATG | ATT | TTT | AAA | ACG | GAT | ACA | GGT | GGT | GAT | CTA | ACC | CTA | 261 |
|---|---|---|---|---|---|---|---|---|---|---|---|---|---|---|---|---|
| Ile | Met | Asn | Met | Ile | Phe | Lys | Thr | Asp | Thr | Gly | Gly | Asp | Leu | Thr | Leu | |
| | | | 825 | | | | | 830 | | | | | 835 | | | |

| GAC | GAA | ATT | TTA | AAG | AAT | CAG | CAG | CTA | CTA | AAT | GAT | ATT | TCT | GGT | AAA | 309 |
|---|---|---|---|---|---|---|---|---|---|---|---|---|---|---|---|---|
| Asp | Glu | Ile | Leu | Lys | Asn | Gln | Gln | Leu | Leu | Asn | Asp | Ile | Ser | Gly | Lys | |
| | | 840 | | | | | 845 | | | | | 850 | | | | |

| TTG | GAT | GGG | GTG | AAT | GGA | AGC | TTA | AAT | GAT | CTT | ATC | GCA | CAG | GGA | AAC | 357 |
|---|---|---|---|---|---|---|---|---|---|---|---|---|---|---|---|---|
| Leu | Asp | Gly | Val | Asn | Gly | Ser | Leu | Asn | Asp | Leu | Ile | Ala | Gln | Gly | Asn | |
| 855 | | | | | 860 | | | | | 865 | | | | | | |

| TTA | AAT | ACA | GAA | TTA | TCT | AAG | GAA | ATA | TTA | AAA | ATT | GCA | AAT | GAA | CAA | 405 |
|---|---|---|---|---|---|---|---|---|---|---|---|---|---|---|---|---|
| Leu | Asn | Thr | Glu | Leu | Ser | Lys | Glu | Ile | Leu | Lys | Ile | Ala | Asn | Glu | Gln | |
| 870 | | | | | 875 | | | | | 880 | | | | | 885 | |

| AAT | CAA | GTT | TTA | AAT | GAT | GTT | AAT | AAC | AAA | CTC | GAT | GCG | ATA | AAT | ACG | 453 |
|---|---|---|---|---|---|---|---|---|---|---|---|---|---|---|---|---|
| Asn | Gln | Val | Leu | Asn | Asp | Val | Asn | Asn | Lys | Leu | Asp | Ala | Ile | Asn | Thr | |
| | | | 890 | | | | | 895 | | | | | 900 | | | |

| ATG | CTT | CGG | GTA | TAT | CTA | CCT | AAA | ATT | ACC | TCT | ATG | TTG | AGT | GAT | GTA | 501 |
|---|---|---|---|---|---|---|---|---|---|---|---|---|---|---|---|---|
| Met | Leu | Arg | Val | Tyr | Leu | Pro | Lys | Ile | Thr | Ser | Met | Leu | Ser | Asp | Val | |
| | | 905 | | | | | 910 | | | | | 915 | | | | |

| ATG | AAA | CAA | AAT | TAT | GCG | CTA | AGT | CTG | CAA | ATA | GAA | TAC | TTA | AGT | AAA | 549 |
|---|---|---|---|---|---|---|---|---|---|---|---|---|---|---|---|---|
| Met |

```
ACT AAA GAA AAT GTG AAA ACA AGT GGC AGT GAG GTC GGA AAT GTT TAT      933
Thr Lys Glu Asn Val Lys Thr Ser Gly Ser Glu Val Gly Asn Val Tyr
            1050                1055                1060

AAC TTC CTA ATT GTA TTA ACA GCT CTG CAA GCA AAA GCT TTT CTT ACT      981
Asn Phe Leu Ile Val Leu Thr Ala Leu Gln Ala Lys Ala Phe Leu Thr
            1065                1070                1075

TTA ACA CCA TGC CGA AAA TTA TTA GGC TTA GCA GAT ATT GAT TAT ACT     1029
Leu Thr Pro Cys Arg Lys Leu Leu Gly Leu Ala Asp Ile Asp Tyr Thr
            1080                1085                1090

TCT ATT ATG AAT GAA CAT TTA AAT AAG GAA AAA GAG GAA TTT AGA GTA     1077
Ser Ile Met Asn Glu His Leu Asn Lys Glu Lys Glu Glu Phe Arg Val
            1095                1100                1105

AAC ATC CTC CCT ACA CTT TCT AAT ACT TTT TCT AAT CCT AAT TAT GCA     1125
Asn Ile Leu Pro Thr Leu Ser Asn Thr Phe Ser Asn Pro Asn Tyr Ala
1110                1115                1120                1125

AAA GTT AAA GGA AGT GAT GAA GAT GCA AAG ATG ATT GTG GAA GCT AAA     1173
Lys Val Lys Gly Ser Asp Glu Asp Ala Lys Met Ile Val Glu Ala Lys
            1130                1135                1140

CCA GGA CAT GCA TTG ATT GGG TTT GAA ATT AGT AAT GAT TCA ATT ACA     1221
Pro Gly His Ala Leu Ile Gly Phe Glu Ile Ser Asn Asp Ser Ile Thr
            1145                1150                1155

GTA TTA AAA GTA TAT GAG GCT AAG CTA AAA CAA AAT TAT CAA GTC GAT     1269
Val Leu Lys Val Tyr Glu Ala Lys Leu Lys Gln Asn Tyr Gln Val Asp
            1160                1165                1170

AAG GAT TCC TTA TCG GAA GTT ATT TAT GGC GAT ATG GAT AAA TTA TTG     1317
Lys Asp Ser Leu Ser Glu Val Ile Tyr Gly Asp Met Asp Lys Leu Leu
            1175                1180                1185

TGC CCA GAT CAA TCT GGA CAA ATC TAT TAT ACA AAT AAC ATA GTA TTT     1365
Cys Pro Asp Gln Ser Gly Gln Ile Tyr Tyr Thr Asn Asn Ile Val Phe
1190                1195                1200                1205

CCA AAT GAA TAT GTA ATT ACT AAA ATT GAT TTC ACT AAA AAA ATG AAA     1413
Pro Asn Glu Tyr Val Ile Thr Lys Ile Asp Phe Thr Lys Lys Met Lys
            1210                1215                1220

ACT TTA AGA TAT GAG GTA ACA GCG AAT TTT TAT GAT TCT TCT ACA GGA     1461
Thr Leu Arg Tyr Glu Val Thr Ala Asn Phe Tyr Asp Ser Ser Thr Gly
            1225                1230                1235

GAA ATT GAC TTA AAT AAG AAA AAA GTA GAA TCA AGT GAA GCG GAG TAT     1509
Glu Ile Asp Leu Asn Lys Lys Lys Val Glu Ser Ser Glu Ala Glu Tyr
            1240                1245                1250

AGA ACG TTA AGT GCT AAT GAT GAT GGG GTG TAT ATG CCG TTA GGT GTC     1557
Arg Thr Leu Ser Ala Asn Asp Asp Gly Val Tyr Met Pro Leu Gly Val
            1255                1260                1265

ATC AGT GAA ACA TTT TTG ACT CCG ATT AAT GGG TTT GGC CTC CAA GCT     1605
Ile Ser Glu Thr Phe Leu Thr Pro Ile Asn Gly Phe Gly Leu Gln Ala
1270                1275                1280                1285

GAT GAA AAT TCA AGA TTA ATT ACT TTA ACA TGT AAA TCA TAT TTA AGA     1653
Asp Glu Asn Ser Arg Leu Ile Thr Leu Thr Cys Lys Ser Tyr Leu Arg
            1290                1295                1300

GAA CTA CTG CTA GCA ACA GAC TTA AGC AAT AAA GAA ACT AAA TTG ATC     1701
Glu Leu Leu Leu Ala Thr Asp Leu Ser Asn Lys Glu Thr Lys Leu Ile
            1305                1310                1315

GTC CCG CCA AGT GGT TTT ATT AGC AAT ATT GTA GAG AAC GGG TCC ATA     1749
Val Pro Pro Ser Gly Phe Ile Ser Asn Ile Val Glu Asn Gly Ser Ile
            1320                1325                1330

GAA GAG GAC AAT TTA GAG CCG TGG AAA GCA AAT AAT AAG AAT GCG TAT     1797
Glu Glu Asp Asn Leu Glu Pro Trp Lys Ala Asn Asn Lys Asn Ala Tyr
            1335                1340                1345
```

```
GTA GAT CAT ACA GGC GGA GTG AAT GGA ACT AAA GCT TTA TAT GTT CAT      1845
Val Asp His Thr Gly Gly Val Asn Gly Thr Lys Ala Leu Tyr Val His
1350                1355                1360                1365

AAG GAC GGA GGA ATT TCA CAA TTT ATT GGA GAT AAG TTA AAA CCG AAA      1893
Lys Asp Gly Gly Ile Ser Gln Phe Ile Gly Asp Lys Leu Lys Pro Lys
                1370                1375                1380

ACT GAG TAT GTA ATC CAA TAT ACT GTT AAA GGA AAA CCT TCT ATT CAT      1941
Thr Glu Tyr Val Ile Gln Tyr Thr Val Lys Gly Lys Pro Ser Ile His
            1385                1390                1395

TTA AAA GAT GAA AAT ACT GGA TAT ATT CAT TAT GAA GAT ACA AAT AAT      1989
Leu Lys Asp Glu Asn Thr Gly Tyr Ile His Tyr Glu Asp Thr Asn Asn
        1400                1405                1410

AAT TTA GAA GAT TAT CAA ACT ATT AAT AAA CGT TTT ACT ACA GGA ACT      2037
Asn Leu Glu Asp Tyr Gln Thr Ile Asn Lys Arg Phe Thr Thr Gly Thr
    1415                1420                1425

GAT TTA AAG GGA GTG TAT TTA ATT TTA AAA AGT CAA AAT GGA GAT GAA      2085
Asp Leu Lys Gly Val Tyr Leu Ile Leu Lys Ser Gln Asn Gly Asp Glu
1430                1435                1440                1445

GCT TGG GGA GAT AAC TTT ATT ATT TTG GAA ATT AGT CCT TCT GAA AAG      2133
Ala Trp Gly Asp Asn Phe Ile Ile Leu Glu Ile Ser Pro Ser Glu Lys
                1450                1455                1460

TTA TTA AGT CCA GAA TTA ATT AAT ACA AAT AAT TGG ACG AGT ACG GGA      2181
Leu Leu Ser Pro Glu Leu Ile Asn Thr Asn Asn Trp Thr Ser Thr Gly
            1465                1470                1475

TCA ACT AAT ATT AGC GGT AAT ACA CTC ACT CTT TAT CAG GGA GGA CGA      2229
Ser Thr Asn Ile Ser Gly Asn Thr Leu Thr Leu Tyr Gln Gly Gly Arg
        1480                1485                1490

GGG ATT CTA AAA CAA AAC CTT CAA TTA GAT AGT TTT TCA ACT TAT AGA      2277
Gly Ile Leu Lys Gln Asn Leu Gln Leu Asp Ser Phe Ser Thr Tyr Arg
    1495                1500                1505

GTG TAT TTC TCT GTG TCC GGA GAT GCT AAT GTA AGG ATT AGA AAT TCT      2325
Val Tyr Phe Ser Val Ser Gly Asp Ala Asn Val Arg Ile Arg Asn Ser
1510                1515                1520                1525

AGG GAA GTG TTA TTT GAA AAA AGA TAT ATG AGC GGT GCT AAA GAT GTT      2373
Arg Glu Val Leu Phe Glu Lys Arg Tyr Met Ser Gly Ala Lys Asp Val
                1530                1535                1540

TCT GAA ATG TTC ACT ACA AAA TTT GAG AAA GAT AAC TTC TAT ATA GAG      2421
Ser Glu Met Phe Thr Thr Lys Phe Glu Lys Asp Asn Phe Tyr Ile Glu
            1545                1550                1555

CTT TCT CAA GGG AAT AAT TTA TAT GGT GGT CCT ATT GTA CAT TTT TAC      2469
Leu Ser Gln Gly Asn Asn Leu Tyr Gly Gly Pro Ile Val His Phe Tyr
        1560                1565                1570

GAT GTC TCT ATT AAG TAAGATCGGG ATCTAATATT AACAGTTTTT AGAAGCTAAT      2524
Asp Val Ser Ile Lys
    1575

TCTTGTATAA TGTCCTTGAT TATGGAAAAA CACAATTTTG TTTGCTAAGA TGTATATATA    2584

GCTCACTCAT TAAAAGGCAA TCAAGCTT                                       2612

(2) INFORMATION FOR SEQ ID NO:32:

(i) SEQUENCE CHARACTERISTICS:
        (A) LENGTH: 789 amino acids
        (B) TYPE: amino acid
        (D) TOPOLOGY: linear (ii) MOLECULE TYPE: protein (xi) SEQUENCE DESCRIPTION: SEQ ID NO:32:

Met Asn Lys Asn Asn Thr Lys Leu Ser Thr Arg Ala Leu Pro Ser Phe
1               5                   10                  15
```

-continued

```
Ile Asp Tyr Phe Asn Gly Ile Tyr Gly Phe Ala Thr Gly Ile Lys Asp
             20                  25                  30

Ile Met Asn Met Ile Phe Lys Thr Asp Thr Gly Gly Asp Leu Thr Leu
         35                  40                  45

Asp Glu Ile Leu Lys Asn Gln Gln Leu Leu Asn Asp Ile Ser Gly Lys
     50                  55                  60

Leu Asp Gly Val Asn Gly Ser Leu Asn Asp Leu Ile Ala Gln Gly Asn
 65                  70                  75                  80

Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Arg Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Pro Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Gly Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430
```

```
Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
        450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
                580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
        610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
                660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
        690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
                740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
770                 775                 780

Asp Val Ser Ile Lys
785

(2) INFORMATION FOR SEQ ID NO:33:

(i) SEQUENCE CHARACTERISTICS:
        (A) LENGTH: 30 base pairs
        (B) TYPE: nucleic acid
        (C) STRANDEDNESS: single
        (D) TOPOLOGY: linear
```

(ii) MOLECULE TYPE: other nucleic acid
         (A) DESCRIPTION: /desc = "forward primer used to make
             pCIB5526"

(iii) HYPOTHETICAL: NO (xi) SEQUENCE DESCRIPTION: SEQ ID NO:33:

GGATCCACCA TGAAGACCAA CCAGATCAGC                                          30

(2) INFORMATION FOR SEQ ID NO:34:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "reverse primer used to make
             pCIB5526"

(iii) HYPOTHETICAL: NO (xi) SEQUENCE DESCRIPTION: SEQ ID NO:34:

AAGCTTCAGC TCCTT                                                          15

(2) INFORMATION FOR SEQ ID NO:35:

(i) SEQUENCE CHARACTERISTICS:
         (A) LENGTH: 2576 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Synthetic DNA"

(iii) HYPOTHETICAL: NO (ix) FEATURE:
         (A) NAME/KEY: CDS
         (B) LOCATION: 9..2564
         (D) OTHER INFORMATION: /note= "Maize optimized sequence
             encoding VIP1A(a) with the Bacillus secretion signal
             removed as contained in pCIB5526"

(xi) SEQUENCE DESCRIPTION: SEQ ID NO:35:

```
GATCCACC ATG AAG ACC AAC CAG ATC AGC ACC ACC CAG AAG AAC CAG CAG          50
         Met Lys Thr Asn Gln Ile Ser Thr Thr Gln Lys Asn Gln Gln
                 825                 830                 835

AAG GAG ATG GAC CGC AAG GGC CTG CTG GGC TAC TAC TTC AAG GGC AAG           98
Lys Glu Met Asp Arg Lys Gly Leu Leu Gly Tyr Tyr Phe Lys Gly Lys
                840                 845                 850

GAC TTC AGC AAC CTG ACC ATG TTC GCC CCC ACG CGT GAC AGC ACC CTG          146
Asp Phe Ser Asn Leu Thr Met Phe Ala Pro Thr Arg Asp Ser Thr Leu
            855                 860                 865

ATC TAC GAC CAG CAG ACC GCC AAC AAG CTG CTG GAC AAG AAG CAG CAG          194
Ile Tyr Asp Gln Gln Thr Ala Asn Lys Leu Leu Asp Lys Lys Gln Gln
        870                 875                 880

GAG TAC CAG AGC ATC CGC TGG ATC GGC CTG ATC CAG AGC AAG GAG ACC          242
Glu Tyr Gln Ser Ile Arg Trp Ile Gly Leu Ile Gln Ser Lys Glu Thr
    885                 890                 895

GGC GAC TTC ACC TTC AAC CTG AGC GAG GAC GAG CAG GCC ATC ATC GAG          290
Gly Asp Phe Thr Phe Asn Leu Ser Glu Asp Glu Gln Ala Ile Ile Glu
900                 905                 910                 915
```

```
ATC AAC GGC AAG ATC ATC AGC AAC AAG GGC AAG GAG AAG CAG GTG GTG          338
Ile Asn Gly Lys Ile Ile Ser Asn Lys Gly Lys Glu Lys Gln Val Val
                920                 925                 930

CAC CTG GAG AAG GGC AAG CTG GTG CCC ATC AAG ATC GAG TAC CAG AGC          386
His Leu Glu Lys Gly Lys Leu Val Pro Ile Lys Ile Glu Tyr Gln Ser
            935                 940                 945

GAC ACC AAG TTC AAC ATC GAC AGC AAG ACC TTC AAG GAG CTG AAG CTT          434
Asp Thr Lys Phe Asn Ile Asp Ser Lys Thr Phe Lys Glu Leu Lys Leu
        950                 955                 960

TTC AAG ATC GAC AGC CAG AAC CAG CCC CAG CAG GTG CAG CAG GAC GAG          482
Phe Lys Ile Asp Ser Gln Asn Gln Pro Gln Gln Val Gln Gln Asp Glu
    965                 970                 975

CTG CGC AAC CCC GAG TTC AAC AAG AAG GAG AGC CAG GAG TTC CTG GCC          530
Leu Arg Asn Pro Glu Phe Asn Lys Lys Glu Ser Gln Glu Phe Leu Ala
980                 985                 990                 995

AAG CCC AGC AAG ATC AAC CTG TTC ACC CAG CAG ATG AAG CGC GAG ATC          578
Lys Pro Ser Lys Ile Asn Leu Phe Thr Gln Gln Met Lys Arg Glu Ile
                1000                1005                1010

GAC GAG GAC ACC GAC ACC GAC GGC GAC AGC ATC CCC GAC CTG TGG GAG          626
Asp Glu Asp Thr Asp Thr Asp Gly Asp Ser Ile Pro Asp Leu Trp Glu
            1015                1020                1025

GAG AAC GGC TAC ACC ATC CAG AAC CGC ATC GCC GTG AAG TGG GAC GAC          674
Glu Asn Gly Tyr Thr Ile Gln Asn Arg Ile Ala Val Lys Trp Asp Asp
        1030                1035                1040

AGC CTG GCT AGC AAG GGC TAC ACC AAG TTC GTG AGC AAC CCC CTG GAG          722
Ser Leu Ala Ser Lys Gly Tyr Thr Lys Phe Val Ser Asn Pro Leu Glu
    1045                1050                1055

AGC CAC ACC GTG GGC GAC CCC TAC ACC GAC TAC GAG AAG GCC GCC CGC          770
Ser His Thr Val Gly Asp Pro Tyr Thr Asp Tyr Glu Lys Ala Ala Arg
1060                1065                1070                1075

GAC CTG GAC CTG AGC AAC GCC AAG GAG ACC TTC AAC CCC CTG GTG GCC          818
Asp Leu Asp Leu Ser Asn Ala Lys Glu Thr Phe Asn Pro Leu Val Ala
                1080                1085                1090

GCC TTC CCC AGC GTG AAC GTG AGC ATG GAG AAG GTG ATC CTG AGC CCC          866
Ala Phe Pro Ser Val Asn Val Ser Met Glu Lys Val Ile Leu Ser Pro
            1095                1100                1105

AAC GAG AAC CTG AGC AAC AGC GTG GAG AGC CAC TCG AGC ACC AAC TGG          914
Asn Glu Asn Leu Ser Asn Ser Val Glu Ser His Ser Ser Thr Asn Trp
        1110                1115                1120

AGC TAC ACC AAC ACC GAG GGC GCC AGC GTG GAG GCC GGC ATC GGT CCC          962
Ser Tyr Thr Asn Thr Glu Gly Ala Ser Val Glu Ala Gly Ile Gly Pro
    1125                1130                1135

AAG GGC ATC AGC TTC GGC GTG AGC GTG AAC TAC CAG CAC AGC GAG ACC          1010
Lys Gly Ile Ser Phe Gly Val Ser Val Asn Tyr Gln His Ser Glu Thr
1140                1145                1150                1155

GTG GCC CAG GAG TGG GGC ACC AGC ACC GGC AAC ACC AGC CAG TTC AAC          1058
Val Ala Gln Glu Trp Gly Thr Ser Thr Gly Asn Thr Ser Gln Phe Asn
                1160                1165                1170

ACC GCC AGC GCC GGC TAC CTG AAC GCC AAC GTG CGC TAC AAC AAC GTG          1106
Thr Ala Ser Ala Gly Tyr Leu Asn Ala Asn Val Arg Tyr Asn Asn Val
            1175                1180                1185

GGC ACC GGC GCC ATC TAC GAC GTG AAG CCC ACC ACC AGC TTC GTG CTG          1154
Gly Thr Gly Ala Ile Tyr Asp Val Lys Pro Thr Thr Ser Phe Val Leu
        1190                1195                1200

AAC AAC GAC ACC ATC GCC ACC ATC ACC GCC AAG TCG AAT TCC ACC GCC          1202
Asn Asn Asp Thr Ile Ala Thr Ile Thr Ala Lys Ser Asn Ser Thr Ala
    1205                1210                1215
```

```
CTG AAC ATC AGC CCC GGC GAG AGC TAC CCC AAG AAG GGC CAG AAC GGC         1250
Leu Asn Ile Ser Pro Gly Glu Ser Tyr Pro Lys Lys Gly Gln Asn Gly
1220                1225                1230                1235

ATC GCC ATC ACC AGC ATG GAC GAC TTC AAC AGC CAC CCC ATC ACC CTG         1298
Ile Ala Ile Thr Ser Met Asp Asp Phe Asn Ser His Pro Ile Thr Leu
                1240                1245                1250

AAC AAG AAG CAG GTG GAC AAC CTG CTG AAC AAC AAG CCC ATG ATG CTG         1346
Asn Lys Lys Gln Val Asp Asn Leu Leu Asn Asn Lys Pro Met Met Leu
            1255                1260                1265

GAG ACC AAC CAG ACC GAC GGC GTC TAC AAG ATC AAG GAC ACC CAC GGC         1394
Glu Thr Asn Gln Thr Asp Gly Val Tyr Lys Ile Lys Asp Thr His Gly
        1270                1275                1280

AAC ATC GTG ACG GGC GGC GAG TGG AAC GGC GTG ATC CAG CAG ATC AAG         1442
Asn Ile Val Thr Gly Gly Glu Trp Asn Gly Val Ile Gln Gln Ile Lys
    1285                1290                1295

GCC AAG ACC GCC AGC ATC ATC GTC GAC GAC GGC GAG CGC GTG GCC GAG         1490
Ala Lys Thr Ala Ser Ile Ile Val Asp Asp Gly Glu Arg Val Ala Glu
1300                1305                1310                1315

AAG CGC GTG GCC GCC AAG GAC TAC GAG AAC CCC GAG GAC AAG ACC CCC         1538
Lys Arg Val Ala Ala Lys Asp Tyr Glu Asn Pro Glu Asp Lys Thr Pro
                1320                1325                1330

AGC CTG ACC CTG AAG GAC GCC CTG AAG CTG AGC TAC CCC GAC GAG ATC         1586
Ser Leu Thr Leu Lys Asp Ala Leu Lys Leu Ser Tyr Pro Asp Glu Ile
            1335                1340                1345

AAG GAG ATC GAG GGC TTG CTG TAC TAC AAG AAC AAG CCC ATC TAC GAG         1634
Lys Glu Ile Glu Gly Leu Leu Tyr Tyr Lys Asn Lys Pro Ile Tyr Glu
        1350                1355                1360

AGC AGC GTG ATG ACC TAT CTA GAC GAG AAC ACC GCC AAG GAG GTG ACC         1682
Ser Ser Val Met Thr Tyr Leu Asp Glu Asn Thr Ala Lys Glu Val Thr
    1365                1370                1375

AAG CAG CTG AAC GAC ACC ACC GGC AAG TTC AAG GAC GTG AGC CAC CTG         1730
Lys Gln Leu Asn Asp Thr Thr Gly Lys Phe Lys Asp Val Ser His Leu
1380                1385                1390                1395

TAC GAC GTG AAG CTG ACC CCC AAG ATG AAC GTG ACC ATC AAG CTG AGC         1778
Tyr Asp Val Lys Leu Thr Pro Lys Met Asn Val Thr Ile Lys Leu Ser
                1400                1405                1410

ATC CTG TAC GAC AAC GCC GAG AGC AAC GAC AAC AGC ATC GGC AAG TGG         1826
Ile Leu Tyr Asp Asn Ala Glu Ser Asn Asp Asn Ser Ile Gly Lys Trp
            1415                1420                1425

ACC AAC ACC AAC ATC GTG AGC GGC GGC AAC AAC GGC AAG AAG CAG TAC         1874
Thr Asn Thr Asn Ile Val Ser Gly Gly Asn Asn Gly Lys Lys Gln Tyr
        1430                1435                1440

AGC AGC AAC AAC CCC GAC GCC AAC CTG ACC CTG AAC ACC GAC GCC CAG         1922
Ser Ser Asn Asn Pro Asp Ala Asn Leu Thr Leu Asn Thr Asp Ala Gln
    1445                1450                1455

GAG AAG CTG AAC AAG AAC CGC GAC TAC TAC ATC AGC CTG TAC ATG AAG         1970
Glu Lys Leu Asn Lys Asn Arg Asp Tyr Tyr Ile Ser Leu Tyr Met Lys
1460                1465                1470                1475

AGC GAG AAG AAC ACC CAG TGC GAG ATC ACC ATC GAC GGC GAG ATA TAC         2018
Ser Glu Lys Asn Thr Gln Cys Glu Ile Thr Ile Asp Gly Glu Ile Tyr
                1480                1485                1490

CCC ATC ACC ACC AAG ACC GTG AAC GTG AAC AAG GAC AAC TAC AAG CGC         2066
Pro Ile Thr Thr Lys Thr Val Asn Val Asn Lys Asp Asn Tyr Lys Arg
            1495                1500                1505

CTG GAC ATC ATC GCC CAC AAC ATC AAG AGC AAC CCC ATC AGC AGC CTG         2114
Leu Asp Ile Ile Ala His Asn Ile Lys Ser Asn Pro Ile Ser Ser Leu
        1510                1515                1520
```

```
CAC ATC AAG ACC AAC GAC GAG ATC ACC CTG TTC TGG GAC GAC ATA TCG          2162
His Ile Lys Thr Asn Asp Glu Ile Thr Leu Phe Trp Asp Asp Ile Ser
    1525                1530                1535

ATT ACC GAC GTC GCC AGC ATC AAG CCC GAG AAC CTG ACC GAC AGC GAG          2210
Ile Thr Asp Val Ala Ser Ile Lys Pro Glu Asn Leu Thr Asp Ser Glu
1540                1545                1550                1555

ATC AAG CAG ATA TAC AGT CGC TAC GGC ATC AAG CTG GAG GAC GGC ATC          2258
Ile Lys Gln Ile Tyr Ser Arg Tyr Gly Ile Lys Leu Glu Asp Gly Ile
                1560                1565                1570

CTG ATC GAC AAG AAA GGC GGC ATC CAC TAC GGC GAG TTC ATC AAC GAG          2306
Leu Ile Asp Lys Lys Gly Gly Ile His Tyr Gly Glu Phe Ile Asn Glu
            1575                1580                1585

GCC AGC TTC AAC ATC GAG CCC CTG CAG AAC TAC GTG ACC AAG TAC GAG          2354
Ala Ser Phe Asn Ile Glu Pro Leu Gln Asn Tyr Val Thr Lys Tyr Glu
        1590                1595                1600

GTG ACC TAC AGC AGC GAG CTG GGC CCC AAC GTG AGC GAC ACC CTG GAG          2402
Val Thr Tyr Ser Ser Glu Leu Gly Pro Asn Val Ser Asp Thr Leu Glu
    1605                1610                1615

AGC GAC AAG ATT TAC AAG GAC GGC ACC ATC AAG TTC GAC TTC ACC AAG          2450
Ser Asp Lys Ile Tyr Lys Asp Gly Thr Ile Lys Phe Asp Phe Thr Lys
1620                1625                1630                1635

TAC AGC AAG AAC GAG CAG GGC CTG TTC TAC GAC AGC GGC CTG AAC TGG          2498
Tyr Ser Lys Asn Glu Gln Gly Leu Phe Tyr Asp Ser Gly Leu Asn Trp
                1640                1645                1650

GAC TTC AAG ATC AAC GCC ATC ACC TAC GAC GGC AAG GAG ATG AAC GTG          2546
Asp Phe Lys Ile Asn Ala Ile Thr Tyr Asp Gly Lys Glu Met Asn Val
            1655                1660                1665

TTC CAC CGC TAC AAC AAG TAGATCTGAG CT                                    2576
Phe His Arg Tyr Asn Lys
        1670

(2) INFORMATION FOR SEQ ID NO:36:

(i) SEQUENCE CHARACTERISTICS:
        (A) LENGTH: 852 amino acids
        (B) TYPE: amino acid
        (D) TOPOLOGY: linear (ii) MOLECULE TYPE: protein (xi) SEQUENCE DESCRIPTION: SEQ ID NO:36:

Met Lys Thr Asn Gln Ile Ser Thr Thr Gln Lys Asn Gln Gln Lys Glu
1               5                   10                  15

Met Asp Arg Lys Gly Leu Leu Gly Tyr Tyr Phe Lys Gly Lys Asp Phe
            20                  25                  30

Ser Asn Leu Thr Met Phe Ala Pro Thr Arg Asp Ser Thr Leu Ile Tyr
        35                  40                  45

Asp Gln Gln Thr Ala Asn Lys Leu Leu Asp Lys Lys Gln Gln Glu Tyr
    50                  55                  60

Gln Ser Ile Arg Trp Ile Gly Leu Ile Gln Ser Lys Glu Thr Gly Asp
65                  70                  75                  80

Phe Thr Phe Asn Leu Ser Glu Asp Glu Gln Ala Ile Ile Glu Ile Asn
                85                  90                  95

Gly Lys Ile Ile Ser Asn Lys Gly Lys Glu Lys Gln Val Val His Leu
            100                 105                 110

Glu Lys Gly Lys Leu Val Pro Ile Lys Ile Glu Tyr Gln Ser Asp Thr
        115                 120                 125

Lys Phe Asn Ile Asp Ser Lys Thr Phe Lys Glu Leu Lys Leu Phe Lys
    130                 135                 140
```

-continued

```
Ile Asp Ser Gln Asn Gln Pro Gln Gln Val Gln Gln Asp Glu Leu Arg
145                 150                 155                 160

Asn Pro Glu Phe Asn Lys Lys Glu Ser Gln Glu Phe Leu Ala Lys Pro
                165                 170                 175

Ser Lys Ile Asn Leu Phe Thr Gln Gln Met Lys Arg Glu Ile Asp Glu
            180                 185                 190

Asp Thr Asp Thr Asp Gly Asp Ser Ile Pro Asp Leu Trp Glu Glu Asn
        195                 200                 205

Gly Tyr Thr Ile Gln Asn Arg Ile Ala Val Lys Trp Asp Asp Ser Leu
    210                 215                 220

Ala Ser Lys Gly Tyr Thr Lys Phe Val Ser Asn Pro Leu Glu Ser His
225                 230                 235                 240

Thr Val Gly Asp Pro Tyr Thr Asp Tyr Glu Lys Ala Ala Arg Asp Leu
                245                 250                 255

Asp Leu Ser Asn Ala Lys Glu Thr Phe Asn Pro Leu Val Ala Ala Phe
            260                 265                 270

Pro Ser Val Asn Val Ser Met Glu Lys Val Ile Leu Ser Pro Asn Glu
        275                 280                 285

Asn Leu Ser Asn Ser Val Glu Ser His Ser Ser Thr Asn Trp Ser Tyr
    290                 295                 300

Thr Asn Thr Glu Gly Ala Ser Val Glu Ala Gly Ile Gly Pro Lys Gly
305                 310                 315                 320

Ile Ser Phe Gly Val Ser Val Asn Tyr Gln His Ser Glu Thr Val Ala
                325                 330                 335

Gln Glu Trp Gly Thr Ser Thr Gly Asn Thr Ser Gln Phe Asn Thr Ala
            340                 345                 350

Ser Ala Gly Tyr Leu Asn Ala Asn Val Arg Tyr Asn Asn Val Gly Thr
        355                 360                 365

Gly Ala Ile Tyr Asp Val Lys Pro Thr Thr Ser Phe Val Leu Asn Asn
    370                 375                 380

Asp Thr Ile Ala Thr Ile Thr Ala Lys Ser Asn Ser Thr Ala Leu Asn
385                 390                 395                 400

Ile Ser Pro Gly Glu Ser Tyr Pro Lys Lys Gly Gln Asn Gly Ile Ala
                405                 410                 415

Ile Thr Ser Met Asp Asp Phe Asn Ser His Pro Ile Thr Leu Asn Lys
            420                 425                 430

Lys Gln Val Asp Asn Leu Leu Asn Asn Lys Pro Met Met Leu Glu Thr
        435                 440                 445

Asn Gln Thr Asp Gly Val Tyr Lys Ile Lys Asp Thr His Gly Asn Ile
    450                 455                 460

Val Thr Gly Gly Glu Trp Asn Gly Val Ile Gln Ile Lys Ala Lys
465                 470                 475                 480

Thr Ala Ser Ile Ile Val Asp Asp Gly Glu Arg Val Ala Glu Lys Arg
                485                 490                 495

Val Ala Ala Lys Asp Tyr Glu Asn Pro Glu Asp Lys Thr Pro Ser Leu
            500                 505                 510

Thr Leu Lys Asp Ala Leu Lys Leu Ser Tyr Pro Asp Glu Ile Lys Glu
        515                 520                 525

Ile Glu Gly Leu Leu Tyr Tyr Lys Asn Lys Pro Ile Tyr Glu Ser Ser
    530                 535                 540

Val Met Thr Tyr Leu Asp Glu Asn Thr Ala Lys Glu Val Thr Lys Gln
545                 550                 555                 560
```

-continued

```
Leu Asn Asp Thr Thr Gly Lys Phe Lys Asp Val Ser His Leu Tyr Asp
            565                 570                 575
Val Lys Leu Thr Pro Lys Met Asn Val Thr Ile Lys Leu Ser Ile Leu
            580                 585                 590
Tyr Asp Asn Ala Glu Ser Asn Asp Asn Ser Ile Gly Lys Trp Thr Asn
            595                 600                 605
Thr Asn Ile Val Ser Gly Gly Asn Asn Gly Lys Lys Gln Tyr Ser Ser
    610                 615                 620
Asn Asn Pro Asp Ala Asn Leu Thr Leu Asn Thr Asp Ala Gln Glu Lys
625                 630                 635                 640
Leu Asn Lys Asn Arg Asp Tyr Tyr Ile Ser Leu Tyr Met Lys Ser Glu
                645                 650                 655
Lys Asn Thr Gln Cys Glu Ile Thr Ile Asp Gly Glu Ile Tyr Pro Ile
                660                 665                 670
Thr Thr Lys Thr Val Asn Val Asn Lys Asp Asn Tyr Lys Arg Leu Asp
            675                 680                 685
Ile Ile Ala His Asn Ile Lys Ser Asn Pro Ile Ser Ser Leu His Ile
    690                 695                 700
Lys Thr Asn Asp Glu Ile Thr Leu Phe Trp Asp Asp Ile Ser Ile Thr
705                 710                 715                 720
Asp Val Ala Ser Ile Lys Pro Glu Asn Leu Thr Asp Ser Glu Ile Lys
                725                 730                 735
Gln Ile Tyr Ser Arg Tyr Gly Ile Lys Leu Glu Asp Gly Ile Leu Ile
                740                 745                 750
Asp Lys Lys Gly Gly Ile His Tyr Gly Glu Phe Ile Asn Glu Ala Ser
            755                 760                 765
Phe Asn Ile Glu Pro Leu Gln Asn Tyr Val Thr Lys Tyr Glu Val Thr
    770                 775                 780
Tyr Ser Ser Glu Leu Gly Pro Asn Val Ser Asp Thr Leu Glu Ser Asp
785                 790                 795                 800
Lys Ile Tyr Lys Asp Gly Thr Ile Lys Phe Asp Phe Thr Lys Tyr Ser
                805                 810                 815
Lys Asn Glu Gln Gly Leu Phe Tyr Asp Ser Gly Leu Asn Trp Asp Phe
            820                 825                 830
Lys Ile Asn Ala Ile Thr Tyr Asp Gly Lys Glu Met Asn Val Phe His
            835                 840                 845
Arg Tyr Asn Lys
    850
```

(2) INFORMATION FOR SEQ ID NO:37:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "forward primer used to make pCIB5527"

(iii) HYPOTHETICAL: NO (xi) SEQUENCE DESCRIPTION: SEQ ID NO:37:

GGATCCACCA TGCTGCAGAA CCTGAAGATC AC        32

(2) INFORMATION FOR SEQ ID NO:38:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "reverse primer used to make pCIB5527"

(iii) HYPOTHETICAL: NO (xi) SEQUENCE DESCRIPTION: SEQ ID NO:38:

```
AAGCTTCCAC TCCTTCTC                                              18
```

(2) INFORMATION FOR SEQ ID NO:39:

(i) SEQUENCE CHARACTERISTICS:
        (A) LENGTH: 1241 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: CDS
        (B) LOCATION: 9..1238
        (D) OTHER INFORMATION: /note= "Maize optimized DNA
           sequence encoding VIP2A(a) with the Bacillus secretion

```
CAG CAG GTG AGC AGC AAG GAG CGC GTG ATC CTG AAG GTG ACC GTC CCC        482
Gln Gln Val Ser Ser Lys Glu Arg Val Ile Leu Lys Val Thr Val Pro
995             1000                1005                1010

AGC GGC AAG GGC AGC ACC ACC CCC ACC AAG GCC GGC GTG ATC CTG AAC        530
Ser Gly Lys Gly Ser Thr Thr Pro Thr Lys Ala Gly Val Ile Leu Asn
                1015                1020                1025

AAC AGC GAG TAC AAG ATG CTG ATC GAC AAC GGC TAC ATG GTG CAC GTG        578
Asn Ser Glu Tyr Lys Met Leu Ile Asp Asn Gly Tyr Met Val His Val
            1030                1035                1040

GAC AAG GTG AGC AAG GTG GTG AAG AAG GGC GTG GAG TGC CTC CAG ATC        626
Asp Lys Val Ser Lys Val Val Lys Lys Gly Val Glu Cys Leu Gln Ile
        1045                1050                1055

GAG GGC ACC CTG AAG AAG AGT CTA GAC TTC AAG AAC GAC ATC AAC GCC        674
Glu Gly Thr Leu Lys Lys Ser Leu Asp Phe Lys Asn Asp Ile Asn Ala
    1060                1065                1070

GAG GCC CAC AGC TGG GGC ATG AAG AAC TAC GAG GAG TGG GCC AAG GAC        722
Glu Ala His Ser Trp Gly Met Lys Asn Tyr Glu Glu Trp Ala Lys Asp
1075                1080                1085                1090

CTG ACC GAC AGC CAG CGC GAG GCC CTG GAC GGC TAC GCC CGC CAG GAC        770
Leu Thr Asp Ser Gln Arg Glu Ala Leu Asp Gly Tyr Ala Arg Gln Asp
                1095                1100                1105

TAC AAG GAG ATC AAC AAC TAC CTG CGC AAC CAG GGC GGC AGC GGC AAC        818
Tyr Lys Glu Ile Asn Asn Tyr Leu Arg Asn Gln Gly Gly Ser Gly Asn
            1110                1115                1120

GAG AAG CTG GAC GCC CAG ATC AAG AAC ATC AGC GAC GCC CTG GGC AAG        866
Glu Lys Leu Asp Ala Gln Ile Lys Asn Ile Ser Asp Ala Leu Gly Lys
        1125                1130                1135

AAG CCC ATC CCC GAG AAC ATC ACC GTG TAC CGC TGG TGC GGC ATG CCC        914
Lys Pro Ile Pro Glu Asn Ile Thr Val Tyr Arg Trp Cys Gly Met Pro
    1140                1145                1150

GAG TTC GGC TAC CAG ATC AGC GAC CCC CTG CCC AGC CTG AAG GAC TTC        962
Glu Phe Gly Tyr Gln Ile Ser Asp Pro Leu Pro Ser Leu Lys Asp Phe
1155                1160                1165                1170

GAG GAG CAG TTC CTG AAC ACC ATC AAG GAG GAC AAG GGC TAC ATG AGC       1010
Glu Glu Gln Phe Leu Asn Thr Ile Lys Glu Asp Lys Gly Tyr Met Ser
                1175                1180                1185

ACC AGC CTG AGC AGC GAG CGC CTG GCC GCC TTC GGC AGC CGC AAG ATC       1058
Thr Ser Leu Ser Ser Glu Arg Leu Ala Ala Phe Gly Ser Arg Lys Ile
            1190                1195                1200

ATC CTG CGC CTG CAG GTG CCC AAG GGC AGC ACT GGT GCC TAC CTG AGC       1106
Ile Leu Arg Leu Gln Val Pro Lys Gly Ser Thr Gly Ala Tyr Leu Ser
        1205                1210                1215

GCC ATC GGC GGC TTC GCC AGC GAG AAG GAG ATC CTG CTG GAT AAG GAC       1154
Ala Ile Gly Gly Phe Ala Ser Glu Lys Glu Ile Leu Leu Asp Lys Asp
    1220                1225                1230

AGC AAG TAC CAC ATC GAC AAG GTG ACC GAG GTG ATC ATC AAG GGC GTG       1202
Ser Lys Tyr His Ile Asp Lys Val Thr Glu Val Ile Ile Lys Gly Val
1235                1240                1245                1250

AAG CGC TAC GTG GTG GAC GCC ACC CTG CTG ACC AAC TAG                   1241
Lys Arg Tyr Val Val Asp Ala Thr Leu Leu Thr Asn
                1255                1260
```

(2) INFORMATION FOR SEQ ID NO:40:

(i) SEQUENCE CHARACTERISTICS:
        (A) LENGTH: 410 amino acids
        (B) TYPE: amino acid
        (D) TOPOLOGY: linear (ii) MOLECULE TYPE: protein (xi) SEQUENCE DESCRIPTION: SEQ ID NO:40:

```
Met Leu Gln Asn Leu Lys Ile Thr Asp Lys Val Glu Asp Phe Lys Glu
 1               5                  10                  15

Asp Lys Glu Lys Ala Lys Glu Trp Gly Lys Glu Lys Glu Lys Glu Trp
             20                  25                  30

Lys Leu Thr Ala Thr Glu Lys Gly Lys Met Asn Asn Phe Leu Asp Asn
         35                  40                  45

Lys Asn Asp Ile Lys Thr Asn Tyr Lys Glu Ile Thr Phe Ser Ile Ala
     50                  55                  60

Gly Ser Phe Glu Asp Glu Ile Lys Asp Leu Lys Glu Ile Asp Lys Met
 65                  70                  75                  80

Phe Asp Lys Thr Asn Leu Ser Asn Ser Ile Ile Thr Tyr Lys Asn Val
                 85                  90                  95

Glu Pro Thr Thr Ile Gly Phe Asn Lys Ser Leu Thr Glu Gly Asn Thr
            100                 105                 110

Ile Asn Ser Asp Ala Met Ala Gln Phe Lys Glu Gln Phe Leu Asp Arg
        115                 120                 125

Asp Ile Lys Phe Asp Ser Tyr Leu Asp Thr His Leu Thr Ala Gln Gln
    130                 135                 140

Val Ser Ser Lys Glu Arg Val Ile Leu Lys Val Thr Val Pro Ser Gly
145                 150                 155                 160

Lys Gly Ser Thr Thr Pro Thr Lys Ala Gly Val Ile Leu Asn Asn Ser
                165                 170                 175

Glu Tyr Lys Met Leu Ile Asp Asn Gly Tyr Met Val His Val Asp Lys
            180                 185                 190

Val Ser Lys Val Val Lys Lys Gly Val Glu Cys Leu Gln Ile Glu Gly
        195                 200                 205

Thr Leu Lys Lys Ser Leu Asp Phe Lys Asn Asp Ile Asn Ala Glu Ala
    210                 215                 220

His Ser Trp Gly Met Lys Asn Tyr Glu Glu Trp Ala Lys Asp Leu Thr
225                 230                 235                 240

Asp Ser Gln Arg Glu Ala Leu Asp Gly Tyr Ala Arg Gln Asp Tyr Lys
                245                 250                 255

Glu Ile Asn Asn Tyr Leu Arg Asn Gln Gly Gly Ser Gly Asn Glu Lys
            260                 265                 270

Leu Asp Ala Gln Ile Lys Asn Ile Ser Asp Ala Leu Gly Lys Lys Pro
        275                 280                 285

Ile Pro Glu Asn Ile Thr Val Tyr Arg Trp Cys Gly Met Pro Glu Phe
    290                 295                 300

Gly Tyr Gln Ile Ser Asp Pro Leu Pro Ser Leu Lys Asp Phe Glu Glu
305                 310                 315                 320

Gln Phe Leu Asn Thr Ile Lys Glu Asp Lys Gly Tyr Met Ser Thr Ser
                325                 330                 335

Leu Ser Ser Glu Arg Leu Ala Ala Phe Gly Ser Arg Lys Ile Ile Leu
            340                 345                 350

Arg Leu Gln Val Pro Lys Gly Ser Thr Gly Ala Tyr Leu Ser Ala Ile
        355                 360                 365

Gly Gly Phe Ala Ser Glu Lys Glu Ile Leu Leu Asp Lys Asp Ser Lys
370                 375                 380

Tyr His Ile Asp Lys Val Thr Glu Val Ile Ile Lys Gly Val Lys Arg
385                 390                 395                 400
```

```
Tyr Val Val Asp Ala Thr Leu Leu Thr Asn
            405                 410

(2) INFORMATION FOR SEQ ID NO:41:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide encoding
            eukaryotic secretion signal used to construct pCIB5527"

(iii) HYPOTHETICAL: NO (xi) SEQUENCE DESCRIPTION: SEQ ID NO:41:

GGATCCACCA TGGGCTGGAG CTGGATCTTC CTGTTCCTGC TGAGCGGCGC CGCGGGCGTG        60

CACTGCCTGC AG                                                           72

(2) INFORMATION FOR SEQ ID NO:42:

(i) SEQUENCE CHARACTERISTICS:
        (A) LENGTH: 1241 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: CDS
        (B) LOCATION: 9..1238
        (D) OTHER INFORMATION: /note= "Maize optimized DNA
            sequence encoding VIP2A(a) with the Bacillus secretion
            signal removed and the eukaryotic secretion signal
            inserted as contained in pCIB5528"

(xi) SEQUENCE DESCRIPTION: SEQ ID NO:42:

GATCCACC ATG CTG CAG AAC CTG AAG ATC ACC GAC AAG GTG GAG GAC TTC        50
         Met Leu Gln Asn Leu Lys Ile Thr Asp Lys Val Glu Asp Phe
                         415                 420

AAG GAG GAC AAG GAG AAG GCC AAG GAG TGG GGC AAG GAG AAG GAG AAG         98
Lys Glu Asp Lys Glu Lys Ala Lys Glu Trp Gly Lys Glu Lys Glu Lys
425                 430                 435                 440

GAG TGG AAG CTT ACC GCC ACC GAG AAG GGC AAG ATG AAC AAC TTC CTG        146
Glu Trp Lys Leu Thr Ala Thr Glu Lys Gly Lys Met Asn Asn Phe Leu
                445                 450                 455

GAC AAC AAG AAC GAC ATC AAG ACC AAC TAC AAG GAG ATC ACC TTC AGC        194
Asp Asn Lys Asn Asp Ile Lys Thr Asn Tyr Lys Glu Ile Thr Phe Ser
            460                 465                 470

ATA GCC GGC AGC TTC GAG GAC GAG ATC AAG GAC CTG AAG GAG ATC GAC        242
Ile Ala Gly Ser Phe Glu Asp Glu Ile Lys Asp Leu Lys Glu Ile Asp
        475                 480                 485

AAG ATG TTC GAC AAG ACC AAC CTG AGC AAC AGC ATC ATC ACC TAC AAG        290
Lys Met Phe Asp Lys Thr Asn Leu Ser Asn Ser Ile Ile Thr Tyr Lys
    490                 495                 500

AAC GTG GAG CCC ACC ACC ATC GGC TTC AAC AAG AGC CTG ACC GAG GGC        338
Asn Val Glu Pro Thr Thr Ile Gly Phe Asn Lys Ser Leu Thr Glu Gly
505                 510                 515                 520
```

-continued

```
AAC ACC ATC AAC AGC GAC GCC ATG GCC CAG TTC AAG GAG CAG TTC CTG        386
Asn Thr Ile Asn Ser Asp Ala Met Ala Gln Phe Lys Glu Gln Phe Leu
            525                 530                 535

GAC CGC GAC ATC AAG TTC GAC AGC TAC CTG GAC ACC CAC CTG ACC GCC        434
Asp Arg Asp Ile Lys Phe Asp Ser Tyr Leu Asp Thr His Leu Thr Ala
            540                 545                 550

CAG CAG GTG AGC AGC AAG GAG CGC GTG ATC CTG AAG GTG ACC GTC CCC        482
Gln Gln Val Ser Ser Lys Glu Arg Val Ile Leu Lys Val Thr Val Pro
            555                 560                 565

AGC GGC AAG GGC AGC ACC ACC CCC ACC AAG GCC GGC GTG ATC CTG AAC        530
Ser Gly Lys Gly Ser Thr Thr Pro Thr Lys Ala Gly Val Ile Leu Asn
            570                 575                 580

AAC AGC GAG TAC AAG ATG CTG ATC GAC AAC GGC TAC ATG GTG CAC GTG        578
Asn Ser Glu Tyr Lys Met Leu Ile Asp Asn Gly Tyr Met Val His Val
585                 590                 595                 600

GAC AAG GTG AGC AAG GTG GTG AAG AAG GGC GTG GAG TGC CTC CAG ATC        626
Asp Lys Val Ser Lys Val Val Lys Lys Gly Val Glu Cys Leu Gln Ile
            605                 610                 615

GAG GGC ACC CTG AAG AAG AGT CTA GAC TTC AAG AAC GAC ATC AAC GCC        674
Glu Gly Thr Leu Lys Lys Ser Leu Asp Phe Lys Asn Asp Ile Asn Ala
            620                 625                 630

GAG GCC CAC AGC TGG GGC ATG AAG AAC TAC GAG GAG TGG GCC AAG GAC        722
Glu Ala His Ser Trp Gly Met Lys Asn Tyr Glu Glu Trp Ala Lys Asp
            635                 640                 645

CTG ACC GAC AGC CAG CGC GAG GCC CTG GAC GGC TAC GCC CGC CAG GAC        770
Leu Thr Asp Ser Gln Arg Glu Ala Leu Asp Gly Tyr Ala Arg Gln Asp
            650                 655                 660

TAC AAG GAG ATC AAC AAC TAC CTG CGC AAC CAG GGC GGC AGC GGC AAC        818
Tyr Lys Glu Ile Asn Asn Tyr Leu Arg Asn Gln Gly Gly Ser Gly Asn
665                 670                 675                 680

GAG AAG CTG GAC GCC CAG ATC AAG AAC ATC AGC GAC GCC CTG GGC AAG        866
Glu Lys Leu Asp Ala Gln Ile Lys Asn Ile Ser Asp Ala Leu Gly Lys
            685                 690                 695

AAG CCC ATC CCC GAG AAC ATC ACC GTG TAC CGC TGG TGC GGC ATG CCC        914
Lys Pro Ile Pro Glu Asn Ile Thr Val Tyr Arg Trp Cys Gly Met Pro
            700                 705                 710

GAG TTC GGC TAC CAG ATC AGC GAC CCC CTG CCC AGC CTG AAG GAC TTC        962
Glu Phe Gly Tyr Gln Ile Ser Asp Pro Leu Pro Ser Leu Lys Asp Phe
            715                 720                 725

GAG GAG CAG TTC CTG AAC ACC ATC AAG GAG GAC AAG GGC TAC ATG AGC       1010
Glu Glu Gln Phe Leu Asn Thr Ile Lys Glu Asp Lys Gly Tyr Met Ser
            730                 735                 740

ACC AGC CTG AGC AGC GAG CGC CTG GCC GCC TTC GGC AGC CGC AAG ATC       1058
Thr Ser Leu Ser Ser Glu Arg Leu Ala Ala Phe Gly Ser Arg Lys Ile
745                 750                 755                 760

ATC CTG CGC CTG CAG GTG CCC AAG GGC AGC ACT GGT GCC TAC CTG AGC       1106
Ile Leu Arg Leu Gln Val Pro Lys Gly Ser Thr Gly Ala Tyr Leu Ser
            765                 770                 775

GCC ATC GGC GGC TTC GCC AGC GAG AAG GAG ATC CTG CTG GAT AAG GAC       1154
Ala Ile Gly Gly Phe Ala Ser Glu Lys Glu Ile Leu Leu Asp Lys Asp
            780                 785                 790

AGC AAG TAC CAC ATC GAC AAG GTG ACC GAG GTG ATC ATC AAG GGC GTG       1202
Ser Lys Tyr His Ile Asp Lys Val Thr Glu Val Ile Ile Lys Gly Val
            795                 800                 805

AAG CGC TAC GTG GTG GAC GCC ACC CTG CTG ACC AAC TAG                   1241
Lys Arg Tyr Val Val Asp Ala Thr Leu Leu Thr Asn
            810                 815                 820
```

-continued (2) INFORMATION FOR SEQ ID NO:43:

(i) SEQUENCE CHARACTERISTICS:
        (A) LENGTH: 410 amino acids
        (B) TYPE: amino acid
        (D) TOPOLOGY: linear (ii) MOLECULE TYPE: protein (xi) SEQUENCE DESCRIPTION: SEQ ID NO:43:

```
Met Leu Gln Asn Leu Lys Ile Thr Asp Lys Val Glu Asp Phe Lys Glu
 1               5                  10                  15

Asp Lys Glu Lys Ala Lys Glu Trp Gly Lys Glu Lys Glu Lys Glu Trp
            20                  25                  30

Lys Leu Thr Ala Thr Glu Lys Gly Lys Met Asn Asn Phe Leu Asp Asn
        35                  40                  45

Lys Asn Asp Ile Lys Thr Asn Tyr Lys Glu Ile Thr Phe Ser Ile Ala
    50                  55                  60

Gly Ser Phe Glu Asp Glu Ile Lys Asp Leu Lys Glu Ile Asp Lys Met
 65                  70                  75                  80

Phe Asp Lys Thr Asn Leu Ser Asn Ser Ile Ile Thr Tyr Lys Asn Val
                85                  90                  95

Glu Pro Thr Thr Ile Gly Phe Asn Lys Ser Leu Thr Glu Gly Asn Thr
            100                 105                 110

Ile Asn Ser Asp Ala Met Ala Gln Phe Lys Glu Gln Phe Leu Asp Arg
        115                 120                 125

Asp Ile Lys Phe Asp Ser Tyr Leu Asp Thr His Leu Thr Ala Gln Gln
    130                 135                 140

Val Ser Ser Lys Glu Arg Val Ile Leu Lys Val Thr Val Pro Ser Gly
145                 150                 155                 160

Lys Gly Ser Thr Thr Pro Thr Lys Ala Gly Val Ile Leu Asn Asn Ser
                165                 170                 175

Glu Tyr Lys Met Leu Ile Asp Asn Gly Tyr Met Val His Val Asp Lys
            180                 185                 190

Val Ser Lys Val Val Lys Gly Val Glu Cys Leu Gln Ile Glu Gly
            195                 200                 205

Thr Leu Lys Lys Ser Leu Asp Phe Lys Asn Asp Ile Asn Ala Glu Ala
210                 215                 220

His Ser Trp Gly Met Lys Asn Tyr Glu Glu Trp Ala Lys Asp Leu Thr
225                 230                 235                 240

Asp Ser Gln Arg Glu Ala Leu Asp Gly Tyr Ala Arg Gln Asp Tyr Lys
                245                 250                 255

Glu Ile Asn Asn Tyr Leu Arg Asn Gln Gly Ser Gly Asn Glu Lys
            260                 265                 270

Leu Asp Ala Gln Ile Lys Asn Ile Ser Asp Ala Leu Gly Lys Lys Pro
    275                 280                 285

Ile Pro Glu Asn Ile Thr Val Tyr Arg Trp Cys Gly Met Pro Glu Phe
290                 295                 300

Gly Tyr Gln Ile Ser Asp Pro Leu Pro Ser Leu Lys Asp Phe Glu Glu
305                 310                 315                 320

Gln Phe Leu Asn Thr Ile Lys Glu Asp Lys Gly Tyr Met Ser Thr Ser
                325                 330                 335

Leu Ser Ser Glu Arg Leu Ala Ala Phe Gly Ser Arg Lys Ile Ile Leu
            340                 345                 350
```

```
Arg Leu Gln Val Pro Lys Gly Ser Thr Gly Ala Tyr Leu Ser Ala Ile
        355                 360                 365

Gly Gly Phe Ala Ser Glu Lys Glu Ile Leu Leu Asp Lys Asp Ser Lys
    370                 375                 380

Tyr His Ile Asp Lys Val Thr Glu Val Ile Ile Lys Gly Val Lys Arg
385                 390                 395                 400

Tyr Val Val Asp Ala Thr Leu Leu Thr Asn
                405                 410
```

(2) INFORMATION FOR SEQ ID NO:44:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide encoding
            vacuolar targetting peptide used to construct pCIB5533"

(iii) HYPOTHETICAL: NO (xi) SEQUENCE DESCRIPTION: SEQ ID NO:44:

```
CCGCGGGCGT GCACTGCCTC AGCAGCAGCA GCTTCGCCGA CAGCAACCCC ATCCGCGTGA      60

CCGACCGCGC CGCCAGCACC CTGCAG                                          86
```

(2) INFORMATION FOR SEQ ID NO:45:

(i) SEQUENCE CHARACTERISTICS:
        (A) LENGTH: 1358 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: CDS
        (B) LOCATION: 9..1355
        (D) OTHER INFORMATION: /note= "Maize optimized VIP2A(a)
            with the Bacillus secretion signal removed and the
            vacuolar
            targetting signal inserted as contained in pCIB5533"

(xi) SEQUENCE DESCRIPTION: SEQ ID NO:45:

```
GATCCACC ATG GGC TGG AGC TGG ATC TTC CTG TTC CTG CTG AGC GGC GCC         50
         Met Gly Trp Ser Trp Ile Phe Leu Phe Leu Leu Ser Gly Ala
                         415                 420

GCG GGC GTG CAC TGC CTC AGC AGC AGC TTC GCC GAC AGC AAC CCC              98
Ala Gly Val His Cys Leu Ser Ser Ser Phe Ala Asp Ser Asn Pro
425                 430                 435                 440

ATC CGC GTG ACC GAC CGC GCC GCC AGC ACC CTG CAG AAC CTG AAG ATC         146
Ile Arg Val Thr Asp Arg Ala Ala Ser Thr Leu Gln Asn Leu Lys Ile
                445                 450                 455

ACC GAC AAG GTG GAG GAC TTC AAG GAG GAC AAG GAG AAG GCC AAG GAG         194
Thr Asp Lys Val Glu Asp Phe Lys Glu Asp Lys Glu Lys Ala Lys Glu
            460                 465                 470

TGG GGC AAG GAG AAG GAG AAG GAG TGG AAG CTT ACC GCC ACC GAG AAG         242
Trp Gly Lys Glu Lys Glu Lys Glu Trp Lys Leu Thr Ala Thr Glu Lys
        475                 480                 485
```

-continued

```
GGC AAG ATG AAC AAC TTC CTG GAC AAC AAG AAC GAC ATC AAG ACC AAC        290
Gly Lys Met Asn Asn Phe Leu Asp Asn Lys Asn Asp Ile Lys Thr Asn
        490                 495                 500

TAC AAG GAG ATC ACC TTC AGC ATA GCC GGC AGC TTC GAG GAC GAG ATC        338
Tyr Lys Glu Ile Thr Phe Ser Ile Ala Gly Ser Phe Glu Asp Glu Ile
505                 510                 515                 520

AAG GAC CTG AAG GAG ATC GAC AAG ATG TTC GAC AAG ACC AAC CTG AGC        386
Lys Asp Leu Lys Glu Ile Asp Lys Met Phe Asp Lys Thr Asn Leu Ser
                525                 530                 535

AAC AGC ATC ATC ACC TAC AAG AAC GTG GAG CCC ACC ACC ATC GGC TTC        434
Asn Ser Ile Ile Thr Tyr Lys Asn Val Glu Pro Thr Thr Ile Gly Phe
            540                 545                 550

AAC AAG AGC CTG ACC GAG GGC AAC ACC ATC AAC AGC GAC GCC ATG GCC        482
Asn Lys Ser Leu Thr Glu Gly Asn Thr Ile Asn Ser Asp Ala Met Ala
        555                 560                 565

CAG TTC AAG GAG CAG TTC CTG GAC CGC GAC ATC AAG TTC GAC AGC TAC        530
Gln Phe Lys Glu Gln Phe Leu Asp Arg Asp Ile Lys Phe Asp Ser Tyr
    570                 575                 580

CTG GAC ACC CAC CTG ACC GCC CAG CAG GTG AGC AGC AAG GAG CGC GTG        578
Leu Asp Thr His Leu Thr Ala Gln Gln Val Ser Ser Lys Glu Arg Val
585                 590                 595                 600

ATC CTG AAG GTG ACC GTC CCC AGC GGC AAG GGC AGC ACC ACC CCC ACC        626
Ile Leu Lys Val Thr Val Pro Ser Gly Lys Gly Ser Thr Thr Pro Thr
                605                 610                 615

AAG GCC GGC GTG ATC CTG AAC AAC AGC GAG TAC AAG ATG CTG ATC GAC        674
Lys Ala Gly Val Ile Leu Asn Asn Ser Glu Tyr Lys Met Leu Ile Asp
            620                 625                 630

AAC GGC TAC ATG GTG CAC GTG GAC AAG GTG AGC AAG GTG GTG AAG AAG        722
Asn Gly Tyr Met Val His Val Asp Lys Val Ser Lys Val Val Lys Lys
        635                 640                 645

GGC GTG GAG TGC CTC CAG ATC GAG GGC ACC CTG AAG AAG AGT CTA GAC        770
Gly Val Glu Cys Leu Gln Ile Glu Gly Thr Leu Lys Lys Ser Leu Asp
    650                 655                 660

TTC AAG AAC GAC ATC AAC GCC GAG GCC CAC AGC TGG GGC ATG AAG AAC        818
Phe Lys Asn Asp Ile Asn Ala Glu Ala His Ser Trp Gly Met Lys Asn
665                 670                 675                 680

TAC GAG GAG TGG GCC AAG GAC CTG ACC GAC AGC CAG CGC GAG GCC CTG        866
Tyr Glu Glu Trp Ala Lys Asp Leu Thr Asp Ser Gln Arg Glu Ala Leu
                685                 690                 695

GAC GGC TAC GCC CGC CAG GAC TAC AAG GAG ATC AAC AAC TAC CTG CGC        914
Asp Gly Tyr Ala Arg Gln Asp Tyr Lys Glu Ile Asn Asn Tyr Leu Arg
            700                 705                 710

AAC CAG GGC GGC AGC GGC AAC GAG AAG CTG GAC GCC CAG ATC AAG AAC        962
Asn Gln Gly Gly Ser Gly Asn Glu Lys Leu Asp Ala Gln Ile Lys Asn
        715                 720                 725

ATC AGC GAC GCC CTG GGC AAG AAG CCC ATC CCC GAG AAC ATC ACC GTG       1010
Ile Ser Asp Ala Leu Gly Lys Lys Pro Ile Pro Glu Asn Ile Thr Val
    730                 735                 740

TAC CGC TGG TGC GGC ATG CCC GAG TTC GGC TAC CAG ATC AGC GAC CCC       1058
Tyr Arg Trp Cys Gly Met Pro Glu Phe Gly Tyr Gln Ile Ser Asp Pro
745                 750                 755                 760

CTG CCC AGC CTG AAG GAC TTC GAG GAG CAG TTC CTG AAC ACC ATC AAG       1106
Leu Pro Ser Leu Lys Asp Phe Glu Glu Gln Phe Leu Asn Thr Ile Lys
                765                 770                 775

GAG GAC AAG GGC TAC ATG AGC ACC AGC CTG AGC AGC GAG CGC CTG GCC       1154
Glu Asp Lys Gly Tyr Met Ser Thr Ser Leu Ser Ser Glu Arg Leu Ala
            780                 785                 790
```

```
GCC TTC GGC AGC CGC AAG ATC ATC CTG CGC CTG CAG GTG CCC AAG GGC    1202
Ala Phe Gly Ser Arg Lys Ile Ile Leu Arg Leu Gln Val Pro Lys Gly
        795                 800                 805

AGC ACT GGT GCC TAC CTG AGC GCC ATC GGC GGC TTC GCC AGC GAG AAG    1250
Ser Thr Gly Ala Tyr Leu Ser Ala Ile Gly Gly Phe Ala Ser Glu Lys
    810                 815                 820

GAG ATC CTG CTG GAT AAG GAC AGC AAG TAC CAC ATC GAC AAG GTG ACC    1298
Glu Ile Leu Leu Asp Lys Asp Ser Lys Tyr His Ile Asp Lys Val Thr
825                 830                 835                 840

GAG GTG ATC ATC AAG GGC GTG AAG CGC TAC GTG GTG GAC GCC ACC CTG    1346
Glu Val Ile Ile Lys Gly Val Lys Arg Tyr Val Val Asp Ala Thr Leu
                845                 850                 855

CTG ACC AAC TAG                                                    1358
Leu Thr Asn
```

(2) INFORMATION FOR SEQ ID NO:46:

(i) SEQUENCE CHARACTERISTICS:
        (A) LENGTH: 449 amino acids
        (B) TYPE: amino acid
        (D) TOPOLOGY: linear (ii) MOLECULE TYPE: protein (xi) SEQUENCE DESCRIPTION: SEQ ID NO:46:

```
Met Gly Trp Ser Trp Ile Phe Leu Phe Leu Leu Ser Gly Ala Ala Gly
 1               5                  10                  15

Val His Cys Leu Ser Ser Ser Phe Ala Asp Ser Asn Pro Ile Arg
            20                  25                  30

Val Thr Asp Arg Ala Ala Ser Thr Leu Gln Asn Leu Lys Ile Thr Asp
         35                  40                  45

Lys Val Glu Asp Phe Lys Glu Asp Lys Glu Lys Ala Lys Glu Trp Gly
     50                  55                  60

Lys Glu Lys Glu Lys Glu Trp Lys Leu Thr Ala Thr Glu Lys Gly Lys
 65                  70                  75                  80

Met Asn Asn Phe Leu Asp Asn Lys Asn Asp Ile Lys Thr Asn Tyr Lys
                 85                  90                  95

Glu Ile Thr Phe Ser Ile Ala Gly Ser Phe Glu Asp Glu Ile Lys Asp
            100                 105                 110

Leu Lys Glu Ile Asp Lys Met Phe Asp Lys Thr Asn Leu Ser Asn Ser
        115                 120                 125

Ile Ile Thr Tyr Lys Asn Val Glu Pro Thr Thr Ile Gly Phe Asn Lys
    130                 135                 140

Ser Leu Thr Glu Gly Asn Thr Ile Asn Ser Asp Ala Met Ala Gln Phe
145                 150                 155                 160

Lys Glu Gln Phe Leu Asp Arg Asp Ile Lys Phe Asp Ser Tyr Leu Asp
                165                 170                 175

Thr His Leu Thr Ala Gln Gln Val Ser Ser Lys Glu Arg Val Ile Leu
            180                 185                 190

Lys Val Thr Val Pro Ser Gly Lys Gly Ser Thr Thr Pro Thr Lys Ala
        195                 200                 205

Gly Val Ile Leu Asn Asn Ser Glu Tyr Lys Met Leu Ile Asp Asn Gly
    210                 215                 220

Tyr Met Val His Val Asp Lys Val Ser Lys Val Val Lys Lys Gly Val
225                 230                 235                 240

Glu Cys Leu Gln Ile Glu Gly Thr Leu Lys Ser Leu Asp Phe Lys
                245                 250                 255
```

-continued

```
Asn Asp Ile Asn Ala Glu Ala His Ser Trp Gly Met Lys Asn Tyr Glu
            260                 265                 270

Glu Trp Ala Lys Asp Leu Thr Asp Ser Gln Arg Glu Ala Leu Asp Gly
            275                 280                 285

Tyr Ala Arg Gln Asp Tyr Lys Glu Ile Asn Asn Tyr Leu Arg Asn Gln
    290                 295                 300

Gly Gly Ser Gly Asn Glu Lys Leu Asp Ala Gln Ile Lys Asn Ile Ser
305                 310                 315                 320

Asp Ala Leu Gly Lys Lys Pro Ile Pro Glu Asn Ile Thr Val Tyr Arg
                325                 330                 335

Trp Cys Gly Met Pro Glu Phe Gly Tyr Gln Ile Ser Asp Pro Leu Pro
            340                 345                 350

Ser Leu Lys Asp Phe Glu Glu Gln Phe Leu Asn Thr Ile Lys Glu Asp
            355                 360                 365

Lys Gly Tyr Met Ser Thr Ser Leu Ser Ser Glu Arg Leu Ala Ala Phe
    370                 375                 380

Gly Ser Arg Lys Ile Ile Leu Arg Leu Gln Val Pro Lys Gly Ser Thr
385                 390                 395                 400

Gly Ala Tyr Leu Ser Ala Ile Gly Gly Phe Ala Ser Glu Lys Glu Ile
                405                 410                 415

Leu Leu Asp Lys Asp Ser Lys Tyr His Ile Asp Lys Val Thr Glu Val
                420                 425                 430

Ile Ile Lys Gly Val Lys Arg Tyr Val Val Asp Ala Thr Leu Leu Thr
            435                 440                 445

Asn
```

(2) INFORMATION FOR SEQ ID NO:47:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:
        (A) NAME/KEY: Peptide
        (B) LOCATION: 1..16
        (D) OTHER INFORMATION: /note= "linker peptide for fusion
            of VIP1A(a) and VIP2A(a) used to construct pCIB5533"

(xi) SEQUENCE DESCRIPTION: SEQ ID NO:47:

```
Pro Ser Thr Pro Pro Thr Pro Ser Pro Ser Thr Pro Pro Thr Pro Ser
1               5                   10                  15
```

(2) INFORMATION FOR SEQ ID NO:48:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA encoding linker peptide used to construct pCIB5533"

(iii) HYPOTHETICAL: NO (xi) SEQUENCE DESCRIPTION: SEQ ID NO:48:

-continued

```
CCCGGGCCTT CTACTCCCCC AACTCCCTCT CCTAGCACGC CTCCGACACC TAGCGATATC     60

GGATCC                                                                66
```

(2) INFORMATION FOR SEQ ID NO:49:

(i) SEQUENCE CHARACTERISTICS:
(A) LENGTH: 4031 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Synthetic DNA"

(iii) HYPOTHETICAL: NO (ix) FEATURE:
(A) NAME/KEY: CDS
(B) LOCATION: 6..4019
(D) OTHER INFORMATION: /note= "Maize optimized DNA sequence encoding a VIP2A(a) - VIP1A(a) fusion protein as contained in pCIB5531"

(xi) SEQUENCE DESCRIPTION: SEQ ID NO:49:

```
GATCC ATG AAG CGC ATG GAG GGC AAG CTG TTC ATG GTG AGC AAG AAG         47
      Met Lys Arg Met Glu Gly Lys Leu Phe Met Val Ser Lys Lys
       450                455                 460

CTC CAG GTG GTG ACC AAG ACC GTG CTG CTG AGC ACC GTG TTC AGC ATC       95
Leu Gln Val Val Thr Lys Thr Val Leu Leu Ser Thr Val Phe Ser Ile
    465                 470                 475

AGC CTG CTG AAC AAC GAG GTG ATC AAG GCC GAG CAG CTG AAC ATC AAC      143
Ser Leu Leu Asn Asn Glu Val Ile Lys Ala Glu Gln Leu Asn Ile Asn
480                 485                 490                 495

AGC CAG AGC AAG TAC ACC AAC CTC CAG AAC CTG AAG ATC ACC GAC AAG      191
Ser Gln Ser Lys Tyr Thr Asn Leu Gln Asn Leu Lys Ile Thr Asp Lys
                500                 505                 510

GTG GAG GAC TTC AAG GAG GAC AAG GAG AAG GCC AAG GAG TGG GGC AAG      239
Val Glu Asp Phe Lys Glu Asp Lys Glu Lys Ala Lys Glu Trp Gly Lys
            515                 520                 525

GAG AAG GAG AAG GAG TGG AAG CTT ACC GCC ACC GAG AAG GGC AAG ATG      287
Glu Lys Glu Lys Glu Trp Lys Leu Thr Ala Thr Glu Lys Gly Lys Met
        530                 535                 540

AAC AAC TTC CTG GAC AAC AAG AAC GAC ATC AAG ACC AAC TAC AAG GAG      335
Asn Asn Phe Leu Asp Asn Lys Asn Asp Ile Lys Thr Asn Tyr Lys Glu
    545                 550                 555

ATC ACC TTC AGC ATA GCC GGC AGC TTC GAG GAC GAG ATC AAG GAC CTG      383
Ile Thr Phe Ser Ile Ala Gly Ser Phe Glu Asp Glu Ile Lys Asp Leu
560                 565                 570                 575

AAG GAG ATC GAC AAG ATG TTC GAC AAG ACC AAC CTG AGC AAC AGC ATC      431
Lys Glu Ile Asp Lys Met Phe Asp Lys Thr Asn Leu Ser Asn Ser Ile
                580                 585                 590

ATC ACC TAC AAG AAC GTG GAG CCC ACC ACC ATC GGC TTC AAC AAG AGC      479
Ile Thr Tyr Lys Asn Val Glu Pro Thr Thr Ile Gly Phe Asn Lys Ser
            595                 600                 605

CTG ACC GAG GGC AAC ACC ATC AAC AGC GAC GCC ATG GCC CAG TTC AAG      527
Leu Thr Glu Gly Asn Thr Ile Asn Ser Asp Ala Met Ala Gln Phe Lys
        610                 615                 620

GAG CAG TTC CTG GAC CGC GAC ATC AAG TTC GAC AGC TAC CTG GAC ACC      575
Glu Gln Phe Leu Asp Arg Asp Ile Lys Phe Asp Ser Tyr Leu Asp Thr
    625                 630                 635

CAC CTG ACC GCC CAG CAG GTG AGC AGC AAG GAG CGC GTG ATC CTG AAG      623
His Leu Thr Ala Gln Gln Val Ser Ser Lys Glu Arg Val Ile Leu Lys
640                 645                 650                 655
```

-continued

```
GTG ACC GTC CCC AGC GGC AAG GGC AGC ACC ACC CCC ACC AAG GCC GGC        671
Val Thr Val Pro Ser Gly Lys Gly Ser Thr Thr Pro Thr Lys Ala Gly
            660                 665                 670

GTG ATC CTG AAC AAC AGC GAG TAC AAG ATG CTG ATC GAC AAC GGC TAC        719
Val Ile Leu Asn Asn Ser Glu Tyr Lys Met Leu Ile Asp Asn Gly Tyr
            675                 680                 685

ATG GTG CAC GTG GAC AAG GTG AGC AAG GTG GTG AAG AAG GGC GTG GAG        767
Met Val His Val Asp Lys Val Ser Lys Val Val Lys Lys Gly Val Glu
            690                 695                 700

TGC CTC CAG ATC GAG GGC ACC CTG AAG AAG AGT CTA GAC TTC AAG AAC        815
Cys Leu Gln Ile Glu Gly Thr Leu Lys Lys Ser Leu Asp Phe Lys Asn
    705                 710                 715

GAC ATC AAC GCC GAG GCC CAC AGC TGG GGC ATG AAG AAC TAC GAG GAG        863
Asp Ile Asn Ala Glu Ala His Ser Trp Gly Met Lys Asn Tyr Glu Glu
720                 725                 730                 735

TGG GCC AAG GAC CTG ACC GAC AGC CAG CGC GAG GCC CTG GAC GGC TAC        911
Trp Ala Lys Asp Leu Thr Asp Ser Gln Arg Glu Ala Leu Asp Gly Tyr
            740                 745                 750

GCC CGC CAG GAC TAC AAG GAG ATC AAC AAC TAC CTG CGC AAC CAG GGC        959
Ala Arg Gln Asp Tyr Lys Glu Ile Asn Asn Tyr Leu Arg Asn Gln Gly
            755                 760                 765

GGC AGC GGC AAC GAG AAG CTG GAC GCC CAG ATC AAG AAC ATC AGC GAC       1007
Gly Ser Gly Asn Glu Lys Leu Asp Ala Gln Ile Lys Asn Ile Ser Asp
            770                 775                 780

GCC CTG GGC AAG AAG CCC ATC CCC GAG AAC ATC ACC GTG TAC CGC TGG       1055
Ala Leu Gly Lys Lys Pro Ile Pro Glu Asn Ile Thr Val Tyr Arg Trp
    785                 790                 795

TGC GGC ATG CCC GAG TTC GGC TAC CAG ATC AGC GAC CCC CTG CCC AGC       1103
Cys Gly Met Pro Glu Phe Gly Tyr Gln Ile Ser Asp Pro Leu Pro Ser
800                 805                 810                 815

CTG AAG GAC TTC GAG GAG CAG TTC CTG AAC ACC ATC AAG GAG GAC AAG       1151
Leu Lys Asp Phe Glu Glu Gln Phe Leu Asn Thr Ile Lys Glu Asp Lys
            820                 825                 830

GGC TAC ATG AGC ACC AGC CTG AGC AGC GAG CGC CTG GCC GCC TTC GGC       1199
Gly Tyr Met Ser Thr Ser Leu Ser Ser Glu Arg Leu Ala Ala Phe Gly
            835                 840                 845

AGC CGC AAG ATC ATC CTG CGC CTG CAG GTG CCC AAG GGC AGC ACT GGT       1247
Ser Arg Lys Ile Ile Leu Arg Leu Gln Val Pro Lys Gly Ser Thr Gly
            850                 855                 860

GCC TAC CTG AGC GCC ATC GGC GGC TTC GCC AGC GAG AAG GAG ATC CTG       1295
Ala Tyr Leu Ser Ala Ile Gly Gly Phe Ala Ser Glu Lys Glu Ile Leu
    865                 870                 875

CTG GAT AAG GAC AGC AAG TAC CAC ATC GAC AAG GTG ACC GAG GTG ATC       1343
Leu Asp Lys Asp Ser Lys Tyr His Ile Asp Lys Val Thr Glu Val Ile
880                 885                 890                 895

ATC AAG GGC GTG AAG CGC TAC GTG GTG GAC GCC ACC CTG CTG ACC AAC       1391
Ile Lys Gly Val Lys Arg Tyr Val Val Asp Ala Thr Leu Leu Thr Asn
            900                 905                 910

TCC CGG GGG CCT TCT ACT CCC CCA ACT CCC TCT CCT AGC ACG CCT CCG       1439
Ser Arg Gly Pro Ser Thr Pro Pro Thr Pro Ser Pro Ser Thr Pro Pro
            915                 920                 925

ACA CCT AGC GAT ATC GGA TCC ACC ATG AAG ACC AAC CAG ATC AGC ACC       1487
Thr Pro Ser Asp Ile Gly Ser Thr Met Lys Thr Asn Gln Ile Ser Thr
            930                 935                 940

ACC CAG AAG AAC CAG CAG AAG GAG ATG GAC CGC AAG GGC CTG CTG GGC       1535
Thr Gln Lys Asn Gln Gln Lys Glu Met Asp Arg Lys Gly Leu Leu Gly
            945                 950                 955
```

-continued

| | |
|---|---|
| TAC TAC TTC AAG GGC AAG GAC TTC AGC AAC CTG ACC ATG TTC GCC CCC<br>Tyr Tyr Phe Lys Gly Lys Asp Phe Ser Asn Leu Thr Met Phe Ala Pro<br>960               965               970               975 | 1583 |
| ACG CGT GAC AGC ACC CTG ATC TAC GAC CAG CAG ACC GCC AAC AAG CTG<br>Thr Arg Asp Ser Thr Leu Ile Tyr Asp Gln Gln Thr Ala Asn Lys Leu<br>               980               985               990 | 1631 |
| CTG GAC AAG AAG CAG CAG GAG TAC CAG AGC ATC CGC TGG ATC GGC CTG<br>Leu Asp Lys Lys Gln Gln Glu Tyr Gln Ser Ile Arg Trp Ile Gly Leu<br>           995               1000             1005 | 1679 |
| ATC CAG AGC AAG GAG ACC GGC GAC TTC ACC TTC AAC CTG AGC GAG GAC<br>Ile Gln Ser Lys Glu Thr Gly Asp Phe Thr Phe Asn Leu Ser Glu Asp<br>        1010               1015             1020 | 1727 |
| GAG CAG GCC ATC ATC GAG ATC AAC GGC AAG ATC ATC AGC AAC AAG GGC<br>Glu Gln Ala Ile Ile Glu Ile Asn Gly Lys Ile Ile Ser Asn Lys Gly<br>        1025               1030             1035 | 1775 |
| AAG GAG AAG CAG GTG GTG CAC CTG GAG AAG GGC AAG CTG GTG CCC ATC<br>Lys Glu Lys Gln Val Val His Leu Glu Lys Gly Lys Leu Val Pro Ile<br>1040               1045             1050             1055 | 1823 |
| AAG ATC GAG TAC CAG AGC GAC ACC AAG TTC AAC ATC GAC AGC AAG ACC<br>Lys Ile Glu Tyr Gln Ser Asp Thr Lys Phe Asn Ile Asp Ser Lys Thr<br>               1060             1065             1070 | 1871 |
| TTC AAG GAG CTG AAG CTT TTC AAG ATC GAC AGC CAG AAC CAG CCC CAG<br>Phe Lys Glu Leu Lys Leu Phe Lys Ile Asp Ser Gln Asn Gln Pro Gln<br>        1075               1080             1085 | 1919 |
| CAG GTG CAG CAG GAC GAG CTG CGC AAC CCC GAG TTC AAC AAG AAG GAG<br>Gln Val Gln Gln Asp Glu Leu Arg Asn Pro Glu Phe Asn Lys Lys Glu<br>               1090             1095             1100 | 1967 |
| AGC CAG GAG TTC CTG GCC AAG CCC AGC AAG ATC AAC CTG TTC ACC CAG<br>Ser Gln Glu Phe Leu Ala Lys Pro Ser Lys Ile Asn Leu Phe Thr Gln<br>        1105               1110             1115 | 2015 |
| CAG ATG AAG CGC GAG ATC GAC GAG GAC ACC GAC ACC GAC GGC GAC AGC<br>Gln Met Lys Arg Glu Ile Asp Glu Asp Thr Asp Thr Asp Gly Asp Ser<br>1120               1125             1130             1135 | 2063 |
| ATC CCC GAC CTG TGG GAG GAG AAC GGC TAC ACC ATC CAG AAC CGC ATC<br>Ile Pro Asp Leu Trp Glu Glu Asn Gly Tyr Thr Ile Gln Asn Arg Ile<br>               1140             1145             1150 | 2111 |
| GCC GTG AAG TGG GAC GAC AGC CTG GCT AGC AAG GGC TAC ACC AAG TTC<br>Ala Val Lys Trp Asp Asp Ser Leu Ala Ser Lys Gly Tyr Thr Lys Phe<br>        1155               1160             1165 | 2159 |
| GTG AGC AAC CCC CTG GAG AGC CAC ACC GTG GGC GAC CCC TAC ACC GAC<br>Val Ser Asn Pro Leu Glu Ser His Thr Val Gly Asp Pro Tyr Thr Asp<br>               1170             1175             1180 | 2207 |
| TAC GAG AAG GCC GCC CGC GAC CTG GAC CTG AGC AAC GCC AAG GAG ACC<br>Tyr Glu Lys Ala Ala Arg Asp Leu Asp Leu Ser Asn Ala Lys Glu Thr<br>        1185               1190             1195 | 2255 |
| TTC AAC CCC CTG GTG GCC GCC TTC CCC AGC GTG AAC GTG AGC ATG GAG<br>Phe Asn Pro Leu Val Ala Ala Phe Pro Ser Val Asn Val Ser Met Glu<br>1200               1205             1210             1215 | 2303 |
| AAG GTG ATC CTG AGC CCC AAC GAG AAC CTG AGC AAC AGC GTG GAG AGC<br>Lys Val Ile Leu Ser Pro Asn Glu Asn Leu Ser Asn Ser Val Glu Ser<br>        1220               1225             1230 | 2351 |
| CAC TCG AGC ACC AAC TGG AGC TAC ACC AAC ACC GAG GGC GCC AGC GTG<br>His Ser Ser Thr Asn Trp Ser Tyr Thr Asn Thr Glu Gly Ala Ser Val<br>               1235             1240             1245 | 2399 |
| GAG GCC GGC ATC GGT CCC AAG GGC ATC AGC TTC GGC GTG AGC GTG AAC<br>Glu Ala Gly Ile Gly Pro Lys Gly Ile Ser Phe Gly Val Ser Val Asn<br>        1250               1255             1260 | 2447 |

```
TAC CAG CAC AGC GAG ACC GTG GCC CAG GAG TGG GGC ACC AGC ACC GGC          2495
Tyr Gln His Ser Glu Thr Val Ala Gln Glu Trp Gly Thr Ser Thr Gly
        1265                1270                1275

AAC ACC AGC CAG TTC AAC ACC GCC AGC GCC GGC TAC CTG AAC GCC AAC          2543
Asn Thr Ser Gln Phe Asn Thr Ala Ser Ala Gly Tyr Leu Asn Ala Asn
1280                1285                1290                1295

GTG CGC TAC AAC AAC GTG GGC ACC GGC GCC ATC TAC GAC GTG AAG CCC          2591
Val Arg Tyr Asn Asn Val Gly Thr Gly Ala Ile Tyr Asp Val Lys Pro
                1300                1305                1310

ACC ACC AGC TTC GTG CTG AAC AAC GAC ACC ATC GCC ACC ATC ACC GCC          2639
Thr Thr Ser Phe Val Leu Asn Asn Asp Thr Ile Ala Thr Ile Thr Ala
        1315                1320                1325

AAG TCG AAT TCC ACC GCC CTG AAC ATC AGC CCC GGC GAG AGC TAC CCC          2687
Lys Ser Asn Ser Thr Ala Leu Asn Ile Ser Pro Gly Glu Ser Tyr Pro
                1330                1335                1340

AAG AAG GGC CAG AAC GGC ATC GCC ATC ACC AGC ATG GAC GAC TTC AAC          2735
Lys Lys Gly Gln Asn Gly Ile Ala Ile Thr Ser Met Asp Asp Phe Asn
        1345                1350                1355

AGC CAC CCC ATC ACC CTG AAC AAG AAG CAG GTG GAC AAC CTG CTG AAC          2783
Ser His Pro Ile Thr Leu Asn Lys Lys Gln Val Asp Asn Leu Leu Asn
1360                1365                1370                1375

AAC AAG CCC ATG ATG CTG GAG ACC AAC CAG ACC GAC GGC GTC TAC AAG          2831
Asn Lys Pro Met Met Leu Glu Thr Asn Gln Thr Asp Gly Val Tyr Lys
                1380                1385                1390

ATC AAG GAC ACC CAC GGC AAC ATC GTG ACG GGC GGC GAG TGG AAC GGC          2879
Ile Lys Asp Thr His Gly Asn Ile Val Thr Gly Gly Glu Trp Asn Gly
        1395                1400                1405

GTG ATC CAG CAG ATC AAG GCC AAG ACC GCC AGC ATC ATC GTC GAC GAC          2927
Val Ile Gln Gln Ile Lys Ala Lys Thr Ala Ser Ile Ile Val Asp Asp
                1410                1415                1420

GGC GAG CGC GTG GCC GAG AAG CGC GTG GCC GCC AAG GAC TAC GAG AAC          2975
Gly Glu Arg Val Ala Glu Lys Arg Val Ala Ala Lys Asp Tyr Glu Asn
        1425                1430                1435

CCC GAG GAC AAG ACC CCC AGC CTG ACC CTG AAG GAC GCC CTG AAG CTG          3023
Pro Glu Asp Lys Thr Pro Ser Leu Thr Leu Lys Asp Ala Leu Lys Leu
1440                1445                1450                1455

AGC TAC CCC GAC GAG ATC AAG GAG ATC GAG GGC TTG CTG TAC TAC AAG          3071
Ser Tyr Pro Asp Glu Ile Lys Glu Ile Glu Gly Leu Leu Tyr Tyr Lys
                1460                1465                1470

AAC AAG CCC ATC TAC GAG AGC AGC GTG ATG ACC TAT CTA GAC GAG AAC          3119
Asn Lys Pro Ile Tyr Glu Ser Ser Val Met Thr Tyr Leu Asp Glu Asn
        1475                1480                1485

ACC GCC AAG GAG GTG ACC AAG CAG CTG AAC GAC ACC ACC GGC AAG TTC          3167
Thr Ala Lys Glu Val Thr Lys Gln Leu Asn Asp Thr Thr Gly Lys Phe
                1490                1495                1500

AAG GAC GTG AGC CAC CTG TAC GAC GTG AAG CTG ACC CCC AAG ATG AAC          3215
Lys Asp Val Ser His Leu Tyr Asp Val Lys Leu Thr Pro Lys Met Asn
        1505                1510                1515

GTG ACC ATC AAG CTG AGC ATC CTG TAC GAC AAC GCC GAG AGC AAC GAC          3263
Val Thr Ile Lys Leu Ser Ile Leu Tyr Asp Asn Ala Glu Ser Asn Asp
1520                1525                1530                1535

AAC AGC ATC GGC AAG TGG ACC AAC ACC AAC ATC GTG AGC GGC GGC AAC          3311
Asn Ser Ile Gly Lys Trp Thr Asn Thr Asn Ile Val Ser Gly Gly Asn
                1540                1545                1550

AAC GGC AAG AAG CAG TAC AGC AGC AAC AAC CCC GAC GCC AAC CTG ACC          3359
Asn Gly Lys Lys Gln Tyr Ser Ser Asn Asn Pro Asp Ala Asn Leu Thr
        1555                1560                1565
```

```
CTG AAC ACC GAC GCC CAG GAG AAG CTG AAC AAG AAC CGC GAC TAC TAC    3407
Leu Asn Thr Asp Ala Gln Glu Lys Leu Asn Lys Asn Arg Asp Tyr Tyr
            1570                1575                1580

ATC AGC CTG TAC ATG AAG AGC GAG AAG AAC ACC CAG TGC GAG ATC ACC    3455
Ile Ser Leu Tyr Met Lys Ser Glu Lys Asn Thr Gln Cys Glu Ile Thr
        1585                1590                1595

ATC GAC GGC GAG ATA TAC CCC ATC ACC ACC AAG ACC GTG AAC GTG AAC    3503
Ile Asp Gly Glu Ile Tyr Pro Ile Thr Thr Lys Thr Val Asn Val Asn
1600                1605                1610                1615

AAG GAC AAC TAC AAG CGC CTG GAC ATC ATC GCC CAC AAC ATC AAG AGC    3551
Lys Asp Asn Tyr Lys Arg Leu Asp Ile Ile Ala His Asn Ile Lys Ser
                1620                1625                1630

AAC CCC ATC AGC AGC CTG CAC ATC AAG ACC AAC GAC GAG ATC ACC CTG    3599
Asn Pro Ile Ser Ser Leu His Ile Lys Thr Asn Asp Glu Ile Thr Leu
            1635                1640                1645

TTC TGG GAC GAC ATA TCG ATT ACC GAC GTC GCC AGC ATC AAG CCC GAG    3647
Phe Trp Asp Asp Ile Ser Ile Thr Asp Val Ala Ser Ile Lys Pro Glu
        1650                1655                1660

AAC CTG ACC GAC AGC GAG ATC AAG CAG ATA TAC AGT CGC TAC GGC ATC    3695
Asn Leu Thr Asp Ser Glu Ile Lys Gln Ile Tyr Ser Arg Tyr Gly Ile
    1665                1670                1675

AAG CTG GAG GAC GGC ATC CTG ATC GAC AAG AAA GGC GGC ATC CAC TAC    3743
Lys Leu Glu Asp Gly Ile Leu Ile Asp Lys Lys Gly Gly Ile His Tyr
1680                1685                1690                1695

GGC GAG TTC ATC AAC GAG GCC AGC TTC AAC ATC GAG CCC CTG CAG AAC    3791
Gly Glu Phe Ile Asn Glu Ala Ser Phe Asn Ile Glu Pro Leu Gln Asn
                1700                1705                1710

TAC GTG ACC AAG TAC GAG GTG ACC TAC AGC AGC GAG CTG GGC CCC AAC    3839
Tyr Val Thr Lys Tyr Glu Val Thr Tyr Ser Ser Glu Leu Gly Pro Asn
            1715                1720                1725

GTG AGC GAC ACC CTG GAG AGC GAC AAG ATT TAC AAG GAC GGC ACC ATC    3887
Val Ser Asp Thr Leu Glu Ser Asp Lys Ile Tyr Lys Asp Gly Thr Ile
        1730                1735                1740

AAG TTC GAC TTC ACC AAG TAC AGC AAG AAC GAG CAG GGC CTG TTC TAC    3935
Lys Phe Asp Phe Thr Lys Tyr Ser Lys Asn Glu Gln Gly Leu Phe Tyr
    1745                1750                1755

GAC AGC GGC CTG AAC TGG GAC TTC AAG ATC AAC GCC ATC ACC TAC GAC    3983
Asp Ser Gly Leu Asn Trp Asp Phe Lys Ile Asn Ala Ile Thr Tyr Asp
1760                1765                1770                1775

GGC AAG GAG ATG AAC GTG TTC CAC CGC TAC AAC AAG TAGATCTGAG         4029
Gly Lys Glu Met Asn Val Phe His Arg Tyr Asn Lys
                1780                1785

CT                                                                 4031
```

(2) INFORMATION FOR SEQ ID NO:50:

(i) SEQUENCE CHARACTERISTICS:
        (A) LENGTH: 1338 amino acids
        (B) TYPE: amino acid
        (D) TOPOLOGY: linear (ii) MOLECULE TYPE: protein (xi) SEQUENCE DESCRIPTION: SEQ ID NO:50:

```
Met Lys Arg Met Glu Gly Lys Leu Phe Met Val Ser Lys Lys Leu Gln
1               5                   10                  15

Val Val Thr Lys Thr Val Leu Leu Ser Thr Val Phe Ser Ile Ser Leu
            20                  25                  30

Leu Asn Asn Glu Val Ile Lys Ala Glu Gln Leu Asn Ile Asn Ser Gln
        35                  40                  45
```

-continued

```
Ser Lys Tyr Thr Asn Leu Gln Asn Leu Lys Ile Thr Asp Lys Val Glu
     50                  55                  60

Asp Phe Lys Glu Asp Lys Glu Lys Ala Lys Glu Trp Gly Lys Glu Lys
 65                  70                  75                  80

Glu Lys Glu Trp Lys Leu Thr Ala Thr Glu Lys Gly Lys Met Asn Asn
                 85                  90                  95

Phe Leu Asp Asn Lys Asn Asp Ile Lys Thr Asn Tyr Lys Glu Ile Thr
                100                 105                 110

Phe Ser Ile Ala Gly Ser Phe Glu Asp Glu Ile Lys Asp Leu Lys Glu
            115                 120                 125

Ile Asp Lys Met Phe Asp Lys Thr Asn Leu Ser Asn Ser Ile Ile Thr
    130                 135                 140

Tyr Lys Asn Val Glu Pro Thr Thr Ile Gly Phe Asn Lys Ser Leu Thr
145                 150                 155                 160

Glu Gly Asn Thr Ile Asn Ser Asp Ala Met Ala Gln Phe Lys Glu Gln
                165                 170                 175

Phe Leu Asp Arg Asp Ile Lys Phe Asp Ser Tyr Leu Asp Thr His Leu
            180                 185                 190

Thr Ala Gln Gln Val Ser Ser Lys Glu Arg Val Ile Leu Lys Val Thr
        195                 200                 205

Val Pro Ser Gly Lys Gly Ser Thr Thr Pro Thr Lys Ala Gly Val Ile
210                 215                 220

Leu Asn Asn Ser Glu Tyr Lys Met Leu Ile Asp Asn Gly Tyr Met Val
225                 230                 235                 240

His Val Asp Lys Val Ser Lys Val Val Lys Gly Val Glu Cys Leu
                245                 250                 255

Gln Ile Glu Gly Thr Leu Lys Lys Ser Leu Asp Phe Lys Asn Asp Ile
                260                 265                 270

Asn Ala Glu Ala His Ser Trp Gly Met Lys Asn Tyr Glu Glu Trp Ala
            275                 280                 285

Lys Asp Leu Thr Asp Ser Gln Arg Glu Ala Leu Asp Gly Tyr Ala Arg
    290                 295                 300

Gln Asp Tyr Lys Glu Ile Asn Asn Tyr Leu Arg Asn Gln Gly Gly Ser
305                 310                 315                 320

Gly Asn Glu Lys Leu Asp Ala Gln Ile Lys Asn Ile Ser Asp Ala Leu
                325                 330                 335

Gly Lys Lys Pro Ile Pro Glu Asn Ile Thr Val Tyr Arg Trp Cys Gly
            340                 345                 350

Met Pro Glu Phe Gly Tyr Gln Ile Ser Asp Pro Leu Pro Ser Leu Lys
        355                 360                 365

Asp Phe Glu Glu Gln Phe Leu Asn Thr Ile Lys Glu Asp Lys Gly Tyr
    370                 375                 380

Met Ser Thr Ser Leu Ser Ser Glu Arg Leu Ala Ala Phe Gly Ser Arg
385                 390                 395                 400

Lys Ile Ile Leu Arg Leu Gln Val Pro Lys Gly Ser Thr Gly Ala Tyr
                405                 410                 415

Leu Ser Ala Ile Gly Gly Phe Ala Ser Glu Lys Glu Ile Leu Leu Asp
            420                 425                 430

Lys Asp Ser Lys Tyr His Ile Asp Lys Val Thr Glu Val Ile Ile Lys
        435                 440                 445

Gly Val Lys Arg Tyr Val Val Asp Ala Thr Leu Leu Thr Asn Ser Arg
    450                 455                 460
```

-continued

```
Gly Pro Ser Thr Pro Pro Thr Pro Ser Pro Ser Thr Pro Pro Thr Pro
465                 470                 475                 480

Ser Asp Ile Gly Ser Thr Met Lys Thr Asn Gln Ile Ser Thr Thr Gln
                485                 490                 495

Lys Asn Gln Gln Lys Glu Met Asp Arg Lys Gly Leu Leu Gly Tyr Tyr
            500                 505                 510

Phe Lys Gly Lys Asp Phe Ser Asn Leu Thr Met Phe Ala Pro Thr Arg
        515                 520                 525

Asp Ser Thr Leu Ile Tyr Asp Gln Gln Thr Ala Asn Lys Leu Leu Asp
    530                 535                 540

Lys Lys Gln Gln Glu Tyr Gln Ser Ile Arg Trp Ile Gly Leu Ile Gln
545                 550                 555                 560

Ser Lys Glu Thr Gly Asp Phe Thr Phe Asn Leu Ser Glu Asp Glu Gln
                565                 570                 575

Ala Ile Ile Glu Ile Asn Gly Lys Ile Ile Ser Asn Lys Gly Lys Glu
            580                 585                 590

Lys Gln Val Val His Leu Glu Lys Gly Lys Leu Val Pro Ile Lys Ile
        595                 600                 605

Glu Tyr Gln Ser Asp Thr Lys Phe Asn Ile Asp Ser Lys Thr Phe Lys
    610                 615                 620

Glu Leu Lys Leu Phe Lys Ile Asp Ser Gln Asn Gln Pro Gln Gln Val
625                 630                 635                 640

Gln Gln Asp Glu Leu Arg Asn Pro Glu Phe Asn Lys Lys Glu Ser Gln
                645                 650                 655

Glu Phe Leu Ala Lys Pro Ser Lys Ile Asn Leu Phe Thr Gln Gln Met
            660                 665                 670

Lys Arg Glu Ile Asp Glu Asp Thr Asp Thr Asp Gly Asp Ser Ile Pro
        675                 680                 685

Asp Leu Trp Glu Glu Asn Gly Tyr Thr Ile Gln Asn Arg Ile Ala Val
    690                 695                 700

Lys Trp Asp Asp Ser Leu Ala Ser Lys Gly Tyr Thr Lys Phe Val Ser
705                 710                 715                 720

Asn Pro Leu Glu Ser His Thr Val Gly Asp Pro Tyr Thr Asp Tyr Glu
                725                 730                 735

Lys Ala Ala Arg Asp Leu Asp Leu Ser Asn Ala Lys Glu Thr Phe Asn
            740                 745                 750

Pro Leu Val Ala Ala Phe Pro Ser Val Asn Val Ser Met Glu Lys Val
        755                 760                 765

Ile Leu Ser Pro Asn Glu Asn Leu Ser Asn Ser Val Glu Ser His Ser
    770                 775                 780

Ser Thr Asn Trp Ser Tyr Thr Asn Thr Glu Gly Ala Ser Val Glu Ala
785                 790                 795                 800

Gly Ile Gly Pro Lys Gly Ile Ser Phe Gly Val Ser Val Asn Tyr Gln
                805                 810                 815

His Ser Glu Thr Val Ala Gln Glu Trp Gly Thr Ser Thr Gly Asn Thr
            820                 825                 830

Ser Gln Phe Asn Thr Ala Ser Ala Gly Tyr Leu Asn Ala Asn Val Arg
        835                 840                 845

Tyr Asn Asn Val Gly Thr Gly Ala Ile Tyr Asp Val Lys Pro Thr Thr
    850                 855                 860

Ser Phe Val Leu Asn Asn Asp Thr Ile Ala Thr Ile Thr Ala Lys Ser
865                 870                 875                 880
```

-continued

```
Asn Ser Thr Ala Leu Asn Ile Ser Pro Gly Glu Ser Tyr Pro Lys Lys
                885                 890                 895

Gly Gln Asn Gly Ile Ala Ile Thr Ser Met Asp Asp Phe Asn Ser His
            900                 905                 910

Pro Ile Thr Leu Asn Lys Lys Gln Val Asp Asn Leu Leu Asn Asn Lys
            915                 920                 925

Pro Met Met Leu Glu Thr Asn Gln Thr Asp Gly Val Tyr Lys Ile Lys
            930                 935                 940

Asp Thr His Gly Asn Ile Val Thr Gly Gly Glu Trp Asn Gly Val Ile
945                 950                 955                 960

Gln Gln Ile Lys Ala Lys Thr Ala Ser Ile Ile Val Asp Asp Gly Glu
                965                 970                 975

Arg Val Ala Glu Lys Arg Val Ala Ala Lys Asp Tyr Glu Asn Pro Glu
            980                 985                 990

Asp Lys Thr Pro Ser Leu Thr Leu Lys Asp Ala Leu Lys Leu Ser Tyr
            995                 1000                1005

Pro Asp Glu Ile Lys Glu Ile Glu Gly Leu Leu Tyr Tyr Lys Asn Lys
            1010                1015                1020

Pro Ile Tyr Glu Ser Ser Val Met Thr Tyr Leu Asp Glu Asn Thr Ala
1025                1030                1035                1040

Lys Glu Val Thr Lys Gln Leu Asn Asp Thr Thr Gly Lys Phe Lys Asp
                1045                1050                1055

Val Ser His Leu Tyr Asp Val Lys Leu Thr Pro Lys Met Asn Val Thr
            1060                1065                1070

Ile Lys Leu Ser Ile Leu Tyr Asp Asn Ala Glu Ser Asn Asp Asn Ser
            1075                1080                1085

Ile Gly Lys Trp Thr Asn Thr Asn Ile Val Ser Gly Gly Asn Asn Gly
            1090                1095                1100

Lys Lys Gln Tyr Ser Ser Asn Asn Pro Asp Ala Asn Leu Thr Leu Asn
1105                1110                1115                1120

Thr Asp Ala Gln Glu Lys Leu Asn Lys Asn Arg Asp Tyr Tyr Ile Ser
            1125                1130                1135

Leu Tyr Met Lys Ser Glu Lys Asn Thr Gln Cys Glu Ile Thr Ile Asp
            1140                1145                1150

Gly Glu Ile Tyr Pro Ile Thr Thr Lys Thr Val Asn Val Asn Lys Asp
            1155                1160                1165

Asn Tyr Lys Arg Leu Asp Ile Ile Ala His Asn Ile Lys Ser Asn Pro
            1170                1175                1180

Ile Ser Ser Leu His Ile Lys Thr Asn Asp Glu Ile Thr Leu Phe Trp
1185                1190                1195                1200

Asp Asp Ile Ser Ile Thr Asp Val Ala Ser Ile Lys Pro Glu Asn Leu
            1205                1210                1215

Thr Asp Ser Glu Ile Lys Gln Ile Tyr Ser Arg Tyr Gly Ile Lys Leu
            1220                1225                1230

Glu Asp Gly Ile Leu Ile Asp Lys Lys Gly Gly Ile His Tyr Gly Glu
            1235                1240                1245

Phe Ile Asn Glu Ala Ser Phe Asn Ile Glu Pro Leu Gln Asn Tyr Val
            1250                1255                1260

Thr Lys Tyr Glu Val Thr Tyr Ser Ser Glu Leu Gly Pro Asn Val Ser
1265                1270                1275                1280

Asp Thr Leu Glu Ser Asp Lys Ile Tyr Lys Asp Gly Thr Ile Lys Phe
            1285                1290                1295
```

```
                                      -continued

Asp Phe Thr Lys Tyr Ser Lys Asn Glu Gln Gly Leu Phe Tyr Asp Ser
            1300                1305                1310

Gly Leu Asn Trp Asp Phe Lys Ile Asn Ala Ile Thr Tyr Asp Gly Lys
            1315                1320                1325

Glu Met Asn Val Phe His Arg Tyr Asn Lys
    1330                1335
```

GENES ENCODING INSECTICIDAL PROTEINS

This is a continuation application of U.S. application Ser. No. 08/469,334, filed Jun. 6, 1995, which is a divisional application of U.S. application Ser. No. 08/463,483, filed Jun. 5, 1995, issued as U.S. Pat. No. 5,849,870, which is a continuation-in-part application of U.S. application Ser. No. 08/314,594 filed Sep. 28, 1994, now abandoned, which is continuation-in-part application of U.S. application Ser. No. 08/218,018 filed Mar. 23, 1994, now abandoned, which is a continuation-in-part of U.S. application Ser. No. 08/037,057 filed Mar. 25, 1993, now abandoned, the disclosures of which are herein incorporated by reference.

FIELD OF THE INVENTION

The present invention is drawn to methods and compositions for controlling plant and non-plant pests.

BACKGROUND OF THE INVENTION

Insect pests are a major factor in the loss of the world's commercially important agricultural crops. Broad spectrum chemical pesticides have been used extensively to control or eradicate pests of agricultural importance. There is, however, substantial interest in developing effective alternative pesticides.

Microbial pesticides have played an important role as alternatives to chemical pest control. The most extensively used microbial product is based on the bacterium *Bacillus thuringiensis* (Bt). Bt is a gram-positive spore forming Bacillus which produces an insecticidal crystal protein (ICP) during sporulation.

Numerous varieties of Bt are known that produce more than 25 different but related ICP's. The majority of ICP's made by Bt are toxic to larvae of certain insects in the orders epidoptera, Diptera and Coleoptera. In general, when an ICP is ingested by a susceptible insect the crystal is solubilized and transformed into a toxic moiety by the insect gut proteases. None of the ICP's active against coleopteran larvae such as Colorado potato beetle (*Leptinotarsa decemlineata*) or Yellow mealworm (*Tenebrio molitor*) have demonstrated significant effects on members of the genus Diabrotica particularly *Diabrotica virgifera virgifera*, the western corn rootworm (WCRW) or *Diabrotica longicornis barberi*, the northern corn rootworm.

*Bacillus cereus* (Bc) is closely related to Bt. A major distinguishing characteristic is the absence of a parasporal crystal in Bc. Bc is a widely distributed bacterium that is commonly found in soil and has been isolated from a variety of foods and drugs. The organism has been implicated in the spoilage of food.

Although Bt has been very useful in controlling insect pests, there is a need to expand the number of potential biological control agents.

BRIEF DESCRIPTION OF THE FIGURE

FIG. 1: Characterization of pCIB6022. Boxed regions represent the extent of VIP1A(a) and VIP2A(a). White box represents the portion of VIP1 encoding the 80 kDa peptide observed in Bacillus. Dark box represents the N-terminal 'propeptide' of VIP1A(a) predicted by DNA sequence analysis. Stippled box represents the VIP2A(a) coding region. Large 'X' represents the location of the frameshift mutation introduced into VIP1A(a). Arrows represent constructs transcribed by the beta-galactosidase promoter. Restriction Sites: C-Cla I; X-Xba I; S-Sca I; RI- Eco RI; B-Bgl II; RV-Eco RV.

SUMMARY OF THE INVENTION

The present invention is drawn to compositions and methods for controlling plant and non-plant pests. Particularly, new pesticidal proteins are disclosed which are isolatable from the vegetative growth stage of Bacillus. Bacillus strains, proteins, and genes encoding the proteins are provided.

The methods and compositions of the invention may be used in a variety of systems for controlling plant and non-plant pests.

DETAILED DESCRIPTION OF THE INVENTION

Compositions and methods for controlling plant pests are provided. In particular, novel pesticidal proteins are provided which are produced during vegetative growth of Bacillus strains. The proteins are useful as pesticidal agents.

The present invention recognizes that pesticidal proteins are produced during vegetative growth of Bacillus strains. To date, all of the identified pesticidal proteins of the invention are secreted from the cell. Prior to the present invention, there was no recognition in the art that a class or classes of pesticidal proteins are produced during vegetative growth of Bacillus. The only report was of a single mosquitocidal toxin from *Bacillus sphaericus* SSII-1 by Myers and Yousten in *Infect. Immun.*, 19:1047–1053 (1978). Having recognized that such a class exists, the present invention embraces all vegetative insecticidal proteins, hereinafter referred to as VIPs, except for the mosquitocidal toxin from *B. sphaericus*.

The present VIPs are not abundant after sporulation and are particularly expressed during log phase growth before stationary phase. For the purpose of the present invention vegetative growth is defined as that period of time before the onset of sporulation. Genes encoding such VIPs can be isolated, cloned and transformed into various delivery vehicles for use in pest management programs.

For purposes of the present invention, pests include but are not limited to insects, fungi, bacteria, nematodes, mites, ticks, protozoan pathogens, animal-parasitic liver flukes, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera and Lepidoptera.

Tables 1–10 gives a list of pests associated with major crop plants and pests of human and veterinary importance. Such pests are included within the scope of the present invention.

TABLE 1

| Lepidoptera (Butterflies and Moths) | |
|---|---|
| Maize | Sunflower |
| *Ostrinia nubilalis*, European corn borer | *Suleima helianthana*, sunflower bud moth |
| *Agrotis ipsilon*, black cutworm | *Homoeosoma electellum*, sunflower moth |

TABLE 1-continued

Lepidoptera (Butterflies and Moths)

| | |
|---|---|
| *Helicoverpa zea*, corn earworm | |
| *Spodoptera frugiperda*, fall armyworm | Cotton |
| *Diatraea grandiosella*, southwestern corn borer | *Heliothis virescens*, cotton boll worm |
| *Elasmopalpus lignosellus*, lesser cornstalk borer | *Helicoverpa zea*, cotton bollworm |
|  | *Spodoptera exigua*, beet armyworm |
| *Diatraea saccharalis*, sugarcane borer | *Pectinophora gossypiella*, pink bollworm |
|  | Rice |
| Sorghum | *Diatraea saccharalis*, sugarcane borer |
| *Chilo partellus*, sorghum borer | |
| *Spodoptera frugiperda*, fall armyworm | *Spodoptera frugiperda*, fall armyworm |
| *Helicoverpa zea*, corn earworm | *Helicoverpa zea*, corn earworm |
|  | Soybean |
| *Elasmopalpus lignosellus*, lesser cornstalk borer | *Pseudoplusia includens*, soybean looper |
| *Feltia subterranea*, granulate cutworm | *Anticarsia gemmatalis*, velvetbean caterpillar |
| Wheat | *Plathypena scabra*, green cloverworm |
| *Pseudaletia unipunctata*, army worm | *Ostrinia nubilalis*, European corn borer |
| *Spodoptera frugiperda*, fall armyworm | *Agrotis ipsilon*, black cutworm |
|  | *Spodoptera exigua*, beet armyworm |
| *Elasmopalpus lignosellus*, lesser cornstalk borer | *Heliothis virescens*, cotton boll worm |
| *Agrotis orthogonia*, pale western cutworm | *Helicoverpa zea*, cotton bollworm |
| *Elasmopalpus lignosellus*, lesser cornstalk borer | Barley |
|  | *Ostrinia nubilalis*, European corn borer |
|  | *Agrotis ipsilon*, black cutworm |

TABLE 2

Coleoptera (Beetles)

Maize

*Diabrotica virgifera* virgifera, western corn rootworm
*Diabrotica longicornis* barberi, northern corn rootworm
*Diabrotica undecimpunctata* howardi, southern corn rootworm
*Melanotus spp.*, wireworms
*Cyclocephala borealis*, northern masked chafer (white grub)
*Cyclocephala immaculata*, southern masked chafer (white grub)
*Popillia japonica*, Japanese beetle
*Chaetocnema pulicaria*, corn flea beetle
*Sphenophorus maidis*, maize billbug Sorghum

*Phyllophaga crinita*, white grub
Eleodes, Conoderus, and *Aeolus spp.*, wireworms
*Oulema melanopus*, cereal leaf beetle
*Chaetocnema pulicaria*, corn flea beetle
*Sphenophorus maidis*, maize billbug Wheat

*Oulema melanopus*, cereal leaf beetle
*Hypera punctata*, clover leaf weevil
*Diabrotica undecimpunctata* howardi, southern corn rootworm

TABLE 2-continued

Coleoptera (Beetles)

Sunflower

*Zygogramma exclamationis*, sunflower beetle
*Bothyrus gibbosus*, carrot beetle

Cotton

*Anthonomus grandis*, boll weevil

Rice

*Colaspis brunnea*, grape colaspis
*Lissorhoptrus oryzophilus*, rice water weevil
*Sitophilus oryzae*, rice weevil Soybean

*Epilachna varivestis*, Mexican bean beetle

TABLE 3

Homoptera (Whiteflies, Aphids etc..)

Maize

*Rhopalosiphum maidis*, corn leaf aphid
*Anuraphis maidiradicis*, corn root aphid Sorghum

*Rhopalosiphum maidis*, corn leaf aphid
*Sipha flava*, yellow sugarcane aphid

Wheat

Russian wheat aphid
*Schizaphis graminum*, greenbug
*Macrosiphum avenae*, English grain aphid Cotton

*Aphis gossypii*, cotton aphid
*Pseudatomoscelis seriatus*, cotton fleahopper
*Trialeurodes abutilonea*, bandedwinged whitefly Rice

*Nephotettix nigropictus*, rice leafhopper

Soybean

*Myzus persicae*, green peach aphid
*Empoasca fabae*, potato leafhopper

Barley

*Schizaphis graminum*, greenbug

Oil Seed Rape

*Brevicoryne brassicae*, cabbage aphid

TABLE 4

Hemiptera (Bugs)

Maize

*Blissus leucopterus* leucopterus, chinch bug

Sorghum

*Blissus leucopterus* leucopterus, chinch bug

Cotton

*Lygus lineolaris*, tarnished plant bug

Rice

*Blissus leucopterus* leucopterus, chinch bug
*Acrostenum hilare*, green stink bug Soybean

*Acrostenum hilare*, green stink bug

TABLE 4-continued

Hemiptera (Bugs)

Barley

*Blissus leucopterus* leucopterus, chinch bug
*Acrostenum hilare*, green stink bug
*Euschistus servus*, brown stink bug

TABLE 5

Orthontera (Grasshoppers, Crickets, and Cockroaches)

Maize

*Melanoplus femurrubrum*, redlegged grasshopper
*Melanoplus sanguinipes*, migratory grasshopper
Wheat

*Melanoplus femurrubrum*, redlegged grasshopper
*Melanoplus differentialis*, differential grasshopper
*Melanoplus sanguinipes*, migratory grasshopper
Cotton

*Melanoplus femurrubrum*, redlegged grasshopper
*Melanoplus differentialis*, differential grasshopper
Soybean

*Melanoplus femurrubrum*, redlegged grasshopper
*Melanoplus differentialis*, differential grasshopper
Structural/Household

*Periplaneta americana*, American cockroach
*Blattella germanica*, German cockroach
*Blatta orientalis*, oriental cockroach

TABLE 6

Diptera (Flies and Mosquitoes)

Maize

*Hylemya platura*, seedcorn maggot
*Agromyza parvicornis*, corn blotch leafminer
Sorghum

*Contarinia sorghicola*, sorghum midge
Wheat

*Mayetiola destructor*, Hessian fly
*Sitodiplosis mosellana*, wheat midge
*Meromyza americana*, wheat stem maggot
*Hylemya coarctata*, wheat bulb fly
Sunflower

*Neolasioptera murtfeldtiana*, sunflower seed midge
Soybean

*Hylemya platura*, seedcorn maggot
Barley

*Hylemya platura*, seedcorn maggot
*Mayetiola destructor*, Hessian fly
Insects attacking humans and animals and disease carriers

*Aedes aegypti*, yellowfever mosquito
*Aedes albopictus*, forest day mosquito
*Phlebotomus papatasii*, sand fly
*Musca domestica*, house fly
*Tabanus atratus*, black horse fly
*Cochliomyia hominivorax*, screwworm fly

TABLE 7

Thysanoptera (Thrips)

Maize

*Anaphothrips obscurus*, grass thrips
Wheat

*Frankliniella fusca*, tobacco thrips
Cotton

*Thrips tabaci*, onion thrips
*Frankliniella fusca*, tobacco thrips
Soybean

*Sericothrips variabilis*, soybean thrips
*Thrips tabaci*, onion thrips

TABLE 8

Hymenoptera (Sawflies, Ants, Wasps, etc.)

Maize

*Solenopsis milesta*, thief ant
Wheat

*Cephus cinctus*, wheat stem sawfly

TABLE 9

Other Orders and Representative Species

Dermaptera (Earwigs)
*Forficula auricularia*, European earwig
Isoptera (Termites)
*Reticulitermes flavipes*, eastern subterranean termite
Mallophaga (Chewing Lice)
*Cuclotogaster heterographa*, chicken head louse
*Bovicola bovis*, cattle biting louse
Anoplura (Sucking Lice)
*Pediculus humanus*, head and body louse
Siphonaptera (Fleas)
*Ctenocephalides felis*, cat flea

TABLE 10

Acari (Mites and Ticks)

Maize

*Tetranychus urticae*, twospotted spider mite
Sorghum

*Tetranychus cinnabarinus*, carmine spider mite
*Tetranychus urticae*, twospotted spider mite
Wheat

*Aceria tulipae*, wheat curl mite
Cotton

*Tetranychus cinnabarinus*, carmine spider mite
*Tetranychus urticae*, twospotted spider mite
Soybean

*Tetranychus turkestani*, strawberry spider mite
*Tetranychus urticae*, twospotted spider mite
Barley

*Petrobia latens*, brown wheat mite

TABLE 10-continued

Acari (Mites and Ticks)

Important human and animal Acari

*Demacentor variabilis*, American dog tick
*Argas persicus*, fowl tick
*Dermatophagoides farinae*, American house dust mite
*Dermatophagoides pteronyssinus*, European house dust mite Now that it has been recognized that pesticidal proteins can be isolated from the vegetative growth phase of Bacillus, other strains can be isolated by standard techniques and tested for activity against particular plant and non-plant pests. Generally Bacillus strains can be isolated from any environmental sample, including soil, plant, insect, grain elevator dust, and other sample material, etc., by methods known in the art. See, for example, Travers et al. (1987) Appl. Environ. Microbiol. 53:1263–1266; Saleh et al. (1969) Can J. Microbiol. 15:1101–1104; DeLucca et al. (1981) Can. J. Microbiol. 27:865–870; and Norris, et al. (1981) "The genera Bacillus and Sporolactobacillus," In Starr et al. (eds.), The Prokaryotes: A Handbook on Habitats, Isolation, and Identification of Bacteria, Vol. II, Springer-Verlog Berlin Heidelberg. After isolation, strains can be tested for pesticidal activity during vegetative growth. In this manner, new pesticidal proteins and strains can be identified.

Such Bacillus microorganisms which find use in the invention include *Bacillus cereus* and *Bacillus thuringiensis*, as well as those Bacillus species listed in Table 11.

TABLE 11

List of Bacillus species

| | Unassigned Strains |
|---|---|
| Morphological Group 1 | |
| *B. megaterium* | Subgroup A |
| *B. cereus** | *B. apiarus** |
| *B. cereus var.* mycoides | *B. filicolonicus* |
| *B. thuringiensis** | *B. thiaminolyticus* |
| *B. licheniformis* | *B. alcalophilus* |
| *B. subtilis** | |
| *B. pumilus* | Subgroup B |
| *B. firmus** | *B. cirroflagellosus* |
| *B. coagulans* | *B. chitinosporus* |
| | *B. lentus* |
| Morphological Group 2 | |
| *B. polymyxa* | Subgroup C |
| *B. macerans* | *B. badius* |
| *B. circulans* | *B. aneurinolyticus* |
| *B. stearothermophilus* | *B. macroides* |
| *B. alvei** | *B. freundenreichii* |
| *B. laterosporus** | |
| *B. brevis* | Subgroup D |
| *B. pulvifaciens* | *B. pantothenticus* |
| *B. popilliae** | *B. epiphytus* |
| *B. lentimorbus** | |
| *B. larvae** | Subgroup E1 |
| | *B. aminovorans* |
| Morphological Group 3 | *B. globisporus* |
| *B. sphaericus** | *B. insolitus* |
| *B. pasteurii* | *B. psychrophilus* |

TABLE 11-continued

List of Bacillus species

| Unassigned Strains |
|---|
| Subgroup E2 |
| *B. psychrosaccharolyticus* |
| *B. macquariensis* |

* = Those Bacillus strains that have been previously found associated with insects Grouping according to Parry, J. M. et al. (1983) Color Atlas of Bacillus species, Wolfe Medical Publications, London.

In accordance with the present invention, the pesticidal proteins produced during vegetative growth can be isolated from Bacillus. In one embodiment, insecticidal proteins produced during vegetative growth, can be isolated. Methods for protein isolation are known in the art. Generally, proteins can be purified by conventional chromatography, including gel-filtration, ion-exchange, and immunoaffinity chromatography, by high-performance liquid chromatography, such as reversed-phase high-performance liquid chromatography, ion-exchange high-performance liquid chromatography, size-exclusion high-performance liquid chromatography, high-performance chromatofocusing and hydrophobic interaction chromatography, etc., by electrophoretic separation, such as one-dimensional gel electrophoresis, two-dimensional gel electrophoresis, etc. Such methods are known in the art. See for example *Current Protocols in Molecular Biology*, Vols. 1 and 2, Ausubel et al. (eds.), John Wiley & Sons, NY (1988). Additionally, antibodies can be prepared against substantially pure preparations of the protein. See, for example, Radka et al. (1983) *J. Immunol.* 128:2804; and Radka et al. (1984) *Immunogenetics* 19:63. Any combination of methods may be utilized to purify protein having pesticidal properties. As the protocol is being formulated, pesticidal activity is determined after each purification step.

Such purification steps will result in a substantially purified protein fraction. By "substantially purified" or "substantially pure" is intended protein which is substantially free of any compound normally associated with the protein in its natural state. "Substantially pure" preparations of protein can be assessed by the absence of other detectable protein bands following SDS-PAGE as determined visually or by densitometry scanning. Alternatively, the absence of other amino-terminal sequences or N-terminal residues in a purified preparation can indicate the level of purity. Purity can be verified by rechromatography of "pure" preparations showing the absence of other peaks by ion exchange, reverse phase or capillary electrophoresis. The terms "substantially pure" or "substantially purified" are not meant to exclude artificial or synthetic mixtures of the proteins with other compounds. The terms are also not meant to exclude the presence of minor impurities which do not interfere with the biological activity of the protein, and which may be present, for example, due to incomplete purification.

Once purified protein is isolated, the protein, or the polypeptides of which it is comprised, can be characterized and sequenced by standard methods known in the art. For example, the purified protein, or the polypeptides of which it is comprised, may be fragmented as with cyanogen bromide, or with proteases such as papain, chymotrypsin, trypsin, lysyl-C endopeptidase, etc. (Oike et al. (1982) *J. Biol. Chem.* 257:9751–9758; Liu et al. (1983) *Int. J. Pept.*

Protein Res. 21:209–215). The resulting peptides are separated, preferably by HPLC, or by resolution of gels and electroblotting onto PVDF membranes, and subjected to amino acid sequencing. To accomplish this task, the peptides are preferably analyzed by automated sequenators. It is recognized that N-terminal, C-terminal, or internal amino acid sequences can be determined. From the amino acid sequence of the purified protein, a nucleotide sequence can be synthesized which can be used as a probe to aid in the isolation of the gene encoding the pesticidal protein.

It is recognized that the pesticidal proteins may be oligomeric and will vary in molecular weight, number of protomers, component peptides, activity against particular pests, and in other characteristics. However, by the methods set forth herein, proteins active against a variety of pests may be isolated and characterized.

Once the purified protein has been isolated and characterized it is recognized that it may be altered in various ways including amino acid substitutions, deletions, truncations, and insertions. Methods for such manipulations are generally known in the art. For example, amino acid sequence variants of the pesticidal proteins can be prepared by mutations in the DNA. Such variants will possess the desired pesticidal activity. Obviously, the mutations that will be made in the DNA encoding the variant must not place the sequence out of reading frame and preferably will not create complementary regions that could produce secondary mRNA structure. See, EP Patent Application Publication No. 75,444.

In this manner, the present invention encompasses the pesticidal proteins as well as components and fragments thereof. That is, it is recognized that component protomers, polypeptides or fragments of the proteins may be produced which retain pesticidal activity. These fragments include truncated sequences, as well as N-terminal, C-terminal, internal and internally deleted amino acid sequences of the proteins.

Most deletions, insertions, and substitutions of the protein sequence are not expected to produce radical changes in the characteristics of the pesticidal protein. However, when it is difficult to predict the exact effect of the substitution, deletion, or insertion in advance of doing. so, one skilled in the art will appreciate that the effect will be evaluated by routine screening assays.

The proteins or other component polypeptides described herein may be used alone or in combination. That is, several proteins may be used to control different insect pests.

Some proteins are single polypeptide chains while many proteins consist of more than one polypeptide chain, i.e., they are oligomeric. Additionally, some VIPs are pesticidally active as oligomers. In these instances, additional protomers are utilized to enhance the pesticidal activity or to activate pesticidal proteins. Those protomers which enhance or activate are referred to as auxiliary proteins. Auxiliary proteins activate or enhance a pesticidal protein by interacting with the pesticidal protein to form an oligomeric protein having increased pesticidal activity compared to that observed in the absence of the auxiliary protein.

Auxiliary proteins activate or increase the activity of pesticidal proteins such as the VIP1 protein from AB78. Such auxiliary proteins are exemplified by, but not limited to, the VIP2 protein from AB78. As demonstrated in the Experimental section of the application, auxiliary proteins can activate a number of pesticidal proteins. Thus, in one embodiment of the invention, a plant, Parent 1, can be transformed with an auxiliary protein. This Parent 1 can be crossed with a number of Parent 2 plants transformed with one or more pesticidal proteins whose pesticidal activities are activated by the auxiliary protein.

The pesticidal proteins of the invention can be used in combination with Bt endotoxins or other insecticidal proteins to increase insect target range. Furthermore, the use of the VIPs of the present invention in combination with Bt δ-endotoxins or other insecticidal principles of a distinct nature has particular utility for the prevention and/or management of insect resistance. Other insecticidal principles include protease inhibitors (both serine and cysteine types), lectins, α-amylase and peroxidase. In one preferred embodiment, expression of VIPs in a transgenic plant is accompanied by the expression of one or more Bt δ-endotoxins. This co-expression of more than one insecticidal principle in the same transgenic plant can be achieved by genetically engineering a plant to contain and express all the genes necessary. Alternatively, a plant, Parent 1, can be genetically engineered for the expression of VIPs. A second plant, Parent 2, can be genetically engineered for the expression of Bt δ-endotoxin. By crossing Parent 1 with Parent 2, progeny plants are obtained which express all the genes introduced into Parents 1 and 2. Particularly preferred Bt δ-endotoxins are those disclosed in U.S. Pat. No. 5,625,136, herein incorporated by reference.

A substantial number of cytotoxic proteins, though not all, are binary in action. Binary toxins typically consist of two protein domains, one called the A domain and the other called the B domain (see *Sourcebook of Bacterial Protein Toxins*, J. E. Alouf and J. H. Freer eds.(1991) Academic Press). The A domain possesses a potent cytotoxic activity. The B domain binds an external cell surface receptor before being internalized. Typically, the cytotoxic A domain must be escorted to the cytoplasm by a translocation domain. Often the A and B domains are separate polypeptides or protomers, which are associated by a protein-protein interaction or a di-sulfide bond. However, the toxin can be a single polypeptide which is proteolytically processed within the cell into two domains as in the case for Pseudomonas exotoxin A. In summary binary toxins typically have three important domains, a cytotoxic A domain, a receptor binding B domain and a translocation domain. The A and B domain are often associated by protein-protein interacting domains.

The receptor binding domains of the present invention are useful for delivering any protein, toxin, enzyme, transcription factor, nucleic acid, chemical or any other factor into target insects having a receptor recognized by the receptor binding domain of the binary toxins described in this patent. Similarly, since binary toxins have translocation domains which penetrate phosopholipid bilayer membranes and escort cytotoxins across those membranes, such translocation domains may be useful in escorting any protein, toxin, enzyme, transcription factor, nucleic acid, chemical or any other factor across a phospholipid bilayer such as the plasma membrane or a vesicle membrane. The translocation domain may itself perforate membranes, thus having toxic or insecticidal properties. Further, all binary toxins have cytotoxic domains; such a cytotoxic domain may be useful as a lethal protein, either alone or when delivered into any target cell(s) by any means.

Finally, since binary toxins comprised of two polypeptides often form a complex, it is likely that there are protein-protein interacting regions within the components of the binary toxins of the invention. These protein-protein interacting domains may be useful in forming associations between any combination of toxins, enzymes, transcription factors, nucleic acids, antibodies, cell binding moieties, or any other chemicals, factors, proteins or protein domains.

Toxins, enzymes, transcription factors, antibodies, cell binding moieties or other protein domains can be fused to pesticidal or auxiliary proteins by producing in frame genetic fusions which, when translated by ribosomes, would produce a fusion protein with the combined attributes of the VIP and the other component used in the fusion. Furthermore, if the protein domain fused to the VIP has an affinity for another protein, nucleic acid, carbohydrate, lipid, or other chemical or factor, then a three-component complex can be formed. This complex will have the attributes of all of its components. A similar rationale can be used for producing four or more component complexes. These complexes are useful as insecticidal toxins, pharmaceuticals, laboratory reagents, and diagnostic reagents, etc. Examples where such complexes are currently used are fusion toxins for potential cancer therapies, reagents in ELISA assays and immunoblot analysis.

One strategy of altering pesticidal or auxiliary proteins is to fuse a 15-amino-acid "S-tag" to the protein without destroying the insect cell binding domain(s), translocation domains or protein-protein interacting domains of the proteins. The S-tag has a high affinity ($K_d=10^{-9}$ M) for a ribonuclease S-protein, which, when bound to the S-tag, forms an active ribonuclease (See F. M. Richards and H. W. Wyckoff (1971) in "The Enzymes", Vol. IV (Boyer, P.D. ed.). pp. 647–806. Academic Press, New York). The fusion can be made in such a way as to destroy or remove the cytotoxic activity of the pesticidal or auxiliary protein, thereby replacing the VIP cytotoxic activity with a new cytotoxic ribonuclease activity. The final toxin would be comprised of the S-protein, a pesticidal protein and an auxiliary protein, where either the pesticidal protein or the auxiliary protein is produced as translational fusions with the S-tag. Similar strategies can be used to fuse other potential cytotoxins to pesticidal or auxiliary proteins including (but not limited to) ribosome inactivating proteins, insect hormones, hormone receptors, transcription factors, proteases, phosphatases, Pseudomonas exotoxin A, or any other protein or chemical factor that is lethal when delivered into cells. Similarly, proteins can be delivered into cells which are not lethal, but might alter cellular biochemistry or physiology.

The spectrum of toxicity toward different species can be altered by fusing domains to pesticidal or auxiliary proteins which recognize cell surface receptors from other species. Such domains might include (but are not limited to) antibodies, transferrin, hormones, or peptide sequences isolated from phage displayed affinity selectable. libraries. Also, peptide sequences which are bound to nutrients, vitamins, hormones, or other chemicals that are transported into cells could be used to alter the spectrum of toxicity. Similarly, any other protein or chemical which binds a cell surface receptor or the membrane and could be internalized might be used to alter the spectrum of activity of VIP1 and VIP2.

The pesticidal proteins of the present invention are those proteins which confer a specific pesticidal property. Such proteins may vary in molecular weight, having component polypeptides at least a molecular weight of 30 kDa or greater, preferably about 50 kDa or greater.

The auxiliary proteins of the invention may vary in molecular weight, having at least a molecular weight of about 15 kDa or greater, preferably about 20 kDa or greater; more preferably, about 30 kDa or greater. The auxiliary proteins themselves may have component polypeptides.

It is possible that the pesticidal protein and the auxiliary protein may be components of a multimeric, insecticidal protein. Such an insecticidal protein which includes the auxiliary proteins as one or more of its component polypeptides may vary in molecular weight, having at least a molecular weight of 50 kDa up to at least 200 kDa, preferably about 100 kDa to 150 kDa.

An auxiliary protein may be used in combination with the pesticidal proteins of the invention to enhance activity or to activate the pesticidal protein. To determine whether the auxiliary protein will affect activity, the pesticidal protein can be expressed alone and in combination with the auxiliary protein and the respective activities compared in feeding assays for pesticidal activity.

It may be beneficial to screen strains for potential pesticidal activity by testing activity of the strain alone and in combination with the auxiliary protein. In some instances an auxiliary protein in combination with the native proteins of the strains yields pesticidal activity where none is seen in the absence of an auxiliary protein.

The auxiliary protein can be modified, as described above, by various methods known in the art. Therefore, for purposes of the invention, the term "Vegetative Insecticidal Protein" (VIP) encompasses those proteins produced during vegetative growth which alone or in combination can be used for pesticidal activity. This includes pesticidal proteins, auxiliary proteins and those proteins which demonstrate activity only in the presence of the auxiliary protein or the polypeptide components of these proteins.

It is recognized that there are alternative methods available to obtain the nucleotide and amino acid sequences of the present proteins. For example, to obtain the nucleotide sequence encoding the pesticidal protein, cosmid clones, which express the pesticidal protein, can be isolated from a genomic library. From larger active cosmid clones, smaller subclones can be made and tested for activity. In this manner, clones which express an active pesticidal protein can be sequenced to determine the nucleotide sequence of the gene. Then, an amino acid sequence can be deduced for the protein. For general molecular methods, see, for example, Molecular Cloning, A Laboratory Manual, Second Edition, Vols. 1–3, Sambrook et al. (eds.) Cold Spring Harbor Laboratory Press, Cold Spring Harbor, N.Y. (1999), and the references cited therein.

The present invention also encompasses nucleotide sequences from organisms other than Bacillus, where the nucleotide sequences are isolatable by hybridization with the Bacillus nucleotide sequences of the invention. Proteins encoded by such nucleotide sequences can be tested for pesticidal activity. The invention also encompasses the proteins encoded by the nucleotide sequences. Furthermore, the invention encompasses proteins obtained from organisms other than Bacillus wherein the protein cross-reacts with antibodies raised against the proteins of the invention. Again the isolated proteins can be assayed for pesticidal activity by the methods disclosed herein or others well-known in the art.

Once the nucleotide sequences encoding the pesticidal proteins of the invention have been isolated, they can be manipulated and used to express the protein in a variety of hosts including other organisms, including microorganisms and plants.

The pesticidal genes of the invention can be optimized for enhanced expression in plants. See, for example U.S. Pat. No. 5,605,136; EPA 0359472; EPA 0385962; WO 91/16432; Perlak et al. (1991) *Proc. Natl. Acad. Sci. USA* 88:3324–3328; and Murray et al. (1989) *Nucleic Acids Research* 17: 477–498. In this manner, the genes can be synthesized utilizing plant preferred codons. That is the preferred codon for a particular host is the single codon which most frequently encodes that amino acid in that host. The maize preferred codon, for example, for a particular amino acid may be derived from known gene sequences from maize. Maize codon usage for 28 genes from maize plants is found in Murray et al. (1989), *Nucleic Acids Research* 17:477–498, the disclosure of which is incorporated herein by reference. Synthetic genes can also be made based on the distribution of codons a particular host uses for a particular amino acid.

In this manner, the nucleotide sequences can be optimized for expression in any plant. It is recognized that all or any part of the gene sequence may be optimized or synthetic. That is, synthetic or partially optimized sequences may also be used.

In like manner, the nucleotide sequences can be optimized for expression in any microorganism. For Bacillus preferred codon usage, see, for example U.S. Pat. No. 5,024,837 and Johansen et al. (1988) *Gene* 65:293–304.

Methodologies for the construction of plant expression cassettes as well as the introduction of foreign DNA into plants are described in the art. Such expression cassettes may include promoters, terminators, enhancers, leader sequences, introns and other regulatory sequences operably linked to the pesticidal protein coding sequence. It is further recognized that promoters or terminators of the VIP genes can be used in expression cassettes.

Generally, for the introduction of foreign DNA into plants Ti plasmid vectors have been utilized for the delivery of foreign DNA as well as direct DNA uptake, liposomes, electroporation, micro-injection, and the use of microprojectiles. Such methods had been published in the art. See, for example, Guerche et al., (1987) *Plant Science* 52:111–116; Neuhause et al., (1987) *Theor. Appl. Genet.* 75:30–36; Klein et al., (1987) *Nature* 327: 70–73; Howell et al., (1980) *Science* 208:1265; Horsch et al., (1985) *Science* 227: 1229–1231; DeBlock et al., (1989) *Plant Physiology* 91:694–701; *Methods for Plant Molecular Biology* (Weissbach and Weissbach, eds.) Academic Press, Inc. (1988); and *Methods in Plant Molecular Biology* (Schuler and Zielinski, eds.) Academic Press, Inc. (1989). See also abandoned U.S. patent application Ser. No. 08/008,374 herein incorporated by reference. See also, EPA 0193259 and EPA 0451878A1. It is understood that the method of transformation will depend upon the plant cell to be transformed.

It is further recognized that the components of the expression cassette may be modified to increase expression. For example, truncated sequences, nucleotide substitutions or other modifications may be employed. See, for example Perlak et al. (1991) *Proc. Natl. Acad. Sci. USA* 88:3324–3328; Murray et al., (1989) *Nucleic Acids Research* 17:477–498; and WO 91/16432.

The construct may also include any other necessary regulators such as terminators, (Guerineau et al., (1991), *Mol. Gen. Genet.*, 226:141–144; Proudfoot, (1991), *Cell*, 64:671–674; Sanfacon et al., (1991), *Genes Dev.*, 5:141–149; Mogen et al., (1990), *Plant Cell*, 2:1261–1272; Munroe et al., (1990), *Gene*, 91:151–158; Ballas et al., (1989), *Nucleic Acids Res.*, 17:7891–7903; Joshi et al., (1987), *Nucleic Acid Res.*, 15:9627–9639); plant translational consensus sequences (Joshi, C. P., (1987), *Nucleic Acids Research*, 15:6643–6653), introns (Luehrsen and Walbot, (1991), *Mol. Gen. Genet.*, 225:81–93) and the like, operably linked to the nucleotide sequence. It may be beneficial to include 5' leader sequences in the expression cassette construct. Such leader sequences can act to enhance translation. Translational leaders are known in the art and include:

Picornavirus leaders, for example, EMCV leader (encephalomyocarditis 5' noncoding region) (Elroy-Stein, O., Fuerst, T. R., and Moss, B. (1989) *PNAS USA* 86:6126–6130);

Potyvirus leaders, for example, TEV leader (Tobacco Etch Virus) (Allison et al., (1986); MDMV leader (Maize Dwarf Mosaic Virus); *Virology*, 154:9–20), and Human immunoglobulin heavy-chain binding protein (BiP), (Macejak, D. G., and Sarnow, P., (1991), *Nature*, 353:90–94;

Untranslated leader from the coat protein mRNA of alfalfa mosaic virus (AMV RNA 4), (Jobling, S. A., and Gehrke, L., (1987), *Nature*, 325:622–625;

Tobacco mosaic virus leader (TMV), (Gallie, D. R. et al., (1989), *Molecular Biology of RNA*, pages 237–256; and Maize Chlorotic Mottle Virus leader (MCMV) (Lommel, S. A. et al., (1991), *Virology*, 81:382–385. See also, Della-Cioppa et al., (1987), *Plant Physiology*, 84:965–968.

A plant terminator may be utilized in the expression cassette. See, Rosenberg et al., (1987), *Gene*, 56:125; Guerineau et al., (1991), *Mol. Gen. Genet.*, 226:141–144; Proudfoot, (1991), *Cell*, 64:671–674; Sanfacon et al., (1991), *Genes Dev.*, 5:141–149; Mogen et al., (1990), *Plant Cell*, 2:1261–1272; Munroe et al., (1990), *Gene*, 91:151–158; Ballas et al., (1989), *Nucleic Acids Res.*, 17:7891–7903; Joshi et al., (1987), *Nucleic Acid Res.*, 15:9627–9639.

For tissue specific expression, the nucleotide sequences of the invention can be operably linked to tissue specific promoters. See, for example, U.S. Pat. No. 5,625,136 herein incorporated by reference.

It is recognized that the genes encoding the pesticidal proteins can be used to transform insect pathogenic organisms. Such organisms include Baculoviruses, fungi, protozoa, bacteria and nematodes.

The Bacillus strains of the invention may be used for protecting agricultural crops and products from pests. Alternatively, a gene encoding the pesticide may be introduced via a suitable vector into a microbial host, and said host applied to the environment or plants or animals. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

Such microorganisms include bacteria, algae, and fungi. Of particular interest are microorganisms, such as bacteria, e.g., Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, e.g., Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum*, Agrobacteria,

*Rhodopseudomonas spheroides, Xanthomonas campestris, Rhizobium melioti, Alcaligenes entrophus, Clavibacter xyli* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans*. Of particular interest are the pigmented microorganisms.

A number of ways are available for introducing a gene expressing the pesticidal protein into the microorganism host under conditions which allow for stable maintenance and expression of the gene. For example, expression cassettes can be constructed which include the DNA constructs of interest operably linked with the transcriptional and translational regulatory signals for expression of the DNA constructs, and a DNA sequence homologous with a sequence in the host organism, whereby integration will occur, and/or a replication system which is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980); and the references cited therein.

Suitable host cells, where the pesticide-containing cells will be treated to prolong the activity of the toxin in the cell when the then treated cell is applied to the environment of the target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such a Saccharomyces and Schizosaccharromyces; and Basidiomycetes yeast, such as Rhodotorula, Aureobasidium, Sporobolomyces, and the like.

Characteristics of particular interest in selecting a host cell for purposes of production include ease of introducing the protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, LactoBacillus sp., Bacillus sp., and the like. Specific organisms include *Pseudomonas aeurginosa, Pseudomonas fluorescens, Saccharomyces cerevisiae, Bacillus thuringiensis, Escherichia coli, Bacillus subtilis,* and the like.

VIP genes can be introduced into micro-organisms that multiply on plants (epiphytes) to deliver VIP proteins to potential target pests. Epiphytes can be gram-positive or gram-negative bacteria for example.

Root colonizing bacteria, for example, can be isolated from the plant of interest by methods known in the art. Specifically, a *Bacillus cereus* strain which colonizes roots could be isolated from roots of a plant (for example see J. Handelsman, S. Raffel, E. Mester, L. Wunderlich and C. Grau, *Appl. Environ. Microbiol.* 56:713–718, (1990)). VIP1 and/or VIP2 could be introduced into a root colonizing *Bacillus cereus* by standard methods known in the art.

Specifically, VIP1 and/or VIP2 derived from *Bacillus cereus* strain AB78 can be introduced into a root colonizing *Bacillus cereus* by means of conjugation using standard methods (J. Gonzalez, B. Brown and B. Carlton, *Proc. Natl. Acad. Sci.* 79:6951–6955, (1982)).

Also, VIP1 and/or VIP2 or other VIPs of the invention can be introduced into the root colonizing Bacillus by means of electro-transformation. Specifically, VIPs can be cloned into a shuttle vector, for example, pHT3101 (D. Lereclus et al., *FEMS Microbiol. Letts.*, 60:211–218 (1989)) as described in Example 10. The shuttle vector pHT3101 containing the coding sequence for the particular VIP can then be transformed into the root colonizing Bacillus by means of electroporation (D. Lereclus et al. 1989, *FEMS Microbiol. Letts.* 60:211–218).

Expression systems can be designed so that VIP proteins are secreted outside the cytoplasm of gram negative bacteria, *E. coli*, for example. Advantages of having VIP proteins secreted are (1) it avoids potential toxic effects of VIP proteins expressed within the cytoplasm and (2) it can increase the level of VIP protein expressed and (3) can aid in efficient purification of VIP protein.

VIP proteins can be made to be secreted in *E. coli*, for example, by fusing an appropriate *E. coli* signal peptide to the amino-terminal end of the VIP signal peptide or replacing the VIP signal peptide with the *E. coli* signal peptide. Signal peptides recognized by *E. coli* can be found in proteins already known to be secreted in *E. coli*, for example the OmpA protein (J. Ghrayeb, H. Kimura, M. Takahara, Y. Masui and M. Inouye, *EMBO J.*, 3:2437–2442 (1984)). OmpA is a major protein of the *E. coli* outer membrane and thus its signal peptide is thought to be efficient in the translocation process. Also, the OmpA signal peptide does not need to be modified before processing as may be the case for other signal peptides, for example lipoprotein signal peptide (G. Duffaud, P. March and M. Inouye, *Methods in Enzymology* 153:492 (1987)).

Specifically, unique BamHil restriction sites can be introduced at the amino-terminal and carboxy-terminal ends of the VIP coding sequences using standard methods known in the art. These BamHI fragments can be cloned, in frame, into the vector pIN-III-ompA1, A2 or A3 (J. Ghrayeb, H. Kimura, M. Takahara, H. Hsiung, Y. Masui and M. Inouye, EMBO J., 3:2437–2442 (1984)) thereby creating ompA:VIP fusion gene which is secreted into the periplasmic space. The other restriction sites in the polylinker of pIN-III-ompA can be eliminated by standard methods known in the art so that the VIP amino-terminal amino acid coding sequence is directly after the ompA signal peptide cleavage site. Thus, the secreted VIP sequence in E. coli would then be identical to the native VIP sequence.

When the VIP native signal peptide is not needed for proper folding of the mature protein, such signal sequences can be removed and replaced with the ompA signal sequence. Unique BamHI restriction sites can be introduced at the amino-ternini of the proprotein coding sequences directly after the signal peptide coding sequences of VIP and at the carboxy-termini of VIP coding sequence. These BamHI fragments can then be cloned into the pIN-III-ompA vectors as described above.

General methods for employing the strains of the invention in pesticide control or in engineering other organisms as pesticidal agents are known in the art. See, for example U.S. Pat. No. 5,039,523 and EP 0480762A2.

VIPs can be fermented in a bacterial host and the resulting bacteria processed and used as a microbial spray in the same manner that Bacillus thuringiensis strains have been used as insecticidal sprays. In the case of a VIP(s) which is secreted from Bacillus, the secretion signal is removed or mutated using procedures known in the art. Such mutations and/or deletions prevent secretion of the VIP protein(s) into the growth medium during the fermentation process. The VIPs are retained within the cell and the cells are then processed to yield the encapsulated VIPs. Any suitable microorganism can be used for this purpose. Psuedomonas has been used to express Bacillus thuringiensis endotoxins as encapsulated proteins and the resulting cells processed and sprayed as an insecticide. (H. Gaertner et al. 1993, In Advanced Engineered Pesticides, L. Kim ed.)

Various strains of Bacillus thuringiensis are used in this manner. Such Bt strains produce endotoxin protein(s) as well as VIPs. Alternatively, such strains can produce only VIPs. A sporulation deficient strain of Bacillus subtilis has been shown to produce high levels of the CryIIIA endotoxin from Bacillus thuringiensis (Agaisse, H. and Lereclus, D., "Expression in Bacillus subtilis of the Bacillus thuringiensis CryIIIA toxin gene is not dependent on a sporulation-specific sigma factor and is increased in a spoOA mutant", J. Bacteriol., 176:4734–4741 (1994)). A similar spoOA mutant can be prepared in Bacillus thuringiensis and used to produce encapsulated VIPs which are not secreted into the medium but are retained within the cell.

To have VIPs maintained within the Bacillus cell the signal peptide can be disarmed so that it no longer functions as a secretion signal. Specifically, the putative signal peptide for VIP 1 encompasses the first 31 amino acids of the protein with the putative consensus cleavage site, Ala-X-Ala, at the C-terminal portion of this sequence (G. von Heijne, J. Mol. Biol. 184:99–105 (1989)) and the putative signal peptide for VIP2 encompasses the first 40 amino acids of the protein with the putative cleavage site after Ala40. The cleavage sites in either VIP 1 or VIP2 can be mutated with methods known in the art to replace the cleavage site consensus sequence with alternative amino acids that are not recognized by the signal peptidases.

Alternatively, the signal peptides of VIP1, VIP2 and/or other VIPs of the invention can be eliminated from the sequence thereby making them unrecognizable as secretion proteins in Bacillus. Specifically, a methionine start site can be engineered in front of the proprotein sequence in VIP1, starting at Asp32, or the proprotein sequence in VIP2, starting at Glu41 using methods known in the art.

VIP genes can be introduced into micro-organisms that multiply on plants (epiphytes) to deliver VIP proteins to potential target pests. Epiphytes can be gram-positive or gram-negative bacteria for example.

The Bacillus strains of the invention or the microorganisms which have been genetically altered to contain the pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein.

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

Preferred methods of applying an active ingredient of the present invention or an agrochemical composition of the present invention which contains at least one of the pesticidal proteins produced by the bacterial strains of the present invention are leaf application, seed coating and soil application. The number of applications and the rate of application depend on the intensity of infestation by the corresponding pest.

In one embodiment of the invention a Bacillus cereus microorganism has been isolated which is capable of killing Diabrotica virgifera virgifera, and Diabrotica longicornis barberi. The novel B. cereus strain AB78 has been deposited in the Agricultural Research Service, Patent Culture Collection (NRRL), Northern Regional Research Center, 1815 North University Street, Peoria, IL 61604, USA and given Accession No. NRRL B-21058.

A fraction protein has been substantially purified from the B. cereus strain. This purification of the protein has been verified by SDS-PAGE and biological activity. The protein has a molecular weight of about 60 to about 100 kDa, particularly about 70 to about 90 kDa, more particularly about 80 kDa, hereinafter VIP.

Amino-terminal sequencing has revealed the N-terminal amino-acid sequence to be: NH$_2$-Lys-Arg-Glu-Ile-Asp-Glu-Asp-Thr-Asp-Thr-Asx-Gly-Asp-Ser-Ile-Pro-(SEQ ID NO:8) where Asx represents either Asp or Asn. The entire amino acid sequence is given in SEQ ID NO:7. The DNA sequence which encodes the amino acid sequence of SEQ ID NO:7 is disclosed in SEQ ID NO:6.

An oligonucleotide probe for the region of the gene encoding amino acids 3–9 of the NH$_2$-terminus has been generated. The probe was synthesized based on the codon usage of a *Bacillus thuringiensis* (Bt) δ-endotoxin gene. The nucleotide sequence of the oligonucleotide is probe used for Southern hybridizations was as follows:

5'-GAA ATT GAT CAA GAT ACN GAT-3' (SEQ ID NO:9)

where N represents any base.

In addition, the DNA probe for the Bc AB78 VIP1 gene described herein, permits the screening of any Bacillus strain or other organisms to determine whether the VIP1 gene (or related gene) is naturally present or whether a particular transformed organism includes the VIP1 gene.

The invention now being generally described, the same will be better understood by reference to the following detailed examples that are provided for the purpose of illustration and are not to be considered limiting of the invention unless so specified.

A standard nomenclature has been developed based on the sequence identity of the proteins encompassed by the present invention. The gene and protein names for the detailed examples which follow and their relationship to the names used in the parent application are shown below.

| Gene/Protein Name under Standard Nomenclature | Gene/Protein Name in Parent | Description of Protein |
|---|---|---|
| VIP1A(a) | VIP1 | VIP1 from strain AB78 as disclosed in SEQ ID NO:5. |
| VIP2A(a) | VIP2 | VIP2 from strain AB78 as disclosed in SEQ ID NO:2. |
| VIP1A(b) | VIP1 homolog | VIP1 from *Bacillus thuringiensis* var. tenebrionis as disclosed in SEQ ID NO:21. |
| VIP2A(b) | VIP2 homolog | VIP2 from *Bacillus thuringiensis* var. tenebrionis as disclosed in SEQ ID NO:20. |
| VIP3A(a) | — | VIP from strain AB88 as disclosed in SEQ ID NO:28 of the present application |
| VIP3A(b) | — | VIP from strain AB424 as disclosed in SEQ ID NO:31 of the present application |

EXPERIMENTAL

EXAMPLE 1

AB78 ISOLATION AND CHARACTERIZATION

*Bacillus cereus* strain AB78 was isolated as a plate contaminant in the laboratory on T3 edia (per liter: 3 g tryptone, 2 g tryptose, 1.5 g yeast extract, 0.05 M sodium phosphate (pH 6.8), and 0.005 g MnCl$_2$; Travers, R. S. 1983). During log phase growth, AB78 gave significant activity against western corn rootworm. Antibiotic activity against gram-positive Bacillus spp. was also demonstrated (Table 12).

TABLE 12

Antibiotic activity of AB78 culture supernatant

| | Zone of inhibition(cm) | |
|---|---|---|
| Bacteria tested | AB78 | Streptomycin |
| E. coli | 0.0 | 3.0 |
| B. megaterium | 1.1 | 2.2 |
| B. mycoides | 1.3 | 2.1 |
| B. cereus CB | 1.0 | 2.0 |
| B. cereus 11950 | 1.3 | 2.1 |
| B. cereus 14579 | 1.0 | 2.4 |
| B. cereus AB78 | 0.0 | 2.2 |
| Bt var. israelensis | 1.1 | 2.2 |
| Bt var. tenebrionis | 0.9 | 2.3 |

Morphological characteristics of AB78 are as follows:

Vegetative rods straight, 3.1–5.0 mm long and 0.5–2.0 mm wide. Cells with rounded ends, single in short chains. Single subterminal, cylindrical-oval, endospore formed per cell. No parasporal crystal formed. Colonies opaque, erose, lobate and flat. No pigments produced. Cells motile. Flagella present.

Growth characteristics of AB78 are as follows:

Facultative anaerobe with optimum growth temperature of 21–30° C. Will grow at 15, 20, 25, 30 and 37° C. Will not grow above 40° C. Grows in 5–7% NaCl.

Table 13 provides the biochemical profile of AB78.

TABLE 13

Biochemical characteristics of *B. cereus* strain AB78.

| Acid from L-arabinose | − | Methylene blue reoxidized | + |
|---|---|---|---|
| Gas from L-arabinose | − | Nitrate reduced | + |
| Acid from D-xylose | − | NO$_3$ reduced to NO$_2$ | + |
| Gas from D-xylose | − | VP | + |
| Acid from D-glucose | + | H$_2$O$_2$ decomposed | + |
| Gas from D-glucose | − | Indole | − |
| Acid from lactose | − | Tyrosine decomposed | + |
| Gas from lactose | − | Dihydroxiacetone | − |
| Acid from sucrose | − | Litmus milk acid | − |
| Gas from sucrose | − | Litmus milk coagulated | − |
| Acid from D-mannitol | − | Litmus milk alkaline | − |
| Gas from D-mannitol | − | Litmus milk peptonized | − |
| Proprionate utilization | + | Litmus milk reduced | − |
| Citrate utilization | + | Casein hydrolyzed | + |
| Hippurate hydrolysis | w | Starch hydrolyzed | + |
| Methylene blue reduced | + | Gelatin liquidified | + |
| | | Lecithinase produced | w | w = weak reaction

EXAMPLE 2

BACTERIAL CULTURE

A subculture of Bc strain AB78 was used to inoculate the following medium, known as TB broth:

| Tryptone | 12 | g/l |
|---|---|---|
| Yeast Extract | 24 | g/l |
| Glycerol | 4 | ml/l |
| KH$_2$PO$_4$ | 2.1 | g/l |
| K$_2$HPO$_4$ | 14.7 | g/l |
| pH 7.4 | | |

The potassium phosphate was added to the autoclaved broth after cooling. Flasks were incubated at 30° C. on a rotary shaker at 250 rpm for 24 h.–36 h, which represents an early to mid-log growth phase.

The above procedure can be readily scaled up to large fermentors by procedures well known in the art.

During vegetative growth, usually 24–36 h. after starting the culture, which represents an early to mid-log growth phase, AB78 bacteria were centrifuged from the culture supernatant. The culture supernatant containing the active protein was used in bioassays.

EXAMPLE 3

INSECT BIOASSAYS

*B. cereus* strain AB78 was tested against various insects as described below.

Western, Northern and Southern corn rootworm, *Diabrotica virgifera virgifera, D. longcornis barberi* and *D. undecempunctata howardi*, respectively: dilutions were made of AB78 culture supernatant grown 24–36 h., mixed with molten artificial diet (Marrone et al. 1985) *J. of Economic Entomology* 78:290–293) and allowed to solidify. Solidified diet was cut and placed in dishes. Neonate larvae were placed on the diet and held at 30° C. Mortality was recorded after 6 days.

*E. coli* clone bioassay: *E. coli* cells were grown overnight in broth containing 100 μg/ml ampicillin at 37° C. Ten ml culture was sonicated 3× for 20 sec each. 500 μl of sonicated culture was added to molten western corn rootworm diet.

Colorado potato beetle, *Leptinotarsa decemlineata*: dilutions in Triton X-100 (to give final concentration of 0.1% TX-100) were made of AB78 culture supernatant grown 24–36 h. Five cm² potato leaf pieces were dipped into these dilutions, air dried, and placed on moistened filter paper in plastic dishes. Neonate larvae were placed on the leaf pieces and held at 30° C. Mortality was recorded after 3–5 days.

Yellow mealworm, *Tenebrio molitor*: dilutions were made of AB78 culture supernatant grown 24–36 h., mixed with molten artificial diet (Bioserv #F9240) and allowed to solidify. Solidified diet was cut and placed in plastic dishes. Neonate larvae were placed on the diet and held at 30° C. Mortality was recorded after 6–8 days.

European corn borer, black cutworm, tobacco budworm, tobacco hornworm and beet armyworm; *Ostrinia nubilalis, Agrotis epsilon, Heliothis virescens, Manduca sexta* and *Spodoptera exigua*, respectively: dilutions, in TX-100 (to give final concentration of 0.1% TX-100), were made of AB78 culture supernatant grown 24–36 hrs. 100 μl was pipetted onto the surface of 18 cm² of solidified artificial diet (Bioserv #F9240) and allowed to air dry. Neonate larvae were then placed onto the surface of the diet and held at 30° C. Mortality was recorded after 3–6 days.

Northern house mosquito, *Culex pipiens*:-dilutions were made of AB78 culture supernatant grown 24–36 h. 100 μl was pipetted into 10 ml water in a 30 ml plastic cup. Third instar larvae were added to the water and held at room temperature. Mortality was recorded after 24–48 hours. The spectrum of entomocidal activity of AB78 is given in Table 14.

TABLE 14

Activity of AB78 culture supernatant against various insect species

| Insect species tested to date | Order | Activity |
| --- | --- | --- |
| Western corn rootworm (*Diabrotica virgifera virgifera*) | Col | +++ |

TABLE 14-continued

Activity of AB78 culture supernatant against various insect species

| Insect species tested to date | Order | Activity |
| --- | --- | --- |
| Northern corn rootworm (*Diabrotica longicornis barberi*) | Col | +++ |
| Southern corn rootworm (*Diabrotica undecimpunctata howardi*) | Col | – |
| Colorado potato beetle (*Leptinotarsa decemlineata*) | Col | – |
| Yellow mealworm (*Tenebrio molitor*) | Col | – |
| European corn borer (*Ostrinia nubilalis*) | Lep | – |
| Tobacco budworm (*Heliothis virescens*) | Lep | – |
| Tobacco hornworm (*Manduca sexta*) | Lep | – |
| Beet armyworm (*Spodoptera exigua*) | Lep | – |
| Black cutworm (*Agrotis ipsilon*) | Lep | – |
| Northern house mosquito (*Culex pipiens*) | Dip | – |

The newly discovered *B. cereus* strain AB78 showed a significantly different spectrum of insecticidal activity as compared to known coleopteran active δ-endotoxins from Bt. In particular, AB78 showed more selective activity against beetles than known coleopteran-active Bt strains in that it was specifically active against Diabrotica W. More specifically, it was most active against *D. virgifera virgifera* and *D. longicornis barberi* but not *D. undecimpunctata howardi*.

A number of Bacillus strains were bioassayed for activity during vegetative growth (Table 15) against western corn rootworm. The results demonstrate that AB78 is unique in that activity against western corn rootworm is not a general phenomenon.

TABLE 15

Activity of culture supernatants from various *Bacillus spp.* against western corn rootworm

| Bacillus strain | Percent WCRW mortality |
| --- | --- |
| *B. cereus* AB78 (Bat.1) | 100 |
| *B. cereus* AB78 (Bat.2) | 100 |
| *B. cereus* (Carolina Bio.) | 12 |
| *B. cereus* ATCC 11950 | 12 |
| *B. cereus* ATCC 14579 | 8 |
| *B. mycoides* (Carolina Bio.) | 30 |
| *B. popilliae* | 28 |
| *B. thuringiensis* HD135 | 41 |
| *B. thuringiensis* HD191 | 9 |
| *B. thuringiensis* GC91 | 4 |
| *B. thuringiensis* isrealensis | 24 |
| Water Control | 4 |

Specific activity of AB78 against western corn rootworm is provided in Table 16.

TABLE 16

Activity of AB78 culture supernatant against neonate western corn rootworm

| Culture supernatant concentration (μl/ml) | Percent WCRW mortality |
|---|---|
| 100 | 100 |
| 25 | 87 |
| 10 | 80 |
| 5 | 40 |
| 2.5 | 20 |
| 1 | 6 |
| 0 | 0 |

The $LC_{50}$ was calculated to be 6.2 μl of culture supernatant per ml of western corn rootworm diet.

The cell pellet was also bioassayed and had no activity against WCRW. Thus, the presence of activity only in the supernatant indicates that this VIP is an exotoxin.

EXAMPLE 4

ISOLATION AND PURIFICATION OF CORN ROOTWORM ACTIVE PROTEINS FROM AB78.

Culture media free of cells and debris was made to 70% saturation by the addition of solid ammonium sulfate (472 g/L). Dissolution was at room temperature followed by cooling in an ice bath and centrifugation at 10,000×g for thirty minutes to pellet the precipitated proteins. The supernatant was discarded and the pellet was dissolved in 1/10 the original volume of 20 mM TRIS-HCl at pH 7.5. The dissolved pellet was desalted either by dialysis in 20 mM TRIS-HCl pH 7.5, or passing through a desalting column.

The desalted material was titrated to pH 3.5 using 20 mM sodium citrate pH 2.5. Following a thirty minute room temperature incubation the solution was centrifuged at 3000×g for ten minutes. The supernatant at this stage contained the greatest amount of active protein.

Following neutralization of the pH to 7.0 the supernatant was applied to a Mono-Q, anion exchange, column equilibrated with 20 mM TRIS pH 7.5 at a flow rate of 300 mL/min. The column was developed with a stepwise and linear gradient employing 400 mM NaCl in 20 mM TRIS pH 7.5.

Bioassay of the column fractions and SDS-PAGE analysis were used to confirm the active fractions. SDS-PAGE analysis identified the biologically active protein as having components of a molecular weight in the range of about 80 kDa and 50 kDa.

EXAMPLE 5

SEQUENCE ANALYSIS OF THE CORN ROOTWORM ACTIVE PROTEIN

The 80 kDa component isolated by SDS-PAGE was transferred to PVDF membrane and was subjected to amino-terminal sequencing as performed by repetitive Edman cycles on an ABI 470 pulsed-liquid sequencer. Transfer was carried out in 10 mM CAPS buffer with 10% methanol pH 11.0 as follows:

Incubation of the gel following electrophoresis was done in transfer buffer for five minutes. ProBlott PVDF membrane was wetted with 100% MeOH briefly then equilibrated in transfer buffer. The sandwich was arranged between foam sponges and filter paper squares with the configuration of cathode-gel-membrane-anode.

Transfer was performed at 70 V constant voltage for 1 hour.

Following transfer, the membrane was rinsed with water and stained for two minutes with 0.25% Coomassie Blue R-250 in 50% MeOH.

Destaining was done with several rinses with 50% MeOH 40% water 10% acetic acid.

Following destaining the membrane was air dried prior to excision of the bands for sequence analysis. A BlottCartridge and appropriate cycles were utilized to achieve maximum efficiency and yield. Data analysis was performed using model 610 Sequence Analysis software for identifying and quantifying the PTH-amino acid derivatives for each sequential cycle.

The N-terminal sequence was determined to be: NH2-Lys-Arg-Glu-Ile-Asp-Glu-Asp-Thr-Asp-Thr-Asx-Gly-Asp-Ser-Ile-Pro-(SEQ ID NO:8) where Asx represents Asp or Asn. The complete amino acid sequence for the 80 kDa component is disclosed in SEQ ID NO:7. The DNA sequence which encodes SEQ ID NO:7 is disclosed in SEQ ID NO:6.

EXAMPLE 6

CONSTRUCTION OF DNA PROBE

An oligonucleotide probe for the region of the gene encoding amino acids 3–9 of the N-terminal sequence (Example 5) was generated. The probe was synthesized based on the codon usage of a *Bacillus thuringiensis* (Bt) δ-endotoxin gene. The nucleotide sequence

5'-GAA ATT GAT CAA GAT ACN GAT-3' (SEQ ID NO:9)

was used as a probe in Southern hybridizations. The oligonucleotide was synthesized using standard procedures and equipment.

EXAMPLE 7

ISOELECTRIC POINT DETERMINATION OF THE CORN ROOTWORM ACTIVE PROTEIN

Purified protein from step 5 of the purification process was analyzed on a 3–9 pI isoelectric focusing gel using the Phastgel electrophoresis system (Pharmacia). Standard operating procedures for the unit were followed for both the separation and silver staining development procedures. The pI was approximated at about 4.9.

EXAMPLE 8

PCR DATA ON AB78

PCR analysis (See, for example U.S. patent application Ser. No. 08/008,006; and, Carozzi et al. (1991) *Appl. Environ. Microbiol.* 57(11):3057–306 1, herein incorporated by reference.) was used to verify that the *B. cereus* strain AB78 did not contain any insecticidal crystal protein genes of *B. thuringiensis* or *B. sphaericus* (Table 17).

TABLE 17

Bacillus insecticidal crystal protein gene primers tested by PCR against AB78 DNA.

| Primers Tested | Product Produced |
|---|---|
| 2 sets specific for CryIIIA | Negative |
| CryIIIB | Negative |
| 2 sets specific for CryIA | Negative |
| CryIA(a) | Negative |
| CryIA(b) specific | Negative |
| CryIB | Negative |

TABLE 17-continued

Bacillus insecticidal crystal protein gene primers tested by PCR against AB78 DNA.

| Primers Tested | Product Produced |
| --- | --- |
| CryIC specific | Negative |
| CryIE specific | Negative |
| 2 sets specific for *B. sphaericus* | Negative |
| 2 sets specific for CryIV | Negative |
| Bacillus control (PI-PLC) | Positive |

EXAMPLE 9

COSMID CLONING OF TOTAL DNA FROM *B. CEREUS* STRAIN AB78

The VIP1A(a) gene was cloned from total DNA prepared from strain AB78 as follows:

Isolation of AB78 DNA was as follows:

1. Grow bacteria in 10 ml L-broth overnight. (Use 50 ml sterile centrifuge tube)
2. Add 25 ml of fresh L-broth and ampicillin (30 μg/ml).
3. Grow cells 2–6 h. at 30° C. with shaking.
4. Spin cells in a 50 ml polypropylene orange cap tube in IEC benchtop clinical centrifuge at ¾ speed.
5. Resuspend cell pellet in 10 ml TES (TES=50 mM TRIS pH 8.0, 100 mM EDTA, 15 mM NaCl).
6. Add 30 mg lysozyme and incubate 2 hrs at 37° C.
7. Add 200 μl 20% SDS and 400 μl Proteinase K stock (20 mg/ml). Incubate at 37° C.
8. Add 200 μl fresh Proteinase K. Incubate 1 hr. at 55° C. Add 5 ml TES to make 15 ml final volume.
9. Phenol extract twice (10 ml phenol, spin at room temperature at ¾ speed in an IEC benchtop clinical centrifuge). Transfer supernatant (upper phase) to a clean tube using a wide bore pipette.
10. Extract once with 1:1 vol. phenol:chloroform/isoamyl alcohol (24:1 ratio).
11. Precipitate DNA with an equal volume of cold isopropanol; Centrifuge to pellet DNA.
12. Resuspend pellet in 5 ml TE.
13. Precipitate DNA with 0.5 ml 3M NaOAc pH 5.2 and 11 ml 95% ethanol. Place at −20° C. for 2h.
14. "Hook" DNA from tube with a plastic loop, transfer to a microfuge tube, spin, pipette off excess ethanol, dry in vacuo.
15. Resuspend in 0.5 ml TE. Incubate 90 min. at 65° C. to help get DNA back into solution.
16. Determine concentration using standard procedures.

Cosmid Cloning of AB78

All procedures, unless indicated otherwise, were performed according to Stratagene Protocol, Supercos 1 Instruction Manual, Cat. No. 251301.

Generally, the steps were as follows:

A. Sau 3A partial digestion of the AB78 DNA.
B. Preparation of vector DNA
C. Ligation and packaging of DNA
D. Tittering the cosmid library
 1. Start a culture of HB101 cells by placing 50 ml of an overnight culture in 5 mls of TB with 0.2% maltose. Incubate 3.5 hrs. at 37° C.
 2. Spin out cells and resuspend in 0.5 ml 10 mM MgSO$_4$.
 3. Add together:
  100 μl cells
  100 μl diluted packaging mixture
  100 μl 10 mM MgSO$_4$
  30 μl TB
 4. Adsorb at room temperature for 30 minutes with no shaking.
 5. Add 1 ml TB and mix gently. Incubate 30 minutes at 37° C.
 6. Plate 200 μl onto L-amp plates. Incubate at 37° C. overnight.

At least 400 cosmid clones were selected at random and screened for activity against western corn rootworm as described in Example 3. DNA from 5 active clones and 5 non-active clones were used in Southern hybridizations. Results demonstrated that hybridization using the above described oligonucleotide probe correlated with western corn rootworm activity (Table 18).

Cosmid clones P3-12 and P5-4 have been deposited with the Agricultural Research Service Patent Culture Collection (NRRL) and given Accession Nos. NRRL B-21061 and NRRL B-21059 respectively.

TABLE 18

Activity of AB78 cosmid clones against western corn rootworm.

| Clone | Mean percent mortality (N = 4) |
| --- | --- |
| Clones which hybridize with probe | |
| P1-73 | 47 |
| P1-83 | 64 |
| P2-2 | 69 |
| P3-12 | 85 |
| P5-4 | 97 |
| Clones which do not hybridize with probe | |
| P1-2 | 5 |
| P3-8 | 4 |
| P3-9 | 12 |
| P3-18 | 0 |
| P4-6 | 9 |

EXAMPLE 10

IDENTIFICATION OF A 6 KB REGION ACTIVE AGAINST WESTERN CORN ROOTWORM.

DNA from P3-12 was partially digested with restriction enzyme Sau 3A, and ligated into the *E. coli* vector pUC 19 and transformed into *E. coli*. A DNA probe specific for the 80 kDa VIP1A(a) protein was synthesized by PCR amplification of a portion of P3-12 DNA. Oligonucleotides MK113 and MK117, which hybridize to portions of VIP1A (a), were synthesized using the partial amino acid sequence of the 80 kDa protein. Plasmid subclones were identified by colony hybridization to the PCR-generated probe, and tested for activity against western corn rootworm. One such clone, PL2, hybridized to the PCR-generated fragment, and was active against western corn rootworm in the assay previously described.

A 6 kb Cla I restriction fragment from pL2 was cloned into the Sma I site of the *E. coli*-Bacillus shuttle vector pHT 3101 (Lereclus, D. et al., *FEMS Microbiology Letters* 60:211–218 (1989)) to yield pCIB6201. This construct confers anti-western corn rootworm activity upon both Bacillus and *E. coli* strains, in either orientation. pCIB6022 contains this same 6 kb Cla I fragment in pBluescript SK(+)

(Stratagene), produces equivalent VIP1A(a) protein (by western blot), and is also active against western corn rootworm.

The nucleotide sequence of pCIB6022 was determined by the dideoxy termination method of Sanger et al., *Proc. Natl. Acad. Sci.* USA, 74:5463–5467 (1977), using PRISM Ready Reaction Dye Deoxy Terminator Cycle Sequencing Kits and PRISM Sequenase® Terminator Double-Stranded DNA Sequencing Kit and analyzed on an ABI 373 automatic sequencer. The sequence is given in SEQ ID NO:1. The 6 kb fragment encodes both VIP1A(a) and VIP2A(a), as indicated by the open reading frames described in SEQ ID NO:1. The sequence encoding VIP1A(a) is further disclosed in SEQ ID NO:4. The relationship between VIP1A(a) and VIP2A(a) within the 6 kb fragment found in pCIB6022 is depicted in FIG. 1. pCIB6022 was deposited with the Agricultural Research Service, Patent Culture Collection, (NRRL), Northern Regional Research Center, 1815 North University Street, Peoria, Ill. 61604, USA, and given the Accession No. NRRL B-21222.

EXAMPLE 11

FUNCTIONAL DISSECTION OF THE VIP1A(a) DNA REGION.

To confirm that the VIP1A(a) open reading frame (ORF) is necessary for insecticidal activity a translational frameshift mutation was created in the gene. The restriction enzyme Bgl II recognizes a unique site located 857 bp into the coding region of VIP1A(a). pCIB6201 was digested with Bgl II, and the single-stranded ends filled-in with DNA polymerase (Klenow fragment) and dNTPS. The plasmid was re-ligated and transformed into *E. coli*. The resulting plasmid, pCIB6203, contains a four nucleotide insertion in the coding region of VIP1A(a). pCIB6203 does not confer WCRW insecticidal activity, confirming that VIP1A(a) is an essential component of western corn rootworm activity.

To further define the region necessary to encode VIP1A(a), subclones of the VIP1A(a) and VIP2A(a) (auxiliary protein) region were constructed and tested for their ability to complement the mutation in pCIB6203. pCIB6023 contains the 3.7 kb Xba I-EcoRV fragment in pBluescript SK(+) (Stratagene). Western blot analysis indicates that pCIB6023 produces VIP1A(a) protein of equal size and quantity as clones PL2 and pCIB6022. pCIB6023 contains the entire gene encoding the 80 kD protein. pCIB6023 was deposited with the Agricultural Research Service, Patent Culture Collection, (NRRL), Northern Regional Research Center, 1815 North University Street, Peoria, Ill. 61604, USA, and given the Accession No. NRRL B-21223N. pCIB6206 contains the 4.3 kb Xba I-Cla I fragment from pCIB6022 in pBluescript SK(+) (Stratagene). pCIB6206 was also deposited with the Agricultural Research Service, Patent Culture Collection, (NRRL), Northern Regional Research Center, 1815 North University Street, Peoria, Ill. 61604, USA, and given the Accession No. NRRL B-21321.

pCIB6023, pCIB6206, and pCIB6203 do not produce detectable western corn rootworm activity when tested individually. However, a mixture of cells containing pCIB6203 (VIP1A(a)-mutated, plus VIP2A(a)) and cells containing pCIB6023 (only VIP1A(a)) shows high activity against western corn rootworm. Similarly, a mixture of cells containing pCIB6206 and cells containing pCIB6203 shows high activity against western corn rootworm.

To further define the limits of VIP2A(a), we constructed pCIB6024, which contains the entirety of VIP2A(a), but lacks most of the VIP1A(a) coding region. pCIB6024 was constructed by gel purifying the 2.2 kb Cla I-Sca I restriction fragment from pCIB6022, filling in the single-stranded ends with DNA polymerase (Kienow fragment) and dNTPs, and ligating this fragment into pBluescript SK(+) vector (Stratagene) digested with the enzyme Eco RV. Cells containing pCIB6024 exhibit no activity against western corn rootworm. However, a mixture of cells containing pCIB6024 and cells containing pCIB6023 shows high activity against western corn rootworm (See FIG. 1).

Thus, pCIB6023 and pCIB6206 must produce a functional VIP1A(a) gene product, while pCIB6203 and pCIB6024 must produce a functional VIP2A(a) gene product. These results suggest a requirement for a gene product(s) from the VIP2A(a) region, in combination with VIP1A(a), to confer maximal western corn rootworm activity. (See FIG. 1)

EXAMPLE 12

AB78 ANTIBODY PRODUCTION

Antibody production was initiated in 2 Lewis rats to allow for both the possibility of moving to production of hybridoma cell lines and also to produce enough serum for limited screening of genomic DNA library. Another factor was the very limited amount of antigen available and the fact that it could only be produced to purity by PAGE and subsequent electrotransfer to nitrocellulose.

Due to the limited availability of antigen on nitrocellulose, the nitrocellulose was emulsified in DMSO and injected into the hind footpads of the animals to elicit B-cell production in the popliteal lymph nodes just upstream. A strong reacting serum was produced as judged by western blot analysis with the first production bleed. Several subsequent injections and bleeds produced enough serum to accomplish all of the screening required.

Hybridoma production with one of the rats was then initiated. The popliteal lymph node was excised, macerated, and the resulting cells fused with mouse myeloma P3×63Ag8.653. Subsequent cell screening was accomplished as described below. Four initial wells were selected which gave the highest emulsified antigen reaction to be moved to limited dilution cloning. An additional 10 wells were chosen for expansion and cryopreservation.

Procedure to Emulsify AB78 on nitrocellulose in DMSO for ELISA screening:

After electrotransfer of AB78 samples run on PAGE to nitrocellulose, the reversible strain Ponceau S is used to visualize all protein transferred. The band corresponding to AB78 toxin, previously identified and N-terminal sequenced, was identified and excised from nitrocellulose. Each band is approximately 1 mm×5 mm in size to minimize the amount of nitrocellulose emulsified. A single band is placed in a microfuge tube with 250 $\mu$l of DMSO and macerated using a plastic pestle (Kontes, Vineland, N.J.). To aid in emulsification, the DMSO mixture is heated for 2–3 minutes at 37° C.–45° C. Some further maceration might be necessary following heating; however, all of the nitrocellulose should be emulsified. Once the AB78 sample is emulsified, it is placed on ice. In preparation for microtiter plate coating with the emulsified antigen, the sample must be diluted in borate buffered saline as follows: 1:5, 1:10, 1:15, 1:20, 1:30, 1:50, 1:100, and 0. The coating antigen must be prepared fresh immediately or to use.

ELISA protocol:

1. Coat with AB78/DMSO in BBS. Incubate overnight at 4° C.

2. Wash plate 3x with 1x ELISA wash buffer.
3. Block (1% BSA & 0.05% Tween 20 in PBS) for 30 minutes at Room Temperature.
4. Wash plate 3x with 1x ELISA wash buffer.
5. Add rat serum. Incubate 1.5 hours at 37° C.
6. Wash plate 3x with 1x ELISA wash buffer.
7. Add goat anti-rat at a concentration of 2 μg/ml in ELISA diluent. Incubate 1 hr. at 37° C.
8. Wash plate 3x with 1x ELISA wash buffer.
9. Add rabbit anti-goat alkaline phosphatase at 2 μg/ml in ELISA diluent. Incubate 1 hr. at 37° C.
10. Wash 3x with 1x ELISA wash buffer.
11. Add Substrate. Incubate 30 minutes at room temperature.
12. Stop with 3N NaOH after 30 minutes.

Preparation of VIP2A(a) Antisera

A partially purified AB78 culture supernatant was separated by discontinuous SDS PAGE (Novex) following manufacturer's instructions. Separated proteins were electrophoresed to nitrocellulose (S&S #21640) as described by Towbin et al., (1979). The nitrocellulose was stained with Ponceau S and the VIP2A(a) band identified. The VIP2A(a) band was excised and emulsified in DMSO immediately prior to injection. A rabbit was initially immunized with emulsified VIP2A(a) mixed approximately 1:1 with Freund's Complete adjuvant by intramuscular injection at four different sites. Subsequent immunizations occurred at four week intervals and were identical to the first, except for the use of Freund' Incomplete adjuvant. The first serum harvested following immunization reacted with VIP2A(a) protein. Western blot analysis of AB78 culture supernatant using this antisera identifies predominately full length VIP2A(a) protein.

EXAMPLE 13

ACTIVATION OF INSECTICIDAL ACTIVITY OF NON-ACTIVE BT STRAINS WITH AB78 VIP CLONES.

Adding pCIB6203 together with a 24 h culture (early to mid-log phase) supernatant from Bt strain GC91 produces 100% mortality in *Diabrotica virgifera virgifera*. Neither pCIB6203 not GC91 is active on *Diabrotica virgifera virgifera* by itself. Data are shown below:

| Test material | Percent Diabrotica mortality |
|---|---|
| pCIB6203 | 0 |
| GC91 | 16 |
| pCIB6203 + GC91 | 100 |
| Control | 0 |

EXAMPLE 14

ISOLATION AND BIOLOGICAL ACTIVITY OF B. CEREUS AB81

A second *B. cereus* strain, designated AB81, was isolated from grain bin dust samples by standard methodologies. A subculture of AB81 was grown and prepared for dioassay as described in Example 2. Biological activity was evaluated as described in Example 3. The results are as follows:

| Insect species tested | Percent Mortality |
|---|---|
| Ostrinia nubilalis | 0 |
| Agrotis ipsilon | 0 |
| Diabrotica virgifera virgifera | 55 |

EXAMPLE 15

ISOLATION AND BIOLOGICAL ACTIVITY OF B. THURINGIENSIS AB6.

A *B. thuringiensis* strain, designated AB6, was isolated from grain bin dust samples by standard methods known in the art. A subculture of AB6 was grown and prepared for bioassay as described in Example 2. Half of the sample was autoclaved 15 minutes to test for the presence of β-exotoxin.

Biological activity was evaluated as described in Example 3. The results are as follows:

| Insect species tested | Percent Mortality |
|---|---|
| Ostrinia nubilalis | 0 |
| Agrotis ipsilon | 100 |
| Agrotis ipsilon (autoclaved sample) | 0 |
| Diabrotica virgifera virgifera | 0 |

The reduction of insecticidal activity of the culture supernatant to insignificant levels by autoclaving indicates that the active principle is not β-exotoxin.

Strain AB6 has been deposited in the Agricultural Research Service, Patent Culture Collection (NRRL), Northern Regional Research Center, 1815 North University Street, Peoria, Ill. 61604, USA, and given Accession No. NRRL B-21060.

EXAMPLE 16

ISOLATION AND BIOLOGICAL CHARACTERIZATION OF B. THURINGIENSIS AB88.

A Bt strain, designated AB88, was isolated from grain bin dust samples by standard methodologies. A subculture of AB88 was grown and prepared for bioassay as described in Example 2. Half of the sample was autoclaved 15 minutes to test for the presence of β-exotoxin. Biological activity was evaluated against a number of insect species as described in Example 3. The results are as follows:

| | | Percent mortality of culture supernatant | |
|---|---|---|---|
| Insect species tested | Order | Non-autoclaved | Autoclaved |
| Agrotis ipsilon | Lepidoptera | 100 | 5 |
| Ostrinia nubilalis | Lepidoptera | 100 | 0 |
| Spodoptera frugiperda | Lepidoptera | 100 | 4 |
| Helicoverpa zea | Lepidoptera | 100 | 12 |
| Heliothis virescens | Lepidoptera | 100 | 12 |

-continued

| Insect species tested | Order | Percent mortality of culture supernatant | |
|---|---|---|---|
| | | Non-autoclaved | Autoclaved |
| Leptinotarsa decemlineata | Coleoptera | 0 | 0 |
| Diabrotica virgifera virgifera | Coleoptera | 0 | 5 |

The reduction of insecticidal activity of the culture supernatant to insignificant levels by autoclaving indicates that the active principle is not β-exotoxin.

Delta-endotoxin crystals were purified from strain AB88 by standard methodologies. No activity from pure crystals was observed when bioassayed against *Agrotis ipsilon*.

EXAMPLE 17

PURIFICATION OF VIPS FROM STRAIN AB88:

Bacterial liquid culture was grown overnight at 30° C. in TB media. Cells were spun out and the supernatant retained. Proteins were precipitated with ammonium sulfate (70% saturation), centrifuged and the pellet retained. The pellet was resuspended in the original volume of 20 mM Tris pH 7.5 and dialyzed against the same buffer. AB88 dialysate was more turbid than comparable material from AB78. AB88 proteins have been separated by several different methods following clarification including isoelectric focusing (Rotofor, BioRad, Hercules, Calif.), precipitation at pH 4.5, ion-exchange chromatography, size exclusion chromatography and ultrafiltration.

European corn borer (ECB)-active protein remained in the pellet obtained by pH 4.5 precipitation of dialysate. When preparative IEF was done on the dialysate using pH 3–10 ampholytes, ECB insecticidal activity was found in all fractions with pH of 7 or greater. SDS-PAGE analysis of these fractions showed protein bands of MW ~60 kDa and ~80 kDa. The 60 kDa and 80 kDa bands were separated by anion exchange HPLC on a Poros-Q column (PerSeptive Biosystems, Cambridge, Mass.). N-terminal sequence was obtained from two fractions containing proteins of slightly differing MW, but both of approximately 60 kDa in size. The sequences obtained were similar to each other and to some δ-endotoxins. anion exchange fraction 23 (smaller): xEPFVSAxxxQxxx (SEQ ID NO:10) anion exchange fraction 28 (larger): xEYENVEPFVSAx (SEQ ID NO:11)

When the ECB-active pH 4.5 pellet was further separated by anion exchange on a Poros-Q column, activity was found only in fractions containing a major band of ~60 kDa.

Black cutworm-active protein also remained in the pellet when AB88 dialysate was brought down to pH 4.5. In preparative IEF using pH 3–10 ampholytes, activity was not found in the ECB-active IEF fractions; instead, it was highest in a fraction of pH 4.5–5.0. Its major components have molecular weights of ~35 and ~80 kDa.

The pH 4.5 pellet was separated by anion exchange HPLC to yield fractions containing only the 35 kDa material and fractions containing both 35 kDa and 80 kDa bands.

EXAMPLE 18

CHARACTERIZATION OF AB88 VIP.

Fractions containing the various lepidopteran active vegetative proteins were generated as described in Example 17. Biological analysis of fractions demonstrated that different VIPs were responsible for the different lepidopteran species activity.

The *Agrotis ipsilon* activity is due to an 80 kDa and/or a 35 kDa protein, either delivered singly or in combination. These proteins are not related to any δ-endotoxins from Bt as evidenced by the lack of sequence homology of known Bt δ-endotoxm sequences. Also, these proteins are not found in the AB88 δ-endotoxin crystal. N-terminal sequences of the major δ-endotoxin proteins were compared with the N-terminal sequences of the 80 kDa and 35 kDa VIP and revealed no sequence homology. A summary of the results follows:

| Agrotis VIP N-terminal sequences | N-terminal sequence of major δ-endotoxin proteins |
|---|---|
| | 130 kDa |
| | MDNNPNINE (SEQ ID NO:14) |
| 80 kDa | 80 kDa |
| MNKNNTKLPTRALP | MDNNPNINE (SEQ ID NO:15) |
| (SEQ ID NO:12) | 60 kDa |
| | MNVLNSGRTTI (SEQ ID NO:16) |
| 35 kDa | |
| ALSENTGKDGGYIVP | |
| (SEQ ID NO:13) | |

The *Ostrinia nubilalis* activity is due to a 60 kDa VIP and the *Spodoptera frugiperda* activity is due to a VIP of unknown size.

*Bacillus thuringiensis* strain AB88 has been deposited in the Agricultural Research Service, Patent Culture Collection (NRRL), Northern Regional Research Center, 1815 North University Street, Peoria, Ill. 61604, USA and given the Accession No. NRRL B-21225.

EXAMPLE 18A

ISOLATION AND BIOLOGICAL ACTIVITY OF B. THURINGIENSIS AB424

A *B. thuringiensis* strain, designated AB424, was isolated from a moss covered pine cone sample by standard methods known in the art. A subculture of AB424 was grown and prepared for bioassay as described in Example 2.

Biological activity was evaluated as described in Example 3. The results are as follows:

| Insect species tested | Percent mortality |
|---|---|
| Ostrinia nubilalis | 100 |
| Agrotis ipsilon | 100 |
| Diabrotica virgifera virgifera | 0 |

Strain AB424 has been deposited in the Agricultural Research Service, Patent Culture Collection (NRRL), Northern Regional Research Center, 1815 North University Street, Peoria, Ill. 61604, USA, and given Accession No. NRR B-21439.

EXAMPLE 18B

CLONING OF THE VIP3A(a) and VIP3A(b) GENES WHICH ENCODE PROTEINS ACTIVE AGAINST BLACK CUTWORM.

DNA from isolates AB88 and AB424 was digested with the restriction enzymes XbaI and EcoRI respectively, ligated into pBluescript vector previously linearized with the same enzymes and dephosphorylated, and transformed into *E. coli* DH5α strain. Recombinant clones were blotted onto nitrocellulose filters which were subsequently probed with a 33-bases long oligonucleotide corresponding to the 11-N terminal amino acids of the 80 kDa protein active against *Agrotis epsilon* (black cutworm). Four out of 400 recombinant clones were positive. Insect bioassays of the positive recombinants exhibited toxicity to black cutworm larvae comparable to that of AB88 or AB424 supernantants.

The nucleotide sequence of pCIB7104, a positive recombinant clone from AB88, and of pCIB7107, a positive recombinant clone from AB424, was determined by the dideoxy termination method of Sanger et al., *Proc. Natl. Acad. Sci. USA*, 74: 5463–5467 (1977), using PRISM Ready Reaction Dye Deoxy Terminator Cycle Sequencing Kits and PRISM Sequenase® Terminator Double-Stranded DNA Sequencing Kit and analysed on an ABI 373 automatic sequencer.

The clone pCIB7104 contains the VIP3A(a) gene whose coding region is disclosed in SEQ ID NO:28 and the encoded protein sequence is disclosed in SEQ ID NO:29. A synthetic version of the coding region designed to be highly expressed in maize is given in SEQ ID NO:30. Any number of synthetic genes can be designed based on the amino acid sequence given in SEQ ID NO:29.

The clone pCIB7107 contains the VIP3A(b) gene whose coding region is disclosed in SEQ ID NO:31 and the encoded protein is disclosed in SEQ ID NO:32. Both pCIB7104 and pCIB7107 have been deposited with the Agricultural Research Service Patent Culture Collection (NRRL) and given Accession Nos. NRRL B-21422 and B-21423, respectively.

EXAMPLE 18C.

IDENTIFICATION OF NOVEL VIP3-LIKE GENES BY HYBRIDIZATION

To identify Bacillus containing genes related to the VIP3A(a) from isolate AB88, a collection of Bacillus isolates was screened by hybridization. Cultures of 463 Bacillus strains were grown in microtiter wells until sporulation. A 96-pin colony stampel was used to transfer the cultures to 150 mm plates containing L-agar. Inoculated plates were kept at 30° C. for 10 hours, then at 4° C. overnight. Colonies were blotted onto nylon filters and probed with a 1.2Kb HindIII VIP3A(a) derived fragment. Hybridization was performed overnight at 62° C. using hybridization conditions of Maniatis et al. *Molecular Cloning: A Laboratory Manual* (1982). Filters were washed with 2×SSC/0.1% SDS at 62° C. and exposed to X-ray film.

Of the 463 Bacillus strains screened, 60 contain VIP3-like genes that could detected by hybridization.

EXAMPLE 18D.

CHARACTERIZATION OF A *B. thuringiensis* STRAIN M2194 CONTAINING A CRYPTIC VIP3-LIKE GENE A *B. thuringiensis* strain, designated M2194, was shown to contain VIP3-like gene(s) by colony hybridization as described in Example 18C. The M2194 VIP3 like gene is considered cryptic since no expression can be detected throughout the bacterial growth phases either by immunoblot analysis using polyclonal antibodies raised against the VIP3A(a) protein isolated from AB88 or by bioassay as described in Example 3.

The M2194 VIP3-like gene was cloned into pKS by following the protocol described in Example 9, which created pCIB7108. *E. coli* containing pCIB7108 which comprises the M2194 VIP3 gene were active against black cutworm demonstrating that the gene encodes a functional protein with insecticidal activity. The plasmid pCIB7108 has been deposited with the Agricultural Research Service Patent Culture Collection (NRRL) and given Accession No. NRRL B-21438.

EXAMPLE 19

ISOLATION AND BIOLOGICAL ACTIVITY OF OTHER BACILLUS SP.

Other Bacillus species have been isolated which produce proteins with insecticidal activity during vegetative growth. These strains were isolated from environmental samples by standard methodologies. Isolates were prepared for bioassay and assayed as described in Examples 2 and 3 respectively. Isolates which produced insecticidal proteins during vegetative growth with activity against *Agrotis ipsilon* in the bioassay are tabulated below. No correlation was observed between the presence of a δ-endotoxin crystal and vegetative insecticidal protein production.

| Bacillus isolate | Presence of δ-endotoxin crystal | Percent mortality |
|---|---|---|
| AB6 | + | 100 |
| AB53 | – | 80 |
| AB88 | + | 100 |
| AB195 | – | 60 |
| AB211 | – | 70 |
| AB217 | – | 83 |
| AB272 | – | 80 |
| AB279 | – | 70 |
| AB289 | + | 100 |
| AB292 | + | 80 |
| AB294 | – | 100 |
| AB300 | – | 80 |
| AB359 | – | 100 |

Isolates AB289, AB294 and AB359 have been deposited in the Agricultural Research Service, Patent Culture Collection (NRRL), Northern Regional Research Center, 1815 North University Street, Peoria Ill. 61604, USA and given the Accession Numbers NRRL B-21227, NRRL B-21229, and NRRL B-21226 respectively.

Bacillus isolates which produce insecticidal proteins during vegetative growth with activity against *Diabrotica virgifera virgifera* are tabulated below.

| Bacillus isolate | Presence of δ-endotoxin crystal | Percent mortality |
|---|---|---|
| AB52 | – | 50 |
| AB59 | – | 71 |
| AB68 | + | 60 |
| AB78 | – | 100 |
| AB122 | – | 57 |
| AB218 | – | 64 |
| AB256 | – | 64 |

Isolates AB59 and AB256 have been deposited in the Agricultural Research Service, Patent Culture Collection (NRRL), Northern Regional Research Center, 1815 North University Street, Peoria Ill. 61604, USA, and given the Accession Numbers NRRL B-21228 and NRRL B-21230, respectively.

EXAMPLE 20

IDENTIFICATION OF NOVEL VIP1/VIP2 LIKE GENES BY HYBRIDIZATION

To identify strains containing genes related to those found in the VIP1A(a)/VIP2A(a) region of AB78, a collection of Bacillus strains was screened by hybridization. Independent cultures of 463 Bacillus strains were grown in wells of 96 well microtiter dishes (five plates total) until the cultures sporulated. Of the strains tested, 288 were categorized as *Bacillus thuringiensis*, and 175 were categorized as other Bacillus species based on the presence or absence of δ-endotoxin crystals. For each microtiter dish, a 96-pin colony stamper was used to transfer approximately 10 μl of spore culture to two 150 mm plates containing L-agar. Inoculated plates were grown 4–8 hours at 30° C., then chilled to 4° C. Colonies were transferred to nylon filters, and the cells lysed by standard methods known in the art. The filters were hybridized to a DNA probe generated from DNA fragments containing both VIP1A(a) and VIP2A(a) DNA sequences. Hybridization was performed overnight at 65° C. using the hybridization conditions of Church and Gilbert (Church, G. M., and W. Gilbert, PNAS, 81:1991–1995 (1984)). Filters were washed with 2×0 SSC containing 0.1% SDS at 65° C. and exposed to X-Ray film.

Of the 463 Bacillus strains screened, 55 strains were identified that hybridized to the VIP1A(a)/VIP2A(a) probe. DNA was isolated from 22 of these strains, and analyzed using a Southern blot with VIP1A(a)/VIP2A(a) DNA as probes. These strains were grouped into 8 classes based on their Southern blot pattern. Each class differed in Southern blot pattern from AB78. One class had a pattern identical to that of the VIP1A(a)/VIP2A(a) homologs from *Bacillus thuringiensis* var *tenebrionis* (see below). Each of the 22 strains was tested for activity against western corn rootworm (WCRW). Three strains, AB433, AB434, and AB435 were found to be active on WCRW. Western blot analysis using VIP2A(a) antisera revealed that strains AB6, AB433, AB434, AB435, AB444, and AB445 produce a protein(s) of equivalent size to VIP2A(a).

Notable among the strains identified was *Bacillus thuringiensis* strain AB6, (NRRL B-1060) which produced a VIP active against black cutworm (*Agrotis ipsilon*) as described in Example 15. Western blot analysis with polyclonal antisera to VIP2A(a) and polyclonal antisera to VIP1A(a) suggests that AB6 produces proteins similar to VIP2A(a) and VIP1A(a). Thus, AB6 may contain VIPs similar to VIP1A(a) and VIP2A(a), but with a different spectrum of insecticidal activity.

EXAMPLE 21

CLONING OF A VIP1A(a)/VIP2A(a) HOMOLOG FROM *BACILLUS THURINGIENSIS* VAR. *TENEBRIONIS*.

Several previously characterized Bacillus strains were tested for presence of DNA similar to VIP1A(a)/VIP2A(a) by Southern blot analysis. DNA from Bacillus strains AB78, AB88, GC91, HD-1 and ATCC 10876 was analyzed for presence of VIP1A(a)/VIP2A(a) like sequences. DNA from Bt strains GC91 and HD-1, and the Bc strain ATCC 10876 did not hybridize to VIP2A(a)/VIP1A(a) DNA, indicating they lack DNA sequences similar to VIP1A(a)/VIP2A(a) genes. Similarly, DNA from the insecticidal strain AB88 (Example 16) did not hybridize to VIP1A(a)/VIP2A(a) DNA region, suggesting that the VIP activity produced by this strain does not result from VIP1A(a)/VIP2A(a) homologs. In contrast, *Bacillus thuringiensis* var. *tenebrionis* (Btt) contained sequences that hybridized to the VIP1A(a)/VIP2A (a) region. Further analysis confirmed that Btt contains VIP1A(a)/VIP2A(a) like sequences.

To characterize the Btt homologs of VIP2A(a) and VIP1A (a), the genes encoding these proteins were cloned. Southern blot analysis identified a 9.5 kb Eco RI restriction fragment likely to contain the coding regions for the homologs. Genomic DNA was digested with Eco RI, and DNA fragments of approximately 9.5 kb in length were gel-purified. This DNA was ligated into pBluescript SK(+) digested with Eco RI, and transformed into *E. coli* to generate a plasmid library. Approximately 10,000 colonies were screened by colony hybridization for the presence of VIP2A(a) homologous sequences. Twenty eight positive colonies were identified. All twenty eight clones are identical, and contain VIP1A(a)/VIP2A(a) homologs. Clone pCIB7100 has been deposited in the Agricultural Research Service, Patent Culture Collection (NRRL), Northern Regional Research Center, 1815 North University Street, Peoria Ill. 61604, USA, and given the Accession Number B-21322. Several subclones were constructed from pCIB7100. A 3.8 kb Xba I fragment from pCIB7100 was cloned into pBluescript SK(+) to yield pCIB7101. A 1.8 kb Hind III fragment and a 1.4 kb Hind III fragment from pCIB7100 were cloned into pBluescript SK(+) to yield pCIB7102 and pCIB7103, respectively. Subclones pCIB7101, pCIB7102 and pCIB7103 have been deposited in the Agricultural Research Service, Patent Culture Collection (NRRL), Northern Regional Research Center, 1815 North University Street, Peoria Ill. 61604, USA, and given the Accession Numbers B-21323, B-21324 and B-21325 respectively.

The DNA sequence of the region of pCIB7100 containing the VIP2A(a)/VIP1A(a) homologs was determined by the dideoxy chain termination method (Sanger et al., 1977, Proc. Natl. Acad. Sci. USA 74:5463–5467). Reactions were performed using PRISM Ready Reaction Dye Deoxy Terminator Cycle Sequencing Kits and PRISM Sequenase® Terminator Double-Stranded DNA Sequencing Kits, and analyzed on an ABI model 373 automated sequencer. Custom oligonucleotides were used as primers to determine the DNA sequence in certain regions. The DNA sequence of this region is shown in SEQ ID NO:19.

The 4 kb region shown in SEQ ID NO:19 contains two open readings frames (ORFs), which encode proteins with a high degree of similarity to VIP1A(a) and VIP2A(a) proteins from strain AB78. The amino acid sequence of the VIP2A(a) homolog, designated as VIP2A(b) using the standardized nomenclature, is found at SEQ ID NO:20 and the amino acid sequence of the VIP1A(a) homolog, designated as VIP1A(b) using the standardized nomenclature, is disclosed at SEQ ID NO:21. The VIP2A(b) protein exhibits 91% amino acid identity to VIP2A(a) from AB78. An alignment of the amino acid sequences of the two VIP2 proteins is provided in Table 19. The VIP1A(b) protein exhibits 77 % amino acid identity to VIP1A(a) from AB78. An alignment of these two VIP1 proteins is provided in Table 20. The alignment shown in Table 20 discloses the similarity between VIP1A(b) and VIP1A(a) from AB78. This alignment reveals that the amino terminal regions of the two VIP1 proteins share higher amino acid identity in the amino-terminal region than in the carboxy terminal region. In fact, the amino terminal two thirds (up to aa 618 of the VIP1A(b) sequence shown in Table 20 ) of the two proteins exhibit 91% identity, while the carboxy-terminal third (from aa 619–833 of VIP1A(b)) exhibit only 35% identity.

Western blot analysis indicated that *Bacillus thuringiensis* var. *tenebrionis* (Btt) produces both VIP1A(a) like and VIP2A(a) like proteins. However, these proteins do not appear to have activity against western corn rootworm. Bioassay for activity against western corn rootworm was performed using either a 24 h culture supernatant from Btt or *E. coli* clone pCIB7100 (which contains the entire region of the VIP1A(a)/VIP2A(a) homologs). No activity against western corn rootworm was detected in either case.

Given the similarity between the VIP2 proteins from Btt and AB78, the ability of VIP2A(b) from Btt to substitute for VIP2A(a) from AB78 was tested. Cells containing pCIB6206 (which produces AB78 VIP1A(a) but not VIP2A (a) protein) were mixed with Btt culture supernatant, and tested for activity against western corn rootworm. While neither Btt culture supernatant nor cells containing pCIB6206 had activity on WCRW, the mixture of Btt and pCIB6206 gave high activity against WCRW. Furthermore, additional bioassay showed that the Btt clone pCIB7100, which contains the Btt VIP 1 A(b)VIP2A(b) genes in *E. coli*, also confers activity against WCRW when mixed with pCIB6206. Thus, the VIP2A(b) protein produced by Btt is functionally equivalent to the VIP2A(a) protein produced by AB78.

Thus, the ability to identify new strains with insecticidal activity by using VIP DNA as hybridization probes has been demonstrated. Furthermore, Bacillus strains that contain VIP1A(a)/VIP2A(a) like sequences, produce VIP1A(a)/VIP2A(a) like protein, yet demonstrate toxicity toward different insect pests. Similar methods can identify many more members of the VIP1/VIP2 family. Furthermore, use of similar methods can identify homologs of other varieties of VIPs (for example, the VIPs from AB88).

TABLE 19

Alignment of VIP2 Amino Acid Sequences
from *Bacillus thuringiensis* var. *tenebrionis*
(VIP2A(b)) vs. AB78 (VIP2A(a))

```
Btt    1  MQRMEGKLFVVSKTLQVVTRTVLLSTVYSITLLNNVVIKADQLNINSQSK  50  SEQ ID NO:20
          |.||||||:|||.||||:||||||||:|.||||  ||||:||||||||
AB78   1  MKRMEGKLFMVSKKLQVVTKTVLLSTVFSISLLNNEVIKAEQLNINSQSK  50  SEQ ID NO:2

51 YTNLQNLKIPDNAEDFKEDKGKAKEWGKEKGEEWRPPATEKGEMNNFLDN 100
          ||||||||.|..||||||:||||||||:.||:.|||||.||||||
       51 YTNLQNLKITDKVEDFKEDKEKAKEWGKEKEKEWKLTATEKGKMNNFLDN 100

101 KNDIKTNYKEITFSMAGSCEDEIKDLEEIDKIFDKANLSSSIITYKNVEP 150
          ||||  ||||||||||||||  ||||||.||||:|||.|||.|||||||||
      101 KNDIXTNYKEITFSMAGSFEDEIKDLKEIDKMFDKTNLSNSIITYKNVEP 150

151 ATIGFNKSLTEGNTINSDAMAQFKEQFLGKDMKFDSYLDTHLTAQQVSSK 200
          .||||||||||||||||||||||||||::|:||||||||||||||||||
      151 TTIGFNKSLTEGNTINSDAMAQFKEQFLDRDIKFDSYLDTHLTAQQVSSK 200

201 KRVILKVTVPSGKGSTTPTKAGVILNNNEYKMLIDNGYVLHVDKVSKVVK 250
          .|||||||||||||||||||||||||.||||||||||::|||||||||
      201 ERVILKVTVPSGKGSTTPTKAGVILNNSEYKMLIDNGYMVHVDKVSKVVK 250

251 KGMECLQVEGTLKKSLDFKNDINAEAHSWGMKIYEDWAKNLTASQREALD 300
          ||:||||:|||||||||||||||||||||||||  ||:|||:||.||||||
      251 KGVECLQIEGTLKKSLDFKNDINAEAHSWGMKNYEEWAKDLTDSQREALD 300

301 GYARQDYKEINNYLRNQGGSGNEKLDAQLKNISDALGKKPIPENITVYRW 350
          |||||||||||||||||||||||||||:||||||||||||||||||||||
      301 GYARQDYKEINNYLRNQGGSGNEKLDAQIKNISDALGKKPIPENITVYRW 350

351 CGMPEFGYQISDPLPSLKDFEEQFLNTIKEDKGYMSTSLSSERLAAFGSR 400
          ||||||||||||||||||||||||||||||||||||||||||||||||||
      351 CGMPEFGYQISDPLPSLKDFEEQFLNTIKEDKGYMSTSLSSERLAAFGSR 400

401 KIILRLQVPKGSTGAYLSAIGGFASEKEILLDKDSKYHIDKATEVIIKGV 450
          ||||||||||||||||||||||||||||||||||||||||||.||||||||
      401 KIILRLQVPKGSTGAYLSAIGGFASEKEILLDKDSKYHIDKVTEVIIKGV 450

451 KRYVVDATLLTN 462
          ||||||||||||
      451 KRYVVDATLLTN 462
```

TABLE 20

Alignment of VIP1 Amino Acid Sequences
from *Bacillus thuringiensis* var. *tenebrionis*
(VIP1A(b)) vs. AB78 (VIP1A(a))

```
Btt   1  MKNMKKKLASVVTCMLLAPMFLNGNVNAVNADSKINQISTTQENQQKEMD 50  SEQ ID NO:21
         ||||||||||||| |||||||||||||||| ||||.|||||||.||||||
Ab78  1  MKNMKKKLASVVTCTLLAPMFLNGNVNAVYADSKTNQISTTQKNQQKEMD 50  SEQ ID NO:5
```

TABLE 20-continued

Alignment of VIP1 Amino Acid Sequences
from *Bacillus thuringiensis* var. *tenebrionis*
(VIP1A(b)) vs. AB78 (VIP1A(a))

```
 51 RXGLLGYYFKGKDFNNLTMFAPTRDNTLMYDQQTANALLDKKQQEYQSIR 100
    ||||||||||||||.||||||||||.||:|||||||| ||||||||||||
 51 RKGLLGYYFKGKDFSNLTMFAPTRDSTLIYDQQTANKLLDKKQQEYQSIR 100

101 WIGLIQRKETGDFTFNLSKDEQAIIEIDGKIISNKGKEKQVVHLEKEKLV 150
    |||||| .||||||||||||.||||||||:|||||||||||||||||:|||
101 WIGLIQSKETGDFTFNLSEDEQAIIEINGKIISNKGKEKQVVHLEKGKLV 150

151 PIKIEYQSDTKFNIDSKTFKELKLFKIDSQNQSQQVQ...LRNPEFNKKE 197
    |||||||||||||||||||||||||||||||||.||||   ||||||||||
151 PIKIEYQSDTKFNIDSKTFKELKLFKIDSQNQPQQVQQDELRNPEFNKKE 200

198 SQEFLAKASKTNLFKQKMKRDIDEDTDTDGDSIPDLWEENGYTIQNKVAV 247
    |||||||:||.|||.|||||:|||||||||||||||||||||||::||
201 SQEFLAKPSKINLFTQKMKREIDEDTDTDGDSIPDLWEENGYTIQNRIAV 250

248 KWDDSLASKGYTKFVSNPLDSHTVGDPYTDYEKAARDLDLSNAKETFNPL 297
    ||||||||||||||||||:|||||||||||||||||||||||||||||
251 KWDDSLASKGYTKFVSNPLESHTVGDPYTDYEKAARDLDLSNAKETFNPL 300

298 VAAFPSVNVSMEKVILSPNENLSNSVESHSSTNWSYTNTEGASIEAGGGP 347
    ||||||||||||||||||||||||||||||||||||||||||:|||| ||
301 VAAFPSVNVSMEKVILSPNENLSNSVESHSSTNWSYTNTEGASVEAGIGP 350

348 LGLSFGVSVTYQHSETVAQEWGTSTGNTSQFNTASAGYLNAVVRYNNVGT 397
    |:||||||.||||||||||||||||||||||||||||||||.||||||||
351 KGISFGVSVNYQHSETVAQEWGTSTGNTSQFNTASAGYLNANVRYNNVGT 400

398 GAIYDVKPTTSFVLNNNTIATITAKSNSTALRISPGDSYPEIGENAIAIT 447
    ||||||||||||||||:|||||||||||||.||||:|||. |:|:||||
401 GAIYDVKPTTSFVLNNDTIATITAKSNSTALNISPGESYPKKGQNGIAIT 450

448 SMDDFNSHPITLNKQQVNQLINNKPIMLETDQTDGGYKIRDTHGNIVTGG 497
    ||||||||||||.||:.|:|||||:||||:|||||||:||||||||||
451 SMDDFNSHPITLNKKQVDNLLNNKPMMLETNQTDGVYKIKDTHGNIVTGG 500

498 EWNGVTQQIKAKTASIIVDDGKQVAEKRVAAKDYGHPEDKTPPLTLKDTL 547
    |||||.||||||||||||||..||||||||||::||||||.|||||.|
501 EWNGVIQQIKAKTASIIVDDGERVAEKRVAAKDYENPEDKTPSLTLKDAL 550

548 KLSYPDEIKETNGLLYYDDKPIYESSVMTYLDENTAKEVKKQINDTTGKF 597
    |||||||||.:|||||.:||||||||||||||||||||.||:||||||
551 KLSYPDEIKEIEGLLYYKNKPIYESSVMTYLDENTAKEVTKQLNDTTGKF 600

598 KDVNHLYDVKLTPKMNFTIKMASLYDGAENNHNSLGTWYLTYNVAGGNTG 647
    |||.|||||||||||.|||:. |||.||.|.||:.|  | |.|||.|
601 KDVSHLYDVKLTPKMNVTIKLSILYDNAESNDNSIGKWTNTNIVSGGNNG 650

648 KRQYRSAHSCAHVALSSEAKKKLNQNANYYLSMYMKADSTTEPTIEVAGE 697
    |:||.|.:. |::.|...:|..|||.| :|||:|:|||.:..|:..|::.||
651 KKQYSSNNPDANLYLNTDAQEKLNKNRDYYISLYMKSEKNTQCEITIDGE 700

698 KSAITSKKVKLNNQNYQRVDILVKNSERNPMDKIYIRGNGTTNVYGDDVT 747
    :||.|.|..:|.:||.|:||:...| ...||:...:.|:.|:....::  ||:.
701 IYPITTKTVNVNKDNYKRLDIIAHNIKSNPISSLHIKTNDEITLFWDDIS 750

748 IPEVSAINPASLSDEEIQEIFKDSTIEYGNPSFVADAVTFK......... 788
    |.:|..|.|..|.|.||.:|:.  .|..::. ::..  ...:.
751 ITDVASIKPENLTDSEIKQTYSRYGIKLEDGILIDKKGGIHYGEFINEAS 800

789 .NIKPLQNYVKEYEIYHK.......SHRYEKKTVFDIMGVHYEYSIAREQ 830
    ||.||||||..|.: ..    |. .|...::.  .::::.   ...
801 FNIEPLQNYVTKYKVTYSSELGQNVSDTLESDKIYKDGTIKFDFTKYSKN 850

831 KKA 833
    ..:
851 EQG 853
```

EXAMPLE 22

FUSION OF VIP PROTEINS TO MAKE A SINGLE POLYPEPTIDE

VIP proteins may occur in nature as single polypeptides, or as two or more interacting polypeptides. When an active VIP is comprised of two or more interacting protein chains, these protein chains can be produced as a single polypeptide chain from a gene resulting from the fusion of the two (or more) VIP coding regions. The genes encoding the two chains are fused by merging the coding regions of the genes to produce a single open reading frame encoding both VIP polypeptides. The composite polypeptides can be fused to produce the smaller polypeptide as the NH$_2$ terminus of the fusion protein, or they can be fused to produce the larger of the polypeptides as the NH$_2$ terminus of the fusion protein. A linker region can optionally be used between the two polypeptide domains. Such linkers are known in the art. This linker can optionally be designed to contain protease cleavage sites such that once the single fused polypeptide is ingested by the target insect it is cleaved in the linker region to liberate the two polypeptide components of the active VIP molecule.

VIP1A(a) and VIP2A(a) from *B. cereus* strain AB78 are fused to make a single polypeptide by fusing their coding regions. The resulting DNA has the sequence given in SEQ ID NO:22 with the encoded protein given in SEQ ID NO:23. In like manner, other fusion proteins may be produced.

The fusion of the genes encoding VIP1A(a) and VIP2A(a) is accomplished using standard techniques of molecular biology. The nucleotides deleted between the VIP1A(a) and VIP2A(a) coding regions are deleted using known mutagenesis techniques or, alternatively, the coding regions are fused using PCR techniques.

The fused VIP polypeptides can be expressed in other organisms using a synthetic gene, or partially synthetic gene, optimized for expression in the alternative host. For instance, to express the fused VIP polypeptide from above in maize, one makes a synthetic gene using the maize preferred codons for each amino acid, see for example patent application U.S. Pat. No. 5,625,136 herein incorporated by reference. Synthetic DNA sequences created according to these methods are disclosed in SEQ ID NO:17 (maize optimized version of the 100 kDa VIP1A(a) coding sequence), SEQ ID NO:18 (maize optimized version of the 80 kDa VIP1A(a) coding sequence) and SEQ ID NO:24 (maize optimized version of the VIP2A(a) coding sequence).

Synthetic VIP1 and VIP2 genes optimized for expression in maize can be fused using PCR techniques, or the synthetic genes can be designed to be fused at a common restriction site. Alternatively, the synthetic fusion gene can be designed to encode a single polypeptide comprised of both VIP1 and VIP2 domains.

Addition of a peptide linker between the VIP1 and VIP2 domains of the fusion protein can be accomplished by PCR mutagenesis, use of a synthetic DNA linker encoding the linker peptide, or other methods known in the art.

The fused VIP polypeptides can be comprised of one or more binding domains. If more than one binding domain is used in the fusion, multiple target pests are controlled using such a fusion. The other binding domains can be obtained by using all or part of other VIPs; *Bacillus thuringiensis* endotoxins, or parts thereof; or other proteins capable of binding to the target pest or appropriate biding domains derived from such binding proteins.

One example of a fusion construction comprising a maize optimized DNA sequence encoding a single polypeptide chain fusion having VIP2A(a) at the N-terminal end and VIP1A(a) at the C-terminal end is provided by pCIB5531. A DNA sequence encoding a linker with the peptide sequence PSTPPTPSPSTPPTPS (SEQ ID NO:47) has been inserted between the two coding regions. The sequence encoding this linker and relevant cloning sites is 5'-<u>CCCGGG</u> CCT TCT ACT CCC CCA ACT CCC TCT CCT AGC ACG CCT CCG ACA CCT AGC <u>GAT ATC GGA TC C</u>-3' (SEQ ID NO:48). Oligonucleotides were synthesized to represent both the upper and lower strands and cloned into a pUC vector following hybridization and phosphorylation using standard procedures. The stop codon in VIP2A(a) was removed using PCR and replaced by the BglII restriction site with a SmaI site. A translation fusion was made by ligating the Bam HI/PstI fragment of the VIP2A(a) gene from pCIB5522 (see Example 24), a PCR fragment containing the PstI-end fragment of the VIP2A(a) gene (identical to that used to construct pCIB5522), a synthetic linker having ends that would ligate with a blunt site at the 5' end and with BamHI at the 3' end and the modified synthetic VIP1A(a) gene from pCIB5526 described below (See SEQ ID NO:35). The fusion was obtained by a four way ligation that resulted in a plasmid containing the VIP2A(a) gene without a translation stop codon, with a linker and the VIP1A(a) coding region without the Bacillus secretion signal. The DNA sequence for this construction is disclosed in SEQ ID NO:49, which encodes the fusion protein disclosed in SEQ ID NO:50. A single polypeptide fusion where VIP1A(a) is at the N-terminal end and VIP2A(a) is at the C-terminal end can be made in a similar fashion. Furthermore, either one or both genes can be linked in a translation fusion with or without a linker at either the 5' or the 3' end to other molecules like toxin encoding genes or reporter genes.

EXAMPLE 23

TARGETING OF VIP2 TO PLANT ORGANELLES

Various mechanisms for targeting gene products are known to exist in plants and the sequences controlling the functioning of these mechanisms have been characterized in some detail. For example, the targeting of gene products to the chloroplast is controlled by a signal sequence found at the amino-terminal end of various proteins. This signal is cleaved during chloroplast import, yielding the mature protein (e.g. Comai et al. J. Biol. Chem. 263: 15104–15109 (1988)). These signal sequences can be fused to heterologous gene products such as VIP2 to effect the import of those products into the chloroplast (van den Broeck et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. Plant Molec. Biol. 13: 411418 (1989)). The cDNAs encoding these products can also be manipulated to effect the targeting of heterologous gene products such as VIP2 to these organelles. Examples of such sequences are the nuclear-encoded ATPases and specific aspartate amino transferase isoforms for mitochondria. Similarly, targeting to cellular protein bodies has been described by Rogers et al. (Proc. Natl. Acad. Sci. USA 82: 6512–6516 (1985)).

By the fusion of the appropriate targeting sequences described above to coding sequences of interest such as VIP2 it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino-terminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the start codon ATG, or alternatively replacement of some amino acids within the coding sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) Methods in Chloroplast Molecular Biology, Elsevier. pp 1081–1091 (1982); Wasmann et al. Mol. Gen. Genet. 205: 446–453 (1986)). These construction techniques are well known in the art and are equally applicable to mitochondria and peroxisomes.

The above described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

A DNA sequence encoding a secretion signal is present in the native Bacillus VIP2 gene. This signal is not present in the mature protein which has the N-terminal sequence of LKITDKVEDF (amino acid residues 57 to 66 of SEQ ID NO:2). It is possible to engineer VIP2 to be secreted out of the plant cell or to be targeted to subcellular organelles such as the endoplasmic reticulum, vacuole, mitochondria or plastids including chloroplasts. Hybrid proteins made by fusion of a secretion signal peptide to a marker gene have been successfully targeted into the secretion pathway. (Itirriaga G. et al., *The Plant Cell*, 1: 381–390 (1989), Denecke et al., *The Plant Cell*, 2:51–59 (1990). Amino-terminal sequences have been identified that are responsible for targeting to the ER, the apoplast, and extracellular secretion from aleurone cells (Koehler & Ho, Plant Cell 2: 769–783 (1990)).

The presence of additional signals are required for the protein to be retained in the endoplasmic reticulum or the vacuole. The peptide sequence KDELIHDEL at the carboxy-terminal of a protein is required for its retention in the endoplasmic reticulum (reviewed by Pelham, *Annual Review Cell Biol.*, 5:1–23 (1989). The signals for retention of proteins in the vacuole have also been characterized. Vacuolar targeting signals may be present either at the amino-terminal portion, (Holwerda et al., *The Plant Cell*, 4:307–318 (1992), Nakamura et al., *Plant Physiol.*, 101:1–5 (1993)), carboxy-terminal portion, or in the internal sequence of the targeted protein. (Tague et al., *The Plant Cell*, 4:307–318 (1992), Saalbach et al., *The Plant Cell*, 3:695–708 (1991)). Additionally, amino-terminal sequences in conjunction with carboxy-terminal sequences are responsible for vacuolar targeting of gene products (Shinshi et al. Plant Molec. Biol. 14: 357–368 (1990)). Similarly, proteins may be targeted to the mitochondria or plastids using specific carboxy terminal signal peptide fusions (Heijne et al., *Eur. J. Biochem.*, 180:535–545 (1989), Archer and Keegstra, *Plant Molecular Biology*, 23:1105–1115 (1993)).

In order to target VIP2, either for secretion or to the various subcellular organelles, a maize optimized DNA sequence encoding a known signal peptide(s) may be designed to be at the 5' or the 3' end of the gene as required. To secrete VIP2 out of the cell, a DNA sequence encoding the eukaryotic secretion signal peptide MGWSWIFLFLLS-GAAGVHCL (SEQ ID NO:25) from U.S. patent application Ser. No. 08/267,641 or any other described in the literature (Itirriaga et al., *The Plant Cell*, 1:381–390 (1989), Denecke, et al., *The Plant Cell*, 2:51–59 (1990)) may be added to the 5' end of either the complete VIP2 gene sequence or to the sequence truncated to encode the mature protein or the gene truncated to nucleotide 286 or encoding a protein to start at amino acid residue 94 (methionine). To target VIP2 to be retained in the endoplasmic reticulum, a DNA sequence encoding the ER signal peptide KDEL/HDEL, in addition to the secretion signal, can be added to the 3' end of the gene. For vacuolar targeting a DNA sequence encoding the signal peptide SSSSFADSNPIRVTDRAAST (SEQ ID NO:3; Holwerda et al., *The Plant Cell*, 4:307–318 (1992)) can be designed to be adjacent to the secretion signal or a sequence encoding a carboxyl signal peptide as described by Dombrowski et al., *The Plant Cell*, 5:587–596 (1993) or a functional variation may be inserted at the 3' end of the gene. Similarly, VIP2 can be designed to be targeted to either the mitochondria or the plastids, including the chloroplasts, by inserting sequences in the VIP2 sequence described that would encode the required targeting signals. The bacterial secretion signal present in VIP2 may be retained or removed from the final construction.

One example of a construction which incorporates a eukaryotic secretion signal fused to a coding sequence for a VIP is provided by pCIB5528. Oligonucleotides corresponding to both the upper and lower strand of sequences encoding the secretion signal peptide of SEQ ID NO:25 was synthesized and has the sequence 5'-GGATCCACC ATG GGC TGG AGC TGG ATC TTC CTG TTC CTG CTG AGC GGC GCC GCG GGC GTG CAC TGC CTGCAG-3' (SEQ ID NO:41). When hybridized, the 5' end of the secretion signal resembled "sticky-ends" corresponding to restriction sites BamHI and PstI. The oligonucleotide was hybridized and phosphorylated and ligated into pCIB5527 (construction described in Example 23A) which had been digested with BamHI/PstI using standard procedures. The resulting maize optimized coding sequence is disclosed in SEQ ID NO:42 which encodes the protein disclosed in SEQ ID NO:43. This encoded protein comprises the eukaryotic secretion signal in place of the Bacillus secretion signal.

One example of a construction which incorporates a vacuolar targetting signal fused to a coding sequence for a VIP is provided by pCIB5533. Oligonucleotides corresponding to both the upper and lower strand of sequences encoding the vacuolar targetting peptide of SEQ ID NO:3 was synthesized and has the sequence 5'-CCG CGGGCG TGC ACT GCC TCA GCA GCA GCA GCT TCG CCG ACA GCA ACC CCA TCC GCG TGA CCG ACC GCG CCG CCA GCA CCC TGC AG-3' (SEQ ID NO:44). When hybridized, the 5' end of the vacuolar targetting signal resembled "sticky-ends" corresponding to restriction sites SacII and PstI. The oligonucleotide was hybridized and phosphorylated and ligated into pCIB5528 (construction described above) which had been digested with SacII/PstI using standard procedures. The resulting maize optimized coding sequence is disclosed in SEQ ID NO:45 which encodes the protein disclosed in SEQ ID NO:46. This encoded protein comprises the vacuolar targetting peptide in addition to the eukaryotic secretion signal.

The VIP1 gene can also be designed to be secreted or targeted to subcellular organelles by similar procedures.

EXAMPLE 23A

REMOVAL OF BACILLUS SECRETION SIGNAL FROM VIP1A(a) AND VIP2A(a)

VIP1A(a) and VIP2A(a) are secreted during the growth of strain AB78. The nature of peptide sequences that act as secretion signals has been described in the literature (Simonen and Palva, Microbiological reviews, pg. 109–137

(1993)). Following the information in the above publication, the putative secretion signal was identified in both genes. In VIP1A(a) this signal is composed of amino acids 1–33 (See SEQ ID NO:5). Processing of the secretion signal probably occurs after the serine at amino acid 33. The secretion signal in VIP2A(a) was identified as amino acids 1–49 (See SEQ ID NO:2). N-terminal peptide analysis of the secreted mature VIP2A(a) protein revealed the N-terminal sequence LKITDKVEDFKEDK. This sequence is found beginning at amino acid 57 in SEQ ID NO:2. The genes encoding these proteins have been modified by removal of the Bacillus secretion signals.

A maize optimized VIP1A(a) coding region was constructed which had the sequences encoding the first 33 amino acids, i.e., the secretion signal, removed from its 5' end. This modification was obtained by PCR using an forward primer that contained the sequence 5'-GGA TCC ACC ATG AAG ACC AAC CAG ATC AGC-3' (SEQ ID NO:33), which hybridizes with the maize optimized gene (SEQ ID NO:26) at nucleotide position 100, and added a BamHI restriction site and a eukaryotic translation start site consensus including a start codon. The reverse primer that contained the sequence 5'-AAG CTT CAG CTC CTT G-3' (SEQ ID NO:34) hybridizes on the complementary strand at nucelotide position 507. A 527 bp amplification product was obtained containing the restriction sites BamHI at the 5' end and HindIII site at the 3' end. The amplification product was cloned into a T-vector (described in Example 24, below) and sequenced to ensure the correct DNA sequence. The BamHI/HindIII fragment was then obtained by restriction digest and used to replace the BamHI/HindIII fragment of the maize optimized VIP1A(a) gene cloned in the root-preferred promoter cassette. The construct obtained was designated pCIB5526. The maize optimized coding region for VIP1A (a) with the Bacillus secretion signal removed is disclosed as SEQ ID NO:35 and the encoded protein is disclosed as SEQ ID NO:36.

The gene encoding the processed form of VIP2A(a), i.e., a coding region with the secretion signal removed, was constructed by a procedure similar to that described for that used to construct the processed form of VIP1 A(a), above. The modification was obtained by PCR using the forward primer 5'-GGA TCC ACC ATG CTG CAG AAC CTG AAG ATC AC -3' (SEQ ID NO:37). This primer hybridizes at nucleotide position 150 of the maize optimized VIP2A(a) gene (SEQ ID NO:27). A silent mutation has been inserted at nucleotide position 15 of this primer to obtain a PstI restriction site. The reverse primer has the sequence 5'-AAG CTT CCA CTC CIT CTC-3' (SEQ ID NO:38). A 259 bp product was obtained with HindIII restriction site at the 3' end. The amplification product was cloned into a T-vector, sequenced and ligated to a BamHI/HindIII digested root-preferred promoter cassette containing the maize optimized VIP2A(a). The construct obtained was designated pCIB5527. The maize optimized coding region for VIP2A (a) with the Bacillus secretion signal removed is disclosed as SEQ ID NO:39 and the encoded protein is disclosed as SEQ ID NO:40.

EXAMPLE 24

CONSTRUCTION AND CLONING OF THE VIP1A(a) AND VIP2A(a) MAIZE OPTIMIZED GENES

Design: The maize optimized genes were designed by reverse translation of the native VIP1 A(a) and VIP2A(a) protein sequences using codons that are used most often in maize (Murray et al., *Nucleic Acid Research*, 17:477498 (1989)). To facilitate cloning, the DNA sequence was further modified to incorporate unique restriction sites at intervals of every 200–360 nucleotides. VIP1 A(a) was designed to be cloned in 11 such fragments and VIP2A(a) was cloned in 5 fragments. Following cloning of the individual fragments, adjacent fragments were joined using the restriction sites common to both fragments, to obtain the complete gene. To clone each fragment, oligonucleotides (50–85 nucleotides) were designed to represent both the upper and the lower strand of the DNA. The upper oligo of the first oligo pair was designed to have a 15 bp single stranded region at the 3' end which was homologous to a similar single stranded region of the lower strand of the next oligo pair to direct the orientation and sequence of the various oligo pairs within a given fragment. The oligos are also designed such that when the all the oligos representing a fragment are hybridized, the ends have single stranded regions corresponding to the particular restriction site to be formed. The structure of each oligomer was examined for stable secondary structures such as hairpin loops using the OLIGO program from NBI Inc. Whenever neccesary, nucleotides were changed to decrease the stability of the secondary structure without changing the amino acid sequence of the protein. A plant ribosomal binding site consensus sequence, TAAACAATG (Joshi et al., *Nucleic Acid Res.*, 15:6643–6653 (1987)) or eukaryotic ribosomal binding site concensus sequence CCACCATG (Kozak, *Nucleic Acid Research*, 12:857–872 (1984)) was inserted at the translational start codon of the gene.

Cloning: Oligos were synthesized by IDT Inc., and were supplied as lyophilized powders. They were resuspended at a concentration of 200 μM. To 30 μl of each oligo formamide was added a final concentration of 25–50% and the sample was boiled for two minutes before separation on a premade 10% polyacryamide/urea gel obtained from Novex. After electrophoresis, the oligo was detected by UV shadowing by placing the gel on a TLC plate containing a fluorescent indicator and exposing it to UV light. The region containing DNA of the correct size was excised and extracted from the polyacryamide by an overnight incubation of the minced gel fragment in a buffer containing 0.4 M LiCl, 0.1 mM EDTA. The DNA was separated from the gel residue by centrifugation through a Millipore UFMC filter. The extracted DNA was ethanol precipitated by the addition of 2 volumes of absolute alcohol. After centrifugation, the precipitate was resuspended in dH$_2$O at a concentration of 2.5 μM. Fragments were cloned either by hybridization of the oligos and ligation with the appropriate vector or by amplification of the hybridized fragment using a equimolar mixture of all the oligos for a particular fragment as a template and end-specific PCR primers.

Cloning by hybridization and ligation: Homologous double stranded oligo pairs were obtained by mixing 5 μl of the upper and of the lower oligo for each oligo pair with buffer containing 1× polynucleotide kinase (PNK) buffer (70 mM Tris-HCl (pH 7.6), 10 mM MgCl$_2$, 5 mM dithiothreitol (DTT)), 50 mM KCl, and 5% formamide in a final volume of 50 μl. The oligos were boiled for 10 minutes and slow cooled to 37° C. or room temperature. 10 μl was removed for analysis on a 4% agarose in a TAE buffer system (Metaphore®; FMC). Each hybridized oligo pair was kinased by the addition of ATP at a final concentration of 1 mM, BSA at a final concentration of 100 μg per ml and 200 units of polynucleotide kinase and 1 μl of 10× PNK buffer in a volume of 10 μl. Following hybridization and phosphorylation, the reaction was incubated at 37° C. for 2 hours to overnight. 10 μl of each of the oligo pairs for a particular fragment, were mixed in a final volume of 50 μl. The oligo pairs were hybridized by heating at 80° C. for 10 minutes and slow cooling to 37° C. 2 ul of oligos was mixed with about 100 ng of an appropriate vector and ligated using a buffer containing 50 mM Tris-HCl (pH 7.8), 10 mM MgCl$_2$, 10 mM DTT, 1 mM ATP. The reaction was incubated at room temp. for 2 hours to overnight and transformed into DH5α strain of E. coli, plated on L- plates containing ampicillin at a concentration of 100 μg/ml using standard procedures. Positive clones were further characterized and confirmed by PCR miniscreen described in detail in U.S. Pat. No. 5/625,136 using the universal primers "Reverse" and M13 "–20" as primers. Positive clones were identified by digestion of DNA with appropriate enzymes followed by sequencing. Recombinants that had the expected DNA sequence were then selected for further work.

PCR Amplification and cloning into T-vector:

PCR amplification was carried out by using a mixture of all the oligomers that represented the upper and the lower strand of a particular fragment (final concentration 5 mM each) as template, specific end primers for the particular fragment (final concentration 2 μM) 200 μM of each dATP, dTTP, dCTP and dGTP, 10 mM Tris-HCl (pH 8.3), 50 mM KCl, 1.5 mM MgCl$_2$, 0.01% gelatin and 5 units of Taq polymerase in a final reaction volume of 50 μl. The amplification reaction was carried out in a Perkin Elmer thermocycler 9600 by incubation at 95° C. for 1 min (1 cycle ), followed by 20 cycles of 95° C. for 45 sec., 50° C. for 45 sec., 72° C. for 30 sec. Finally the reaction was incubated for 5 min at 72° C. before analyzing the product. 10μl of the reaction was analyzed on a 2.5% Nusieve (FMC) agarose gel in a TAE buffer system. The correct size fragment was gel purified and used for cloning into a PCR cloning vector or T-vector. T-vector construction was as described by Marchuk et al., *Nucleic Acid Research*, 19:1154 (1991). pBluescriptsk+ (Stratagene®, Ca.) was used as the parent vector. Transformation and identification of the correct clone was carried out as described above.

Fragments 1, 3, 4, 5, 6, 8, and 9 of VIP1A(a) and fragments 2 and 4 of VIP2A(a) were obtained by cloning of PCR amplification products; whereas, fragments 2, 7, 10 and 11 of VIP1A(a) and fragments 1, 3, and 5 of VIP2A(a) were obtained by hybridization/ligation.

Once fragments with the desired sequence were obtained, the complete gene was assembled by cloning together adjacent fragments. The complete gene was resequenced and tested for activity against WCRW before moving it into plant expression vectors containing the root preferred promoter (disclosed in U.S. Pat. No. 5,466,785, herein incorporated by reference) and the rice actin promoter.

One such plant expression vector is pCIB5521. The maize optimized VIP1A(a) coding region (SEQ ID NO:26) was cloned in a plant expression vector containing the root preferred promoter at the 5' of the gene with the PEP Carboxylase intron #9 followed by the 35S terminator at the 3' end. The plasmid also contains sequences for ampicillin resistance from the plasmid pUC19. Another plant expression vector is pCIB5522, which contains the maize optimized VIP2A(a) coding region (SEQ ID NO:27) fused to the root preferred promoter at the 5' of the gene with the PEP Carboxylase intron #9 followed by the 35S terminator at the 3' end.

EXAMPLE 25

NAD AFFINITY CHROMATOGRAPHY

A purification strategy was used based on the affinity of VIP2 for the substrate NAD. The supernatant from the pH 3.5 sodium citrate buffer treatment described in Example 4 was dialyzed in 20 mM TRIS pH 7.5 overnight. The neutralized supematant was added to an equal volume of washed NAD agarose and incubated with gentle rocking at 4° C. overnight. The resin and protein solution were added to a 10 ml disposable polypropylene column and the protein solution allowed to flow out. The column was washed with 5 column volumes of 20 mM TRIS pH 7.5 then washed with 2–5 column volumes of 20 mM TRIS pH 7.5, 100 mM NaCl, followed by 2–5 column volumes of 20 mM TRIS 7.5. The VIP proteins were eluted in 20 mM TRIS pH 7.5 supplemented with 5 mM NAD. Approximately 3 column volumes of the effluent were collected and concentrated in a Centricon −10. Yield is typically about 7–15 μg of protein per ml of resin.

When the purified proteins were analyzed by SDS-PAGE followed by silver staining, two polypeptides were visible, one with Mr of approximately 80,000 and one with Mr of approximately 45,000. N-terminal sequencing revealed that the Mr 80,000 protein corresponded to a proteolytically processed form of VIP1A(A) and the Mr 45,000 form corresponded to a proteolytically processed form of VIP2A (a). The co-purification of VIP1A(a) with VIP2A(a) indicates that the two proteins probably form a complex and have protein-protein interacting regions. VIP1A(a) and VIP2A(a) proteins purified in this manner were biologically active against western corn rootworm.

EXAMPLE 26

EXPRESSION OF MAIZE OPTIMIZED VIP1A(a) AND VIP2A(a)

*E. coli* strains containing different plasmids comprising VIP genes were assayed for expression of VIPs. *E. coli* strains harboring the individual plasmids were grown overnight in L-broth and expressed protein was extracted from the culture as described in Example 3, above. Protein expression was assayed by Western Blot analysis using antibodies developed using standard methods known in the art, similar to those described in Example 12, above. Also, insecticidal activity of the expressed proteins were tested against Western corn rootworm according to the method in Example 3, above. The results of the *E. coli* expression assays are described below.

Expression of VIPs in *E. coli*

| Extract of *E. coli* Strain Harboring Indicated Plasmid | Assay No. 1 % Mortality | Assay No. 2 | Protein Detected |
|---|---|---|---|
| Control | 0 | 0 | no |
| pCIB5521 (maize optimized VIP1A(a)) | 47 | 27 | yes |
| pCIB5522 (maize optimized VIP2A(a)) | 7 | 7 | yes |
| pCIB6024 (native VIP2A(a)) | 13 | 13 | yes |
| pCIB6206 (native VIP1A(a)) | 27 | 40 | yes |
| Extracts pCIB5521 + pCIB5522 combined | 87 | 47 | |
| Extracts pCIB5521 + pCIB6024 combined | 93 | 100 | |
| Extracts pCIBSS22 + pCIB6206 combined | 100 | 100 | |
| Extracts pCIB6024 + pCIB6206 combined | 100 | 100 | |

The DNA from these plasmids was used to transiently express the VIPs in a maize protoplast expression system.

Protoplasts were isolated from maize 2717 Line 6 suspension cultures by digestion of the cell walls using Cellulase RS and Macerase R10 in appropriate buffer. Protoplasts were recovered by sieving and centrifugation. Protoplasts were transformed by a standard direct gene transfer method using approximately 75 μg plasmid DNA and PEG40. Treated protoplasts were incubated overnight in the dark at room temperature. Analysis of VIP expression was accomplished on protoplast explants by Western blot analysis and insecticidal activity against Western corn rootworm as described above for the expression in *E. coli*. The results of the maize protoplast expression assays are described below.

Expression of VIPs in Plant Protoplasts

| Extract Tested | Assay No. 1 % Mortality | Assay No. 2 | Protein Detected |
|---|---|---|---|
| No DNA Control | 27 | 10 | no |
| pCIB5521 (p) (maize optimized VIP1A(a)) | 20 (0) | 30 | yes |
| pCIB5522 (p) (maize optmizied VIP2A(a)) | 20 (0) | 20 | yes |
| Extracts pCIB5521 (p) + pCIB5522 (p) combined | 87 (82) | 90 | |
| Extracts pCIB5521 (p) + pCIB5522 (e) combined | 100 | — | |
| Extracts pCIB5522 (p) + pCIB5521 (e) combined | 53 (36) | — | |
| Extracts pCIB5521 (p) + pCIB6024 (e) combined | 100 | — | |
| Extracts pCIB5522 (p) + pCIB6206 (e) combined | 100 | — | |
| pCIB6024 (e) (native VIP2A(a)) | 0 | — | yes |
| pCIB6206 (e) (native VIP1A(a)) | 20 | — | yes |
| pCIB5521 + pCIB 5522 plasmids delivered by cotransformation | 100 | 100 | yes |

(p) = extract of protoplast culture transformed with indicated plasmid
(e) = extract of *E. coli* strain harboring indicated plasmid The expression data obtained with both *E. coli* and maize protoplasts show that the maize optimized VIP1A(a) and VIP2A(a) genes make the same protein as the native VIP1A (a) and VIP2A(a) genes, respectively, and that the proteins encoded by the maize optimized genes are functionally equivalent to the proteins encoded by the native genes.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The following deposits have been made at Agricultural Research Service, Patent Culture Collection (NRRL), Northern Regional Research Center, 1815 North University Street, Peoria, Ill. 61604, USA:

| | | |
|---|---|---|
| 1. | *E. coli* PL2 | Accession No. NRRL B-21221N |
| 2. | *E. coli* pCIB6022 | Accession No. NRRL B-21222 |
| 3. | *E. coli* pCIB6023 | Accession No. NRRL B-21223N |
| 4. | *Bacillus thuringiensis* HD73-78VIP | Accession No. NRRL B-21224 |
| 5. | *Bacillus thuringiensis* AB88 | Accession No. NRRL B-21225 |
| 6. | *Bacillus thuringiensis* AB359 | Accession No. NRRL B-21226 |
| 7. | *Bacillus thuringiensis* AB289 | Accession No. NRRL B-21227 |
| 8. | Bacillus sp. AB59 | Accession No. NRRL B-21228 |
| 9. | Bacillus sp. AB294 | Accession No. NRRL B-21229 |
| 10. | Bacillus sp. AB256 | Accession No. NRRL B-21230 |
| 11. | *E. coli* P5-4 | Accession No. NRRL B-21059 |
| 12. | *E. coli* P3-12 | Accession No. NRRL B-21061 |
| 13. | *Bacillus cereus* AB78 | Accession No. NRRL B-21058 |
| 14. | *Bacillus thuringiensis* AB6 | Accession No. NRRL B-21060 |
| 15. | *E. coli* pCIB6202 | Accession No. NRRL B-21321 |
| 16. | *E. coli* pCIB7100 | Accession No. NRRL B-21322 |
| 17. | *E. coli* pCIB7101 | Accession No. NRRL B-21323 |
| 18. | *E. coli* pCIB7102 | Accession No. NRRL B-21324 |
| 19. | *E. coli* pCIB7102 | Accession No. NRRL B-21325 |
| 20. | *E. coli* pCIB7104 | Accession No. NRRL B-21422 |
| 21. | *E. coli* pCIB7107 | Accession No. NRRL B-21423 |
| 22. | *E. coli* PCIB7108 | Accession No. NRRL B-21438 |
| 23. | *Bacillus thuringiensis* AB424 | Accession No. NRRL B-21439 |

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid molecule comprising a nucleotide sequence that encodes an insecticidal protein comprising an amino acid sequence that is the translation product of a nucleic acid sequence whose complement hybridizes to a sequence selected from the group consisting of nucleotides 1082–2467 of SEQ ID NO:1, nucleotides 2475–5126 of SEQ ID NO:1, nucleotides 1–1386 of SEQ ID NO:19, and nucleotides 1394–3895 of SEQ ID NO:19 under hybridization conditions of 65° C. followed by washing at 65° C. in 2×SSC containing 0.1 % SDS.

2. An isolated nucleic acid molecule according to claim 1, wherein said amino acid sequence is the translation product of a nucleic acid sequence whose complement hybridizes to nucleotides 1082–2467 of SEQ ID NO:1 or nucleotides 1–1386 of SEQ ID NO:19 under hybridization conditions of 65° C. followed by washing at 65° C. in 2×SSC containing 0.1% SDS.

3. An isolated nucleic acid molecule according to claim 1, wherein said amino acid sequence is the translation product of a nucleic acid sequence whose complement hybridizes to nucleotides 2475–5126 of SEQ ID NO:1 or nucleotides 1394–3895 of SEQ ID NO:19 under hybridization conditions of 65° C. followed by washing at 65° C. in 2×SSC containing 0.1% SDS.

4. An isolated nucleic acid molecule according to claim 2, wherein the nucleotide sequence that encodes the insecticidal protein is a synthetic sequence that has been designed for optimum expression in a plant.

5. An isolated nucleic acid molecule according to claim 4, wherein the plant is maize.

6. An isolated nucleic acid molecule according to claim 3, wherein the nucleotide sequence that encodes the insecticidal protein is a synthetic sequence that has been designed for optimum expression in a plant.

7. An isolated nucleic acid molecule according to claim 6, wherein the plant is maize.

8. A chimeric gene comprising a heterologous promoter sequence operatively linked to the nucleic acid molecule of claim 2.

9. A chimeric gene comprising a heterologous promoter sequence operatively linked to the nucleic acid molecule of claim 3.

10. A recombinant vector comprising the chimeric gene of claim 8.

11. A recombinant vector comprising the chimeric gene of claim 7.

12. A transgenic host cell comprising the chimeric gene of claim 8.

13. A transgenic host cell comprising the chimeric gene of claim 9.

14. A transgenic host cell according to claim 12, which is a transgenic plant cell.

15. A transgenic host cell according to claim 13, which is a transgenic plant cell.

16. A transgenic plant comprising the transgenic plant cell of claim 14.

17. A transgenic plant comprising the transgenic plant cell of claim 15.

18. Seed from the transgenic plant of claim 16.

19. Seed from the transgenic plant of claim 17.

20. An isolated nucleic acid molecule comprising a nucleotide sequence that encodes an insecticidal protein, wherein the complement of said nucleotide sequence hybridizes to a sequence selected from the group consisting of nucleotides 1082–2467 of SEQ ID NO:1, nucleotides 2475–5126 of SEQ ID NO:1, nucleotides 1–1386 of SEQ ID NO:19, and nucleotides 1394–3895 of SEQ ID NO:19 under hybridization conditions of 65° C. followed by washing at 65° C. in 2×SSC containing 0.1% SDS.

21. An isolated nucleic acid molecule according to claim 20, wherein the complement of said nucleotide sequence hybridizes to nucleotides 1082–2467 of SEQ ID NO:1 or nucleotides 1–1386 of SEQ ID NO:19 under hybridization conditions of 65° C. followed by washing at 65° C. 2×SSC containing 0.1% SDS.

22. An isolated nucleic acid molecule according to claim 20, wherein the complement of said nucleotide sequence hybridizes to nucleotides 2475–5126 of SEQ ID NO:1 or nucleotides 1394–3895 of SEQ ID NO:19 under hybridization conditions of 65° C. followed by washing at 65° C. in 2×SSC containing 0.1% SDS.

23. A chimeric gene comprising a heterologous promoter sequence operatively linked to the nucleic acid molecule of claim 21.

24. A clinieric gene comprising at heterologous promoter sequence operatively linked to the nucleic acid molecule of claim 22.

25. A recombinant vector comprising the chimeric gene of claim 23.

26. A recombinant vector comprising the chimeric gene of claim 24.

27. A transgenic host cell comprising the chimeric gene of claim 23.

28. A transgenic host cell comprising the chimeric gene of claim 24.

29. A transgenic host cell according to claim 27, which is a transgenic plant cell.

30. A transgenic host cell according to claim 28, which is a transgenic plant cell.

31. A transgenic plant comprising the transgenic plant cell of claim 29.

32. A transgenic plant comprising the transgenic plant cell of claim 30.

33. Seed from the transgenic plant of claim 31.

34. Seed from the transgenic plant of claim 32.

* * * * *